US008574635B2

(12) United States Patent
Lee-Huang et al.

(10) Patent No.: US 8,574,635 B2
(45) Date of Patent: Nov. 5, 2013

(54) COMPOSITIONS AND METHODS FOR TREATING OBESITY, OBESITY RELATED DISORDERS AND FOR INHIBITING THE INFECTIVITY OF HUMAN IMMUNODEFICIENCY VIRUS

(75) Inventors: Sylvia Lee-Huang, New York, NY (US); Paul L. Huang, Boston, MA (US); Philip Lin Huang, Maple Glen, PA (US); Dawei Zhang, Elmhurst, NY (US); John Z. H. Zhang, New York, NY (US); Young Tae Chang, New York, NY (US); Jae Wook Lee, San Diego, CA (US); Ju Bao, Brooklyn, NY (US); Yongtao Sun, Xi'an (CN)

(73) Assignees: New York University, New York, NY (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 12/932,018

(22) Filed: Feb. 16, 2011

(65) Prior Publication Data
US 2011/0142973 A1 Jun. 16, 2011

Related U.S. Application Data

(62) Division of application No. 11/827,135, filed on Jul. 9, 2007, now abandoned.

(60) Provisional application No. 60/819,172, filed on Jul. 7, 2006, provisional application No. 60/897,702, filed on Jan. 26, 2007.

(51) Int. Cl.
*A01N 65/00* (2009.01)
(52) U.S. Cl.
USPC .......................................................... 424/725
(58) Field of Classification Search
None
See application file for complete search history.

(56) References Cited

U.S. PATENT DOCUMENTS 6,893,627 B2 * 5/2005 Ribnicky et al. ............... 424/725
2004/0028751 A1 * 2/2004 Mae et al. ..................... 424/684

OTHER PUBLICATIONS

Bray, et al., Pharmacological Treatment of Obesity, Am J Clin Nutr 55:151S-319S, 1992.
Connolly, et al., Valvular Heart Disease Associated With Fenfluramine-Phentermine, New Engl J Med 337-581-588, 1997.
Degawa-Yamauchi M, Serum Resistin (FIZZ3) Protein Is Increased in Obese Humans, J. Clin. Endocrinol. Metab., 88: 5452-5455, (2003).
Bachman ES, Dhillon H, Zhang C-Y, et al. BetaAR signaling required for diet-induced thermogenesis and obesity resistance. Science 297:843, 2002.
Danforth (2000) Nature Genetics 26: 13.
Spiegelman et al. J. Biol. Chem. 268: 6823-6826, 1993.
Yu and Hausman, Exp Cell Res Dec. 15, 1998; 245(2): 343-9.
MacDougald, O. A. et al. (1995) Annu. Rev. Biochem 64:345-73.
Smas, C. M. et al. (1995) Biochem J. 309, 697-710.
Cornelius, P. et al. (1994) Annu. Rev. Nutr. 14:99-129.
Kirkland, J. L., et al.(1997) J. Amer. Geriatr. Soc. 45:959-67.
Lin, F. T., et al (1994) Proc. Natl. Acad: Sci. USA 91:8757-8761.
Hu, E. et al. (1995) Proc. Natl. Acad. Sci. USA 92:8956-60.
Wu, Z., et al. (1995) Genes Defer 9:2350-63.
Yeh, W. C., et al. (1995) Genes Devel. 9:168-81.
Wu et al. (1999) Transcriptional activation of adipogenesis Current Opin. Cell Biol 11:689-694.
Rosen and Spiegelman (2000) Molecular regulation of adipogenesis Annu Rev Cell Dev Biol 16:145-171.
Hopkinson et al. (1997) Am J Clin Nutr 65(2): 432-8.
Butte et al. (1999) Am J Clin Nutr 69(2): 299-307.
Anal Chem. May 15, 2006;78(10):3271-6.
Endocrine. Feb. 2006;29(1):81-90.
Proc Natl Acad Sci U S A. Apr. 27, 2004;101(17):6780-5. Epub Apr. 16, 2004.
Int J Obes (Lond). May 16, 2006.
Endocrinology. Jun. 2006;147(6):2690-5. Epub Mar. 2, 2006.
Biochem Biophys Res Commun. Jun. 23, 2006;345(1):332-9. Epub Apr. 27, 2006.
J Endocrinol Invest. Mar. 2006;29(3):231-6).
Br J Nutr. Aug. 2004;92 Suppl 1:S47-57.
Clin Exp Pharmacol Physiol. Apr. 2006;33(4):395-9.
HIF-alpha, beta, Diabetologia. May 2006;49(5):1049-63 Epub Feb. 28, 2006.
Biochem Biophys Res Commun. Mar. 10, 2006;341(2):549-56.
Am J Physiol Endocrinol Metab. Mar. 2006;290(3):E591-7. Epub Oct. 18, 2005.
Fleming, H.P. et al. (1973), Applied Microbiol. 26: 777-782.
Zanichelli, D. et al. (2005) J. Food Prot. 68(7):1492-1496.
Micol et al.(Micol, V. et al. (2005).
Carluccio, M.A. et al. (2003) Arterioscler Thromb Vasc Biol. 23: 622-629.

(Continued)

*Primary Examiner* — Michael Meller
(74) *Attorney, Agent, or Firm* — Klauber & Jackson LLC

(57) ABSTRACT

The present invention relates to methods and pharmaceutical compositions for treating obesity or obesity-related disorders in a subject suffering from or predisposed to developing obesity or an obesity-related disorder, or for inhibiting the infectivity of HIV, by administering oleuropein, an analogue or derivative thereof, or the major metabolites of oleuropein including oleuropein aglycone, hydroxytyrosol, and elenolic acid or their analogues, or derivatives thereof, an iridoid glycoside, or a secoiridoid glycoside or analogues or derivatives thereof, or any combination of the foregoing including olive leave extract. The invention also relates to methods for screening/diagnosing a subject having, or predisposed to having obesity or a related disorder by measuring the expression profiles of an adipogenic gene selected from PPARγ2, LPL and αP2 gene and gene product, or other adipogenic, lipogenic, or lipolytic genes and gene products in an individual. The invention further provides for screening for novel oleuropein analogues.

9 Claims, 28 Drawing Sheets

(56) References Cited

OTHER PUBLICATIONS

Hamdi, H.K. et al. (2005) Biochem Biophys. Res. Commun. Jul. 14 Epub.
Miles, E.A. et al. (2005), Nutrition, 21(3): 389-394.
Manna C. et al. (2004) J. Nutr. Biochem. 15(8): 461-466.
Puel, C. et al. (2004) 92(1): 119-127.
Coni E. et al. (2000), Lipids, 35(1): 45-54.
Caruso, D. (1999) Nutr. Metab. Cardiovasc. Dis. 9(3) :102-107.
Lee-Huang et al Biochemical & biophysical research communications.2003;307:1029.
Kliewer, et al., Recent Progress in Hormone Research, (2001), 56: 239-63.
Kersten et als, Peroxisome proliferator-activated receptor alpha mediates the adaptive response to fasting. J Clin Invest, 1999. 103: p. 1489-98.
Barak, et als, PPAR gamma is required for placental, cardiac, and adipose tissue development. Mol Cell, 1999. 4: p. 585-95.
Kubota, et als, PPAR gamma mediates high-fat diet-induced adipocyte hypertrophy and insulin resistance. Mol Cell, 1999. 4: p. 597-609.
Rosen, et als, , PPAR gamma is required for the differentiation of adipose tissue in vivo and in vitro. Mol Cell, 1999. 4: p. 611-7.
Tontonoz, et al, Stimulation of adipogenesis in fibroblasts by PPAR gamma 2, a lipid-activated transcription factor. Cell, 1994. 79: p. 1147-56.
Wang, et als, Peroxisome-proliferator-activated receptor delta activates fat metabolism to prevent obesity. Cell 2003. 113: p. 159-70.
Willson, et al., Journal of Medicinal Chemistry, (2000), 43: 527-550.
Auwerx, J., Diabetologia, (1999), 42: 1033-1049.
Koeffler H P Clin Cancer Res. 9(1):1-9 (2003).
Kuenzli S, et al., Br J. Dermatol. 149(2):229-36 (2003).
Duque G, Drug News Perspect. 16(6):341-6 (2003).
Jackson S M, et al., FEBS Lett. 471(1):119-24 (2000).
Feinstein D L, Diabetes Technol Ther. 5(1):67-73 (2003).
Ricote, et al., Nature, 391:79-82 (1998) and Jiang, et al., Nature, 391:82-86 (1998).
Eur J Pharmacol. Apr. 24, 2006;536(1-2):182-91. Epub Feb. 28, 2006.
Curr Opin Investig Drugs. Apr. 2006;7(4):360-70).
Lee-Huang, et als, Anti-HIV activity of olive leaf extract (OLE) and modulation of host cell gene expression by HIV-1 . . . Biochem Biophys Res Commun 307 (2003) 1029-1037.
Brown, Retroviruses, in Coffin, J., Hughes, S., and Varmus, H., (Eds.) Cold Spring Harbor Press, Cold Spring Harbor, 1998, 161-203.
T. K. Chiu and D. R. Davies, Structure and function of HIV-1 integrase, Curr Top Med Chem 4 (2004) 965-977.
Zhu, et als, Requirement for integrase during reverse transcription of human immunodeficiency virus . . . J Virol 78 (2004) 5045-5055.
Pommier, A. A. Johnson, and C. Marchand, Integrase inhibitors to treat HIV/AIDS, Nat Rev Drug Discov 4 (2005) 236-248.
Sherman, et als, "Human immunodeficiency virus integration protein expressed in *Escherichia coli* . . . " Proc Natl Acad Sci U S A 87 (1990) 5119-5.
Micol, et al., "Synergetic mixed nutritional ingredients enhance and maintain weight loss in humans," AgroFood Industry Hi-Tech, 2005; 16(5): 13-16.

\* cited by examiner

Aortic lesions in apoE ko mice fed a Western diet for 4 months

FIG. 5A
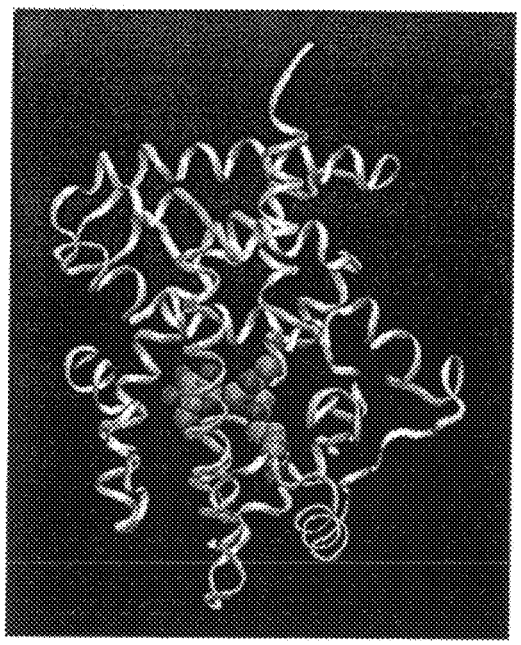
FIG. 5B
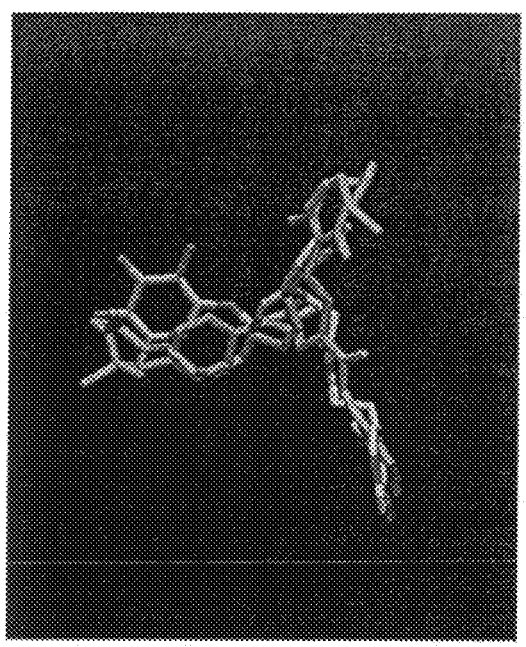
FIG. 5C
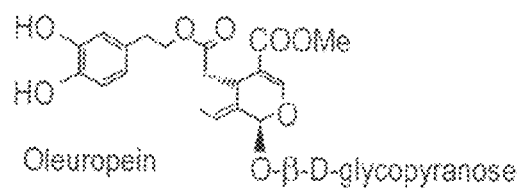
Oleuropein
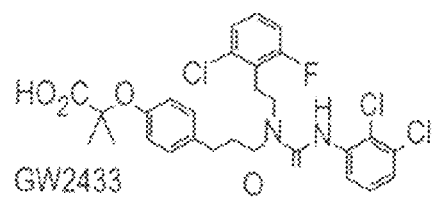
GW2433
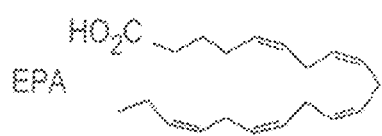
EPA
FIG. 5D
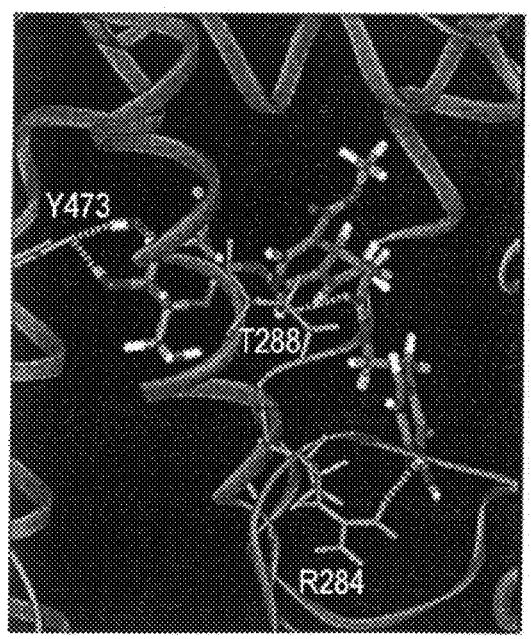

FIG. 6A
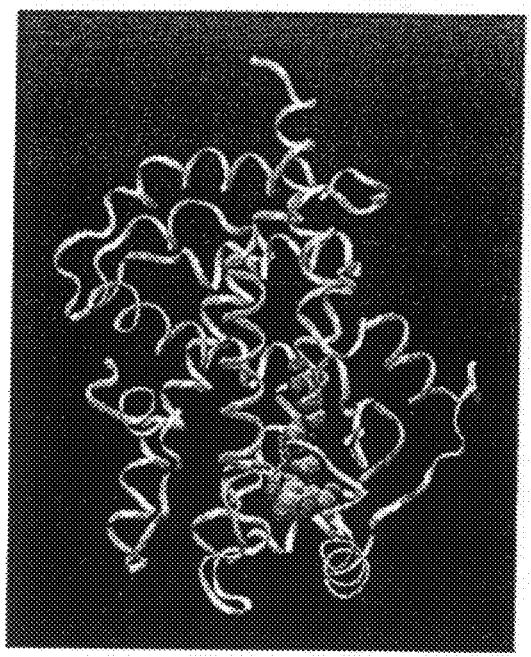
FIG. 6B
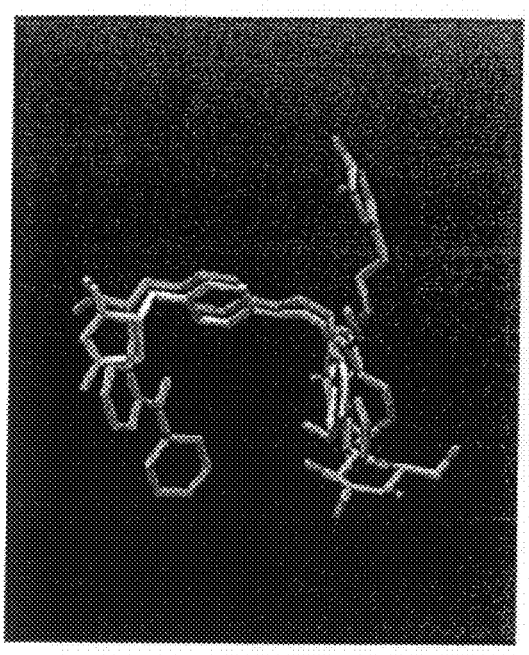
FIG. 6C
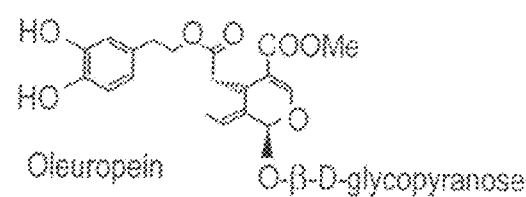
Oleuropein
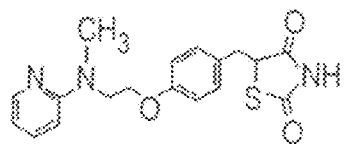
Rosiglitazone
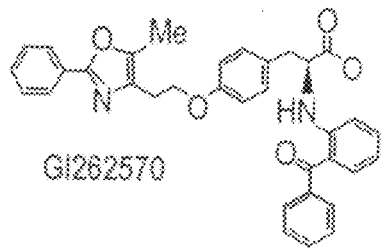
GI262570
FIG. 6D
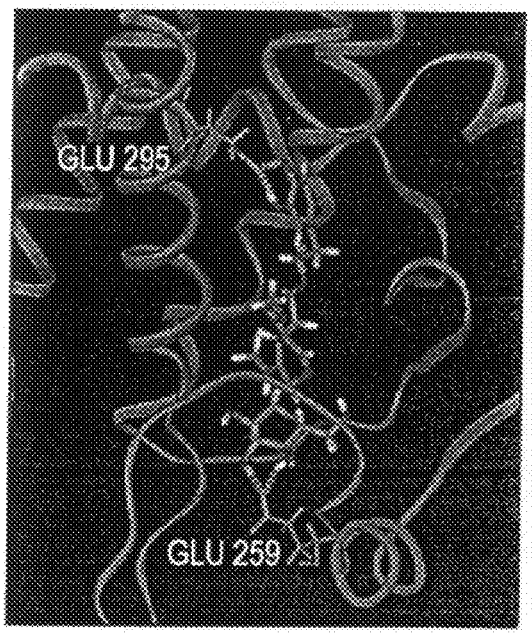

FIG. 7A
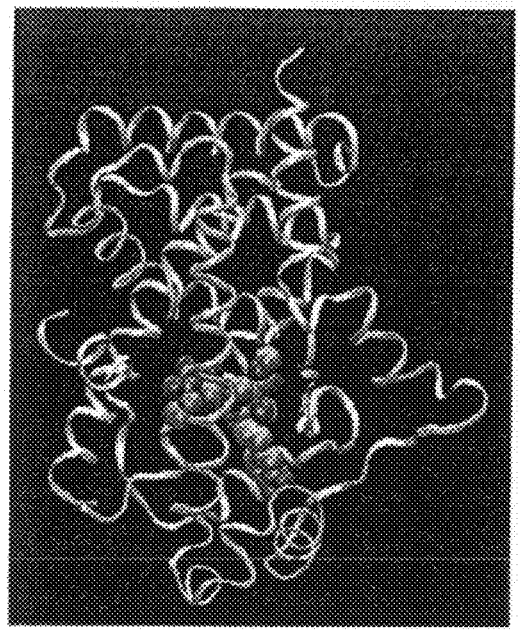
FIG. 7B
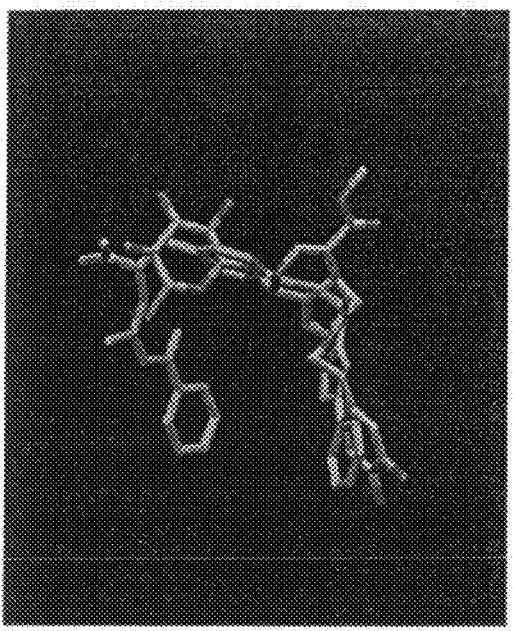
FIG. 7C
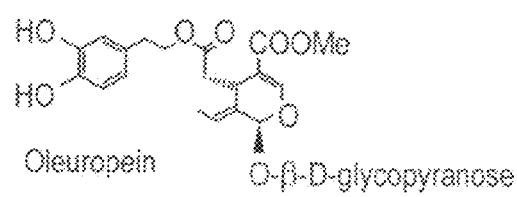
Oleuropein
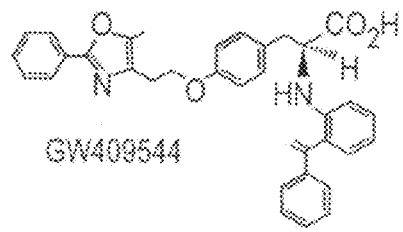
GW409544
FIG. 7D
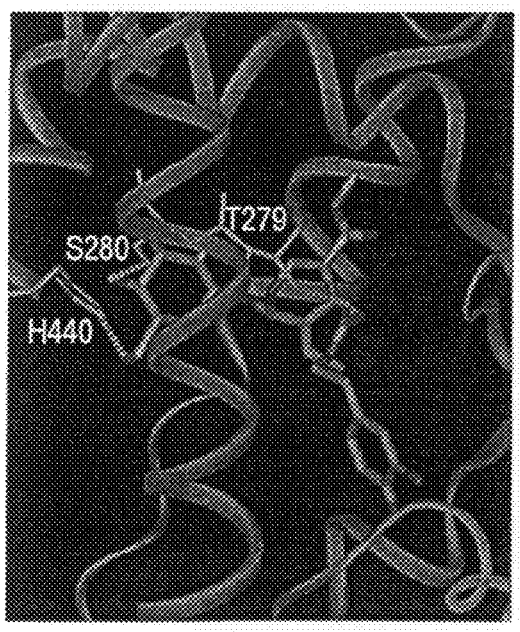

Oleuropein (glycoside)

Oleuropein LC (280 nm, 230 nm, and MSD

Oleuropein Mass (m/z=539)

Oleuropein LC (280 nm, 230 nm, and MSD)

Serum Hydroxytyrosol Mass (m/z=153)

FIG. 12E
Urine LC (280 nm, 230 nm, and MSDC.
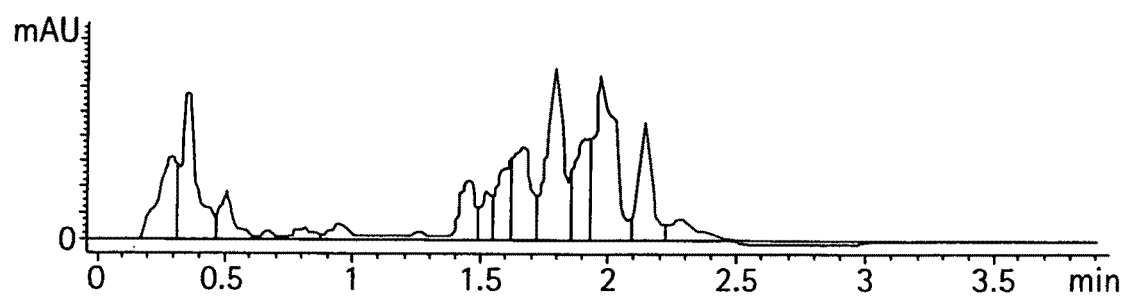
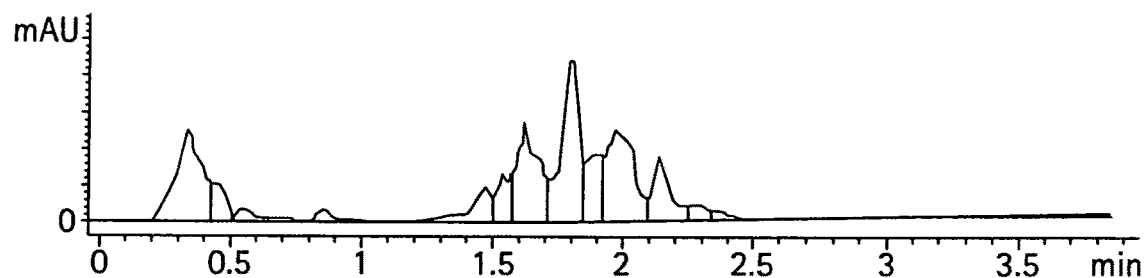
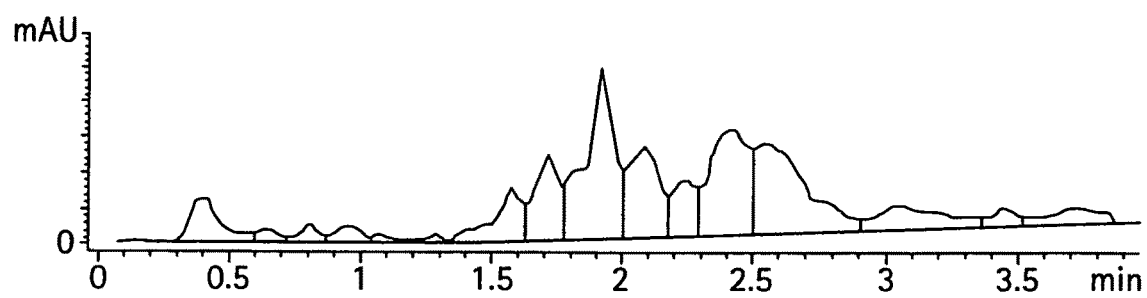

Urine Mass (m/z=100-600)

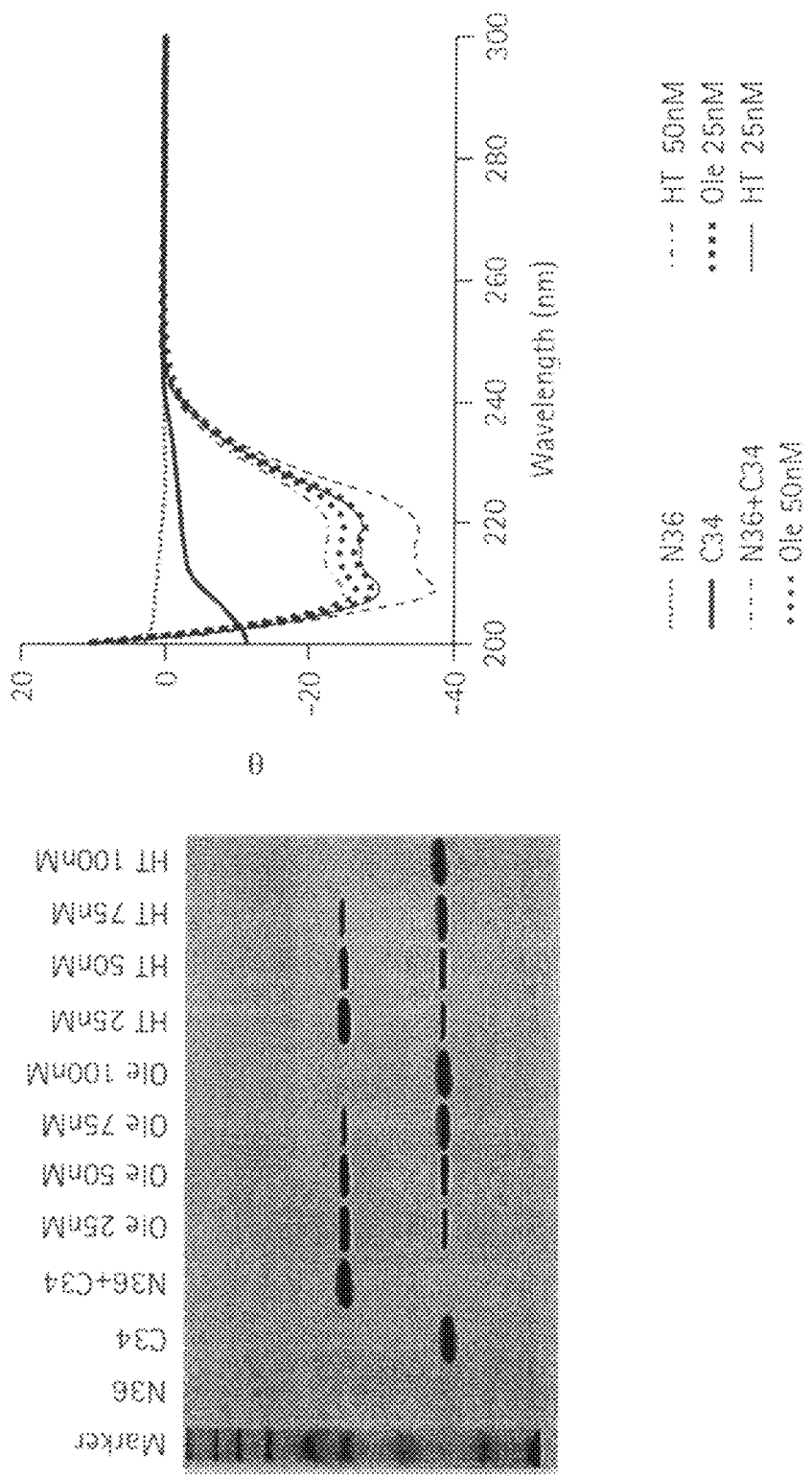

Disintegration

COMPOSITIONS AND METHODS FOR TREATING OBESITY, OBESITY RELATED DISORDERS AND FOR INHIBITING THE INFECTIVITY OF HUMAN IMMUNODEFICIENCY VIRUS

The present application is a division of U.S. Ser. No. 11/827,135 filed Jul. 9, 2007 now abandoned, which is a non-provisional application claiming the priority of U.S. Provisional Application Ser. No. 60/819,172, filed Jul. 7, 2006 and U.S. Provisional Application Ser. No. 60/897,702, filed Jan. 26, 2007, the disclosures of which are incorporated by reference herein in their entireties. Applicants claim the benefits of U.S. Provisional Application Ser. Nos. 60/819,172 and 60/897,702 under 35 U.S.C. §119(e).

FIELD OF THE INVENTION

Background of the Invention

Obesity, which is defined in general terms as an excess of body fat relative to lean body mass, is now a world wide epidemic, and is one of the most serious contributors to increased morbidity and mortality. Obesity is prevalent in the United States, affecting more than 61% of the total population (Flegal, et al., Overweight and Obesity in the United States: Prevalence and Trends, 1960-1994. Int J Obes 22:39-47, 1998). Obesity is defined more specifically by the United States Centers for Disease Control and Prevention (CDC) as an excessively high amount of body fat or adipose tissue in relation to lean body mass and overweight is defined as an increased body weight in relation to height, when compared to some standard of acceptable or desirable weight. The CDC alternatively defines overweight as a person with a body mass index (BMI) between 25.0 and 29.9 and obesity is defined as a BMI greater than or equal to 30.0. Obesity is often associated with psychological and medical morbidities, the latter of which includes increased joint problems, vascular diseases such as coronary artery disease, hypertension, stroke, and peripheral vascular disease. Obesity also causes metabolic abnormalities such as insulin resistance and Type II diabetes (non-insulin-dependent diabetes mellitus (NIDDM)), hyperlipidemia, and endothelial dysfunction. These abnormalities predispose the vasculature to injury, cellular proliferation and lipid oxidation, with resulting atherosclerosis leading to heart attack, stroke, and peripheral vascular diseases. In 1998, consumers spent $33 billion in the United States for weight-loss products and services with a less than positive outcome (Serdula, et al., Prevalence of Attempting Weight Loss and Strategies for Controlling Weight, JAMA 282:1353-1358, 1999). Thus, obesity and its associated complications continue to be a major problem throughout the worldwide health care system.

Obesity is clearly an important clinical problem with very broad reaching implications. There is a pressing need for more research on the molecular mechanisms that underlie obesity and its medical consequences, as well as new approaches for its treatment. To date, these approaches have been limited to diet and exercise (therapeutic lifestyle changes), surgical procedures such as gastric bypass, and pharmacologic agents. Drug treatment for obesity has been disappointing since almost all drug treatments for obesity are associated with undesirable side effects that contributed to their termination. A number of monoamines and neuropeptides are known to reduce food intake (Bray, et al., Pharmacological Treatment of Obesity, Am J Clin Nutr 55:151 S-319S, 1992). Available pharmacotherapies have included Sibutramine (an appetite suppressant), Orlistat (a lipase inhibitor), fenfluramine and dexfenfluramine. Although body weight loss is effective, these sympathomimetic drugs cause side effects including pulmonary hypertension, neuroanatomic changes, and a typical valvular heart diseases. For example, fenfluramine and dexfenfluramine were withdrawn from the market in 1997 because of associated cardiac valvulopathy (Connolly, et al., Valvular Heart Disease Associated With Fenfluramine-Phentermine, New Engl J Med 337-581-588, 1997). Thus, nutrition and dietary restriction are most desirable for weight loss. However, long-term success of dietary regulation is low because of noncompliance. The loss of motivation to change dietary habits necessary to consume less fat and fewer calories results in regaining weight.

Thus, there are no real treatments based on the biology of the primary metabolic abnormalities found in obesity and its related conditions, such as metabolic syndrome or atherosclerosis. Accordingly, there is still a need for new compositions and methods that address treating individuals suffering from obesity and obesity-related disorders. There is also a need for new agents and compositions for treating individuals infected with human immunodeficiency virus (HIV). It is toward the development of new compositions and methods for treating obesity and obesity-related disorders and for treating individuals infected with HIV that the present invention is directed.

The citation of any reference herein should not be construed as an admission that such reference is prior art to the instant invention.

SUMMARY OF THE INVENTION

In accordance with the broadest aspect of the invention, methods and compositions comprising oleuropein, or an analogue or derivative thereof, or the major metabolites of oleuropein including oleuropein aglycone, hydroxytyrosol, and elenolic acid or their analogues, or derivatives thereof, or an iridoid glycoside, or a secoiridoid glycoside or their analogues or derivatives thereof, or any combination of the foregoing including but not limited to olive leave extract, are disclosed for treating obesity and obesity-related conditions or disorders, as well as for inhibiting the infectivity of HIV. In particular, these compositions modulate adipogenesis, lipodystrophy, reduce fat accumulation and weight gain. These agents also prevent HIV viral fusion/entry into a host cell and bind the catalytic site of the HIV integrase. Thus, these agents provide an advantage over other anti-viral therapies in that both viral entry and integration are inhibited. They exert their effect by modulating adipocyte differentiation (adipogenesis), de-differentiation, transdifferentiation, and by decreasing the number of adipocytes (fat cells), or by modulating adipocyte metabolism (lipid synthesis, storage, accumulation, and utilization) so as to decrease fat accumulation and decrease the size of the fat cell (decrease fat mass), increase fat burning and expenditure. These compositions also have an effect on adipogenic, lipogenic and lipolytic gene/gene product expression, perturbation of pre-adipocyte to adipocyte balance by promoting de-differentiation or transdifferentiation of adipocytes, the end result being a reduction in fat accumulation (adipose mass) and a reduction in weight gain. Accordingly, these compositions are useful for treating obesity and obesity-related disorders. In addition, these compositions have been shown to reduce diet-induced atherogenesis, thus allowing for a means of treating one of the major conditions or disorders associated with, or resulting from, obesity. Moreover, the compositions disclosed may also be utilized for treating other obesity-related disorders, including but not limited to, coronary artery disease, hypertension, stroke, peripheral vascular disease, insulin resistance, glucose intolerance, diabetes mellitus, hyperlipidemia, atherosclerosis, cellular proliferation and endothelial dysfunction, diabetic dyslipidemia, HIV-related lipodystrophy, e.g. Highly Active Anti-Retroviral Therapy (HAART)-induced lipodystrophy, and metabolic syndrome, type II diabetes, hyperinsulinemia, diabetic complications including diabetic neuropathy, nephropathy, retinopathy or cataracts, heart failure, hypercholesterolemia, inflammation, thrombosis, congestive heart failure, and any other cardiovascular disease related to obesity or an overweight condition, or obesity induced asthma, airway dysfunction and pulmonary disorders. The compositions may also be contemplated for use in the production of lean meat from meat animals, e.g., beef cattle, lambs, hogs, chickens and turkeys.

Accordingly, a first aspect of the invention provides a method of modulating adipocyte differentiation or adipogenic gene expression, comprising administering a therapeutically effective amount of oleuropein or an analogue, or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives thereof, or any combination of any of the foregoing thereof including but not limited to olive leaf extract, to a mammalian subject in need thereof.

In one embodiment, oleuropein or its analogues, or derivatives thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives thereof, or any combinations of any of the foregoing including but not limited to olive leaf extract, up-regulates fat utilization, energy uncoupling, related regulators, factors and enzymes including but not limited to lipolytic genes/gene products in these pathways.

In another embodiment, oleuropein or an analogue, or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives thereof, or any combinations of any of the foregoing including but not limited to olive leaf extract, blocks or down-regulates adipocyte differentiation, regulators, factors, and enzymes involved in the adipogenic pathway. In yet another embodiment, oleuropein or an analogue, or derivative thereof or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives thereof, or any combinations of any of the foregoing thereof including but not limited to olive leaf extract, enhances de-differentiation of adipocytes and allows for transdifferentiation into osteoblasts, muscle cells, cartilage, and bone as well as regulators and enzymes involved in these pathways.

In yet another embodiment, the adipogenic gene whose expression is modulated by oleuropein or an analogue, or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives thereof, or any combinations of any of the foregoing including but not limited to olive leaf extract, is selected from the group consisting of Peroxisome Proliferator-Activated Receptor $\gamma$ (PPAR$\gamma$), lipoprotein lipase (LPL) and the $\alpha$P2 gene or gene product. Oleuropein or its analogues, or derivatives, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives thereof, or any combinations of any of the foregoing thereof including but not limited to olive leaf extract, also modulate the expression of all of the three types of PPARs $\alpha$, $\delta$, and $\gamma$ resulting in a coordinated regulation of adipocyte differentiation, de-differentiation, transdifferentiation, adipocyte metabolism and energy homeostasis. In yet another embodiment, the lipogenic, lipolytic and energy uncoupling genes and gene products whose expression is modulated includes, but is not limited to, PPAR $\delta$ and its modulated genes and gene products. In yet another embodiment, the lipogenic, lipolytic and energy uncoupling genes whose expression is modulated includes, but is not limited to, PPAR $\alpha$ and its modulated genes and gene products.

A second aspect of the invention provides a method of treating, controlling or preventing obesity, or of reducing body weight, or of inhibiting fat accumulation, or of promoting fat burning and energy uncoupling in vivo, or of treating, controlling or preventing the onset of one or more obesity-related disorders or conditions, comprising administering a therapeutically effective amount of oleuropein or an analogue, or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives, or any combinations of any of the foregoing thereof including but not limited to olive leaf extract, to a mammalian subject in need thereof.

In one embodiment, the one or more obesity-related disorders or conditions are selected from the group consisting of coronary artery disease, hypertension, stroke, peripheral vascular disease, insulin resistance, glucose intolerance, diabetes mellitus, hyperglycemia, hyperlipidemia, hypercholesteremia, hypertriglyceridemia, hyperinsulinemia, atherosclerosis, cellular proliferation and endothelial dysfunction, diabetic dyslipidemia, HIV-related lipodystrophy and metabolic syndrome, type II diabetes, diabetic complications including diabetic neuropathy, nephropathy, retinopathy or cataracts, heart failure, inflammation, thrombosis, congestive heart failure, any other asthmatic or pulmonary disease related to obesity and any other viral infection related diseases and any other cardiovascular disease related to obesity or an overweight condition.

A third aspect provides a method of treating, controlling or preventing the onset of one or more obesity related disorders or conditions selected from the group consisting of Asthma and related diseases including but not limited to, Allergy, Atopic Dermatitis (Eczema), Gastroesophageal Reflux Disease, Airway, Pulmonary and Lung disorders, in a mammalian subject in need of treatment, comprising administering a therapeutically effective amount of oleuropein or an analogue, derivative or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives, or any component or any combinations of any of the foregoing thereof including but not limited to olive leave extract.

A fourth aspect provides a method of treating, controlling or preventing the onset of one or more obesity related disorders or conditions selected from the group consisting of AIDS and HAART related diseases including but not limited to lipodystrophy in a human and or mammalian subject in need of treatment, comprising administering a therapeutically effective amount of oleuropein or an analogue, derivative or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives, or any component or any combinations of any of the foregoing thereof including but not limited to olive leave extract.

A fifth aspect provides a method of treating, controlling or preventing the onset of one or more viral infection related disorders or conditions selected from the group consisting of viral infection related diseases including but not limited to the AIDS virus HIV-1, and other viruses including but not limited to simian immunodeficiency viruses (SW), Sendai virus, feline immunodeficiency virus (FIV), respiratory syncytial virus (RSV), measles virus, Ebola virus, Nipah and Hendra viruses, the severe acute respiratory syndrome associated coronavirus (SARS-CoV), and the avain flu virus in a humans, mammalian, avian, poultry, non human primates subjects in need of treatment, comprising administering a therapeutically effective amount of oleuropein or an analogue, or derivative, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives, or any component or any combinations of any of the foregoing thereof including but not limited to olive leave extract.

A sixth aspect of the invention provides a method for modulating Peroxisome Proliferator Activation Receptor (PPAR) activity, comprising administering to a mammal in need thereof a therapeutically effective amount of oleuropein or an analogue, or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives, or any component or any combinations of any of the foregoing thereof or an iridoid glycoside, or a secoiridoid glycoside or their analogues, or derivatives, or any components or any combinations thereof including but not limited to olive leave extract.

A seventh aspect provides a method of treating a subject suffering from, or at risk for developing a disease or condition for which PPAR modulation provides a therapeutic benefit, comprising administering to said subject a therapeutically effective amount of oleuropein, or an analogue or derivative thereof or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives, or any component or any combinations of any of the foregoing thereof including but not limited to olive leave extract.

In one embodiment, the subject is a human or a non-human mammal. In a preferred embodiment, the subject is a mammal. In another preferred embodiment, the subject is a non-human mammal selected from the group consisting of cows, horses, pigs, sheep, goats, birds, rodents, dogs, cats and other domestic animals or farm animals.

In yet another particular embodiment, the condition for which PPAR modulation provides a therapeutic benefit is selected from the group consisting of obesity, obesity-related disorders and the sequelae thereof. In yet another embodiment, accordingly, the present invention provides for a method of treating inflammatory diseases or conditions comprising administering a PPAR gamma modulator to a subject in need of such therapy. In one particular embodiment, the method provides for treating neurological or neurodegenerative diseases or conditions caused in part by the presence or influx of inflammatory cells, such as for example, multiple sclerosis, stroke or Alzheimer's disease. The use of a PPAR modulator for treating a nervous system injury is also contemplated, for example, a spinal cord injury or traumatic brain injury. The use of a PPAR modulator for wound healing is also contemplated. In one particular embodiment, the PPAR modulator is a PPAR gamma, alpha, or delta agonist, or a combined agonist.

In yet another particular embodiment, the PPAR is selected from PPAR $\delta$, $\gamma$ or $\alpha$, or a dual, or pan PPAR $\delta$, $\gamma$ and $\alpha$ modulators.

In yet another particular embodiment, the obesity-related disorder or sequelae is selected from the group consisting of coronary artery disease, hypertension, stroke, peripheral vascular disease, insulin resistance, diabetes mellitus, hyperlipidermia, atherosclerosis, cellular proliferation and endothelial dysfunction, diabetic dyslipidemia, type II diabetes, hyperinsulinemia, diabetic complications including diabetic neuropathy, nephropathy, retinopathy or cataracts, heart failure, hypercholesterolemia, inflammation, thrombosis, congestive heart failure, and any other cardiovascular disease related to obesity or an overweight condition.

An eighth aspect of the invention provides a method of reducing or preventing formation of atherosclerotic lesions or preventing diet-induced atherogenesis, comprising administering to a mammal in need thereof a therapeutically effective amount of oleuropein or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives, or any combinations of any of any of the foregoing thereof.

A ninth aspect of the invention provides a method of modulating endothelial dysfunction comprising administering to a mammal in need thereof a therapeutically effective amount of oleuropein or an analogue, or derivative, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, derivatives, or any combinations of any of the foregoing thereof including but not limited to olive leave extract.

A tenth aspect of the invention provides a method for treating obesity or obesity related disorders or other disorders for which PPAR modulation provides a therapeutic benefit comprising administering a second agent in combination with oleuropein, or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, derivatives, or any combination of any of the foregoing thereof including but not limited to olive leaf extract.

In one particular embodiment, the second agent is selected from the group consisting of a different PPAR modulating agent, a cholesterol or lipid lowering agent, a biguanide, insulin, an antihyperglycemic agent, GLP-1 or analogues thereof, DPP4 inhibitors, a weight loss agent, and any agent useful for treating metabolic syndrome or type 2 diabetes.

In another particular embodiment, the different PPAR modulating agent is a thiazolidinedione selected from the group consisting of troglitazone, pioglitazone and rosiglitazone.

In yet another particular embodiment, the cholesterol or lipid lowering agent is a HMG-CoA reductase inhibitor, and wherein the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin. In yet another particular embodiment, the cholesterol or lipid lowering agent is niacin or a fibrate.

In yet another particular embodiment, the biguanide is selected from the group consisting of metformin, phenformin, and buformin.

In yet another particular embodiment, the antihyperglycemic is a prandial glucose regulator or an alpha-glucosidase inhibitor.

In yet another particular embodiment, the prandial glucose regulator is repaglinide or nateglinide.

In yet another particular embodiment, the alpha-glucosidase inhibitor is selected from the group consisting of acarbose, voglibose and miglitol.

In yet another particular embodiment, the agent useful for treating metabolic syndrome or type 2 diabetes is a sulfonylurea selected from the group consisting of glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide.

In yet another particular embodiment, the agent useful for treating AIDS and Highly Active Anti-Retroviral Therapy (HAART)-induced lipodystrophy, metabolic syndrome or type 2 diabetes is a thiazolidinedione (TZD) and a fibrate.

In yet another particular embodiment, the agent useful for treating HIV-1 infection and AIDS is a component or the full composition of the Highly Active Anti-Retroviral Therapy (HAART), including a protease inhibitor (PI), a nucleotide reverse transcriptase inhibitor (NRTI), and a non-nucleotide reverse transcriptase inhibitor (NNRTI).

In yet another particular embodiment, the agent useful for treating obesity induced asthma and related disorders is selected from the group consisting of a glucocorticoid, an antileukotriene and an antihistamine.

An eleventh aspect of the invention provides a pharmaceutical composition comprising a therapeutically effective amount of oleuropein, or an analogue or derivative thereof or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, derivatives, or any combinations thereof including but not limited to olive leave extract, and a pharmaceutically acceptable carrier for delivery to a mammal in need of such therapy.

In one particular embodiment, the pharmaceutical composition may be administered orally, nasally, transdermally, intravenously, intramuscularly, or subcutaneously.

In another particular embodiment, the subject has or is at risk for unwanted weight gain, obesity or an obesity related disorder, e.g., diabetes or glucose intolerance, insulin resistant states, hypertension, HIV-1 infection, or any of the other disorders disclosed herein. In preferred embodiments, the method includes identifying a subject as being in need of treatment or prevention of unwanted weight gain, obesity or an obesity related disorder. In another particular embodiment, the pharmaceutical composition is formulated for delivery to a human or non-human mammal. In a preferred embodiment, the mammal is a human. In another preferred embodiment, the subject is a non-human mammal selected from the group consisting of cows, horses, pigs, sheep, goats, birds, rodents (including rats, mice and gerbils), dogs, cats and other domestic animals or farm animals.

A twelfth aspect of the invention provides a pharmaceutical composition directed to combination therapy, whereby oleuropein or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues or derivatives, or any combination thereof including but not limited to olive leave extract, is combined with one or more other therapeutic agents that are useful in the treatment of disorders associated with the development and progression of obesity and obesity related disorders, such as atherosclerosis, hypertension, hyperlipidemias, dyslipidemias, diabetes and other related disorders as described herein.

In one particular embodiment, the composition for combination therapy comprises oleuropein and at least one other agent. In another particular embodiment, the composition for combination therapy comprises oleuropein and at least two or more other agents.

In one particular embodiment, the at least one other therapeutic agent is a different PPAR modulating agent other than oleuropein.

In a more particular embodiment, the different PPAR modulating agent is a thiazolidinedione selected from the group consisting of troglitazone, pioglitazone and rosiglitazone.

In yet another particular embodiment, the at least one other therapeutic agent is a cholesterol-lowering agent.

In yet another particular embodiment, the cholesterol lowering agent is a HMG-CoA reductase inhibitor.

In yet another particular embodiment, the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin.

In yet another particular embodiment, oleuropein is combined with a therapy useful for the treatment of metabolic syndrome or type 2 diabetes.

In yet another particular embodiment, the therapy useful for the treatment of metabolic syndrome or type 2 diabetes and its associated complications is selected from the group consisting of a biguanide drug, (including metformin, phenformin and buformin), insulin (synthetic insulin analogues, amylin) and oral antihyperglycemics.

In yet another particular embodiment, oleuropein is combined with an oral antihyperglycemic agent, which is a prandial glucose regulator or an alpha-glucosidase inhibitor. In yet another particular embodiment, the prandial glucose regulator is repaglinide or nateglinide. In yet another particular embodiment, the alpha-glucosidase inhibitor is acarbose, voglibose or miglitol.

In yet another particular embodiment, oleuropein is combined with a sulfonylurea.

In yet another particular embodiment, the sulfonylurea is selected from the group consisting of glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide.

In one particular embodiment, the composition comprises a mixture of oleuropein or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues or derivatives, or any combination thereof including but not limited to olive leaf extract, and the at least one or two other agents, wherein the at least one or two other agents may be administered prior to, concurrent with, or subsequent to, oleuropein or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues or derivatives, or any combination thereof including but not limited to olive leaf extract.

In another particular embodiment, the composition comprising oleuropein or an analogue or derivative thereof or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues or derivatives, or any combination thereof including but not limited to olive leaf extract, interacts with, e.g., binds to, PPARδ, PPARγ and PPARα.

In yet another particular embodiment, oleuropein or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues or derivatives, or any combination thereof including but not limited to olive leaf extract, is combined with a therapy useful for the treatment of the AIDS virus HIV-1, and other viruses with a type I transmembrane envelope glycoprotein, such as simian immunodeficiency viruses (SIV), Sendai virus, feline immunodeficiency virus (FIV), respiratory syncytial virus (RSV), measles virus, Ebola virus, Nipah and Hendra viruses, the severe acute respiratory syndrome associated coronavirus (SARS-CoV), and the avain flu virus H5N1 including but not limited to PI, NRTI, NNRTI, HAART, tamiflu, ribavirin, steroid, recombinant nematode anticoagulant protein c2 (rNAPC2).

In yet another particular embodiment, oleuropein is combined with a therapy useful for the treatment of obesity induced asthma and related disorders, including but not limited to the PPARs, glucocorticoids, antileukotrienes and antihistamines.

In another particular embodiment, the oleuropein or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, an iridoid glycoside, or a secoiridoid glycoside, or their analogues, or derivatives thereof, or any combination thereof including but not limited to olive leaf extract, is targeted to adipose tissue in a subject. The oleuropein or an analogue or derivative thereof or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or an analogue, or derivative thereof, or any combination thereof including but not limited to olive leaf extract, may be targeted to adipose tissue by virtue of an inherent characteristic, e.g., lipid solubility. In other embodiments, the agent may include (e.g., the agent can be linked, fused or conjugated to, or enveloped in) a targeting reagent that targets the agent to an adipose tissue. The targeting reagent can be a nucleic acid, a protein (e.g., a hormone, e.g., leptin, conjugate or an antibody to an adipocyte-specific antigen), a lipid (e.g., a liposome), a carbohydrate, or other molecule that is targeted to an adipose tissue.

In yet another particular embodiment, the oleuropein or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside, or their analogues or derivatives thereof, or any combination of the foregoing including but not limited to olive leaf extract, is targeted to adipose tissue via Resistin (resistance to insulin) or Resistin-Like Molecules (RELMs or FIZZ1-3) (Degawa-Yamauchi M, Serum Resistin (FIZZ3) Protein Is Increased in Obese Humans, J. Clin. Endocrinol. Metab., 88: 5452-5455, (2003); (Diabetologia. (2006) May 10; Anal Chem. (2006) May 15; 78(10):3271-6; Hum Reprod. (2006) May 12) or Adipocyte-Specific Secretory Factor (ADSF) Proteins (Endocrine. (2006) February; 29(1):81-90 Proc Natl Acad Sci USA. (2004) Apr. 27; 101(17):6780-5. Epub (2004) Apr. 16) or antibodies to such proteins, as well as Leptin (Int J Obes (Lond). (2006) May 16) or Leptin Receptor antibodies, Acrp30/Adiponectin (Endocrinology. (2006) June; 147(6): 2690-5. Epub (2006) March 2; (Hum Reprod. (2006) May 12; [Epub ahead of print]; Biochem Biophys Res Commun. (2006) Jun. 23; 345(1):332-9. Epub (2006) Apr. 27. J Endocrinol Invest. (2006) March; 29(3):231-6) (Hum Reprod. 2006 May 12; [Epub ahead of print]; Biochem Biophys Res Commun. 2006 Jun. 23; 345(1):332-9. Epub 2006 Apr. 27. J Endocrinol Invest. 2006 March; 29(3):231-6) or Adipsin antibodies, Orexins (Br J. Nutr. 2004 August; 92 Suppl 1:S47-57) or Orexins Receptor antibodies, a Glucose Transporter (Glut1-Glut14) (Clin Exp Pharmacol Physiol. 2006 April; 33(4):395-9; Am J. Med. 2006 May; 119(5 Suppl 1):S10-6) antibody, or an antibody to a Hypoxia Induced Factor (HIF-alpha, beta) (HIF-alpha, beta, Diabetologia. 2006 May; 49(5):1049-63. Epub 2006 Feb. 28; Biochem Biophys Res Commun. 2006 Mar. 10; 341(2):549-56.) Am J Physiol Endocrinol Metab. 2006 March; 290(3):E591-7. Epub 2005 Oct. 18.

In yet another particular embodiment, the oleuropein or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogue or derivative, or any combination thereof including but not limited to olive leaf extract, is targeted to a preadipocyte and its specific proteins such as pref-1 and C1q to modulate adipocyte differentiation and maturation.

In yet another particular embodiment, the oleuropein or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside, or their analogues, or derivatives thereof, or any combination of the foregoing including but not limited to olive leaf extract, is targeted to a mesenchymal stem cell (MSC) or an embryonic stem cell. MSCs differentiate into adipocytes, chondrocytes, osteoblasts, and myoblasts. Thus, these stem cells are promising candidates for adipogenesis management by oleuropein and derivatives or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogue or derivative, or any combination thereof including but not limited to olive leaf extract, targeting and/or ex-vivo treatment so as to modulate adipocyte differentiation, de-differentiation and trans-differentiation. The application of oleuropein and derivatives in this system is not only effective in treating obesity and related metabolic syndromes by modulating adipocyte differentiation and development but also provide tools to manipulate adult stem cells for cell-based approaches in regenerative medicine. For example, aged and osteoporotic patients have a high fat to bone ratio in their bones compared with young and healthy counterparts, an outcome possibly due to the conversion of bone to fat cells. Application of oleuropein or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogue or derivative, or any combination thereof including but not limited to olive leaf extract to mediate transdifferentiation between osteoblasts and adipocytes should be of relevance to the development of therapeutic control of bone loss in osteoporosis. For specific targeting of MSC, these cells express leukemia inhibitory factor, macrophage colony-stimulating factor, and stem cell factor specifically. Thus, these proteins and antibodies specific for or that bind these proteins can be used for targeting.

In another particular embodiment, the targeting reagent is lipid soluble.

In another particular embodiment, the administration of the compositions of the invention can be initiated, e.g., (a) when the subject begins to show signs of unwanted weight gain, obesity or an obesity-related disease; (b) when obesity or an obesity-related disease is diagnosed; (c) before, during or after a treatment for obesity or an obesity-related disease is begun or begins to exert its effects; or (d) generally, as is needed to maintain health, e.g., normal weight. The period over which the agent is administered (or the period over which clinically effective levels are maintained in the subject) can be long term, e.g., for six months or more or a year or more, or short term, e.g., for less than a year, six months, one month, two weeks or less.

In another particular embodiment, the pharmaceutical compositions described herein, including oleuropein, or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues, or derivatives thereof, or any combination thereof including but not limited to olive leaf extract and any second agent to be administered with oleuropein or its analogues or derivatives thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside or their analogues or derivatives thereof, or any combination thereof including but not limited to olive leaf extract as described above, are administered in a therapeutically effective dose.

In yet another particular embodiment, oleuropein or an analogue, or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside, or their analogues, or derivatives thereof, or any combination thereof including but not limited to olive leaf extract may have an effect on white or brown adipose tissue or a combination thereof. For example, since PPAR delta is involved in thermogenesis and energy uncoupling (the main function of brown fat) and oleuropein has high affinity for PPAR delta, it may also have an effect on brown adipose tissue. Accordingly, oleuropein may be involved in the dissipation of stored fat as heat in brown adipose tissue. Brown fat plays an important role in the control of body weight, and mitochondrial uncoupling proteins may be one of many factors involved in the development of obesity. An interesting demonstration of this is found in a report in which transgenic mice with genetic ablation of brown fat developed obesity in the absense of overeating (Bachman E S, Dhillon H, Zhang C-Y, et al. BetaAR signaling required for diet-induced thermogenesis and obesity resistance. Science 297:843, 2002).

A thirteenth aspect of the invention provides a method for identifying a candidate compound or an analogue or derivative of oleuropein that modulates adipocyte differentiation, de-differentiation, trans-differentiation, fat accumulation and adipogenic gene expression or for treating obesity or obesity-related disorders, comprising:

a. treating a cell with an inducing agent in the presence or absence of a candidate compound;

b. determining whether the candidate compound inhibits differentiation of the pre-adipocyte cell to an adipocyte, or whether the candidate compound down-regulates adipogenic and lipogenic gene or gene product expression and/or up-regulates lipolytic and/or an energy uncoupling gene or gene product expression;

c. comparing the results obtained with the candidate compound in vitro with the results obtained using oleuropein;

d. testing the candidate compound and oleuropein in an animal model of obesity to determine the in vivo effects of both the candidate compound and oleuropein;

e. determining whether the candidate compound decreases the amount of adipose tissue in vivo or whether the test compound prevents further fat accumulation in vivo; and f. selecting a candidate compound that has equivalent or better activity than oleuropein.

In one particular embodiment, the invention relates to a method for identifying a therapeutic agent having analogous activity to oleuropein comprising treating a type of cell that expresses a type of PPAR with a candidate compound/therapeutic; and determining the level of expression of at least one gene selected from the group consisting of PPARγ2, lipoprotein lipase (LPL), and αP2 lipid binding protein, wherein a change in the profile of expression of at least one of these genes in the cell treated with the candidate compound/therapeutic relative to a cell that was not treated with the candidate compound/therapeutic indicates that the candidate compound/therapeutic is a therapeutic for treating a disease associated with a PPAR. The "profile", "profiling" or "profile of expression" refers to both the level of expression of one or more genes and also the activity or function of one or more of these genes. Accordingly, the candidate compound may have an effect not only on the expression of one or more genes, but on the function or activity of one or more genes. In one particular embodiment, an increase in the profile of expression of at least one of these genes following treatment with a candidate compound/therapeutic indicates that the candidate compound/therapeutic is a therapeutic for treating a disease associated with a PPAR. The profile in expression of one or more of these genes relates to the differentiation or maturation of the adipocyte. In another particular embodiment, the inducing agent that is used for in vitro analysis is any compound or molecule that induces differentiation of a pre-adipocyte or a mesenchymal stem cell into a mature adipocyte, eg. dexamethasone, insulin and methyl xanthine. In another particular embodiment, following contacting/treating a cell containing PPAR with a candidate compound/therapeutic, one may determine the profile of expression of other genes selected from the group consisting of leptin, TNFα, IL-6, PAI-1, adipsin, complement factor C3 and angiotensinogen. In yet another particular embodiment, in addition to classic markers of adipogenesis such as hormone-sensitive lipase (HSL), lipoprotein lipase (LPL), adiponectin, fatty acid-binding protein 4, perilipin and CCAAT enhancer binding protein, and enzymes of energy metabolism such as glycerol-3-phosphate dehydrogenase 1, acetyl-coenzyme A carboxykinase, phosphoenolpyruvate carboxykinase and pyruvate dehydrogenase kinase, profiles on the expression of other related genes including PPARα, PPARδ, PPARγ, AP2, MARPK3, SREBP-1, leptin, and GLUT4 are envisioned following treatment of a type of cell with a candidate compound/therapeutic. These are important because they are not only adipocyte "markers" but also important in adipocyte function and pathogenesis. Any agent that affects adipogenesis would modulate the expression of these genes. In one particular embodiment, an adipogenic agent would up-regulate while an anti-adipogenic agent would down regulate the expression of one or more of these genes. However, physiologically it is not a simple up or down regulation. It involves the regulation of other related genes upstream and downstream as including PPARδ, PPARα, enzymes involve in lipid metabolism, fatty acid oxidation, energy uncoupling as well as genes modulated by the PPARs. In addition to monitoring the up or down regulation of these genes, another particular embodiment provides for measuring the differential expression as well as polymorphisms of these genes. In yet another particular embodiment, the PPAR is selected from the group consisting of α, γ, or δ.

In another embodiment of the invention, the candidate therapeutic is selected from the group consisting of proteins, peptides, peptidomimetics, antibodies, nucleic acids, including RNA (eg. siRNA), DNA, derivatives of fatty acids, and small molecules. The small molecules may be synthetic or may be derived from a natural source, such as a plant, animal, microbe, or soil.

In another embodiment, the disease is obesity or an obesity-related disorder, such as, but not limited to, Type II diabetes.

In another embodiment, the expression level of at least one of the genes noted above is detected. In another particular embodiment, the expression level of at least two or more of the genes noted above is detected.

In another embodiment, the composition is an oral capsule or tablet, a liquid suspension, or a chip or wafer for oral delivery. In another embodiment, the composition is formulated for intravenous use, for intramuscular use, for subcutaneous delivery or for intraperitoneal injection.

In another embodiment, the composition comprising oleuropein or an analogue, derivative of oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside, or their analogues, or derivatives thereof, or any combination thereof including but not limited to olive leaf extract may be targeted to (e.g., the oleuropein or analogue or derivative thereof can be linked, fused or conjugated to, or enveloped in) the adipocyte by attachment of the oleuropein or analogue or derivative thereof to adipose tissue via Resistin or Resistin-Like Molecules (RELMs or FIZZ1-3) or Adipocyte-Specific Secretory Factor (ADSF) Proteins or antibodies to such proteins, as well as Leptin or Leptin Receptor antibodies, Acrp30/Adiponectin or Adipsin antibodies, Orexins or Orexins Receptor antibodies, a Glucose Transporter (Glut1-Glut14) antibody, or an antibody to a Hypoxia Induced Factor (HIF-alpha, beta).

In yet another particular embodiment, the composition comprising the oleuropein or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside, or their analogues, or derivatives thereof, or any combination thereof including but not limited to olive leaf extract, is targeted to a preadipocyte and its specific proteins such as Preadipocyte factor-1 (Pref-1), which is an epidermal growth factor-like domain-containing transmembrane protein and is implicated in inhibiting preadipocytes differentiation and component of complement (C1) or C1q, which is a serum glycoprotein involved in immune complexes to modulate adipocyte differentiation and maturation.

In yet another particular embodiment, the composition comprising the oleuropein or an analogue or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside, or their analogues, or derivatives thereof, or any combination thereof including but not limited to olive leaf extract, is targeted to a mesenchymal stem cell (MSC). MSCs differentiate into adipocytes, chondrocytes, osteoblasts, and myoblasts. Accordingly, in yet another embodiment, the invention provides a method of transdifferentiating adipocytes into osteoblasts, myoblasts and chondrocytes, wherein the method comprises administering to a mammal in need thereof a therapeutically effective amount of oleuropein or an analogue, or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside, or their analogues, or derivatives thereof, or any combination thereof including but not limited to olive leaf extract. Thus, these stem cells are promising candidates for adipogenesis management by oleuropein and derivatives (as mentioned above) targeting and/or ex-vivo treatment so as to modulate adipocyte differentiation, trans-differentiation and de-differentiation. The application of oleuropein and derivatives (as mentioned above) in this system is not only effective in treating obesity and related metabolic syndromes by modulating adipocyte differentiation and development but also provide tools to manipulate adult stem cells for cell-based approaches in regenerative medicine. For example, aged and osteoporotic patients have a high fat to bone ratio in their bones compared with young and healthy counterparts, an outcome possibly due to the conversion of bone to fat cells. Application of oleuropein or an analogue, or derivative thereof, or oleuropein aglycone or their analogues, or derivatives thereof, or hydrotyrosol, or dihydroxy phenol or their analogues, or derivatives thereof, or elenolic acid or their analogues, or derivatives thereof, or an iridoid glycoside, or a secoiridoid glycoside, or their analogues, or derivatives thereof, or any combination thereof including but not limited to olive leave extract to mediate transdifferentiation between osteoblasts and adipocytes should be of relevance to the development of therapeutic control of bone loss in osteoporosis. For specific targeting of MSC, these cells express leukaemia inhibitory factor, macrophage colony-stimulating factor, and stem cell factor specifically. Thus these proteins and their antibodies can be used for targeting.

In another particular embodiment, the targeting reagent is lipid soluble.

In a fourteenth aspect, the invention provides a method of determining whether a subject is responsive to treatment with a therapeutic such as oleuropein or a therapeutic having analogous activity to oleuropein, comprising determining the level of expression of one or more genes or gene products selected from the group consisting of PPARγ2, LPL, or αP2 in a cell or a bodily fluid sample of the subject, and/or determining the differential expression of the adipogenic, lipogenic and lipolytic genes or gene products, wherein a change in level of expression of any one or more of these genes or gene products in a cell or bodily fluid sample of the subject relative to that in a cell or bodily fluid sample of a subject that was not treated with oleuropein or a therapeutic having analogous activity to oleuropein, or a change of the profiles and or functions of adipogenic, lipogenic and lipolytic genes, indicates that the subject is responsive to treatment with oleuropein or an oleuropein analogue or derivative.

A fifteenth aspect of the invention provides a method for determining whether a subject is responsive to treatment with a therapeutic having analogous activity to oleuropein, comprising determining the profile of expression of adipogenic, lipogeneic and lipolytic, genes or gene products selected from the group consisting of PPARδ, PPARγ and PPARα in cells of the subject, wherein a higher or lower level of expression or function/activity of any one of these genes in the cells of the subject relative to that in cells of a subject that was not treated with a PPAR ligand indicates that the subject is responsive to treatment with the PPAR ligand.

In one particular embodiment, the cells are obtained from whole blood, e.g. peripheral blood mononuclear cells (PBMC). In another particular embodiment, the cells are adipocytes. In yet another particular embodiment, the cells are pre-adipocytes. In yet another embodiment, the cells are mesenchymal stem cells. In yet another particular embodiment, the bodily fluid sample is plasma or serum.

In a sixteenth aspect, the invention provides a method for predicting whether a subject would be responsive to treatment with a compound having analogous activity to oleuropein, comprising treating the subject with the candidate or test compound followed by collecting preadipocytes or whole blood of the subject and determining the profile of expression of at least one of the genes selected from the group consisting of PPARγ2, LPL, αP2, leptin, TNFα, IL-6, PAI-1, adipsin, complement factor C3, angiotensinogen, hormone-sensitive lipase (HSL), lipoprotein lipase (LPL), adiponectin, fatty acid-binding protein 4, perilipin and CCAAT enhancer binding protein, and enzymes of energy metabolism such as glycerol-3-phosphate dehydrogenase 1, acetyl-coenzyme A carboxykinase, phosphoenolpyruvate carboxykinase and pyruvate dehydrogenase kinase, wherein a change in the profile of expression (the level of expression and/or the change in function or activity) of at least one of these genes relative to expression in cells or in a whole blood sample of subjects not treated with oleuropein, indicates that the subject would be responsive to treatment with the compound having analogous activity to oleuropein. In another particular embodiment, a method for predicting whether a subject would be responsive to treatment with a compound having analogous activity to oleuropein, comprises incubating cells of the subject with oleuropein and determining the level of expression of at least one of the genes selected from the group consisting of PPARα and PPARδ as well as their responsive genes in lipid metabolism, lipid utilization and energy uncoupling. The expression of these genes can be profiled in a cellular sample or in a blood sample, for example, whole blood, or plasma or serum. In addition to PPARα, PPARδ and PPARγ and their responsive genes, the levels of glucose, fasting insulin, insulin AUC, total cholesterol, LDL cholesterol, HDL cholesterol, triglyceride, adiponectin, free fatty acid and TNFα, are also indications of an effect of oleuropein or an analogue or derivative thereof.

In one embodiment, the PPAR is selected from the group consisting of α, γ, or δ.

A seventeenth aspect of the invention provides a method for purifying biologically active oleuropein, an oleuropein derivative, or an oleuropein metabolite from olive leave extract, the method comprising the steps:

a) extracting the oleuropein, or a derivative or metabolite thereof by heating olive leaves to at least 80° C. but not above 85° C. for about 10-12 hours in water, saline or phosphate buffer;

b) collecting the liquid from step a) and repeating the extracting procedure of step a) at least one additional time;

c) combining the liquid from steps a) and b) and centrifuging at least 20,000×g for at least 30 minutes to remove small particulates or insoluble material;

d) concentrating the liquid from step c) by lyophilization until dried;

e) dissolving the dried extract from step d) into sterile water to a concentration of about 10-20 mg/ml and filter sterilizing;

f) distributing the material from step e) into sterile cryotubes under aseptic conditions and storing at a temperature of at least −80° C.;

g) fractionation, characterization and analyzing the extract by a method selected from the group consisting of high pressure liquid chromatography (HPLC), thin layer chromatography (TLC) and liquid chromatography-mass spectrometry (LC-MS); and h) comparing the material obtained in step g) with a known standard.

In one embodiment, the ratio of dried leaves to water, saline or phosphate buffer in step c) above is about 1 gram of dried leaves to about 40 ml of water, saline or phosphate buffer.

In another embodiment, the filter sterilizing is accomplished using a filter of about 0.45 microns.

An eighteenth aspect of the invention provides a method for synthesizing biologically active hydroxytyrosol, or a hydroxytyrosol analogue or derivative, comprising:
a) providing 3,4-dihydroxylphenylacetic acid;
b) reacting 3,4-dihydroxylphenylacetic acid with acetyl chloride and methanol by stirring at room temperature overnight to yield 3,4-dihydroxylphenylacetic ester
c) purifying the 3,4-dihydroxylphenylacetic ester by column chromatography.
d) dissolving the 3,4-dihydroxylphenylacetic ester of step c) in tetrahydrofuran;
e) adding 1 molar LiAlH4 into the reaction mixture from step d); stirring at 0° C. for about 2 hours;
f) purifying the hydroxytyrosol, or a hydroxytyrosol analogue or derivative by column chromatography; and
g) characterizing the hydroxytyrosol, or a hydroxytyrosol analogue or derivative by liquid chromatography-mass spectrometry.

A nineteenth aspect of the invention provides for the preparation of biologically active hydroxytyrosol, comprising:
a) providing oleuropein;
b) treating the oleuropein of step a) with beta-glycosidase to yield oleuropein aglycone;
c) hydrolyzing the oleuropein aglycone to yield hydroxytyrosol and elenolic acid.

In one embodiment, the hydrolyzing of step c) above is accomplished by treating the oleuropein aglycone of step b) with an esterase to yield hydroxytyrosol and elenolic acid.

A twentieth aspect of the invention provides for a method of inhibiting human immunodeficiency virus (HIV) infectivity, comprising administering a therapeutically effective amount of oleuropein or hydroxytyrosol, or a derivative or analogue thereof. In one embodiment, the administering may be in vitro or in vivo.

In another embodiment, the oleuropein or hydroxytyrosol, or a derivative or analogue thereof, prevents the fusion of the virus to the host cell, and/or prevents cell to cell transmission of the virus, and/or prevents viral replication by binding to the active/catalytic site of the HIV integrase.

In yet another embodiment, the inhibiting of HIV infectivity is the result of the binding of oleuropein or hydroxytyrosol, or a derivative or analogue thereof, to a conserved hydrophobic pocket on the surface of the central trimeric coiled-coil of the HIV gp41 fusion domain.

In yet another embodiment, the oleuropein or hydroxytyrosol, or a derivative or analogue thereof, interacts with the N-terminal heptad repeat (NHR) coiled-coil trimer N36 helices and interferes with the formation of 6HB with the C-terminal heptad repeat (CHR), C34.

In yet another embodiment, the oleuropein or hydroxytyrosol, or a derivative or analogue thereof, inhibits 6HB formation.

In yet another embodiment, the oleuropein or hydroxytyrosol, or a derivative or analogue thereof, binds to both regions I and II of said integrase.

In yet another embodiment, the oleuropein or hydroxytyrosol, or a derivative or analogue thereof, inhibits one or more of the following activities of the integrase:
a) inhibition of 3' processing activity of the HIV integrase;
b) inhibition of strand-transfer activity of the HIV integrase; or
c) inhibition of the disintegration activity of the HIV integrase.

In yet another embodiment, the human immunodeficiency virus is HIV-1 or HIV-2.

In yet another embodiment, the oleuropein or hydroxytyrosol, or a derivative or analogue thereof, inhibits the fusion or replication of any one of an M tropic or a T tropic strain from different HIV clades.

Other objects and advantages will become apparent from a review of the ensuing detailed description and attendant claims taken in conjunction with the following illustrative drawings. All references cited in the present application are incorporated herein in their entirety.

BRIEF DESCRIPTION OF THE DRAWINGS

FIG. 16. The effect of Ole and HT on the formation of 6HB between HIV-1 peptides N36 and C34
A. Native PAGE was carried out in Tris-glycine 18% gels, at 120 V constant voltages at room temperature for 2 h. The gel was then stained with Coomassie Blue and analyzed by densitometry. Lane 1, molecular weight markers; lane 2, N36; lane 3, C34; lane 4 fusion complex, (N36+C34); lanes 5-8 and 9-12, in the presence of Ole and HT at 25, 50, 75 and 100 nM.
B. CD analysis, CD spectra for N36 (Green), C34 (Red), (N36+C34) 6HB (Blue), and N36+C34 in the presence of 25 and 50 nM of Ole or HT.

DETAILED DESCRIPTION OF THE INVENTION

Figure 1:
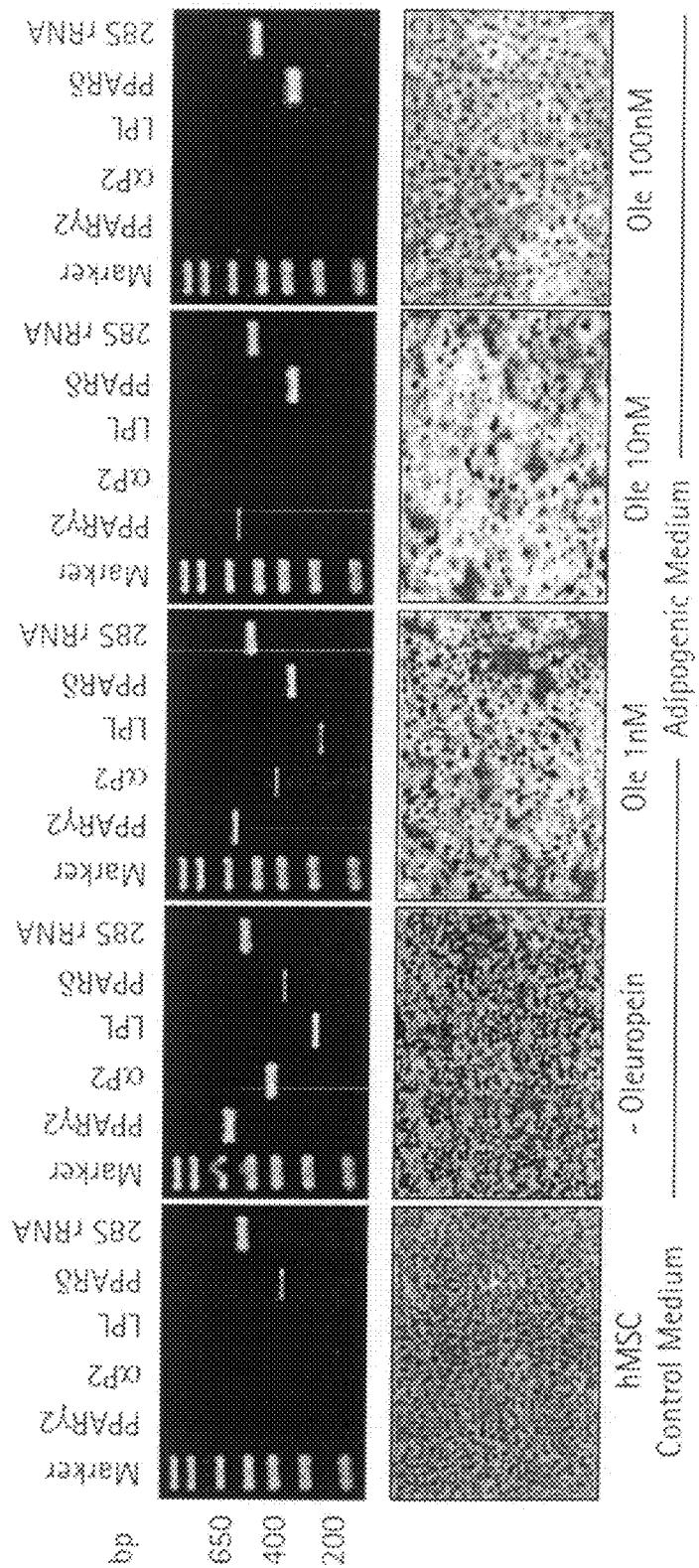
FIG. 1 Demonstrates that oleuropein modulates adipocyte differentiation

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

DEFINITIONS

The terms used herein have the meanings recognized and known to those of skill in the art, however, for convenience and completeness, particular terms and their meanings are set forth below.

The term "adipocyte" refers to a cell existing in or derived from fat tissue which is terminally differentiated. In their differentiated state, adipocytes assume a rounded morphology associated with cytoskeletal changes and loss of mobility. They further accumulate lipid as multiple small vesicles that later coalesce into a single, large lipid droplet displacing the nucleus. The term "human adipocyte" refers to an adipocyte existing in or isolated from human fat tissue. Adipocytes play a critical role in energy homeostasis. They synthesize and store lipids when nutrients are plentiful, and release fatty acids into the circulation when nutrients are required. Numerous adipogenic genes are expressed in functional adipocytes, whereas they are not expressed in preadipocytes in which lipid are not accumulated either. Adipocyte development has been extensively studied in cell culture as well as in animal models. There are several lines of evidence supporting that adipose tissue dysfunction plays an important role in the pathogenesis of type II diabetes mellitus, i.e. failure of adipocyte differentiation is a predisposition to developing diabetes, (see, e.g., Danforth (2000) Nature Genetics 26: 13).

The term "adipogenic gene expression" refers to the expression of several genes known as "adipogenesis marker genes" and more particularly refers to one or more genes specifically associated with a specific adipogenesis/differentiation stage. Such marker genes are well-known in the art. For example, Peroxisome Proliferator-Activated Receptor γ2 (PPARγ2), lipoprotein lipase (LPL), and the adipocyte-selective fatty acid binding protein (the αP2 gene). In addition, other differentiated adipocyte marker genes include glycerophosphate dehydrogenase (GPDH), fatty acid synthase, acetyl CoA carboxylase, malic enzyme, Glut 4, and the insulin receptor (see Spiegelman et al. J. Biol. Chem. 268: 6823-6826, 1993, incorporated herein by reference). Preadipocytes also have characteristic marker genes, such as the cell surface antigen recognized by the monoclonal antibody AD-3. Expression level changes of the various isoforms of the C/EBP (CCAAT/enhancer-binding proteins) family of transcription factors may also indicate different stages of adipogenesis (see Yu and Hausman, Exp Cell Res Dec. 15, 1998; 245(2): 343-9). Other genes include the lipolytic genes involved in the mobilization and β-oxidation of stored fat as well as those in the mitochrondia involved in thermogenesis (the uncoupling enzymes, factors and modulators) such as PPAR α, PPARδ, and their related genes, hormone-sensitive lipase (HSL), lipoprotein lipase (LPL), and enzymes of energy metabolism such as glycerol-3-phosphate dehydrogenase 1, acetyl-coenzyme A carboxykinase, phosphoenolpyruvate carboxykinase and pyruvate dehydrogenase kinase.

The phrase "essentially pure" refers to a cell population, e.g., a human adipocyte population, that has been isolated from its natural source (e.g., has been isolated or purified from fat tissue, for example, from human fat tissue) and, through a purification step or series of purification steps, has been separated from other cells (e.g., non-adipocyte cells) and cellular debris. An essentially pure cell population, as defined according to the instant invention, is at least 90% pure, i.e., at least 90% of the cells are of the desired cell type (e.g., human adipocytes) and less then 10% are contaminating (e.g. non-adipocyte) cells. In a preferred embodiment, an essentially pure cell population (e.g., an essentially pure adipocyte population) is at least 95% pure. In a more preferred embodiment, an essentially pure cell population (e.g., an essentially pure adipocyte population) is at least 96%, 97%, 98%, 99% or 100% pure).

The phrase "differentiation-inducing agent" refers to a compound or agent that initiates or stimulates the differentiation of preadipocytes into adipocytes. Preferred "differentiation-inducing agents" include but are not limited to insulin, insulin-sensitizing agents, substrates for lipid synthesis, PPAR ligands (e.g., natural ligands, for example, prostaglandin $J_2$, and synthetic ligands, for example, thiazolidinediones, and the like). The phrase "differentiation-promoting agent" refers to a compound or an agent that enhances or accelerates the differentiation of preadipocytes into adipocytes. Preferred "differentiation-inducing agents" include but are not limited to insulin, insulin-sensitizing agents, substrates for lipid synthesis, PPAR ligands, and the like. "Differentiation-inducing agents" or "differentiation-promoting agents" vary considerably in effectiveness but share common effects on several cellular signaling pathways including, but not limited to: (1) tyrosine kinase pathways (e.g., IGF-1-mediated tyrosine kinase pathway); (2) adenylyl cyclase/phosphodiesterase signaling pathways; (3) steroid/thyroid/peroxisome proliferator activated (PPAR)/retinoid nuclear receptors signaling pathways; and (4) protein kinase signaling pathways (MacDougald, O. A. et al. (1995) Annu. Rev. Biochem 64:345-73; Smas, C. M. et al. (1995) Biochem J. 309, 697-710; Cornelius, P. et al. (1994) Annu. Rev. Nutr. 14:99-129). Following induction of differentiation through these signal transduction pathways, coordinated changes in the expression of over 600 genes occurs leading to the acquisition and maintenance of the fat cell phenotype (MacDougald, O. A. et al. (1995) Annu. Rev. Biochem 64:345-73; Smas, C. M. et al. (1995) Biochem J. 309, 697-710; Cornelius, P. et al. (1994) Annu. Rev. Nutr. 14:99-129). These changes in differentiation-dependent gene expression are orchestrated by several transcription factors including CCAAT enhancer binding proteins (C/EBPα, β, and γ), PPARγ, and others (reviewed in MacDougald, O. A. et al. (1995) Annu. Rev. Biochem 64:345-73; Smas, C. M. et al. (1995) Biochem J. 309, 697-710; Kirkland, J. L., et al. (1997) J. Amer. Geriatr. Soc. 45:959-67). Overexpression of some of these transcription factors, including C/EBPα and PPAR γ, is sufficient to induce the differentiation of preadipocytes (Lin, F. T., et al (1994) Proc. Natl. Acad: Sci. USA 91:8757-8761; Hu, E. et al. (1995) Proc. Natl. Acad. Sci. USA 92:8956-60; Wu, Z., et al. (1995) Genes Defer 9:2350-63; Yeh, W. C., et al. (1995) Genes Devel. 9:168-81).

Markers of differentiation include (presented in order of detectable changes in expression): (1) cytoskeletal genes; (2) lipoprotein lipase (LPL) and collagen isoforms; (3) adipocyte fatty acyl binding protein (aP2) and glycerol-3-phosphate dehydrogenase (G3PD); and/or (4) the insulin sensitive glucose transporter (GLUT4), angiotensinogen (ang), apolipoprotein E (apoE), leptin, adipsin (complement factor D), protein C3, factor B, and other genes occur that contribute to the endocrine/paracrine function of adipose tissue. Increased fat cell mass, which is dependent on the balance between rates of adipogenesis, lipogenesis and lipolysis.

"Modulation" or "modulates" or "modulating" refers to up regulation (i.e., activation or stimulation), down regulation (i.e., inhibition or suppression) of a response, or the two in combination or apart. As used herein, a fat cell, preadipocyte or adipocyte "modulator" or "modulating" compound or agent is a compound or agent that modulates at least one biological marker or biological activity characteristic of fat cells and/or fat tissue. The term "modulating" as related to adipocyte differentiation or adipogenic gene expression, refers to the ability of a compound or agent to exert an effect on adipocyte differentiation, de-differentiation or transdifferentiation or to alter the expression of at least one gene (as noted above) related to adipogenesis. In addition, compounds or agents of the invention modulate at least one of (1) differentiation-specific gene expression, (2) lipid metabolism (e.g., lipogenesis and/or lipolysis), (3) fatty acid uptake, (4) fat accumulation and/or (5) accumulation of cytoplasmic lipid and (6) modulation of PPAR activity.

"Differentiate" or "differentiation" as used herein, generally refers to the process by which precursor or progenitor cells differentiate into specific cell types. In the matter of the present invention, the term refers to the process by which pre-adipocytes become adipocytes. Differentiated cells can be identified by their patterns of gene expression and cell surface protein expression. The genes associated with adipocyte differentiation are noted above. As an example, cells of adipocyte lineage typically express the following genes: ob, Ucp, PPARγ and C/EBPs (see, e.g., Kozak and Kozak, Endocrinology 134(2):906-13 (1994)) and Lee et al., J. Clin. Invest. 111 (4): 453-461 (2003). As used herein, the term "differentiate" refers to having a different character or function from the original type of tissues or cells. Thus, "differentiation" is the process or act of differentiating.

"Dedifferentiate" or "dedifferentiation" as used herein, refers to the process by which lineage committed cells reverse their lineage commitment and become precursor or progenitor cells. Dedifferentiated cells can be identified by loss of patterns of gene expression and cell surface protein expression associated with the lineage committed cells. A loss of expression or decrease in expression levels of one or more of the adipocyte genes noted above indicates that an adipocyte has undergone dedifferentiation.

"Transdifferentiation" refers to the process by which precursor or progenitor cells pre-committed to cell types of one lineage differentiate into specific cell types of another lineage, e.g., pre-adipocytes can transdifferentiate into osteoblasts and vice versa. Transdifferentiated cells can be identified by their patterns of gene expression and cell surface protein expression. Typically, cells of an osteoblast lineage express genes such as, for example, alkaline phosphatase, collagen type I, osteocalcin, and osteoponin; and bone specific transcription factors such as, for example, Cbfa 1/Runx2, Osx, gsc, Dlx1, Dlx5, Msx1, Cart1, Hoxa1, Hoxa2, Hoxa3, Hoxb1, rae28, Twist, AP-2, Mfl, Pax1, Pax3, Pax9, TBX3, TBX4, TBX5, and Brachyury (see, e.g., Olsen et al, 2000 supra and Nakashima et al., Cell 108(1):17-29 (2002). The cells can be transdifferentiated within the same progenitors. For example, mesenchymal stem cells or marrow stromal cells (MSC), are stem cells that can differentiate into osteoblasts, chondrocytes, myocytes, adipocytes, neuronal cells, and, as described lately, into beta-pancreatic islets cells. Thus these cells can be cross transdifferentiated under optimal culture conditions and/or growth factors. MSCs cultured in the presence of transformation growth factor (TGF), specifically bone morphogenetic protein (BMP), will differentiate into chondrocytes, whereas MSCs cultured in serum with ascorbic acid, inorganic phosphate and dexamethasone will differentiate into osteoblasts. On the other hand, MSCs cultured under adipogenic conditions in the presence of dexamethasone, insulin and isobutyl-methylxanthine will differentiate into adipocytes.

Adipocyte differentiation is a multistep process controlled by the action of a complex interactive network of transcription factors in mammals. In the fruit fly the serpent gene is critical for the genesis of the fruit fly fat body, which corresponds to mammalian liver and adipose tissue. The GATA family of transcription factors in mice are the mammalian homologues of the *Drosophila* serpent gene. Both GATA-2 and GATA-3 directly bind to specific sites in the proximal promoter of the adipogenic transcription factor, peroxisome proliferaror activated receptor-gamma (PPAR-gamma), and negatively regulate its activity. Both GATA-2 and GATA-3 expression are severely defective in the white adipose tissue of several different models of obesity. These results indicate that GATA-2 and GATA-3 are preadipocyte markers and play an important role in adipogenesis.

As used herein, the term "candidate compound" or "candidate therapeutic" or "test compound" or "agent" or "test agent" refers to any compound or molecule that is to be tested. As used herein, the terms, which are used interchangeably, refer to biological or chemical compounds such as simple or complex organic or inorganic molecules, peptides, proteins, antibodies, oligonucleotides, polynucleotides, carbohydrates, or lipoproteins. A vast array of compounds can be synthesized, for example oligomers, such as oligopeptides and oligonucleotides, and synthetic organic compounds based on various core structures, and these are also included in the terms noted above. In addition, various natural sources can provide compounds for screening, such as plant or animal extracts, and the like. Compounds can be tested singly or in combination with one another. Agents or candidate compounds can be randomly selected or rationally selected or designed. As used herein, an agent or candidate compound is said to be "randomly selected" when the agent is chosen randomly without considering the specific interaction between the agent and the target compound or site. As used herein, an agent is said to be "rationally selected or designed", when the agent is chosen on a nonrandom basis which takes into account the specific interaction between the agent and the target site and/or the conformation in connection with the agent's action. Moreover, the agent may be selected by its effect on the gene expression profile obtained from screening in vitro or in vivo. For example, the gene expression data for primary human preadipocytes and adipocytes can be accessed online through databases including Pub Med, Human Genome Project (HGP), Gene Bank and PDB (Protein Data Bank).

Biochemically, "adipogenesis" is referred to as the process of fat cell formation. It involves commitment, differentiation and maturation of adipocytes. Adipogenic genes, gene products, enzymes, factors, and pathways are the genes, gene products, enzymes, factors, and pathways for adipocyte differentiation (adipogenesis or fat cell formation), and these genes are described throughout the present application. "Lipogenesis" is referred to as the process of lipid biosynthesis (fat formation), the conversion of carbohydrate or protein to fat and the synthesis of triglycerides from 2-monogylcerol and free fatty acids as well as from glycerol-3-phosphate and fatty acyl CoA. In addition, the synthesis of long chain fatty acids, using acetyl CoA as the primer and malonyl CoA as the addition unit also refers to as lipogenesis. Lipogenic genes, gene products, enzymes, factors, and pathways are the genes, gene products, enzymes, factors, and pathways for lipid biosynthesis (fat formation), and these genes are also described throughout the present application. Thus, adipogenesis is different from lipogenesis and the two terms are not synonymous. In addition, "adipogenesis" refers to the process whereby adipose tissue, a mesodermal derivative, develops from preadipocytes. "Adipogenesis" refers to the process by which an undifferentiated precursor cell differentiates into an adipocyte (a fat cell, which is a cell characterized by the cellular function of fat storage e.g., in cytoplasmic lipid droplets). Precursor cells that are involved in the process of adipogensis include pre-adipocytes, mesenchymal stem cells and progenitor cells. Generally, diseases associated with adipogenesis include body weight disorders such as obesity and cachexia, and nonshivering and shivering thermogenesis. Accordingly, in one aspect of the invention, the agents identified as modulators of adipogenesis are potentially useful for modulating body weight-related processes, including, for example, treatment of body weight disorders such as obesity and cachexia, and thermogenesis. Treatment of other obesity related disorders or conditions are also contemplated. Obesity related disorders or conditions may be selected from the group consisting of coronary artery disease/cardiovascular disease, hypertension, cerebrovascular disease, stroke, peripheral vascular disease, insulin resistance, glucose intolerance, diabetes mellitus, hyperglycemia, hyperlipidemia, dyslipidemia, hypercholesteremia, hypertriglyceridemia, hyperinsulinemia, atherosclerosis, cellular proliferation and endothelial dysfunction, diabetic dyslipidemia, HIV-related lipodystrophy, peripheral vessel disease, cholesterol gallstones, cancer, menstrual abnormalities, infertility, polycystic ovaries, osteoarthritis, sleep apnea, metabolic syndrome (Syndrome X), type II diabetes, diabetic complications including diabetic neuropathy, nephropathy, retinopathy, cataracts, heart failure, inflammation, thrombosis, congestive heart failure, and any other cardiovascular disease related to obesity or an overweight condition. Obesity induced or related asthma, airway dysfunction and pulmonary disorders are also important diseases linked to obesity. "Lipolysis" or "lipolytic" refers to the process of lipid degradation/oxidation (fat burning, utilization, energy production). Lipolytic genes, gene products, enzymes, factors, and pathways are the genes, gene products, enzymes, factors, and pathways for lipid oxidation (fat burning, (β-oxidation). "Thermogenesis" refers to the process of heat and energy generation, also known as energy uncoupling. Thermogenic genes, gene products, enzymes, factors, and pathways are the genes, gene products, enzymes, factors, and pathways for body heat generation and energy uncoupling. This process also increases metabolic rate.

The PPARs play a central role in adipocyte differentiation. PPAR gamma responsive genes in human adipocyte differentiation are briefly discussed below: Affymetrix profiling of gene expression in human adipocytes identified about 1000 genes that were significantly up-regulated subsequent to induction of differentiation and 278 statistically significantly down-regulated genes [*Gene.* 2006 Mar. 15; 369:90-9]. In addition, it is also necessary to consider PPAR alpha and delta responsive genes. A recent report (*Diabetologia.* 2005 September; 48(9):1776-83. Epub 2005 Jul. 30) on microarray gene profiling of isolated abdominal subcutaneous adipocytes from 20 non-obese (BMI 25±3 kg/m$^2$) and 19 obese (BMI 55±8 kg/m$^2$) non-diabetic Pima Indians using Affymetrix HG-U95 GeneChip arrays showed that the most differentially expressed genes in adipocytes of obese individuals consisted of 433 upregulated and 244 down-regulated genes. Of these, 410 genes could be classified into 20 functional Gene Ontology categories. The analyses indicated that the inflammation/immune response category was over-represented, and that most inflammation-related genes were upregulated in adipocytes of obese subjects. This study provides evidence supporting the active role of mature adipocytes in obesity-related inflammation. It also provides potential candidate genes for susceptibility to obesity.

Depending on the desired result, an agent identified to induce adipogenesis is potentially useful for increasing body weight and an agent identified to prevent adipogenesis is potentially useful for decreasing body weight. Adipogenesis in vivo and in vitro is subject to hormonal and transcriptional control, in part mediated by a cascade of transcription factors including members of the CCAAT/enhancer binding protein family, basic helix-loop-helix leucine zipper (bBLH-LZ) family, e.g., ADD1/SREBP1 and peroxisome proliferator activated receptor gamma (PPARgamma) (See, e.g., Wu et al. (1999) Transcriptional activation of adipogenesis Current Opin. Cell Biol 11:689-694, Rosen and Spiegelman (2000) Molecular regulation of adipogenesis Annu Rev Cell Dev Biol 16:145-171, for recent reviews, as well as Kim and Spiegelman (1996) ADD1/SREBP1 promotes adipocyte differentiation and gene expression linked fatty acid metabolism Genes Devel 10:1096-1107). However details regarding cellular targets of such transcription factors remain largely undetermined, as do the mechanisms underlying their action in physiological and pathological processes.

"Subject" or "patient" refers to a mammal, preferably a human, in need of treatment for a condition, disorder or disease.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E.W. Martin.

A "therapeutically effective amount" or "an effective amount", which are used interchangeably, is an amount sufficient to decrease or prevent the symptoms associated with the conditions disclosed herein, including diseases associated with obesity, or an amount to inhibit the infectivity of human immunodeficiency virus (HIV-1 and HIV-2) and other related conditions contemplated for therapy with the compositions of the present invention. The effect on HIV infectivity may be measured by any of the commonly used methods known to those skilled in the art, for example, cell fusion may be measured by assessing the level of syncitia formation. Viral replication may be measured by using PCR procedures to monitor the level of viral nucleic acid in a host cell.

"Metabolic Syndrome" or otherwise known as "Syndrome X" means a disease characterized by spontaneous hypertension, dyslipidemia, insulin resistance, hyperinsulinemia, increased abdominal fat and increased risk of coronary heart disease. As used herein, the terms "Syndrome X", "Metabolic Syndrome" and "Metabolic Syndrome X" shall mean a disorder that presents risk factors for the development of Type II diabetes mellitus and cardiovascular disease and is characterized by insulin resistance and hyperinsulinemia and may be accompanied by one or more of the following: (a) glucose intolerance, (b) Type II diabetes, (c) dyslipidemia, (d) hypertension and (e) obesity.

"Obesity" refers to a condition in which the body weight of a mammal exceeds medically recommended limits by at least about 20%, based upon age and skeletal size. "Obesity" is characterized by fat cell hypertrophy and hyperplasia. "Obesity" may be characterized by the presence of one or more obesity-related phenotypes, including, for example, increased body mass (as measured, for example, by body mass index, or "BMI"), altered anthropometry, basal metabolic rates, or total energy expenditure, chronic disruption of the energy balance, increased Fat Mass as determined, for example, by DEXA (Dexa Fat Mass percent), altered maximum oxygen use (VO2), high fat oxidation, high relative resting rate, glucose resistance, hyperlipidemia, insulin resistance, and hyperglycemia. See also, for example, Hopkinson et al. (1997) Am J Clin Nutr 65(2): 432-8 and Butte et al. (1999) Am J Clin Nutr 69(2): 299-307. "Overweight" individuals are generally having a body mass index (BMI) between 25 and 30. "Obese" individuals or individuals suffering from "obesity" are generally individuals having a BMI of 30 or greater. Obesity may or may not be associated with insulin resistance.

An "obesity-related disease" or "obesity related disorder" or "obesity related condition", which are all used interchangeably, refers to a disease, disorder, or condition, which is associated with, related to, and/or directly or indirectly caused by obesity. The "obesity-related diseases", or the "obesity-related disorders" or the "obesity related conditions" include but are not limited to, coronary artery disease/cardiovascular disease, hypertension, cerebrovascular disease, stroke, peripheral vascular disease, insulin resistance, glucose intolerance, diabetes mellitus, hyperglycemia, hyperlipidemia, dyslipidemia, hypercholesteremia, hypertriglyceridemia, hyperinsulinemia, atherosclerosis, cellular proliferation and endothelial dysfunction, diabetic dyslipidemia, HIV-related lipodystrophy, peripheral vessel disease, cholesterol gallstones, cancer, menstrual abnormalities, infertility, polycystic ovaries, osteoarthritis, sleep apnea, metabolic syndrome (Syndrome X), type II diabetes, diabetic complications including diabetic neuropathy, nephropathy, retinopathy, cataracts, heart failure, inflammation, thrombosis, congestive heart failure, and any other cardiovascular disease related to obesity or an overweight condition and/or obesity related asthma, airway and pulmonary disorders.

An individual "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of obesity or an obesity-related disease or a disease for which PPAR modulation provides a therapeutic benefit, or an individual who is more likely to acquire HIV through use of shared needles or those individuals who may practice unprotected sexual activity. An individual having one or more of these risk factors has a higher probability of developing obesity or an obesity-related disease, or HIV than an individual without these risk factors. Examples (i.e., categories) of risk groups are well known in the art and discussed herein.

"Development" or "progression" of obesity herein means initial manifestations and/or ensuing progression of the disorder. Development of obesity can be detectable and assessed using standard clinical techniques, such as measurement of increased body mass (as measured, for example, by body mass index, or "BMI"), altered anthropometry, basal metabolic rates, or total energy expenditure, chronic disruption of the energy balance, increased Fat Mass as determined, for example, by DEXA (Dexa Fat Mass percent), altered maximum oxygen use (VO2), high fat oxidation, high relative resting rate, glucose resistance, hyperlipidemia, insulin resistance, and hyperglycemia. See also, for example, Hopkinson et al. (1997) Am J Clin Nutr 65(2): 432-8 and Butte et al. (1999) Am J Clin Nutr 69(2): 299-307. However, development also refers to disease progression that may be undetectable. For purposes of this invention, development or progression refers to the biological course of the disease state. "Development" includes occurrence, recurrence, and onset. As used herein "onset" or "occurrence" of obesity includes initial onset and/or recurrence.

As used herein, "delaying development" of obesity, or an obesity-related disease, means to defer, hinder, slow, retard, stabilize, and/or postpone development of the disease. This delay can be of varying lengths of time, depending on the history of the disorder and/or the medical profile of the individual being treated. As is evident to one skilled in the art, a sufficient or significant delay can, in effect, encompass prevention, in that the individual does not develop detectable disease. A method that "delays" development of disease is a method that reduces the extent of the disease in a given time frame, when compared to not using the method. Such comparisons are typically based on animal or clinical studies, using a statistically significant number of subjects, although this knowledge can be based upon anecdotal evidence. "Delaying development" can mean that the extent and/or undesirable clinical manifestations are lessened and/or time course of the progression is slowed or lengthened, as compared to not administering the agent. Thus the term also includes, but is not limited to, alleviation of symptoms, diminishment of extent of disease, stabilized (i.e., not worsening) state of disease, delay or slowing of disease progression, and remission (whether partial or total) whether detectable or undetectable.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder" as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholecystitis and cholelithiasis, gout, obstructive sleep apnea and respiratory problems, osteoarthritis, and prevention and treatment of bone loss, e.g. osteoporosis.

"Alpha-glucosidase inhibitors" act to inhibit alpha-glucosidase, which is an enzyme that converts fructose to glucose, thus these inhibitors delay the digestion of carbohydrates. The undigested carbohydrates are subsequently broken down in the gut, thereby reducing the post-prandial glucose peak. Suitable examples include, but are not limited to, acarbose, voglibose and miglitol.

"Sulfonylureas" increase insulin production by stimulating pancreatic beta cells, and therefore act as insulin secretagogues. The primary mechanism of action of sulfonylureas is to close ATP-sensitive potassium channels in the beta-cell plasma membrane, initiating a chain of events that result in insulin release. Suitable examples of sulfonylureas include, but are not limited to chlorpropamide, tolazamide, tolbutamide, glyburide, glipizide, glimepiride, and like. Meglitinides, another class of insulin secretagogues, that have a mechanism of action distinct from that of the sulfonylureas. Suitable examples of meglitinides include, but are not limited to repaglinide. Agents which modify insulin secretion such as Glucagon-like Peptide-1(GLP-1) and it's mimetics, Glucose-insulinotropic peptide (GIP) and it's mimetics, Exendin and it's mimetics, and Dipeptyl Protease Inhibitors (DPP1V) are also contemplated for use with the invention.

"Biguanides" are compounds that decrease liver glucose production and increase the uptake of glucose. Suitable examples include, but are not limited to metformin, phenformin and buformin.

A "peroxisome proliferator activated receptor" or "PPAR" is a member of a family of nuclear receptors, distinguished in alpha (α), delta (δ), and gamma (γ) subtypes as described herein. As used herein the term "PPAR" refers to a peroxisome proliferator-activated receptor as recognized in the art. As indicated above, the PPAR family includes PPAR α (also referred to as PPARa or PPARalpha), PPAR δ (also referred to as PPAR beta, PPARd or PPARdelta), and PPAR γ (also referred to as PPARa or PPARgamma). The individual PPARs can be identified by their sequences, where exemplary reference sequence accession numbers are: NM_005036 (cDNA sequence for hPPARa (SEQ ID NO:1)), NP_005027 (protein sequence for hPPARa (SEQ ID NO: 2)), NM_015869 (cDNA sequence for hPPARg isoform 2 (SEQ ID NO: 3)), NP_056953 (protein sequence for hPPARg isoform 2 (SEQ ID NO: 4)), NM_006238 (cDNA sequence for hPPARd (SEQ ID NO: 5)), and NP_006229 (protein sequence for hPPARd (SEQ ID NO: 6)). One of ordinary skill in the art will recognize that sequence differences will exist due to allelic variation, and will also recognize that other animals, particularly other mammals have corresponding PPARs, which have been identified or can be readily identified using sequence alignment and confirmation of activity, can also be used. One of ordinary skill in the art will also recognize that modifications can be introduced in a PPAR sequence without destroying PPAR activity. Such modified PPARs can also be used in the present invention, e.g., if the modifications do not alter the binding site conformation to the extent that the modified PPAR lacks substantially normal ligand binding.

A "PPAR modulating agent" or "PPAR modulator" refers to any agent that binds to any of the PPAR receptors and acts to either enhance the activity or function of that particular receptor (agonist) or acts to inhibit or depress the activity or function of that particular receptor (antagonist). The PPAR receptors include the α, γ, and δ receptors. It is also possible to have the following types of PPAR modulators:

Selective PPAR modulators that serve as selective or partial agonist/antagonist and uncouple therapeutic effects from adverse side effects. For example, a selective/partial PPAR γ agonist/antagonist that uncouples the therapeutic effect of insulin sensitizing activity from adipogenic effect (side effect for weight gain during treatment)

Dual PPAR modulators that act on two PPARs collectively, selectively or partially either as agonists or agonist-antagonists combined. For example, the dual PPARγ/PPARα agonists have two separate therapeutic targets in metabolic pathways in adipose tissue and liver. They may improve both hyperglycemia and atherogenic dyslipidaemia and may further reduce the inflammatory component of atherogenesis.

Pan PPAR modulators that interact with all of the three PPARs collectively, selectively or partially either as agonists or agonist-antagonists combined. For example, the pan PPARγ/PPARα/PPAR δ agonists have three separate therapeutic targets—metabolic pathways in adipose tissue, liver and muscle (and other tissue). They may improve hyperglycemia, atherogenic dyslipidemia, inflammatory component of atherogenesis, energy uncoupling and weight reduction.

"Thiazolidinediones" are insulin sensitizing drugs, which decrease peripheral insulin resistance by enhancing the effects of insulin at target organs and tissues. These drugs bind and activate the nuclear receptor, peroxisome proliferator-activated receptor-gamma (PPAR-gamma) which increases transcription of specific insulin-responsive genes. Suitable examples of PPAR-gamma agonists are the thiazolidinediones which include, but are not limited to rosiglitazone, pioglitazone, troglitazone, isaglitazone (known as MCC-555), 2-[2-[(2R)-4-hexyl-3,4-dihydro-3-oxo-2H-1,4-benzoxazin-2-yl]ethoxy]-benzene acetic acid, and the like. Additionally, the non-thiazolidinediones also act as insulin sensitizing drugs, and include, but are not limited to GW2570, and the like.

The concept of "combination therapy" is well exploited in current medical practice. Treatment of a pathology by combining two or more agents that target the same pathogen or biochemical pathway sometimes results in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect can be synergistic (the efficacy of the combination is greater than the sum of the effects of each drug given alone). As used herein, the term "combination therapy" means the two compounds can be delivered in a simultaneous manner, e.g. concurrently, or wherein one of the compounds is administered first, followed by the second agent, e.g sequentially. The desired result can be either a subjective relief of one or more symptoms or an objectively identifiable improvement in the recipient of the dosage.

"Atherogenesis" is a process of forming atheromas, that is, plaques in the inner lining (the intima) of arteries. It is a process in which the immune system appears to take an active part, and refers to the build-up of plaque in the blood vessels. Accordingly, activated lymphocytes have been detected in human and murine plaques, sometimes even preceding the infiltrating lipid-laden macrophages. The atherosclerotic process entails a proliferative phenotype, involving, apart from lymphocytes and macrophages, also smooth muscle cells, which occupy lesions that are relatively more advanced. Furthermore, atherosclerosis is the accumulation of lipid, inflammatory cells, and fibrous tissue in the intima, which causes intimal thickening of large and mid-sized arteries. The clinical manifestations differ depending on the circulatory bed affected. The coronary arteries are particularly susceptible to atherogenesis; atherosclerosis of the coronary arteries may lead to angina pectoris and myocardial infarction. Dyslipidemia is a primary, major risk factor for coronary artery disease (CAD) and may even be a prerequisite for CAD, occurring before other major risk factors come into play. "Diet-induced atherogenesis" refers to the induction or initiation of the atherogenic process by consumption of food that contains a high fat content, which ultimately results in build-up of plaque in the blood vessels.

"Endothelial dysfunction" is a physiological dysfunction of normal biochemical processes carried out by endothelial cells, the cells that line the inner surface of all blood vessels, arteries and veins. Compromise of normal function of endothelial cells is characteristic of endothelial dysfunction. Normal functions of endothelial cells include mediation of coagulation, platelet adhesion, immune function, control of volume and electrolyte content of the intravascular and extravascular spaces. An important consequence of endothelial dysfunction is the inability of a vessel to dilate in response to physiological stimuli, such as increases in blood flow, reflecting impaired flow-dependent, endothelium-mediated vasodilation (FDD). Accumulating evidence suggests that endothelial dysfunction contributes to exercise intolerance, impaired myocardial perfusion, and left ventricular remodelling in congestive heart failure. Moreover, impaired endothelial function is associated with a number of disease states, including cardiovascular disease (CVD) and its major risk factors. Endothelial dysfunction precedes overt vascular disease by years and may itself be a potentially modifiable CVD risk factor. Although no gold standard for the measurement of endothelial function exists, the measurement of flow-mediated dilation (FMD) in the brachial artery, assessed with Doppler ultrasonography, is the most studied method and shows the most promise for clinical application. It is a well-tolerated, noninvasive, and low-risk procedure. Brachial artery FMD is an attractive screening tool for assessing endothelial dysfunction.

"Treatment" or "treating" refers to therapy, prevention and prophylaxis and particularly refers to the administration of medicine or the performance of medical procedures with respect to a patient, for either prophylaxis (prevention) or to cure (if possible) or reduce the extent of or likelihood of occurrence of the infirmity or malady or condition or event in the instance where the patient is afflicted. More particularly, as related to the present invention, "treatment" or "treating" is defined as the application or administration of a therapeutic agent to a patient, or application or administration of a therapeutic agent to an isolated tissue or cell line from a patient, who has a disease, a symptom of disease or a predisposition toward development of a disease. Treatment can slow, cure, heal, alleviate, relieve, alter, remedy, ameliorate, improve or affect the disease, a symptom of the disease or the predisposition toward disease, e.g., by at least 10%. In the present invention, the treatments using the agents described may be provided to slow or halt weight gain, or to aid in weight reduction, or to prevent fat accumulation or obesity, or to inhibit adipocyte differentiation or adipogenic gene expression, or to increase the amount or quality of lean muscle mass present in the mammal, or to prevent the infectivity of HIV, or to slow viral spread, or to alleviate one or more symptoms associated with the presence of the viral disease. More preferably, the goal is the treatment of obesity or obesity-related diseases, disorders or conditions and the morbidity associated with such conditions and the treatment of human immunodeficiency virus infections and the symptoms and sequelae associated with the presence of the viral infection.

"Diagnosis" or "screening" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

A "small molecule" refers to a composition that has a molecular weight of less than 3 kilodaltons (kDa), and preferably less than 1.5 kilodaltons, and more preferably less than about 1 kilodalton. Small molecules may be nucleic acids, peptides, polypeptides, peptidomimetics, carbohydrates, lipids or other organic (carbon-containing) or inorganic molecules. As those skilled in the art will appreciate, based on the present description, extensive libraries of chemical and/or biological mixtures, often fungal, bacterial, or algal extracts, may be screened with any of the assays of the invention to identify compounds that modulate a bioactivity. A "small organic molecule" is an organic compound (or organic compound complexed with an inorganic compound (e.g., metal)) that has a molecular weight of less than 3 kilodaltons, and preferably less than 1.5 kilodaltons, and more preferably less than about 1 kilodalton.

"Disease associated with PPAR γ, δ, or α" or "a disease associated with a PPAR γ, δ, or α receptor" includes diseases treatable with a ligand of any of the above-noted PPAR receptors, such as but not limited to Type II diabetes and obesity, or other obesity related disorders. Diseases related to PPAR expression and/or activity would also be considered as associated with the PPAR receptor, such as obesity or other disorders expected to be affected by alterations in the PPAR's role in adipocyte differentiation, de-differentiation and trans-differentiation as well as adipocyte functions including fat synthesis, storage, utilization and energy uncoupling. The diseases associated with the modulation of the different PPAR receptors are known to those skilled in the art. For example, possible diseases and/or risk factors associated with PPARs are: the metabolic syndrome and its associated risk factors for atherosclerotic cardiovascular disease (ASCVD) and diabetes, atherogenic dyslipidemia, elevated blood pressure, elevated plasma glucose, a prothrombotic state and a pro-inflammatory state. In addition, other conditions, including fatty liver, polycystic ovary disease, sleep apnea, cholesterol gallstones, asthma and cancer.

"Prophylactic" or "therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

"Therapeutic agent" or "therapeutic" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents are known in the art and may be identified by their effects. Certain therapeutic agents are capable of regulating cell proliferation and differentiation. Examples include chemotherapeutic nucleotides, drugs, hormones, non-specific (non-antibody) proteins, oligonucleotides (e.g., antisense oligonucleotides that bind to a target nucleic acid sequence (e.g., mRNA sequence)), peptides, and peptidomimetics. Examples of other therapeutic agents that modulate PPAR gamma, alpha and delta are the thiazolidinediones, firbrates, fatty acids and eicosanoids.

"Therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human.

"Agonist" refers to an agent that mimics or up-regulates (e.g., potentiates or supplements) the bioactivity of a protein. An agonist may be a wild-type protein or derivative thereof having at least one bioactivity of the wild-type protein. An agonist may also be a compound that up-regulates expression of a gene or which increases at least one bioactivity of a protein. An agonist may also be a compound which increases the interaction of a polypeptide with another molecule, e.g., a target peptide or nucleic acid. An agonist may also be a compound that increase or up-regulate the activity and/or function of a protein, peptide, an enzyme or biofactor.

"Antagonist" refers to an agent that down-regulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that down-regulates expression of a gene or which reduces the amount of expressed protein present. An antagonist may also be a compound that decrease or down-regulate the activity and/or function of a protein, peptide, an enzyme or biofactor.

"Analog" or "analogue" as used herein, refers to a chemical compound, a nucleotide, a protein, or a polypeptide that possesses similar or identical activity or function(s) as the chemical compounds, nucleotides, proteins or polypeptides having the desired activity and therapeutic effect of the present invention (eg. to inhibit fat accumulation, or to modulate adipocyte differentiation or adipogenic gene expression or to treat obesity or obesity-related diseases, disorders or conditions), but need not necessarily comprise a compound that is similar or identical to those compounds of the preferred embodiment, or possess a structure that is similar or identical to the agents of the present invention. An agent having activity "analogous to oleuropein" is an agent that possesses similar functions and activities as oleuropein, including the effects on the adipogenic and lipolytic genes described herein, and on adipocyte metabolism, differentiation, de-differentiation, or transdifferentiation or effects on the PPAR receptors described herein.

"Derivative" refers to the chemical modification of molecules, either synthetic organic molecules or proteins, nucleic acids, or any class of small molecules such as fatty acids, or other small molecules that are prepared either synthetically or isolated from a natural source, such as a plant, that retain at least one function of the active parent molecule, but may be structurally different. Chemical modifications may include, for example, replacement of hydrogen by an alkyl, acyl, or amino group. It may also refer to chemically similar compounds which have been chemically altered to increase bioavailability, absorption, or to decrease toxicity. A derivative polypeptide is one modified by glycosylation, pegylation, or any similar process that retains at least one biological or immunological function of the polypeptide from which it was derived.

As used herein in connection with the design or development of PPAR ligands, the term "bind" and "binding" and like terms refer to a non-convalent energetically favorable association between the specified molecules (i.e., the bound state has a lower free energy than the separated state, which can be measured calorimetrically). For binding to a target, the binding is at least selective, that is, the compound binds preferentially to a particular target or to members of a target family at a binding site, as compared to non-specific binding to unrelated proteins not having a similar binding site. For example, BSA is often used for evaluating or controlling for non-specific binding. In addition, for an association to be regarded as binding, the decrease in free energy going from a separated state to the bound state must be sufficient so that the association is detectable in a biochemical assay suitable for the molecules involved.

By "binding pocket" is meant a specific volume within a binding site. A binding pocket is a particular space within a binding site at least partially bounded by target molecule atoms. Thus a binding pocket is a particular shape, indentation, or cavity in the binding site. Binding pockets can contain particular chemical groups or structures that are important in the non-covalent binding of another molecule such as, for example, groups that contribute to ionic, hydrogen bonding, van der Waals, or hydrophobic interactions between the molecules.

In the context of target molecules in the present invention, the term "crystal" refers to an ordered complex of target molecule, such that the complex produces an X-ray diffraction pattern when placed in an X-ray beam. Thus, a "crystal" is distinguished from a disordered or partially ordered complex or aggregate of molecules that do not produce such a diffraction pattern. Preferably a crystal is of sufficient order and size to be useful for X-ray crystallography. A crystal may be formed only of target molecule (with solvent and ions) or may be a co-crystal of more than one molecule, for example, as a co-crystal of target molecule and binding compound, and/or of a complex of proteins (such as a holoenzyme).

By "designing a ligand", "preparing a ligand", "discovering a ligand", and like phrases is meant the process of considering relevant data (especially, but not limited to, any individual or combination of binding data, X-ray co-crystallography data, molecular weight, clogP, and the number of hydrogen bond donors and acceptors) and making decisions about advantages that can be achieved with resort to specific structural modifications to a molecule, and implementing those decisions. This process of gathering data and making decisions about structural modifications that can be advantageous, implementing those decisions, and determining the result can be repeated as many times as necessary to obtain a ligand with desired properties.

By "docking" is meant the process of attempting to fit a three-dimensional configuration of a binding pair member into a three-dimensional configuration of the binding site or binding pocket of the partner binding pair member, which can be a protein, and determining the extent to which a fit is obtained. The extent to which a fit is obtained can depend on the amount of void volume in the resulting binding pair complex (or target molecule-ligand complex). The configuration can be physical or a representative configuration of the binding pair member, e.g., an in silico representation or other model.

In the context of development of modulators using molecular scaffolds, by "ligand" is meant a molecular scaffold that has been chemically modified at one or more chemically tractable structures to bind to the target molecule with altered or changed binding affinity or binding specificity relative to the molecular scaffold. The ligand can bind with a greater specificity or affinity for a member of the molecular family relative to the molecular scaffold. A ligand binds non-covalently to a target molecule, which can preferably be a protein or enzyme.

By "orientation", in reference to a binding compound bound to a target molecule is meant the spatial relationship of the binding compound and at least some of its consitituent atoms to the binding pocket and/or atoms of the target molecule at least partially defining the binding pocket.

Binding compounds can be characterized by their affinity for the target molecule as measured by determining the dissociation constant or by measuring their effect on the activity of the target molecule. For example, the IC50 (or EC50) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured. For PPAR agonists, activities can be determined as described in the Examples, or using other such assay methods known in the art.

In addition, the interaction of a ligand with its target structure can be assessed by measurement of the free energy in kcal/mol using approaches that involve AutoDock, Molecular Dynamics (MD) and Molecular Mechanics/Poisson-Boltzmann Solvent Accessible surface area (MM-PBSA) calculations. This is done using the crystal structures of the ligand binding domains of the PPAR receptors. Molecular docking is used to generate several distinct binding orientations. Molecular dynamics simulation is used to further relax the complex. MM-PBSA is then used to estimate the affinity for each binding mode. The binding modes with the lowest free energy are expected to be the most favorable. The energetically most favorable binding mode would provide for a free energy of <0 kcal/mol (negative value), and larger the free energy, the less favorable the interaction. The binding between a ligand and its target is unique in each system and can not be compared to other systems. However, it can be stated that the smaller the free energy the more favorable the binding. For favorable interactions, the free energy is negative. The more negative, the more favorable the interaction is.

The MM/PBSA approach uses a set of structures collected with molecular dynamics to evaluate free energies of binding. This method combines the molecular mechanical energies with the continuum solvent approaches. The molecular mechanical energies are determined based on AMBER force field and represent the internal energy (bond, angle and dihedral), van der Waals and electrostatic interactions. The electrostatic contribution to the solvation free energy is calculated with the Poisson-Boltzmann (PB) method. The hydrophobic contribution to the solvation free energy is determined with solvent-accessible-surface-area dependent terms. And estimates of conformational entropies can be made with the nmode module from AMBER. Briefly, MM/PBSA methodology involves the following steps:

1. Perform short molecular dynamics simulation.
2. Calculate average molecular mechanical and solvation energies from a set of simulation snapshots.
3. Use the quasi-harmonic approximation to/approximate/ the entropy of the system.

By putting energy terms together, free energy of binding can be estimated with the formula $$\Delta G \approx U(EE) + \Delta G(\text{solv}) - T\Delta S$$

Where $\Delta G$=standard free energy (kcal/mol), U (EE)=MM energy (kcal/mol), $\Delta G$ (sols)=free energy of solvent (kcal/mol), T=temperature (Kelvin) and A S=entropy (kcal/mol K).

"Resistin" (resistance to insulin) or "Resistin-Like Molecules" "RELMs" or "FIZZ 1-3" are found in the inflammatory zone involved in allegory and inflammation. Resistin is an adipokine associated with obesity and type 2 diabetes. Serum resistin level is related to insulin resistance. (Degawa-Yamauchi M, Serum Resistin (FIZZ3) Protein Is Increased in Obese Humans, J. Clin. Endocrinol. Metab., 88: 5452-5455, (2003); *Anal Chem*. (2006) May 15; 78(10):3271-6)

"Adipocyte-Specific Secretory Factor" (ADSF) is a small cysteine-rich protein secreted from adipose tissue (adipocyte-derived hormones, adipokines) that belongs to a gene family found in inflammatory zone (FIZZ) or found in resistin-like molecule (RELM). ADSF has been implicated in modulating adipogenesis and insulin resistance. It inhibits adipogenesis, decreases plasma triglyceride and free fatty acid, improves glucose tolerance and insulin sensitivity. (*Endocrine*. (2006) February; 29(1):81-90; *Proc Natl Acad Sci USA*. (2004) Apr. 27; 101(17):6780-5. Epub (2004) Apr. 16).

"Leptin" is a 16 kDa adipokine (protein hormone), encoded by the obese (ob) gene, expressed predominantly by adipocytes. It is important in regulating body weight, metabolism and reproductive function. Smaller amounts of leptin are also secreted by cells in the epithelium of the stomach and in the placenta. Leptin receptors are highly expressed in areas of the hypothalamus known to be important in regulating body weight, as well as in T lymphocytes and vascular endothelial cells (*Int J Obes* (Lond). (2006) May 16)

"Acrp30/Adiponectin" (adipocyte complement-related protein of 30 kDa) also known as AdipoQ, APM1, Adiponectin, Gelatin binding protein 28 kDa/GBP28 or adipocyte most abundant gene transcript is identified as a novel adipocyte-specific synthesized and secreted protein with structural resemblance to complement factor C1q. Like adipsin, Acrp30 secretion is induced ~10-fold during adipocyte differentiation. Plasma levels are reduced in obese humans, and low levels are associated with insulin-resistance. (*Endocrinology*. (2006) June; 147(6):2690-5. Epub (2006) Mar. 2). Adiponectin is an adipokine with insulin-sensitizing, anti-inflammatory, and anti-atherogenic properties. Plasma levels of adiponectin are reduced in insulin resistant states such as obesity, type 2 diabetes and cardiovascular disease. (*Hum Reprod*. (2006) May 12; [Epub ahead of print]; *Biochem Biophys Res Commun*. (2006) Jun. 23; 345(1):332-9. Epub (2006) Apr. 27. *J Endocrinol Invest*. (2006) March; 29(3):231-6).

"Orexins" is a neuropeptide that stimulates appetite (Br J. Nutr. (2004) *August*; 92 Suppl 1:S47-57)

"Glucose Transporter" (Glut1-Glut14) "Glut 4" is a glucose transporter expressed uniquely in muscle and fat tissues. It moves from intracellular sites to the plasma membrane following insulin stimulation and thus increases the rate of glucose transport into these tissues. GLUT4 expression is absent or low in most cultured cell models, which is a disadvantage for studies of glucose metabolism. However, in conditionally immortalized muscle there is a clear rise in GLUT4 levels following differentiation. (Clin Exp Pharmacol Physiol. 2006 April; 33(4):395-9; Am J. Med. 2006 May; 119(5 Suppl 1):S10-6).

"Hypoxia-inducible factor-1" (HIF-1) is a transcription factor. It plays a critical role in the transduction of the metabolic response to hypoxia. HIF-1 is composed of $\alpha$ and/$\beta$ subunits, the $\beta$-subunit is expressed constitutively whereas the $\alpha$-subunit is induced by hypoxia. HIF-1 is activated in hypoxia by the stimulation of the expression of the HIF-1$\alpha$ subunit to form the functional transcription factor. HIF-1 are expressed in adipocytes and hypoxia cell culture leads to increased levels of adipokines. Insulin activates hypoxia-inducible factor-1 alpha in human vascular smooth muscle cells via phosphatidylinositol-3 kinase and mitogen-activated protein kinase pathways (HIF-alpha, beta, Diabetologia. (2006) May; 49(5):1049-63. Epub (2006) February 28; Biochem Biophys Res Commun. (2006) Mar. 10; 341(2):549-56.) Am J Physiol Endocrinol Metab. (2006) March; 290(3):E591-7. Epub 2005 Oct. 18

"Pref-1" or Preadipocyte factor −1 is a transmembrane protein with epidermal growth factor-like domain. It is highly expressed in preadipocytes. Pref-1 expression is, however, completely abolished in adipocytes.

"Adipsin" is a serine protease that is secreted by adipocytes. It is deficient in several animal model of obesity. Adipsin has now been identified as the same protein as complement factor D or C3 convertase activator or properdin factor D. Its expression is induced upon differentiation of preadipocytes.

General Description

Olive leaf has a number of constituents, including oleuropein and several types of flavinoids, including rutin, apigenin, luteolin. In the studies presented herein, "ole" refers to oleuropein, and "OLE" refers to Olive Leaves Extract. Recent studies have centered on oleuropein (ole), which is a non-toxic glucoside isolated from olive leaves, which has been shown to have a number of beneficial medicinal properties. For example, early studies by Fleming et al. demonstrated the anti-microbial effects of oleuropein (Fleming, H. P. et al. (1973), Applied Microbiol. 26: 777-782). This work was further supported by the studies of Zanichelli, et al. (Zanichelli, D. et al. (2005) J. Food Prot. 68(7):1492-1496) and Micol et al. (Micol, V. et al. (2005), Antiviral Res. 66(2-3): 129-136). Carluccio et al. have shown in vitro that oleuropein inhibits endothelial adhesion molecule expression (Carluccio, M. A. et al. (2003) Arterioscler Thromb Vasc Biol. 23: 622-629). Hamdi et al. have shown that oleuropein has anti-tumor properties and acts to disrupt actin filaments in cells in culture (Hamdi, H. K. et al. (2005) Biochem Biophys. Res. Commun. July 14 Epub). Miles et al. demonstrated that oleuropein inhibits certain inflammatory cytokines (Miles, E. A. et al. (2005), Nutrition, 21(3): 389-394). Further studies by Manna, et al. demonstrated that oleuropein prevents ischemia and reperfusion induced myocardial injury (Manna C. et al. (2004) J. Nutr. Biochem. 15(8): 461-466). Studies by Puel et al. demonstrated that oleuropein prevented inflammation-induced osteopenia in ovariectomised rats (Puel, C. et al. (2004) 92(1): 119-127). Earlier studies by Visioli et al. demonstrated that oleuropein protects low density lipoprotein from $CuSO_4$-induced oxidation. Coni et al (2000) have subsequently demonstrated that oleuropein can increase the ability of low density lipoprotein to resist oxidation in vivo (Coni E. et al. (2000), Lipids, 35(1): 45-54), while Caruso et al. have also shown that oleuropein can prevent cholesterol oxide formation in vitro (Caruso, D. (1999) Nutr. Metab. Cardiovasc. Dis. 9(3):102-107).

Oleuropein is reported herein to be a novel modulator of adipocyte differentiation, de-differentiation, trans-differentiation, and adipogenic and lipolytic genes and gene products expression and also decreases in fat accumulation and increases in fat burning. The oleuropein was prepared from olive leave extract as reported in Lee-Huang et al. (Lee-Huang S; Zhang L; Huang P L; Chang Y T; Huang P L. "Anti-HIV activity of olive leaf extract (OLE) and modulation of host cell gene expression by HIV-1 infection and OLE treatment". *Biochemical & biophysical research communications*. 2003; 307:1029); 307:1029. Commercial oleuropein was used as a standard for the comparison with the oleuropein preparations used in the present studies. In addition, oleuropein has been found to be effective in modulation of endothelial dysfunction and to reduce diet induced atherosclerosis. Moreover, oleuropein and derivatives or analogues thereof reduce the number of fat cells by modulating adipocyte differentiation, de-differentiation and trans-differentiation. Likewise, oleuropein and its derivatives or analogues thereof reduce fat accumulation, decrease the size of the fat cells, increase fat burning and expenditure by modulating adipocyte metabolism in terms of down-regulation of lipogenesis (fat formation), up-regulation of lipolysis (fat burning) and thermogenesis via modulating the lipogenic, lipolytic and thermogenic genes, gene products, enzymes, factors, and pathways. Accordingly, based on the findings presented here, oleuropein is proposed to be useful for treating obesity or obesity related disorders, such as, but not limited to, coronary artery disease/cardiovascular disease, hypertension, cerebrovascular disease, stroke, peripheral vascular disease, insulin resistance, glucose intolerance, diabetes mellitus, hyperglycemia, hyperlipidemia, dyslipidemia, hypercholesteremia, hypertriglyceridemia, hyperinsulinemia, atherosclerosis, cellular proliferation and endothelial dysfunction, diabetic dyslipidemia, HIV-related lipodystrophy, peripheral vessel disease, cholesterol gallstones, cancer, menstrual abnormalities, infertility, polycystic ovaries, osteoarthritis, sleep apnea, metabolic syndrome (Syndrome X), type II diabetes, diabetic complications including diabetic neuropathy, nephropathy, retinopathy, cataracts, heart failure, inflammation, thrombosis, congestive heart failure, and any other cardiovascular disease related to obesity or an overweight condition. Moreover, while not wishing to be bound by theory it has also been determined that oleuropein binds to all of the PPAR receptors $\alpha$, $\delta$, and $\gamma$ and modulate their actions coordinately. Whether or not this is the mechanism by which oleuropein acts remains to be determined. Furthermore, with the discovery that oleuropein selectively modulates all of the PPAR receptors, the potential for using high throughput assays to identify other similar/analogous PAN-PPAR modulators pharmacologically useful oleuropein-like compounds which modulate these receptors stimulatanously is feasible. Such compounds will be useful in the treatment of PPAR-mediated diseases and conditions as well as any for which oleuropein was previously considered to be useful. In addition, oleuropein may be used in diagnostic assays to monitor the progression of disease or to monitor the effectiveness of therapy with agents that are administered to patients suffering from obesity or an obesity related condition, or who are prone to development of such conditions.

Proliferator-Activated Receptors (PPARs)

The Proliferator-Activated Receptors (PPARs) are members of the nuclear receptor superfamily, which upon binding to specific DNA response elements and in response to ligand binding, result in the activation of several genes. The PPARs contain a DNA-binding domain, a ligand-binding domain, and a flexible hinge connecting the two. The PPARs function as ligand-regulated transcription factors that control the expression of target genes by binding to their responsive DNA sequence (DNA response elements or PPREs) as heterodimers with the retinoid X receptor (RXR). The target genes encode enzymes involved in lipid metabolism and differentiation of adipocytes. The PPAR receptor experiences a conformational change upon ligand binding, which results in activation of gene transcription. The term "nuclear receptor" mainly refers to factors which control transcription of a target gene by binding upstream from the target gene promoter in a nuclear receptor ligand-dependent fashion. However, some nuclear receptors lack nuclear receptor ligands. Consequently, even nuclear receptors which lack nuclear receptor ligands are called "nuclear receptors" if their structural and functional homology places them in the nuclear receptor gene superfamily. Nuclear receptors include estrogen receptors (ER), vitamin D receptors (VDR), peroxisome proliferator-activated receptors (PPAR), liver X receptors (LXR), retinoic acid receptors (RAR), retinoid X receptors (RXR), androgen receptors (AR), glucocorticoid receptors (GR), farnesoid x receptors (FXR), mineralcorticoid receptors (MR) and the like for example, but are not limited by these.

There are three known subtypes of PPARs. They include the subtypes PPAR alpha, PPAR gamma, and PPAR delta. Natural agonists of the three types of PPARs include fatty acids, which implicates them as critical regulators in metabolic pathways involving energy storage and utilization. Furthermore, this also suggests that the PPARs may be potential targets for development of therapeutics against disorders such as obesity, and obesity-related disorders, including diabetes and dyslipidemia (Kliewer, et al., Recent Progress in Hormone Research, (2001), 56: 239-63).

PPARα is expressed predominantly in the liver and, to a lesser extent, in cardiac and skeletal muscle. It plays a crucial role in fatty acid oxidation in response to fasting, providing ketone bodies that serve as an energy source for peripheral tissues. PPARα knockout mice cannot meet energy demands during fasting, and develop hypoglycemia, hyperlipidemia, and fatty liver (Kersten S, Seydoux J, Peters J M, Gonzalez F J, Desvergne B, and Wahli W, *Peroxisome proliferator-activated receptor alpha mediates the adaptive response to fast-* ing: J Clin Invest, 1999. 103: p. 1489-98.). PPARα agonists include the fibrates, which are used clinically to treat hypertriglyceridemia.

PPARγ has several critical roles. First, PPARγ is essential for fat cell differentiation. PPARγ knockout mice lack adipose tissue (Barak Y, Nelson M C, Ong E S, Jones Y Z, Ruiz-Lozano P, Chien K R, Koder A, and Evans R M, *PPAR gamma is required for placental, cardiac, and adipose tissue development*. Mol Cell, 1999. 4: p. 585-95; Kubota N, Terauchi Y, Mild H, Tamemoto H, Yamauchi T, Komeda K, Satoh S, Nakano R, Ishii C, Sugiyama T, Eto K, Tsubamoto Y, Okuno A, Murakami K, Sekihara H, Hasegawa G, Naito M, Toyoshima Y, Tanaka S, Shiota K, Kitamura T, Fujita T, Ezaki O, Aizawa S, Kadowaki T, and et al., PPAR gamma mediates high-fat diet-induced adipocyte hypertrophy and insulin resistance. Mol Cell, 1999. 4: p. 597-609; Rosen E D, Sarraf P, Troy A E, Bradwin G, Moore K, Milstone D S, Spiegelman B M, and Mortensen R M, *PPAR gamma is required for the differentiation of adipose tissue in vivo and in vitro*. Mol Cell, 1999. 4: p. 611-7.), and overexpression of PPARγ converts non-adipocytes into fat cells (Tontonoz P, Hu E, and Spiegelman B M, Stimulation of adipogenesis in fibroblasts by PPAR gamma 2, a lipid-activated transcription factor. Cell, 1994. 79: p. 1147-56.). Second, PPARγ acts as a fatty acid sensor that regulates whole-body glucose homeostasis. PPARγ activates genes involved in lipogenesis and lipid storage. It also modulates adipokine expression, increasing production of adiponectin, while it blocks expression of TNF-α, and resistin. The net result of these changes increases insulin sensitivity. PPARγ is the molecular target for the thiazolidinedione class of drugs that improve insulin sensitivity.

PPARδ, also known as PPARβ, is expressed ubiquitously, and regulates expression of genes involved in fatty acid catabolism and adaptive thermogenesis. Transgenic expression of PPARδ results in lean mice that are resistant to obesity and hyperlipidemia, while PPARδ knockout mice show reduced energy uncoupling, and are prone to obesity (Wang Y X, Lee C H, Tiep S, Yu R T, Ham J, Kang H, and Evans R M, *Peroxisome-proliferator-activated receptor delta activates fat metabolism to prevent obesity*. Cell, 2003. 113: p. 159-70.).

PPARs may modulate vascular effects by affecting insulin resistance, and by expression of adipokines. In addition, PPARs may have direct effects on gene transcription in vascular tissues and endothelial cells.

The significance of these receptors in physiology and disease is evidenced by the fact that PPAR-γ and PPARα are respective molecular targets for the insulin-sensitizing thiazolidinedione (TZD) and lipid-lowering fibrate drugs that total more than $5 billion in annual sales.

PPARδagonist GW501516 (2-methyl-4-(((4-methyl-2-(4-trifluoromethylphenyl)-1,3-thiazol-5-yl)-methyl) sulfanyl) phenoxy)acetic acid) and PPARδ, α, γ, pan agonist GW2433 (2-(4-(3-(1-(2-(2-chloro-6-fluoro-phenyl)-ethyl)-3-(2,3-dichloro-phenyl)-ureido)-propyl)-phenoxy)-2-methyl-propionic acid) were shown to lower plasma triglyceride levels in obese monkeys while raising high-density lipoprotein levels, prompting the initiation of clinical trials to assess efficacy in hyperlipidemic patients. The medical potential of PPAR δ agonist and PPARδ, α, γ, pan agonist is believed to exceed that of both PPARα and PPARγ single agonist or dual agonists.

The findings presented herein demonstrate that oleuropein interacts with PPARα, PPARδ and PPARγ, and as such, offers a novel application for therapeutic pan modulation of these important transcription factors in the treatment of obesity and related disorders.

PPAR gamma: Out of the three subtypes, PPAR gamma has been most extensively studied. It is known to play an important role in the regulation of glucose and lipid homeostasis as well as in adipocyte differentiation (Willson, et al., Journal of Medicinal Chemistry, (2000), 43: 527-550). The PPAR gamma protein is conserved across several species including mice and humans. One of the first synthetic ligands of PPAR gamma identified as agonists was a class of antidiabetic compounds known as thiazolidinediones (TZDs). The efficacy of individual TZDs in anti-diabetic therapy appears to correlate with their ability to bind and activate the PPAR gamma receptor (Auwerx, J., Diabetologia, (1999), 42: 1033-1049). This class of compounds has also been shown to induce gene expression in adipocytes, which correlates with lowered glucose levels (Willson, et al.). TZDs have also been shown to reduce lipid and insulin levels. Known thiazolidinediones include Rosiglitazone, Troglitazone, Pioglitazone, and MCC-555. Each of these compounds binds preferentially to PPAR gamma over the other PPAR subtypes. Pioglitazone and rosiglitazone are Food and Drug Administration approved drugs that are currently sold for the treatment of Type II diabetes. Troglitazone was also FDA approved for Type II diabetes, but has been withdrawn from commercial use due to the occurrence of undesirable side effects.

Although the advances made with the thiazolidinedione class of antidiabetes agents is significant, there are unacceptable side effects associated with this class of drugs, which have limited their clinical use. Accordingly, there remains a need for potent, selective modulators of PPAR gamma, of which the activators of PPAR gamma will be useful for the treatment of NIDDM and other disorders related to lipid metabolism and energy homeostasis. Still further, compounds that block PPAR gamma activity would be useful for interfering with the maturation of preadipocytes into adipocytes and thus would be useful for the treatment of obesity and obesity-related disorders associated with undesirable adipocyte maturation. In addition, the response of patients to particular TZDs is variable, with about 20-30% of patients using these compounds being classified as non-responders. Accordingly, it is highly desirable to identify compounds for treating diabetes, as well as for treating obesity and other obesity-related disorders that are more therapeutically effective with fewer side effects. There is also a need to develop more accurate methods for predicting whether a subject is likely to respond to a particular treatment as well as methods that determine the extent to which a patient has responded to the treatment.

PPAR gamma has been shown to be expressed in an adipose tissue-specific manner. Furthermore, it is induced early during the course of differentiation of preadipocytes. Further studies have now demonstrated that PPAR gamma not only plays a pivotal role in the adipogenic signaling cascade, but also regulates the ob/leptin gene which is involved in regulating energy homeostasis. PPAR gamma also plays a role in adipocyte differentiation, which has been shown to be a critical step for targeting therapeutics for treating obesity and obesity-related conditions, such as diabetes.

PPAR gamma ligands also have in vitro anticancer activity against a wide variety of neoplastic cells and in vivo anticancer effects and chemotherapeutic or chemopreventive effects have been seen in animal studies. PPAR gamma ligands may slow the growth of cancer cells and may induce the partial differentiation of some cancer cells. Overall, much literature indicates that PPAR gamma ligands have antiproliferative activity and may be useful in the treatment of cancer, including particularly several common cancers, including those of the colon, prostate, and breast. (See, Koeffler H P Clin Cancer Res. 9(1):1-9 (2003)).

Furthermore, there is evidence to suggest that PPAR (e.g., PPAR-gamma) acts by a number of mechanisms to influence the permeability of skin, inhibit the growth of epidermal cells, promote the terminal differentiation of epidermis, and regulate the inflammatory response of skin. Accordingly, PPAR ligands may be useful in the modulation of skin conditions characterized by hyperproliferation, inflammatory infiltrates and abnormal differentiation (e.g., psoriasis), including inflammatory skin diseases (e.g. atopic dermatitis), proliferative skin diseases, acne vulgaris, protease inhibitor associated lipodystrophia and wound healing. (See, Kuenzli S, et al., Br J. Dermatol. 149(2):229-36 (2003)).

Additional studies suggest that PPAR gamma plays a role in the pathophysiology of senile osteoporosis. For example, adipogenesis in bone marrow increases with aging. Mesenchymal stem cells expressing a subtype of this receptor (PPAR gamma 2) differentiate into adipocytes. Appropriate modulation of this receptor may promote mesenchymal stem cell differentiation into osteoblasts. Furthermore, activators of PPAR alpha, delta, and gamma have been reported to induce alkaline phosphatase activity and bone matrix calcification. Accordingly, pharmacological use of PPAR activators should promote bone mineral density by modulating osteoblastic maturation. (See, Duque G, Drug News Perspect. 16(6):341-6 (2003); Jackson S M, et al., FEBS Lett. 471(1): 119-24 (2000). Based on the studies presented herein, another aspect of the present invention is the use of oleuropein, or an analogue or derivative thereof for the treatment of osteoporosis, or other diseases or conditions associated with bone loss.

The anti-proliferative and anti-inflammatory effects of PPAR gamma are observed in glial cells and lymphocytes. It has been postulated that activation of such cells may be involved in the pathophysiology of neurological diseases associated with brain inflammation (e.g, Alzheimer's disease and multiple sclerosis). Studies indicate that PPAR gamma modulators would be therapeutically useful in such diseases. (See, Feinstein D L, Diabetes Technol Ther. 5(1):67-73 (2003)). Accordingly, the present invention provides for a method of treating inflammatory diseases or conditions comprising administering a PPAR gamma modulator to a subject in need of such therapy. In one particular embodiment, the method provides for treating neurological or neurodegenerative diseases or conditions caused in part by the presence or influx of inflammatory cells, such as for example, multiple sclerosis, stroke or Alzheimer's disease. The use of a PPAR modulator for treating a nervous system injury is also contemplated, for example, a spinal cord injury or traumatic brain injury. In one particular embodiment, the PPAR modulator is a PPAR gamma agonist.

Based on the studies done with the PPAR family of receptors in various disease conditions, it is possible that compounds that interact with the various PPAR receptors may be useful in treating these various diseases. Depending on the biological environment (e.g., cell type, pathological condition of the host, etc.), these compounds can activate or block the actions of PPARgamma. By activating the PPAR gamma receptor, the compounds find use as therapeutic agents capable of modulating conditions mediated by the PPAR gamma receptor. As noted above, an example of such a condition is non-insulin dependent diabetes mellitus (NIDDM). Additionally, the compounds may be useful for the prevention and treatment of complications of diabetes (e.g., neuropathy, retinopathy, glomerulosclerosis, and cardiovascular disorders), and treating hyperlipidemia. Still further, the compounds may be useful for the modulation of inflammatory conditions which most recently have been found to be controlled by PPAR gamma (see, Ricote, et al., Nature, 391:79-82 (1998) and Jiang, et al., Nature, 391:82-86 (1998). Examples of inflammatory conditions include asthma, rheumatoid arthritis and atherosclerosis. Such compounds may also be useful in the treatment of other skin diseases such as acne, atopic dermatitis, psoriasis, photodermatitis, eczema, and seborrhea.

It has also been described in WO 96/33724 that compounds selective for PPAR gamma receptors, such as prostaglandin-J2 or -D2, may be potentially active agents for the treatment of obesity and diabetes. Compounds that act via antagonism of PPAR gamma may be useful for treating obesity, hypertension, hyperlipidemia, hypercholesterolemia, hyperlipoproteinemia, and metabolic disorders.

Compounds which are PPAR gamma agonists or activators by virtue of their anti-inflammatory effects can have neuroprotective effects and find use in the treatment of brain inflammatory conditions such as Alzheimer's disease and multiple sclerosis. PPAR alpha, PPAR delta and their ligands are important for lipid oxidation and energy uncoupling. They increase fat consumption and decrease fat accumulation, thus they can have weight reduction and anti-obesity effects. A ligand such as oleuropein with the capability to bind all of the three PPARs has the potential to act as a PAN modulator. These are discussed below.

PPAR Gamma

Owing to their ability to induce gene expression in adipocytes and to enhance adipocyte differentiation, TZDs induce weight gain in often already obese patients. For this reason, efforts are being made to identify new partial agonists or antagonists for PPARγ in an attempt to combine their antidiabetic and anti-obesity effects.

Combined PPARα/PPARγ Agonists

The effects of TZDs on the lipid profile in diabetic patients are not optimal. Given the favorable effect of PPAR activators on plasma lipoprotein metabolism, combined activation of PPARα and PPARγ could lead to a complementary and synergistic action on lipid metabolism, insulin sensitivity and inflammation control. Dual activation of PPARα and γ could, in theory, also limit the occurrence of side effects associated with TZD therapy, such as edema and body-weight gain, although this has not been observed so far in clinical trials with coagonists. Thus, combined PPARα/γ activation has recently emerged as an intriguing concept and spawned the development of co-agonists.

PPAR-Delta and PPARαδγ Pan Agonist or Modulator

Because of its ubiquitous expression and the paucity of selective ligands, PPAR-delta is the least understood PPAR subtype. Nevertheless, early PPAR-δ-selective agonists were found to elevate HDL-C levels in diabetic mice, an observation that indicated that PPARδ ligands might have beneficial effects on dyslipidemia (*Eur J. Pharmacol.* 2006 Apr. 24; 536(1-2):182-91. Epub 2006 Feb. 28). Subsequently, the potent PPARδagonist GW501516 was shown to increase HDL-C while decreasing elevated TG and insulin levels in obese rhesus monkeys. GW501516 also attenuates weight gain and insulin resistance in mice fed high-fat diets by increasing the expression in skeletal muscle of genes that promote lipid catabolism and mitochondrial uncoupling, thereby increasing β-oxidation of fatty acids in skeletal muscle (*Curr Opin Investig Drugs.* 2006 April; 7(4):360-70).

Expected Results of PPAR Pan Modulator Such as OLE/Oleuropein/Hydroxytyrosol) on Metabolic Endpoints Our discovery that Oleuropein is able to act as a PPAR pan agonist that targets all of the three isoforms of PPARs, PPARα, PPARγ and PPARγ offers a new class of orally available potential novel drug. A compound targeting all of these PPAR subtypes could provide a combination of triglyceride, LDL and glucose lowering activities, coupled with increases in insulin sensitivity, HDL and reverse cholesterol transport (see Table 1). Its antihyperglycemic, lipid-modulating, insulin-sensitizing activities could be used in the treatment of a variety of metabolic and cardiovascular diseases, including Type II diabetes, impaired glucose tolerance, dyslipidemia, hypertension, metabolic syndrome X, asthma and HIV/HAART associated lipodystrophys. Furthermore, synergies of such a combination may enable lower dosing and consequently mitigate side effects and toxicities observed with current therapies. Although treatment options for Type II diabetes are available, their usefulness is significantly limited due to their failure to ameliorate concurrent hyperglycemia and hyperlipidemia (e.g. triglycerides, LDL-cholesterol) or to raise HDL, in addition to their side effects.

Clinical practice. Management of newly diagnosed HIV infection, N Engl J Med 353 (2005) 1702-1710]. These agents can be classified according to their mechanism of action: reverse transcriptase inhibitors (RTIs) (nucleoside, NRTIs and non-nucleoside, NNRTIs), protease inhibitors (PIs), fusion inhibitors, and multi-class combination products (MCCP). The combination of RTIs and PIs, commonly known as Highly Active Antiretroviral Therapy (HAART) [S. M. Hammer, Clinical practice. Management of newly diagnosed HIV infection, N Engl J Med 353 (2005) 1702-1710, J. Cohen, Therapies. Confronting the limits of success, Science 296 (2002) 2320-2324], has significantly reduced morbidity and mortality, transforming HIV/AIDS into a manageable chronic illness. Although HAART can favorably influence disease progression, it does not cure HIV infection. Antiviral therapy must be maintained long-term, and serious chronic toxicity, therapy fatigue, and drug resistance have become major issues.

TABLE 1

Cardiovascular Disease PPAR Pan-Agonist Fact Sheet and Expected Results of OLE/Oleuropein/Hydroxytyrosol on Metabolic Endpoints

| Target | Glucose | Insulin | TG | FAA | LDL | HDL | Limitations |
| --- | --- | --- | --- | --- | --- | --- | --- |
| PPARα | No effect | No effect | ↓ | ↓ | ↓ | ↑ | Ineffective on glucose and insulin sensitivity |
| PPARδ | No effect | ↑ | ↓↓ | ↓ | ↓ | ↑ | Less validation for PPARδ |
| PPARγ* | ↓↓ | ↑ | ↓ | ↓ | ↑↑ | No effect | Edema, weight gain, anemia, LDL/cholesterol↑, need to monitor liver function |
| PPARαγ* | ↓ | ↑ | ↓ | ↓ | ↓ | ↑ | Edema, weight gain, anemia, LDL/cholesterol↑, need to monitor liver function |
| PPARαδγ** | ↓↓ | ↑↑ | ↓↓↓ | ↓↓ | ↓↓ | ↑↑↑ | Less validation for PPARδ |

Abbreviations:
Insulin S, insulin sensitivity;
TG, triglycerides;
FFA, free fatty acids;
LDL, low-density lipoprotein cholesterol;
HDL, high-density lipoprotein
*Reported clinical effects in obese, rhesus monkeys and in patients Edema, weight gain, anemia,
↑LDL cholesterol, requirement to monitor liver
**Predicted effect of oleuropein and derivatives Use of Oleuroein and/or Hydroxytyrosol for Inhibiting Viral Infectivity The work presented herein also demonstrates that oleuropein (Ole) and hydroxytyrosol (HT) are a unique class of HIV-1 inhibitors from olive leaf extracts, which are effective against viral fusion and integration. Molecular docking simulation was used to study the interactions of Ole and HT with viral targets. It was determined that Ole and HT bind to the conserved hydrophobic pocket on the surface of the HIV-gp41 fusion domain by hydrogen bonds with Q577 and hydrophobic interactions with 1573, G 572, and L 568 on gp41 N-terminal heptad repeat peptide N36, interfering with formation of the gp41 fusion-active core. To test and confirm modeling predications, the effect of Ole and HT on HIV-1 fusion complex formation was studied using native polyacrylamide gel electrophoresis and circular dichroism spectroscopy. Ole and HT exhibit dose dependent inhibition on HIV-1 fusion core formation with $EC_{50}$s of 66-58 nM, with no detectable toxicity.

At present, 29 drugs are licensed by the FDA for the treatment of HIV-1 infection in the United States [S. M. Hammer, New therapeutic approaches include the fusion inhibitor Fuzeon (T-20, enfuvirtide), the non-peptidic PI Tipranavir, the new PI darunavir and the recently approved MCCP Atripla. However, existing experience with HIV-1 highlights the need to use multiple effective agents in combination for maximal and durable effect. Thus, the search for novel anti-HIV agents continues to be of great significance, especially those capable of affecting multiple stages of the viral life cycle.

We previously reported that olive leaf extract is potent against HIV-1 [S. Lee-Huang, L. Zhang, P. L. Huang, and Y. T. Chang, Anti-HIV activity of olive leaf extract (OLE) and modulation of host cell gene expression by HIV-1 infection and OLE treatment, Biochem Biophys Res Commun 307 (2003) 1029-1037]. Subsequent studies as described herein demonstrate that the anti-HIV properties of oleuropein (Ole) and its main metabolite, hydroxytyrosol (HT) are the key anti-HIV components of Olive Leaf Extract. They are active against multiple stages of the HIV-1 life cycle, inhibiting cell-to-cell HIV-1 transmission and viral core antigen p24 production. Molecular docking simulations indicate that Ole and HT interact with the conserved hydrophobic pocket on the surface of the central trimeric coiled-coil of HIV-41 fusion complex, the six helical bundle (6HB), and the catalytic core domain (CCD) of HIV-1 integrase active site.

Molecular modeling and functional confirmation of Ole and HT binding to HIV-1 integrase was also studied and the results summarized herein. Docking simulations identified two binding regions for Ole within the integrase active site. Region I encompasses the conserved D64-D116-E152 motif, while region II involves the flexible loop region formed by amino acid residues 140-149. HT, on the other hand, binds to region II. Both Ole and HT exhibit favorable interactions with important amino acid residues through strong H-bonding and van der Waals contacts, predicting integrase inhibition. To test and confirm modeling predictions, we examined the effect of Ole and HT on HIV-1 integrase activities including 3'-processing, strand transfer and disintegration. Ole and HT exhibit dose-dependent inhibition on all three activities, with $EC_{50}$s in the nM range. These studies demonstrate that molecular modeling of target-ligand interaction coupled with structural-activity analysis should facilitate the design and identification of innovative integrase inhibitors and other therapeutics.

HIV-1 integrase is one of three viral enzymes required for viral replication, along with RT and protease [P. O. Brown, Retroviruses, in Coffin, J., Hughes, S., and Varmus, H., (Eds.) Cold Spring Harbor Press, Cold Spring Harbor, 1998, 161-203; T. K. Chiu, and D. R. Davies, Structure and function of HIV-1 integrase, Curr Top Med Chem 4 (2004) 965-977; K. Zhu, C. Dobard, and S. A. Chow, Requirement for integrase during reverse transcription of human immunodeficiency virus type 1 and the effect of cysteine mutations of integrase on its interactions with reverse transcriptase, J Virol 78 (2004) 5045-5055]. Integration of HIV-1 cDNA into the host chromosome is essential for stable maintenance of the viral genome, efficient viral gene expression and productive infection. Thus, viral integrase is a critical target for anti-HIV therapy [Y. Pommier, A. A. Johnson, and C. Marchand, Integrase inhibitors to treat HIV/AIDS, Nat Rev Drug Discov 4 (2005) 236-248; P. A. Sherman, and J. A. Fyfe, Human immunodeficiency virus integration protein expressed in *Escherichia coli* possesses selective DNA cleaving activity, Proc Natl Acad Sci USA 87 (1990) 5119-5123]. The first step leading to viral DNA integration is the binding of viral integrase to HIV long terminal repeat (LTR) sequences. This is followed by three sequential reactions: 1) 3'-processing, the removal of two nucleotides, GT, from the 3'-end of HIV-LTR, 2) strand transfer, a concerted cleavage-ligation reaction, in which the integrase makes a staggered cut in the target DNA and ligates the recessed 3' ends of the viral DNA to the 5' ends of the target DNA, and 3) gap repair, removal of the two unpaired nucleotides at the 5' end of the viral DNA and repair of the gap between the viral and the target DNA. In the presence of a DNA substrate that mimics the product of viral integration, integrase can catalyze the reversal of strand transfer, known as "disintegration" [S. A. Chow, K. A. Vincent, V. Ellison, and P. O. Brown, Reversal of integration and DNA splicing mediated by integrase of human immunodeficiency virus, Science 255 (1992) 723-726 S. A. Chow, K. A. Vincent, V. Ellison, and P. O. Brown, Reversal of integration and DNA splicing mediated by integrase of human immunodeficiency virus, Science 255 (1992) 723-726], in which viral DNA is released and the target DNA is sealed.

Therapeutic and Prophylactic Compositions and their Use

Candidates for therapy with the agents identified by the methods described herein are patients either suffering from, or at risk for development of obesity, or an obesity related disease, disorder or condition, including diabetes, dyslipidemia, hypertension and cardiovascular diseases, asthma to name a few. Other obesity related disorders have been described previously. In addition, patients who are obese or are prone to developing obesity or an obesity related disorder based on a genetic predisposition are also considered to be candidates for therapy using oleuropein or a compound having activity analogous to oleuropein. Furthermore, patients who have limited mobility or patients who are bed-ridden due to a surgical procedure or illness and are not capable of exercise and are thus prone to accumulation of body fat may be candidates for therapy with the agents identified by the methods described. In addition, the present invention contemplates the use of oleuropein, hydroxytyrosol, and their derivatives, analogues or mimics thereof, for inhibiting the growth and/or infectivity of HIV-1 by virtue of the effects of oleuroein and hydroxytyrosol on inhibition of viral fusion and/or by their effects on the viral integrase.

The invention provides methods of treatment comprising administering to a subject an effective amount of an agent of the invention. In a preferred aspect, the compound is substantially purified (e.g., substantially free from substances that limit its effect or produce undesired side-effects). The subject is preferably an animal, including but not limited to animals such as monkeys, cows, pigs, horses, chickens, cats, dogs, etc., and is preferably a mammal, and most preferably human. In one specific embodiment, a non-human mammal is the subject. In another specific embodiment, a human mammal is the subject. Accordingly, the agents identified by the methods described herein may be formulated as pharmaceutical compositions to be used for prophylaxis or therapeutic use to treat these patients. Moreover, the agents of the invention may be useful for administering to non-human mammals to aid in the build-up of lean muscle which may then prove highly beneficial for the meat industry.

Various delivery systems are known and can be used to administer a compound of the invention, e.g., encapsulation in liposomes, microparticles, or microcapsules. Methods of introduction can be enteral or parenteral and include but are not limited to intradermal, intramuscular, intraperitoneal, intravenous, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment.

Such compositions comprise a therapeutically effective amount of an agent, and a pharmaceutically acceptable carrier. In a particular embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E.W. Martin. Such compositions will contain a therapeutically effective amount of the compound, preferably in purified form, together with a suitable amount of carrier so as to provide the form for proper administration to the subject. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

In a specific embodiment, it may be desirable to administer the pharmaceutical compositions of the invention locally to the area in need of treatment; this may be achieved, for example, and not by way of limitation, by local infusion during surgery, by topical application, by injection, by means of a catheter, or by means of an implant, said implant being of a porous, non-porous, or gelatinous material, including membranes, such as sialastic membranes, or fibers or co-polymers such as Elvax (see Ruan et al, (1992), Proc Natl Acad Sci USA, 89:10872-10876). In one embodiment, administration can be by direct injection by aerosol inhaler.

In another embodiment, the compound can be delivered in a vesicle, in particular a liposome (see Langer (1990) Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound can be delivered in a controlled release system. In one embodiment, a pump may be used (see Langer, supra; Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. (1983) Macromol. Sci. Rev. Macromol. Chem. 23:61; see also Levy et al. (1985) Science 228:190; During et al. (1989) Ann. Neurol. 25:351; Howard et al. (1989) J. Neurosurg. 71:105). In yet another embodiment, a controlled release system can be placed in proximity of the therapeutic target, i.e., the airways, thus requiring only a fraction of the systemic dose (see, e.g., Goodson, in Medical Applications of Controlled Release (1984) supra, vol. 2, pp. 115-138). Other suitable controlled release systems are discussed in the review by Langer (1990) Science 249:1527-1533.

Effective Doses

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to unaffected cells and, thereby, reduce side effects.

The data obtained from cell culture assays and animal studies can be used in formulating a dose range for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to optimize efficacious doses for administration to humans. Plasma levels can be measured by any technique known in the art, for example, by high performance liquid chromatography.

In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. Normal dose ranges used for particular therapeutic agents employed for specific diseases can be found in the Physicians' Desk Reference, $54^{th}$ Edition (2000).

While the subject is being treated, the health of the patient may be monitored by measuring one or more relevant indices at predetermined times during a 24-hour period. For example, lipid levels may be monitored during the course of therapy using standard procedures known to those skilled in the art, in order to minotor the effectiveness of therapy. Alternatively, for patients suffering from HIV, blood samples may be obtained during the course of therapy to monitor levels of viral nucleic acid using standard PCR procedures known to those skilled in the art. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other therapeutic agents, may reduce the required dosage for any individual component because the onset and duration of effect of the different components may be complimentary. In such combined therapy, the different active agents may be delivered together or separately, and simultaneously or at different times within the day.

The invention includes use of any modifications or equivalents of the above agents which do not exhibit a significantly reduced activity. The statements of effect and use contained herein are therefore to be construed accordingly, with such uses and effects employing modified or equivalent gene products being part of the invention.

Oleuropein is a phenolic secoiridoid glycoside with the structure as shown in the figure below. It is an organic molecule that consists of a dihydroxy phenol moiety, a secoiridoid moiety and a glucose moiety. The glucose moiety can be removed by β-glycosidase to yield oleuropein aglycone. Oleuropein aglycone can than be hydrolyzed into hydroxytyrosol and elenolic acid. These are the metabolites of oleuropein and they are all physiological active (See FIG. 10).

The present agents that prevent fat accumulation, or that modulate differentiation, de-differentiation and trans-differentiation of adipocytes or that have an effect on the expression of adipogenic, lipogenic and lipolytic genes and gene products can be used as the sole active agents, or can be used in combination with other active ingredients Combination Therapy The compounds of the invention may be combined with another therapeutic agent that is useful in the treatment of obesity or disorders associated with the development and progression of obesity and obesity related disorders, such as, diabetes, atherosclerosis, hypertension, hyperlipidaemias, dyslipidaemias, and cardiovascular disease. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to lower blood sugar or to treat complications associated with diabetes, including nephropathy, neuropathy, retinopathy, cardiovascular disease, stroke, or any other complication associated with diabetes.

Accordingly, the compounds of the invention may be used alongside other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide. Alternatively, oleuropein and/or hydroxytyrosol may be used in combination with other anti-virals known in the art to be effective against HIV.

In another aspect of the invention, the agents of the invention, e.g. oleuropein or an analogue or derivative thereof, or a pharmaceutically acceptable salt, solvate, solvate of such a salt or a prodrug thereof, may be administered in association with another PPAR modulating agent. PPAR modulating agents include but are not limited to a PPAR alpha, delta and/or gamma agonist, or pharmaceutically acceptable salts, solvates, solvates of such salts or prodrugs thereof. Suitable PPAR alpha, delta and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, r0 (5), 623-634 and J Med Chem, 2000, 43, 527, which are all incorporated herein by reference in their entireties. Particularly a PPAR alpha and/or gamma agonist refers to NN622/Ragaglitazar, BMS 298585, WY-14643, clofibrate, fenofibrate, bezafibrate, gemfibrozil and ciprofibrate; GW 9578, ciglitazone, troglitazone, pioglitazone, rosiglitazone, eglitazone, proglitazone, BRL-49634, KRP-297, JTT-501, SB 213068, GW 1929, GW 7845, GW 0207, L-796449, L-165041, GW 2433 and a PPAR alpha and/or gamma agonist such as (S)-2-ethoxy-3-[4-(2-{4-methanesulphonyloxyphenyl}ethox-y)-phenyl]propanoic acid and pharmaceutically acceptable salts thereof.

In addition the combination of the invention may be used in conjunction with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of obesity or an obesity related disorder, such as, type 2 diabetes and its associated complications will be those known in the art and approved for use by regulatory bodies for example the FDA and may be found in the Orange Book published by the FDA. Alternatively smaller doses may be used as a result of the benefits derived from the combination. The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and simvastatin, or a pharmaceutically acceptable salt, especially sodium or calcium, or a solvate thereof, or a solvate of such a salt. A particular statin is atorvastatin, or a pharmaceutically acceptable salt, solvate, solvate of such a salt or a prodrug thereof. More particular statins are rosuvastatin and atorvastatin calcium salts.

In the present application, the term "cholesterol-lowering agent" also includes chemical modifications of the HMG-CoA reductase inhibitors, such as esters, prodrugs and metabolites, whether active or inactive.

Diabetes mellitus is a syndrome resulting from the interaction of hereditary and environmental factors; it is characterized by disturbances in insulin secretion and other metabolic and vascular abnormalities, i.e. an elevated concentration of glucose in the blood, non-specific accelerated arteriosclerosis, neuropathy and thickening of the capillary basal lamina caused by a degeneration of the kidney and the retina.

According to a modern classification, the diabetes is divided into two main categories:

Insulin-dependent diabetes mellitus (also known as Type 1 diabetes); patients with this type of diabetes literally depend on insulin to prevent ketoacidosis and death. As far as the endogenous insulin secretion is concerned, patients with Type 1 diabetes mellitus exhibit insulinopenia.

Noninsulin-dependent diabetes mellitus (also known as Type 2 diabetes); patients with this type of diabetes do not need insulin to live: they can decide whether using it or not to control the symptoms of the diabetes. As far as the endogenous insulin secretion is concerned, patients with Type 2 diabetes can be further classified into two groups. In the first group, insulin levels are either normal or lower than normal; in the second group, insulin values are higher than normal and patients exhibit insulin resistance.

Accordingly, given the data presented herein, oleuropein may be useful as a stand-alone agent for the treatment of obesity, or for preventing fat accumulation in individuals prone to obesity. However, it is also to be understood that oleuropein may be used as adjunct therapy with other known agents used to treat obesity or obesity related disorders.

Monitoring a Patient's Response to the Therapeutic

Monitoring a patient's response to the therapeutic is usually done by measuring metabolic endpoints including plasma levels of glucose, insulin, TG, FAA, LDL, HDL in addition to adipogenic, lipogenic and lipolytic genes and gene products (proteins and/or enzymes). These are usually evaluated from whole blood, blood cells, plasma or serum of the patient's blood by specific bioassays. These assays are routinely used in clinical analysis of patient's blood samples. The modulation of the PPARs (genes or proteins), adipogenic, lipogenic and lipolytic genes and gene products, cytokines, hormones (insulin etc), adipokines as well as other genes and gene products involved in the targeted regulatory pathways can be determined from peripheral blood mononuclear cells (PBMC) purified from the blood sample using RT-PCR, cDNA microarray blots for specific genes and ELISA or proteomics for gene products (proteins). Specific enzyme assays can be used for monitoring enzymatic activities. An example of the metabolic variables to be measured in a proposed clinical trial is presented in Table 2 below. However, in addition to the variables described below, other measurements may include, but not be limited to, determination of the specific levels of cytokine and adipokines such as IL-6, resistin, MCP-1, PAI-1, adiponection or leptin.

TABLE 2

Metabolic Variables at Baseline and the Changes Observed after, for example, 3 months, 6 Months and 12 Months of Treatment with Oleuropein, and derivatives (including but not limit to its metabolites) for diabetics/obesity/cardiovascular disease

| | Baseline | | Mean Change after 3, 6, or 12 Months or other defined times | | |
| --- | --- | --- | --- | --- | --- |
| Variable | Placebo Group (n = xx) | OLE Group (n = xx) | Placebo Group (n = xx) | OLE Group (n = xx) | P Value† |
| Metabolic characteristics | | | | | |
| Ratio of glucose disposal rate to mean serum insulin level at steady state | | | | | |
| Fasting glucose level, mmol/L (mg/dL) | | | | | |
| 2-h glucose level, mmol/L (mg/dL) | | | | | |
| Fasting insulin level, pmol/L | | | | | |
| Insulin AUC level, pmol/L × $10^4$ (120 min) | | | | | |
| Total cholesterol level, mmol/L (mg/dL) | | | | | |
| LDL cholesterol level, mmol/L (mg/dL) | | | | | |
| HDL cholesterol level, mmol/L (mg/dL) | | | | | |
| Triglyceride level, mmol/L (mg/dL) | | | | | |
| Adiponectin level, μg/mL | | | | | |
| Free fatty acid level, mmol/L | | | | | |
| TNFα, IL-6, adipokines | | | | | |
| PPARα, PPARδ, PPARγ | | | | | |

TABLE 2-continued

Metabolic Variables at Baseline and the Changes Observed after, for example, 3 months, 6 Months and 12 Months of Treatment with Oleuropein, and derivatives (including but not limit to its metabolites) for diabetics/obesity/cardiovascular disease

| Variable | Baseline | | Mean Change after 3, 6, or 12 Months or other defined times | | P Value† |
|---|---|---|---|---|---|
| | Placebo Group (n = xx) | OLE Group (n = xx) | Placebo Group (n = xx) | OLE Group (n = xx) | |
| Adipogenic genes and gene products | | | | | |
| Lipogenic genes and gene products | | | | | |
| Lipolytic genes and gene products | | | | | |
| Safety variables | | | | | |
| Hemoglobin level, g/L | | | | | |
| ALT level, U/L | | | | | |

* All values are means ± SD.
ALT = alanine aminotransferase;
AUC = area under the curve;
HDL = high-density lipoprotein;
LDL = low-density lipoprotein.
†P values for mean change from baseline represent between-group effect from analysis of covariance with baseline value as covariate. For treating AIDS related lipodystrophy one also measure $CD^+$ counts and Log HIV RNA level, copies/mL The present invention further provides for methods of diagnosing a patient's response to treatment with oleuropein or an analogue or derivative thereof. Furthermore, the present invention provides prognostic methods for evaluating the progression of treatment with oleuropein or an analogue or derivative thereof. The invention provides a array of genes and gene products identified as being modulated following treatment with oleuropein or an analogue or derivative thereof and which may be used to monitor a therapeutic response to treatment with oleuropein or an analogue or derivative thereof. The genes and gene products, which are up- or down-regulated in response to treatment with oleuropein may be used diagnostically and prognostically for treatment of a PPAR associated disease, such as obesity or an obesity related disorder or disease such as Type II diabetes, with a PPAR ligand. These genes or gene products (proteins or enzymes) can be monitored from the patient's blood (whole blood cells, serum or plasma) by enzyme assay, ELISA (antibody), RT-PCR, microarray, and/or proteomics techniques. Exemplary diagnostic tools and assays are set forth below, under followed by exemplary methods for conducting these assays.
Diagnostic Tools and Assays and Methods for Identifying Novel Therapeutics for Treating a Disease Associated with a PPAR Receptor One aspect of the invention provides a means of determining whether a subject is responsive to treatment with oleuropein or an analogue or derivative thereof or a combination of oleuropein and a second agent used to treat obesity or an obesity related disorder, or of assessing the final outcome of therapy with oleuropein or an analogue or derivative thereof or a combination of oleuropein and a second agent used to treat obesity or an obesity related disorder in a subject in need of such therapy. Another aspect of the invention provides for the use of methods for screening for novel therapeutics for treating a disease associated with a PPAR receptor. The methods described herein are merely exemplary and are not meant to be limiting, and as such, it is to be recognized that one of skill in the art would be cognizant of the various other methodologies that may be used to determine effectiveness of therapy with oleuropein or analogues or derivatives thereof, or to identify novel analogues or derivatives or metabolites of oleuropein for use in treating obesity or obesity related disorders.

In one particular embodiment, the method comprises measuring any one or more of the following clinical parameters: lipid profile, glucose levels, insulin levels, or any one or more cytokines or adipokines present in the serum or plasma of a subject undergoing treatment with oleuropein, or an analogue or derivative or metabolite of oleuropein. Any one or more of these sensitive and reliable end-points may be effective at determining whether oleuropein, or an analogue, or a derivative, or a metabolite thereof, or a combination of oleuropein or an analogue or derivative or metabolite thereof together with one or more agents useful for treating obesity or an obesity related disorder has proven to be effective in treating these patients suffering from these conditions.

In another particular embodiment, the effectiveness of therapy with oleuropein or hydroxytyrosol or an analogue or derivative thereof in patients infected with HIV may be measured by standard procedures known to those skilled in the art. For example, in the early stages of infection, HIV often causes no symptoms and the infection can be diagnosed only by testing a person's blood. Two tests are available to diagnose HIV infection—one that looks for the presence of antibodies produced by the body in response to HIV and the other that looks for the virus itself. The first test is an (Enzyme Linked Immunosorbent Assay). an ELISA test and it is used to measure antibodies produced by the patient against the virus. When the body is infected with HIV, one looks for such antibodies in blood.

If antibodies are present, the test gives a positive result, but this must be confirmed by another test called Western Blot or Immunofluoroscent Assay (IFA). All positive tests by ELISA may not be accurate and hence Western Blot and repeated tests are necessary to confirm a person's HIV status. A person infected with HIV is termed HIV-positive or seropositive.

Antibodies to HIV generally do not reach detectable levels in the blood till about three months after infection. This period, from the time of infection till the blood is tested positive for antibodies, is called the Window Period. Some times, the antibodies might take even six months to show up. Even if the tests are negative, during the Window Period, the amount of virus is very high in an infected person. Hence, if a person is newly infected, the risk of transmission is higher.

If a person is highly likely to be infected with HIV and yet both the tests are negative, a doctor may suggest a repetition of the tests after three months or six months when the antibodies are more likely to have developed.

The second test is called PCR (Polymerase Chain Reaction), which looks for HIV itself in the blood. This test, which recognizes the presence of the virus' genetic material in the blood, can detect the virus within a few days of infection.

There are also tests like Radio Immuno Precipitation Assay (RIPA), a confirmatory blood test that may be used when antibody levels are difficult to detect or when Western Blot test results are uncertain. Other available tests are Rapid Latex Agglutination Assay, a simplified, inexpensive blood test that may prove useful in medically disadvantaged areas where there is a high prevalence of HIV infection, and p24 Antigen Capture Assay.

In another particular embodiment, the responsiveness of a subject to treatment with oleuropein or an analogue or derivative or metabolite thereof can be assessed by measuring body mass index (BMI) or by monitoring the weight of the subject. In a particular embodiment, one would expect to see an improvement in the BMI or a decrease in body weight or at least a stabilization in body mass (eg. no additional weight gain over a given period of time).

In another particular embodiment, such a method comprises determining the levels of expression of one or more genes or gene products (proteins) which are modulated in a cell of the subject undergoing treatment with oleuropein (or an oleuropein analogue, derivative, or metabolite thereof) and comparing these levels of expression with the levels of expression of the genes and gene products in a cell of a subject not treated with oleuropein (or an oleuropein analogue, derivative, or metabolite thereof), or of the same subject before treatment with oleuropein (or an oleuropein analogue, derivative, or metabolite thereof), such that the modulation (either up or down-regulation of the gene or gene product) of one or more genes is indicative that the subject is responsive to treatment with oleuropein (or with an analogue, derivative or metabolite thereof). In one embodiment, the cell is obtained from a sample of whole blood, for example, white blood cells, including lymphocytes, monocytes, neutrophils and the like, although other cells expressing these genes are also contemplated for analysis. In one embodiment, the genes may be any of the adipogenic genes or gene products selected from the group consisting of Peroxisome Proliferator-Activated Receptor γ2 (PPARγ2), lipoprotein lipase (LPL), and the adipocyte-selective fatty acid binding protein (the αP2 gene). In addition, other differentiated adipocyte marker genes include glycerophosphate dehydrogenase (GPDH), fatty acid synthase, acetyl CoA carboxylase, malic enzyme, Glut 4, and the insulin receptor (see Spiegelman et al. J. Biol. Chem. 268: 6823-6826, 1993, incorporated herein by reference). Preadipocytes also have characteristic marker genes, such as the cell surface antigen recognized by the monoclonal antibody AD-3. Expression level changes of the various isoforms of the C/EBP (CCAAT/enhancer-binding proteins) family of transcription factors may also indicate different stages of adipogenesis (see Yu and Hausman, Exp Cell Res Dec. 15, 1998; 245(2): 343-9). A person of skill in the art will recognize that in certain diagnostic and prognostic assays, it will be sufficient to assess the level of expression of a single adipogenic, lipogenic or lipolytic gene as noted above and that in others, the expression of two or more is preferred. For example, the level of expression of a gene or gene product (protein) may be determined by a method selected from, but not limited to, cDNA microarray, reverse transcription-polymerase chain reaction (RT-PCR), real time PCR and proteomics analysis. Other means such as electrophoretic gel analysis, enzyme immunoassays (ELISA assays), Western blots, dot-blot analysis, Northern blot analysis and in situ hybridization may also be contemplated for use, although it is to be understood that the former assays that are noted (eg. microarrays, RT-PCR, real time PCR and proteomics analysis) provide a more sensitive, quantitative and reliable measurement of genes or gene products that are modulated by oleuropein or analogues, derivatives or metabolites thereof. Sequences of the genes or cDNA from which probes are made (if needed) for analysis may be obtained, e.g., from GenBank, other public databases or publications, and are shown here for certain of the exemplary markers shown in Tables 3 and 4. Magnetic resonance imaging may also be used for assessing the effect of oleuropein or analogues or derivatives or metabolites thereof on protein expression.

In another particular embodiment, novel candidate therapeutics (eg. oleuropein analogues or derivatives or metabolites thereof) may be tested for activity by measuring their effect on adipocyte differentiation, de-differentiation or trans-differentiation, as described herein. The candidate therapeutics may be selected from the following classes of compounds: proteins, peptides, peptidomimetics, antibodies, derivatives of fatty acids, nucleic acids, including DNA or RNA, antisense molecules or siRNA molecules, or other small organic molecules, either synthetic or naturally derived. In some embodiments, the candidate therapeutics are selected from a library of compounds. These libraries may be generated using combinatorial synthetic methods.

Use of Microarrays for Determining Gene Expression Levels

Microarrays may also be used for determining gene expression levels and may be prepared by methods known in the art, or they may be custom made by companies, e.g., Affymetrix (Santa Clara, Calif.) (see www.affymetrix.com). Numerous articles describe the different microarray technologies, (e.g., Shena, et al., Tibtech, (1998), 16:301; Duggan, et al., Nat. Genet., (1999), 21:10; Bowtell, et al., Nat. Genet., (1999), 21:25; Hughes, et al., Nat. Biotechn., (2001), 19:342). While many of the microarrays utilize nucleic acids and relevant probes for the analysis of gene expression profiles, protein arrays, in particular, antibody arrays or glycosylation arrays also hold promise for studies related to protein or glycoprotein expression from biological samples (see for example, RayBiotech, Inc. at www.raybiotech.com/product.htm, Panomics at www.panomics.com, Clontech Laboratories, inc. at www.clontech.com, Procognia in Maidenhead, UK and Qiagen at www.qiagen.com.

Samples for Analysis

While the efficacy of oleuropein or an analogue, derivative, or metabolite thereof may be tested in a subject for its effect on, for example, glucose levels, insulin levels, lipid profile, body mass index or weight loss, it may also be of interest to assess its effects on the modulation of the genes or gene products listed in Table 4. While it may be possible to look at the level of a particular gene in certain cellular samples (whole blood cells or peripheral blood mononuclear cells), a more particular method would involve the analysis of the protein expression in these cell types or in the plasma or serum form the subjects exposed or treated with oleuropein or an analogue or derivative thereof. For example, protein and nucleic acid prepared fromn specimens may be obtained from an individual to be tested using either "invasive" or "non-invasive" sampling means. A sampling means is said to be "invasive" if it involves the collection of the biosamples from within the skin or organs of an animal (including, especially, a human, a murine, an ovine, an equine, a bovine, a porcine, a canine, or a feline animal). Examples of invasive methods include needle biopsy, pleural aspiration, etc. Examples of such methods are discussed by Kim, C. H. et al., J. Virol., (1992), 66:3879-3882; Biswas, B. et al., Annals NY Acad. Sci., (1990), 590:582-583; Biswas, B., et al., J. Clin. Microbiol., (1991), 29:2228-2233. Extraction of adipose tissue from individuals used in some embodiments of this invention is well known to those skilled in the art, for example as described by Lonnroth, et al., Diabetes, (1983), 32980: 748-54.

In one embodiment the assays of the present invention will be performed on cells including but not limited to whole blood cells, or isolated white blood cells from a mammal, or from adipocyte cultures propagated for laboratory purposes, 3T3-L1 adipocytes, cells of skeletal muscle derived from a mammal, skeletal muscle cells propagated for laboratory purposes, C2C12 myotube cells, or mesenchymal stem cells, etc. Primary cultures or cell lines can be used. Alternatively, embroyonic stem (ES) cells differentiated into adipocytes can be used, for example, as described in Poliard, et al., Journal of Cell Biology, (1995), 130: 1461-72. Appropriate cell lines that can be obtained for screening purposes are commercially available from the ATCC. In yet another embodiment, a sample of whole blood, blood plasma or serum is obtained for further analysis.

Other Methods for Determining Gene Expression Levels

In certain embodiments, it is sufficient to determine the expression of one or only a few genes, as opposed to hundreds or thousands of genes. Although microarrays may be used in these embodiments, various other methods of detection of gene expression are available.

For example, the modulation of gene expression can be performed using a RT-PCR or Real Time-PCR assay. Total RNA is extracted using procedures known to those skilled in the art and subjected to reverse transcription using an RNA-directed DNA polymerase, such as reverse transcriptase isolated from AMV, MoMuLV or recombinantly produced. The cDNAs produced can be amplified in the presence of Taq polymerase and the amplification monitored in an appropriate apparatus in real time as a function of PCR cycle number under the appropriate conditions that yield measurable signals, for example, in the presence of dyes that yield a particular absorbance reading when bound to duplex DNA. The relative concentrations of the mRNAs corresponding to chosen genes can be calculated from the cycle midpoints of their respective Real Time-PCR amplification curves and compared between cells exposed to a candidate therapeutic relative to a control cell in order to determine the increase or decrease in mRNA levels in a quantitative fashion.

In addition, a method for high throughput analysis of gene expression is the serial analysis of gene expression (SAGE) technique, first described in Velculescu, et al., Science, (1995), 270, 484-487. Among the advantages of SAGE is that it has the potential to provide detection of all genes expressed in a given cell type, provides quantitative information about the relative expression of such genes, permits ready comparison of gene expression of genes in two cells, and yields sequence information that may be used to identify the detected genes. Thus far, SAGE methodology has proved itself to reliably detect expression of regulated and nonregulated genes in a variety of cell types (Velculescu, et al., (1997), Cell, 88, 243-251; Zhang, et al., Science, (1997), 276, 1268-1272 and Velculescu, et al., Nat Genet, (1999), 23, 387-388. Techniques for producing and probing nucleic acids are further described, for example, in Sambrook, et al., Molecular Cloning: A Laboratory Manual (New York, Cold Spring Harbor Laboratory, 1989).

In other methods, the level of expression of a gene is detected by measuring the level of protein encoded by the gene. In the case of polypeptides which are secreted from cells, the level of expression of these polypeptides may be measured in biological fluids. While methods such as immunoprecipitation, ELISA, Western blot analysis, or immunohistochemistry using an agent, e.g., an antibody, that specifically detects the protein encoded by the gene may be contemplated, other more sensitive and quantitative methods are preferred, as described below. The invention is not limited to a particular assay procedure, and therefore is intended to include both homogeneous and heterogeneous procedures. General techniques to be used in performing the various immunoassays noted above are known to those of ordinary skill in the art.

Proteomics: Rationale for Use

While genomic profiling provides information about susceptibility to disease, proteomic profiling reflects snapshots of metabolic dynamics, reveals heterogeneous gene expression, identifies biologically relevant phenotypes and generates information on protein structure-function relationships in the severity and prognosis of a disease. Thus, results from proteomic studies should offer insight into the pathology of obesity and effects by oleuropein therapy. Many forms of protein alterations can be associated with pathophysiological changes and therapeutic treatments. In addition to expression levels and patterns, these include alternative splicing, post-translational modifications, proteolytic processes, co-secretion and protein-protein interactions. Thus, the identification and quantification of proteins alone is not sufficient to understand functional interactions. Changes as small as the addition of a single phosphate, cleavage of a leader peptide, amidation, or oxidation, can drastically alter the biological function of a protein. Thus, it is important to detect these minute changes using sensitive and accurate proteomic technology.

Sample Preparation

Serum or plasma proteins may be differentially expressed in response to pathophysiological changes in obesity and related diseases and to therapeutic treatments of these disorders. Proteomic study of plasma proteins in normal and obese patients demonstrated significant differences in protein patterns. Plasma will be prepared from blood samples and used in proteomic analyses.

Proteomics: The Use of 2DE, MS, MALDI-TOF, MS/MS, LC/MS, and SELDI-TOF 2-dimensional polyacrylamide gel electrophoresis (2DE) coupled to mass spectrometry (MS) is currently the standard analysis in proteomics. Plasma samples may be subjected to 2DE (first dimension isoelectric focusing, second dimension SDS-PAGE). Selected spots from 2DE may be extracted from the gels, digested with trypsin and subjected to MS analysis to determine their identities (Aebersold, R. & Mann, M. Mass spectrometry-based proteomics. *Nature* 422, 198-207 (2003)). MALDI-TOF (matrix-assisted laser desorption/ionization coupled with time of flight (TOF)) is a method of choice to be used for proteins (Tanaka, K. The origin of macromolecule ionization by laser irradiation (Nobel lecture). *Angew Chem Int Ed Engl* 42, 3860-70 (2003).). Tandem MS (MS/MS) may be used for selective isolation of peptide fragments to read out the (partial) amino acid sequence, and LC/MS (liquid chromatography coupled to MS) may be used for the identification of small peptides. However, the 2DE/MS detection is restricted to pI between 4 and 10 and proteins within an MW range of 10-200 kDa. Thus, peptides or small proteins (0.5-10 kDa), such as hormones, adipokines and growth factors, which are related to obesity pathogenesis may not be detected by 2DE/MS. Thus, additional initial separation systems such as C/MS using HPLC coupled MALDI-TOF for differential small peptide display is contemplated for use (America, A. H., Cordewener, J. H., van Geffen, M. H., Lommen, A., Vissers, J. P., Bino, R. J. & Hall, R. D. Alignment and statistical difference analysis of complex peptide data sets generated by multidimensional LC-MS. *Proteomics* 6, 641-53 (2006). Surface enhanced laser desorption ionization and time of flight (SELDI-TOF) using chromatographic chip surfaces based on amino acid sequence, protein structure, charge or hydrophobicity is also contemplated for use (Weinberger, S. R., Dalmasso, E. A. & Fung, E. T. Current achievements using ProteinChip Array technology. *Curr Opin Chem Biol* 6, 86-91 (2002)), as well as antibody proteomics based on immunoaffinity (Ingvarsson, J., Lindstedt, M., Borrebaeck, C. A. & Wingren, C. One-step fractionation of complex proteomes enables detection of low abundant analytes using antibody-based microarrays. *J Proteome Res* 5, 170-6 (2006).).

TABLE 4

Sequence Identifiers for Relevant Proteins Whose Genes may be Modulated by Exposure to Oleuropein or Analogues or Derivatives thereof.

| Name of Protein | GenBank Accession Number | DNA/Protein | SEQ. I.D. NO. |
|---|---|---|---|
| PPAR-gamma isoform 2 | NP_056953 | Protein | 15 |
| Leptin | DD247154 | DNA | 16 |
| P2 Adipocyte Protein | XM_939801 | DNA | 17 |
| Adipsin | M84526 | DNA | 18 |
| Angiotensinogen Protein | AAD14288 | Protein | 19 |
| Angiotensinogen DNA | BC011519 | DNA | 20 |
| Complement Factor H | AAH58009 | Protein | 21 |
| Complement Factor D | BC057807 | DNA | 22 |
| Lipoprotein Lipase | M15856 | DNA | 23 |
|  | BC011353 | DNA | 24 |
|  | NM_000237 | DNA | 29 |
| Perilipin | NM_002666 | DNA | 25 |
| Glucose Transporter 4 (GLUT4) | NP_001033 | Protein | 26 |
| SREBF1 | NM_004176 | DNA | 27 |

TABLE 3

PCR primers for differentiation specific genes

| Gel lane | Gene | Primer sequence (sense/antisense) | Product size (bp) | Gen ID # |
|---|---|---|---|---|
| 1 | Marker | 1 kb plus DNA ladder of 200, 300, 400, 500, 650, 850, and 1000 bp | 200-1,000 | |
| 2 | PPARγ2 Adipogenic | 5'-GGATGTCGTGTCTGTGGAGA-3' (SEQ ID NO: 1) 5'-TGAGGAGAGTTACTTGGTCG-3' (SEQ ID NO: 2) | 630 | BC006811 |
| 3 | LPL Adipogenic | 5'-GAGATTTCTCTGTATGGCACC-3' (SEQ ID NO: 3) 3'-CTGCAAATGAGACACTTTCTC-3' (SEQ ID NO: 4) | 276 | BC011353 |
| 4 | αP2 Adipogenic | 5'-GTACCTGGAAACTTGTCTCC-3' (SEQ ID NO: 5) 5'-GTTCAATGCGAACTTCAGTC-3' (SEQ ID NO: 6) | 418 | BC007538 |
| 5 | PPARδ Anti-adipogenic | 5'-GGTGAATGGCCTGCCTCCCTACAA-3' (SEQ ID NO: 7) 5'-CACAGAATGATGGCC GCAATGAAT-3' (SEQ ID NO: 8) | 380 | BC007578 |
| 6 | ALP Osteogenic | 5'-TGGAGCTTCAGAAGCTCAACACCA-3' (SEQ ID NO: 9) 5'-ATCTCGTTGTCTGAGTACCAGTCC-3' (SEQ ID NO: 10) | 452 | BC014139 |
| 7 | OC Osteogenic | 5'-CATGAGAGCCCTCACA-3' (SEQ ID NO: 11) 5'-AGAGCGACACCTAGAC-3' (SEQ ID NO: 12) | 310 | NM199173 |
| 8 | 28S rRNA Internal Control | 5'-GTGCAGATC'TTGGTGGTAGTAGC-3' (SEQ ID NO: 13) 5'-AGAGCCAATCCTTATCCCGAAGTT-3' (SEQ ID NO: 14) | 589 | BC000380 |

TABLE 4-continued

Sequence Identifiers for Relevant Proteins Whose Genes may be Modulated by Exposure to Oleuropein or Analogues or Derivatives thereof.

| Name of Protein | GenBank Accession Number | DNA/Protein | SEQ. I.D. NO. |
|---|---|---|---|
| CCAAT | NM_005194 | DNA | 28 |
| Plasminogen Activator Inhibitor-1 | NP_000593 | Protein | 30 |
| Adiponectin | NM_004797 | DNA | 31 |
| Interleukin-6 | NM_000600 | DNA | 32 |
| Interleukin-6 | NP_000591 | Protein | 33 |
| TNF-alpha | NP_000585 | Protein | 34 |
| PPAR-alpha | NM_005036 | DNA | 35 |
| PPAR-alpha | NP_005027 | Protein | 36 |
| PPAR-gamma | NM_015869 | DNA | 37 |
| PPAR-gamma | NP_056953 | Protein | 38 |
| PPAR-delta | NM_006238 | DNA | 39 |
| PPAR-delta | NP_006229 | Protein | 40 |

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Modulation of Adipogenesis and Lipodystrophy by Oleuropein

Oleuropein Modulates Adipocyte Differentiation
Methods

Human mesenchymal stem cells (hMSCs) at $10^4$ cells/cm$^2$ were cultured in MSC growth medium first to confluence. Adipogenesis was induced two days post confluence by culturing the cells in adipogenic medium (AIM) containing 10 µM dexamethasone, 1 µg/ml insulin, and 0.5 mM 3-isobutyl-1-methylxanthine, in the absence and presence of oleuropein at 1, 10 and 100 nM. Fresh culture medium was changed every 3 days. Full differentiation of hMSC to adipocytes was detected by Oil Red O staining at day 12. Gene expression was monitored by RT-PCR, using primers shown in Table 3.
Results It was determined that oleuropein down-regulates adipocyte differentiation, fat accumulation and adipogenic gene expression in human mesenchymal stem cells (hMSCs). As seen in FIG. 1, hMSCs grown in control medium do not stain with Oil Red O (counterstained with hematoxylin), while hMSCs grown in AIM contain lipid droplets that stain with Oil Red O. Oleuropein shows dose dependent inhibition of adipocyte differentiation. We are confirming these results using flow cytometry. Oleuropein down-regulates the expression of adipogenic genes PPARγ2, LPL (lipoprotein lipase), and αP2 (lipid binding protein). Oleuropein up-regulates PPARδ expression while the expression of the internal control 28S rRNA remains relatively constant.

Figure 2:
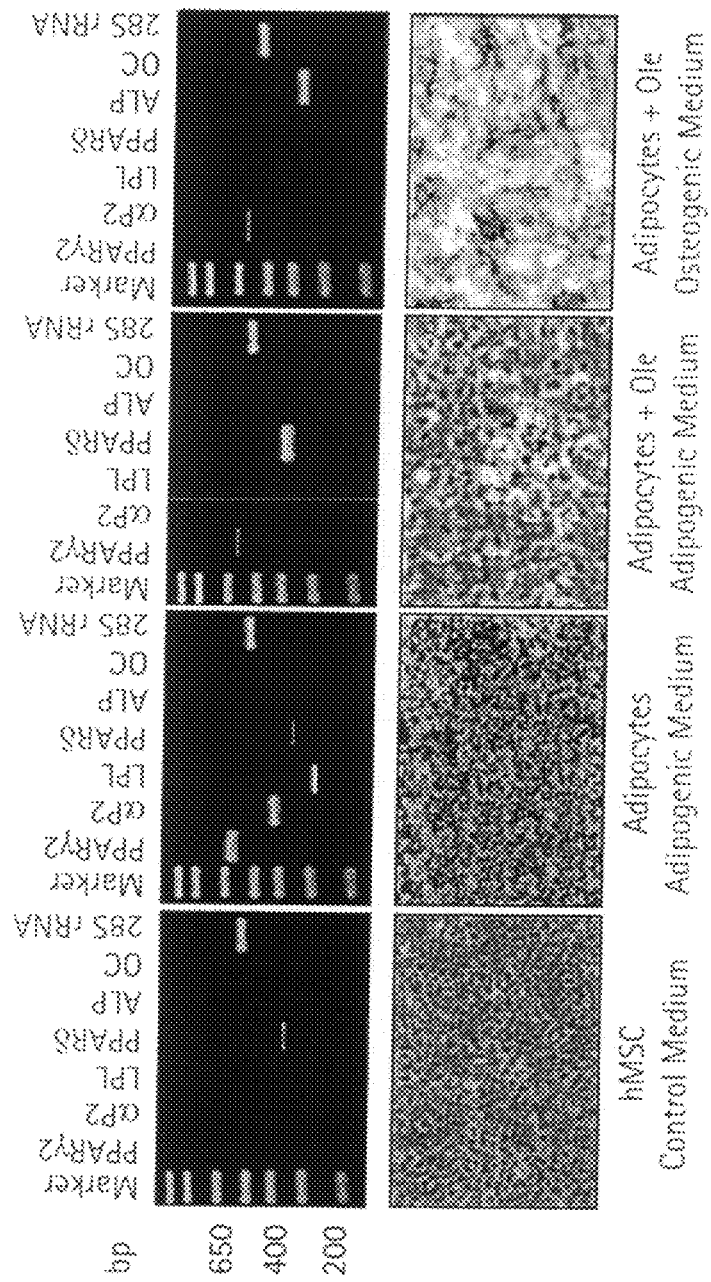
FIG. 2 Demonstrates that oleuropein de-differentiates adipocytes and allows transdifferentiation FIG. 3 Represents aortas from apoE knock out mice fed a Western diet for 4 months, and then stained with Oil Red O FIG. 4 Shows aortic lesions in apoE knock out mice fed a Western diet for 4 months FIG. 5 Shows the predicted PPARδ-oleuropein binding structure FIG. 6 Shows the predicted PPARγ-oleuropein binding structure FIG. 7 Shows the predicted PPARα-oleuropein binding structure FIG. 8 Shows the chemical structure of oleuropein FIG. 9 Shows the HPLC elution profile of Olive Leaf Extract (OLE). The numbers represent the identified peaks. The identities of the peaks are shown in Table 5. Peak 6 is oleuropein, and contains the bulk of the biological activity.

Oleuropein De-Differentiates Adipocytes and Allows Transdifferentiation into Osteoblasts
Methods For transdifferentiation studies, hMSCs were cultured in adipogenic medium for 12 days, allowing full differentiation into adipocytes. Oleuropein (80 nM) was added to the culture medium for 48 hours. De-differentiation of adipocytes was detected by the disappearance of the accumulated lipid by Oil Red O staining. Oleuropein-treated cells were collected by trypsinization and cultured in osteogenic medium containing 10 nM dexamethasone, 10 mM β-glycerophosphate, 50 µg/ml L-ascorbate 2-phosphate, and 10 nM 1α, 25-dihydroxyvitamin D3 for 6 days.
Results As seen in FIG. 2, fully differentiated adipocytes from hMSC lost their Oil Red O staining after the addition of oleuropein. Furthermore, treatment with osteogenic medium resulted in transdifferentiation into osteoblasts. In contrast, hMSC-derived adipocytes treated with osteogenic medium, but not with oleuropein, showed little change at day 6. 48 hours after the addition of oleuropein, the expression of adipogenic marker genes PPARγ2, LPL, and αP2 were down-regulated, while PPARδ was up-regulated. Upon the switch to osteogenic medium, expression of osteocalcin (OC) and alkaline phosphatase (ALP) are observed.
Summary of Results It was determined that oleuropein can modulate adipogenic differentiation of cultured hMSC, and can de-differentiate hMSC-derived adipocytes, allowing transdifferentiation. These results are important because they show that oleuropein can modulate the differentiation and commitment steps in adipogenesis, and offer a possible cellular mechanism for anti-obesity effects.

Example 2

Modulation of Endothelial Dysfunction and Atherosclerosis by Oleuropein

Oleuropein Reduces Diet-Induced Atherosclerosis in the Western Diet-Fed apoE ko Mouse
Methods It was previously demonstrated that oleuropein and OLE, following administration to mice, could be detected in the blood and urine by LC-MS. To test whether oleuropein reduces diet-induced atherosclerosis, oleuropein was administered to apoE ko mice at various doses from 0.25 mg/ml, 2.5 mg/ml, and 25 mg/ml in the drinking water followed by feeding them with a Western diet containing 42% of calories from fat (Harlan-Teklad). At the 4 month time-point for the 0.25 mg/ml dose (daily dose 1.25 mg), serum levels of oleuropein achieved with this dose are comparable to those in animals fed a diet supplemented with olive oil.

Figure 3:
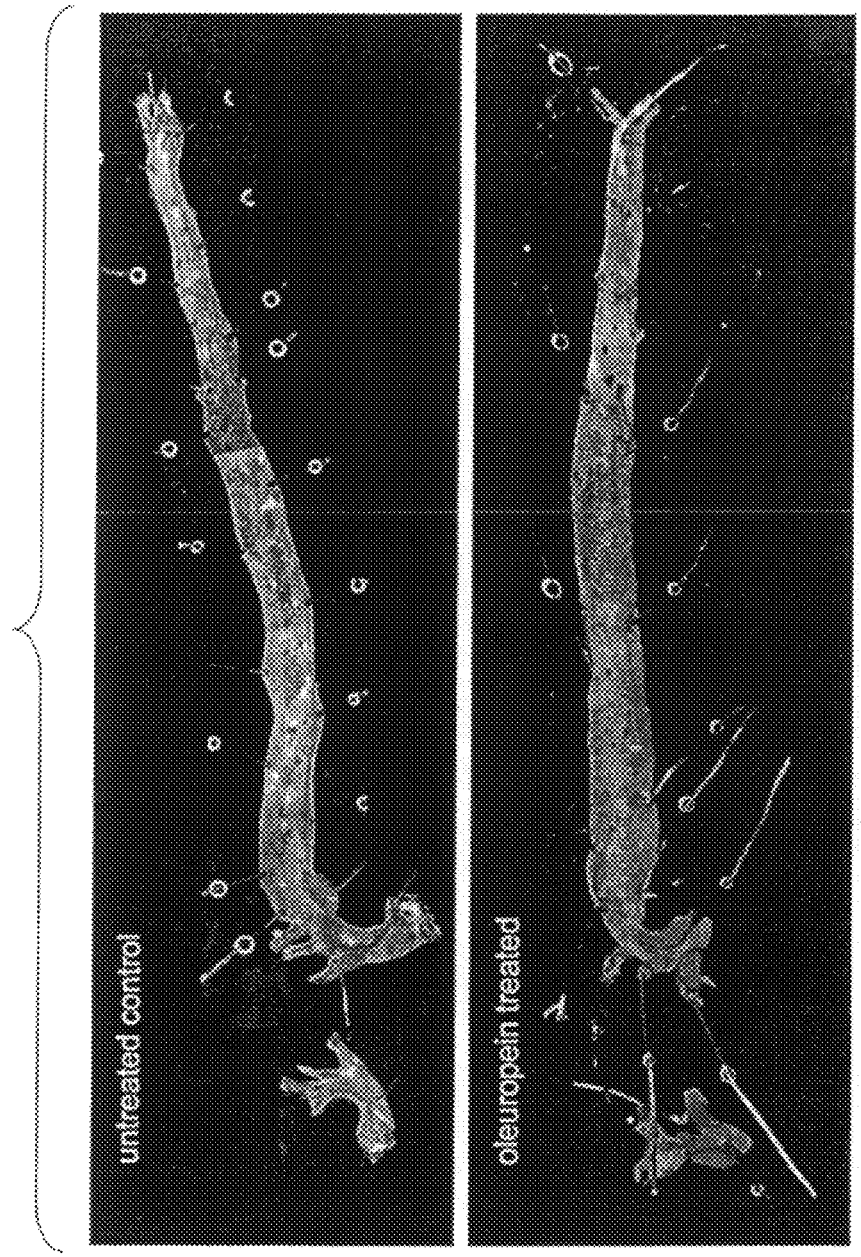
Figure 4:
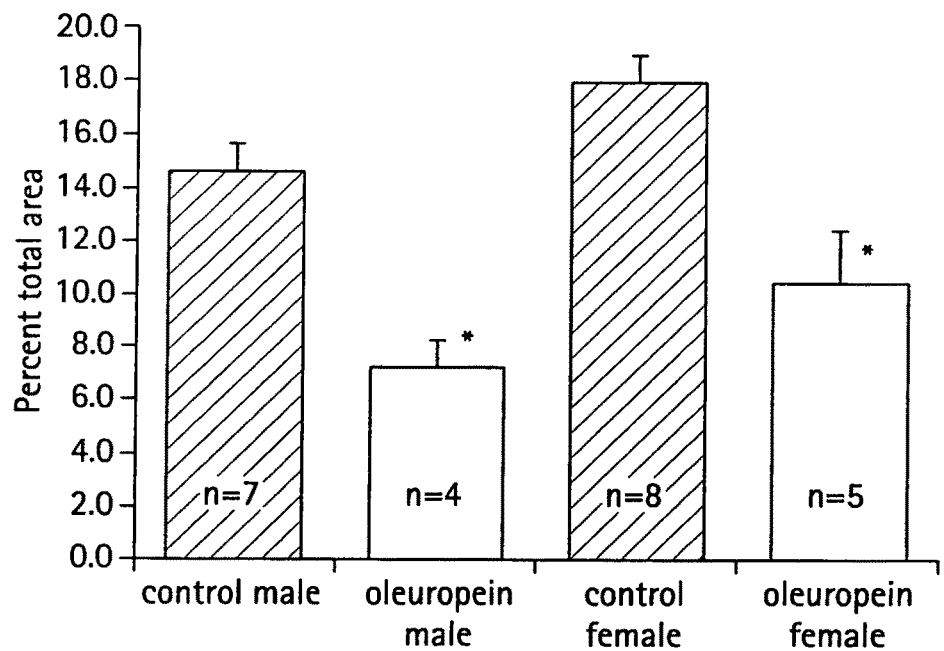

The mice were sacrificed, blood and tissues collected. Aortas were dissected from the aortic valve to the iliac bifurcation, opened longitudinally, and pinned to a black wax surface. Atherosclerotic lesions were stained with Oil Red O. The total area of the aorta and the atherosclerotic lesion areas were determined by planimetry using Image Pro software. FIG. 3 shows representative aortas stained with Oil Red O from untreated and oleuropein treated apoE ko mice.
Results As seen in FIG. 4, there was a significant reduction in lesion area at 4 months in both male and female apoE ko mice that were treated with oleuropein. Female mice had more lesions than male mice in both control and oleuropein-treated groups, consistent with the known gender effects in the apoE ko model. Error bars indicate SEM; differences between control and oleuropein-treated mice were significant for both genders (*) at $p<0.05$.

Summary of these Results

It was demonstrated that oleuropein modulates diet-induced atherogenesis in the Western diet-fed apoE ko mouse model, at doses comparable to those achievable by diet. These results suggest that the beneficial effects of a Mediterranean diet may not be due solely to effects of olive oil on the lipid profile, but may also be mediated in part by non-lipid components such as oleuropein.

Example 3

Computational Approaches to New Treatments for Obesity

Methods

Detailed theoretical and computational analysis for binding of oleuropein to PPARγ, PPARγ and PPARα was performed, using an approach that combines AutoDock, MD and MM-PBSA calculations. We used the crystal structure of PPARδ and PPARγ ligand binding domains. The large ligand-binding site is formed by several α-helices, including the C-terminal AF-2 helix. We first used molecular docking to generate several distinct binding orientations, and performed molecular dynamics simulation to further relax the complex. Then, we applied MM-PBSA to estimate the affinity for each binding mode. The binding modes with the lowest free energy are expected to be the most favorable. We then analyzed the detailed interactions based on these binding modes.

Oleuropein Mimics the Binding Mode of High Affinity Ligands for PPARδ

FIG. 5a shows docking of oleuropein to PPARγ in the energetically most favorable binding mode (II), with free energy of −52.73 kcal/mol. In the predicted structure, oleuropein occupies the Y-shaped ligand-binding pocket, identical to two known ligands of PPARδ: the synthetic agonist GW2433, which is a high-affinity ligand, and the natural fatty acid eicosapentanoic acid (EPA), which binds efficiently to all three PPARs.

FIG. 5b shows an overlay of oleuropein (red and blue), GW2433 (green) and EPA (purple) in their bound configurations. Oleuropein's sugar group is located in a similar position and orientation as the carboxyl groups in GW2433 and EPA. The two hydroxyls on the sugar ring are oriented toward the AF-2 helix and held in place through a network of hydrogen bonds with Y473, and hydrophobic interactions with L469 and T84, as seen in FIG. 5d. Both Y473 and L469 are part of the AF-2 helix. The same network of hydrogen bonds occurs in the binding of ligands to PPARδ and γ, and is believed to be important for ligand-mediated activation of these receptors.

Oleuropein Shows Different Binding Modes than High Affinity Ligands for PPARγ

FIG. 6 shows docking of oleuropein with PPARγ in the most favorable binding mode (I), with free energy of −27.09 kcal/mol. In the predicted structure, oleuropein binds into the large PPARγ pocket in an extended (up-down) conformation rather than the U-shaped conformation of other known ligands such as GI262570 and rosiglitazone. FIG. 6b shows an overlay of oleuropein (red and blue), rosiglitazone (yellow) and the PPARγ agonist GI262570 (green). Unlike known ligands, oleuropein does not interact directly with AF-2 helix. At one end of the molecule, the dihydroxyl phenol group is directed into the solvent-accessible channel between H3 and the β strands. At the other end, the oleuropein sugar headgroup is inserted 4.0 Å deeper than the phenyloxazole tail of GI262570 into the lipophilic pocket adjacent to the β sheet, forming two strong hydrogen bonds with the carboxyl group of E259 (shown in FIG. 6d).

Oleuropein Shows Different Binding Modes than High Affinity Ligands for PPARα

FIG. 7a shows the binding structure of PPARα-oleuropein complex with free energy of −24.71 kcal/mole. The PPARα backbone is represented by the yellow ribbon, and oleuropein is represented with vdw and is color coded as follows: carbon, cyan and oxygen, red. In the predicted structure as shown, oleuropein adopts a Y-shaped configuration when it binds to PPARα, similar to how it binds to PPARγ. This is consistent with the similarities between the binding sites of PPARα and PPARδ. This conformation differs from the U-shaped conformation of other known ligands of PPARα, such as GW409544. FIG. 7b represents superposition of the structures of GW409544 (green) and oleuropein (red and blue) bound to PPARα. FIG. 7c shows the chemical structures of oleuropein and GW409544. FIG. 7d shows hydrogen bonds formed by oleuropein and the surroundings (indicated as green dotted lines).

Summary of these Results

The known ligand binding domains of PPAR δ is large and Y-shaped. Our molecular modeling results show binding modes for oleuropein that are as favorable as the currently known ligands. Oleuropein mimics precisely the binding mode of high affinity ligands for PPARδ, indicates that oleuropein is capable of moduating PPARδ activity similar to that of know PPARδ agonist. Oleruopein has the potential to increase fat oxidation, increase energy uncoupling and thermogenesis and thus decrease fat accumulation, reduce body weight and prevent obesity. For PPARδ, on the other hand, in the predicted structure, oleuropein binds to PPARδ in an extended (up-down) conformation rather than the U-shaped conformation of other known ligands such as GI262570 and rosiglitazone. Unlike these ligands, oleuropein does not interact directly with AF-2 helix. These results predicate that oleuropein has the potential to interact with PPARγ distinct from PPARγ known agonists including TDZ. Oleruopein does not act on the AF2 helix of PPARγ, the region that involves in adipogenesis, thus suggesting an important mechanism for regulation of PPARγ activity in uncoupling adipogenesis from insulin sensitivity and other activities. For PPARα, in the predicted structure, oleuropein adopts a Y-shaped configuration when it binds to PPARα. This is similar to how it binds to PPARδ. This is consistent with the similarities between the binding sites of PPARα and PPARδ as well as their functions. Both PPARα and PPARδ are involved in fat oxidation and energy utilization. In this context, the energetically favorable Y configuration of oleuropein may offer insight into its biological effects. Studies are underway to confirm the biological significance of these modeling results, and correlating them with in vitro and in vivo data. We are studying the experimental binding and co-crystallization of oleuropein with the ligand binding domains of PPAR α, δ and γ. We are analyzing the expression and activity of PPAR α, δ and γ in tissues from oleuropein-treated apoE ko mice that show reduction in diet-induced atherosclerosis, to identify the importance of these isoforms to the observed biological activity.

Example 4

Preparation of Oleuropein from Olive Leaf Extract

LC-MS Standardization of Olive Leaf Extract (OLE) Containing Oleuropein as the Active Moiety A. Preparation of Olive Leaf Extract Selection Cleaning and Processing of the Olive Leaves.

Healthy whole olive leaves were selected and cleaned to remove dust, residual insecticides and contaminating material. The leaves were cut into small pieces or powdered into fine powders and placed in a sterile flask just before extraction, with sterile distilled water and pre-heated to 80° C.

Extraction Media and Ratio.

A comparison was made between the extraction with water, PBS (Phosphate Buffered Saline, 10 mM sodium phosphate buffer, pH 6.8, containing 0.15% NaCl) and organic solvents (50% methanol, or 40% ethanol). No significant differences were found in biological activity using the different extraction methods. Since the therapeutic ingredients in olive leaf are apparently water-soluble, a decision was made to use water extraction, because it gives stable extracts that can be concentrated with ease. For efficient extraction, it was determined that the optimal ratio is one gram of dry leaves to 40 ml of water.

Extraction Conditions:

The extraction mixture was covered and incubated with agitation for 10-12 hours at 80° C. in a water bath. It is important that the extraction temperature be kept under 85° C. Heating above 86° C. inactivates oleuropein, one of the principle ingredients of OLE. Alternative methods for extraction including but not limited to microwave for two repeats of 5-10 min, or ultrasound for 25 min.

Concentration of the Extract by Lyophilization.

At the end of 10-12 hours at 80° C., proper extraction results in a medium brown colored OLE with about 70-80% of the original volume. The liquid was poured off and collected. The leaves were extracted again for a second time under the same conditions to ensure complete extraction of the active ingredients. Small pieces of leaves and insoluble material in the extract were removed by centrifugation at 20,000×g for 30 min. The clear supernatant was collected and labeled as Step 1 OLE. Step 1 OLE was concentrated by freeze-drying using a Lyophilizer. The dried OLE was collected, and labeled as Step 2 OLE.

Sterilization by Millipore Filtration.

Step 2 OLE was dissolved in sterile water at 10-20 mg/ml, sterilized by Millipore filtration with a 0.45 micron filter, distributed at small lots in sterile cryo-tubes under aseptic conditions and stored at −80° C. This is Step 3 OLE and its oleuropein content was quantitated by LC-MS using known oleuropein standard. Standardized OLE was used in all of our experiments.

Preparation and LC-MS Standardization of Oleuropein

Oleuropein was prepared and quantitated by LC-MS as noted above. This process was performed using an HP1100 equipped with diode array detector and ESI-mass spectrometer. LC was done using a C18 column, using a gradient of 5-95% $CH_3CN$—$H_2O$ containing 1% acetic acid. The diode array recordings were made at 280 nm and 230 nm, and the ESI mass spectrum was made in negative detection mode. Purified oleuropein, was used as a standard. Experiments were optimized by infusion of the standards in negative scan mode to investigate the [M-H] ion of oleuropein glycoside (m/z 539). Oleuropein fractionates as a single peak by HPLC at 1.846 min, and contains predominantly oleuropein glycoside (m/z 539). The oleuropein content in the lyophilized OLE ranges from 20-25% as standardized by LC-MS.

Preparation and LC-MS Standardization of Hydroxytyrosol

Hydroxytyrosol was prepared from homogeneous oleuropein isolated from OLE. The procedure involves treatment of oleuropein with β-glycosidase (including but not limited to Sigma G4511) in 80 mM sodium acetate pH 5.0 using 1 Unit of enzyme/μmole of substrate at 37° C. for 1 hr to remove the glucose moiety and to yield oleuropein aglycone. The oleuropein aglycone was then be treated with esterase (including but not limited to Sigma E0887) in sodium phosphate buffer at pH 7.5 using 1 Unit of enzyme/μmole of substrate at 25° C. for 1 hr to yield hydroxytyrosol and elonelic acid. The final products were resolved and quantitated by LC-MS as described above. Detection and quantification were performed at 280 and 320 nm for hydroxytyrosol at 0.698 min (m/z 153) and oleuropein aglycone at 2.087 min (m/z 377), while 240 nm was used for the detection of elenolic acid at 1.846 min (m/z 241).

LC-MS Standards

Synthesis of Hydroxytyrosol

Hydroxytyrosol, the major metabolite of oleuropein is biological active. We have designed a unique method for chemical synthesis of hydroxytyrosol. Chemically synthesized hydroxytyrosol is as active as its natural counterpart from OLE. Major steps in chemical synthesis of hydroxytyrosol are briefly outlined below:

We started our hydroxytyrosol synthesis from 3,4-dihydroxylphenylacetic ester. It was prepared by the following procedure. The reaction mixture of 3,4-dihydroxylphenylacetic acid 168 mg in $CH_3OH$ was treated with Acetyl chloride and $CH_3OH$ mixture. The reaction mixture was stirred at room temperature overnight. The reaction mixture was purified by column chromatography. A total of 140 mg of oily compound was obtained

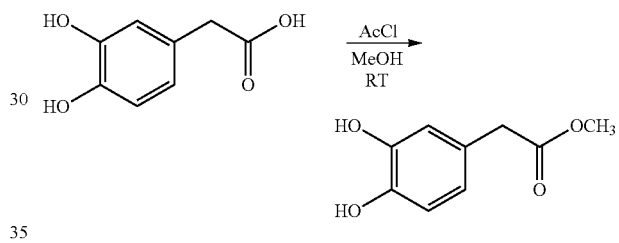

Hydroxytyrosol was prepared from 3,4-dihydroxylphenylacetic ester by $LiAlH_4$ reduction. 140 mg of 3,4-dihydroxylphenylacetic ester was dissolved in tetrahydrofuran (TI-IF). 1M of $LiAlH_4$ (4 ml) solution was added to the reaction mixture. The mixture was stirred at 0° C. for 2 hours. The reaction mixture was purified by column chromatography to give hydroxyltyrosol and characterized by LC-MS.

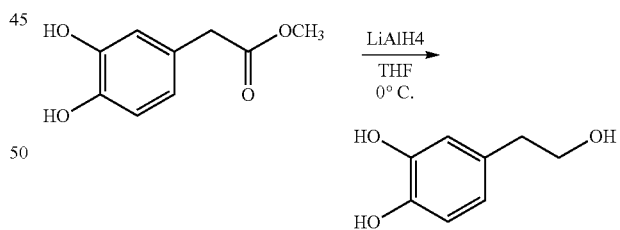

B. HPLC Analysis of OLE Components

Figure 8:
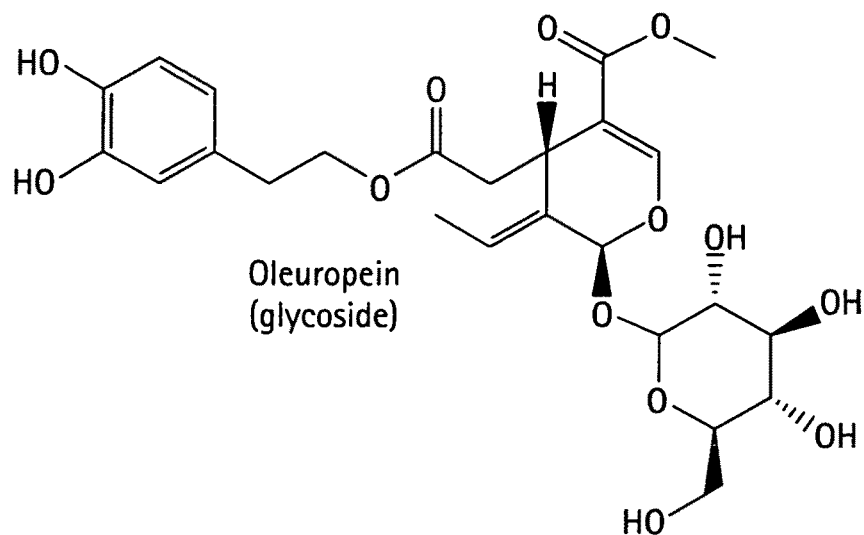
Figure 9:
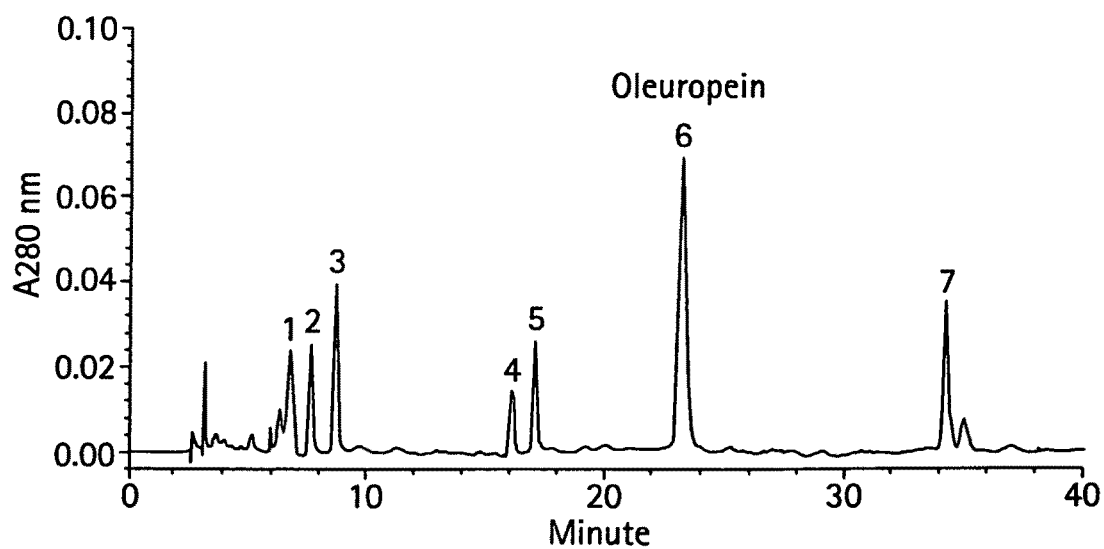

Step 3 OLE was subjected to HPLC using a Waters two solvents delivery system with photodiode array detector. A Symmetry C18 column (5 μm, 3.9×250 mm) column with a Sentry Guard 3.9×20 mm insert was used. Data acquisition and quantitation were performed with Millennium 32 software (version 3.0). The mobile phase was 79% distilled water and 21% acetonitrile (HPLC grade), both acidified to pH 3 with 0.1 M orthophosphoric acid. This solvent system is designed for resolution and quantitation of polypheolic compounds. The flow rate was 1 ml/min, and the injection volume was 20 μl. Polyphenolic compounds were monitored by absorbance at 280 nm. The run time was 35 minutes. The structure of oleuropein is shown in FIG. 8. The elution profile is shown in FIG. 9. A total of seven major peaks were resolved from the included material. The solvent front and excluded material appear before peak 1, with retention time (Rt) less than 6 minutes.

C. Identification of OLE Components

The major OLE components were identified by TLC and HPLC with known standards. TLC was carried out on silica gel 60 F254 (Merck) with chloroform/methanol/acetic acid (70:30:10). Secoiridoids and flavonoids were detected by visualization under UV light at 254 nm with 10% ferric chloride and 10% aminoethyl diphenylborate spray, using known standards. HPLC verification was conducted by repeated HPLC of peak material with known amounts of standards. The identities of the polyphenolic compounds in each peak are shown in Table 5, along with their relative levels in the OLE and their cytotoxicity.

TABLE 5

Identity and characterizations of phenolic compounds in OLE

| Peak | Rt (min) | Compound | % (w/w) | Cytotoxicity |
|---|---|---|---|---|
| Excl. | <6 | Solvent front | — | — |
| 1 | 6.6 | Rutin | 0.34 | — |
| 2 | 7.8 | Verbascoside | 0.38 | — |
| 3 | 8.9 | Luteolin7-glucoside | 0.68 | — |
| 4 | 16.0 | Apigenin7-glucoside | 0.18 | — |
| 5 | 17.0 | Flavonid x | 0.56 | — |
| 6 | 22.8 | Oleuropein | 12.8 | — |
| 7 | 34.0 | Oleuroside | 0.51 | — |

D. LC-MS Analysis

Samples:

The standard and peak 6 oleuropein were prepared in sterile water with a final concentration of 1 mg/ml. Step 3 OLE was prepared as described above at a final concentration of 10 mg/ml. All samples were Millipore filtered and stored at −20° C. until use.

Experimental Protocol:

LC-MS was performed using an HP1100 equipped with diodearray detector and ESI-mass spectrometer. LC was done using a C18 column (20×4.0 mm), with 4 minute elution using a gradient of 5-95% $CH_3CN$ (containing 1% acetic acid)-H2O (containing 1% acetic acid). The diodearray records were made at 280 nm and 230 nm, and ESI mass spectrum was made in negative detection mode. The standard and peak 6 oleuropein were diluted to a final concentration of 0.5 mg/ml, and OLE was diluted to 5 mg/ml. The injection volumes were all 5 µl. Experiments were optimized by infusion of the standards in negative scan mode to investigate the [M-H] ion of oleuropein (m/z 539).

Results

Peak 6 oleuropein showed similar purity to the oleuropein standard by LC FIG. 11 shows the LC-MS results of oleuropein standard (11A), peak 6 oleuropein (11B) and OLE (11C). As seen in FIGS. 11A-LC and 11B-LC, peak 6 oleuropein is as pure as the standard. A single major peak was observed at 1.827 min and a minor peak at 1.696 min (less than 1%) in both samples.

Figure 11A:
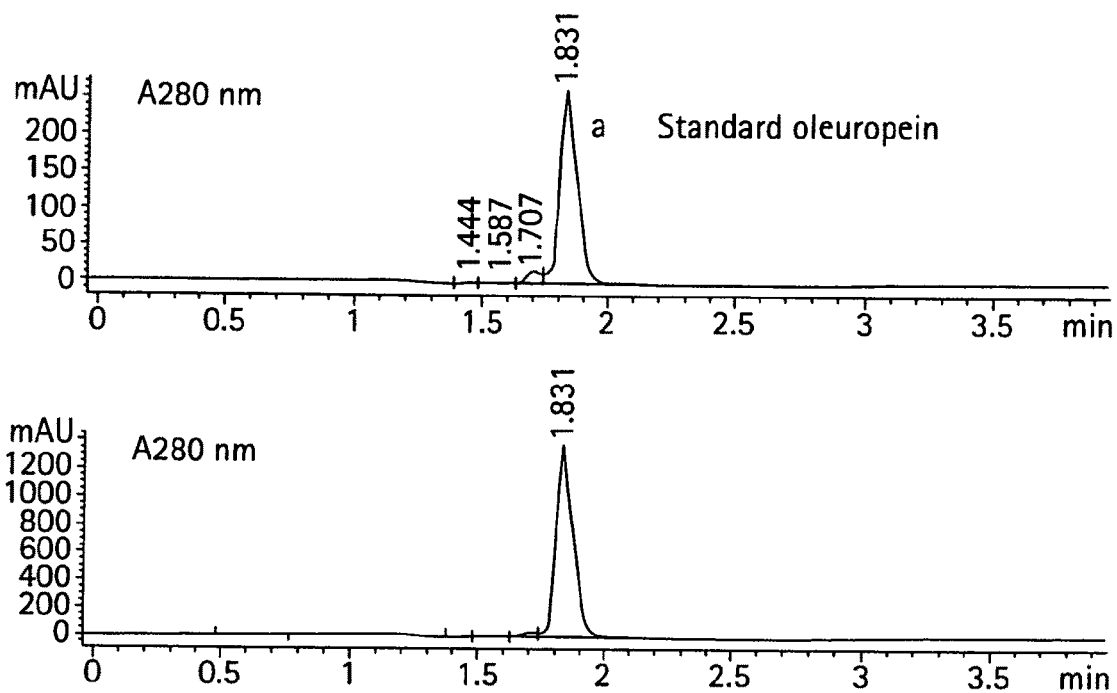
FIG. 11 Shows the results of the standardization of olive leaf extract by liquid chromatography-mass spectrometry (LC-MS) based on oleuropein content.
Figure 11B:
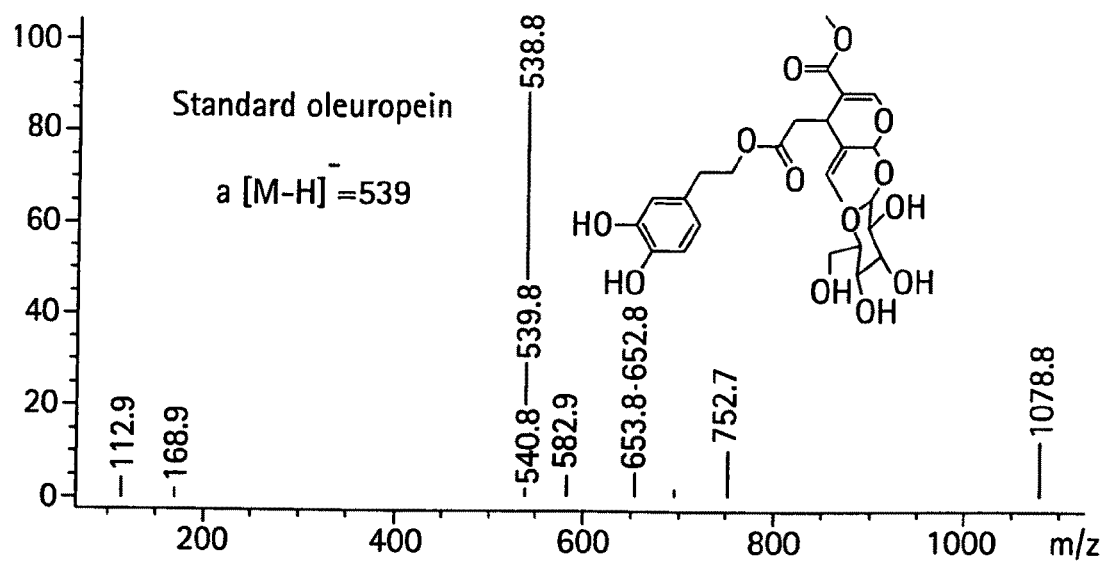

Peak 6 oleuropein showed a single mass as the oleuropein standard by MS MS of the standard and the peak 6 oleuropein are seen in FIGS. 11A-MS and 11B-MS. A single mass peak at $[M-H]^-=539$ corresponds to oleuropein was detected in both samples. A minor peaks was observed at mass $[M-H]^-=1079$ it represents [2M-H].

Ole Contains Several Components by LC

Figure 11C:
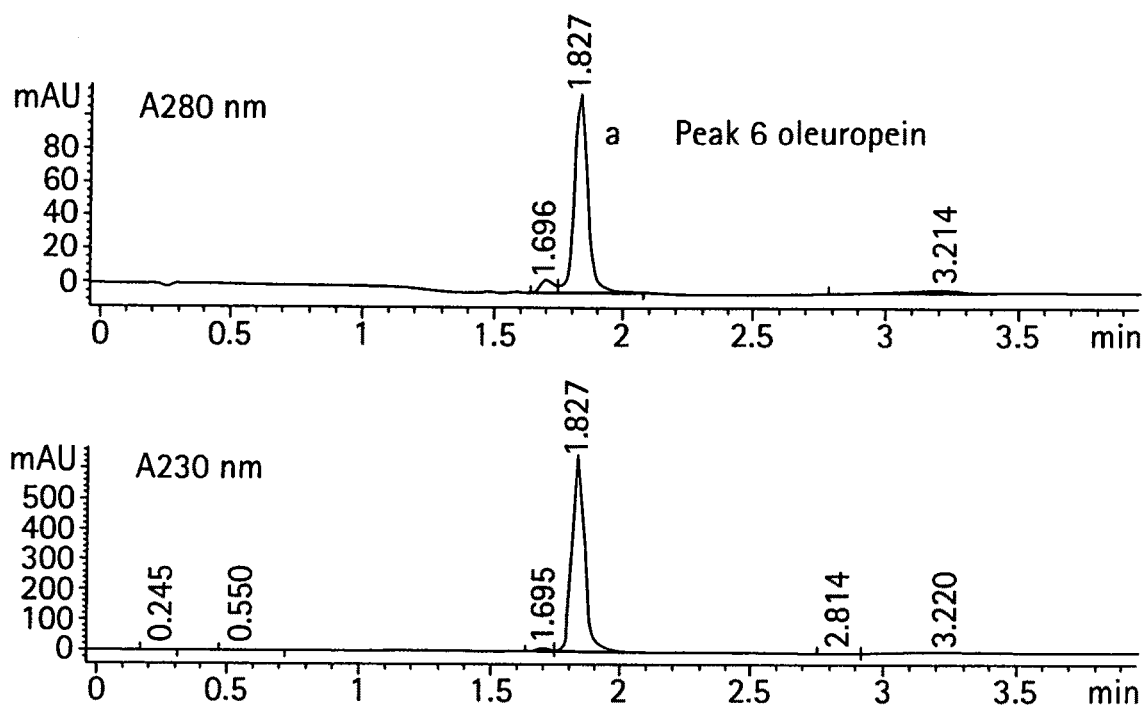
Figure 11D:
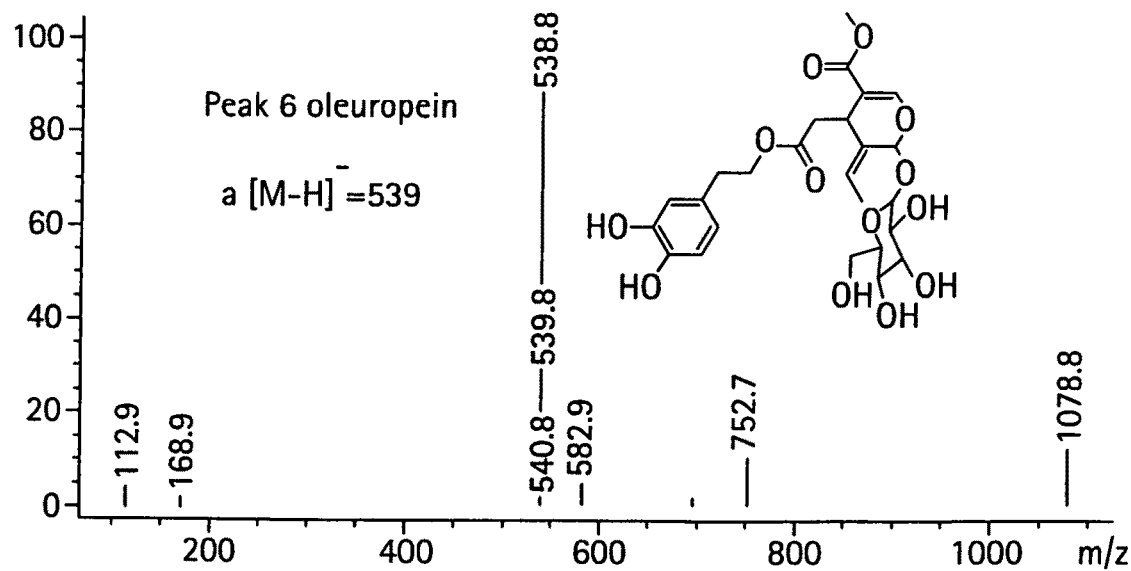
Figure 11E:
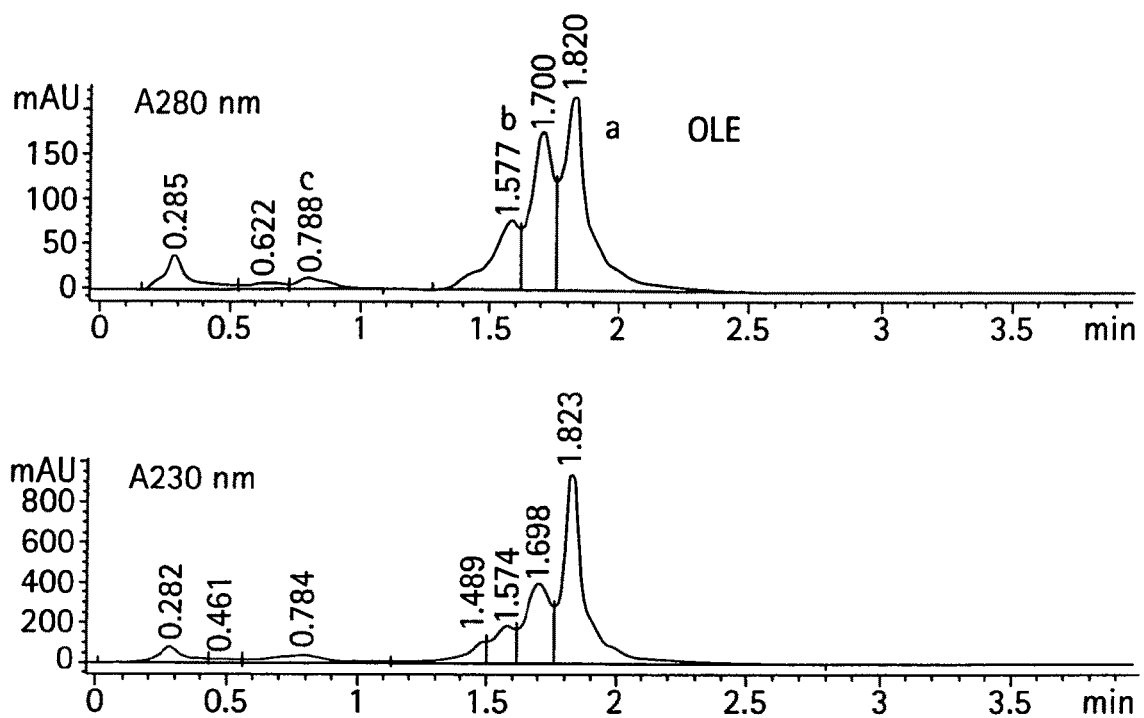
Figure 11F:
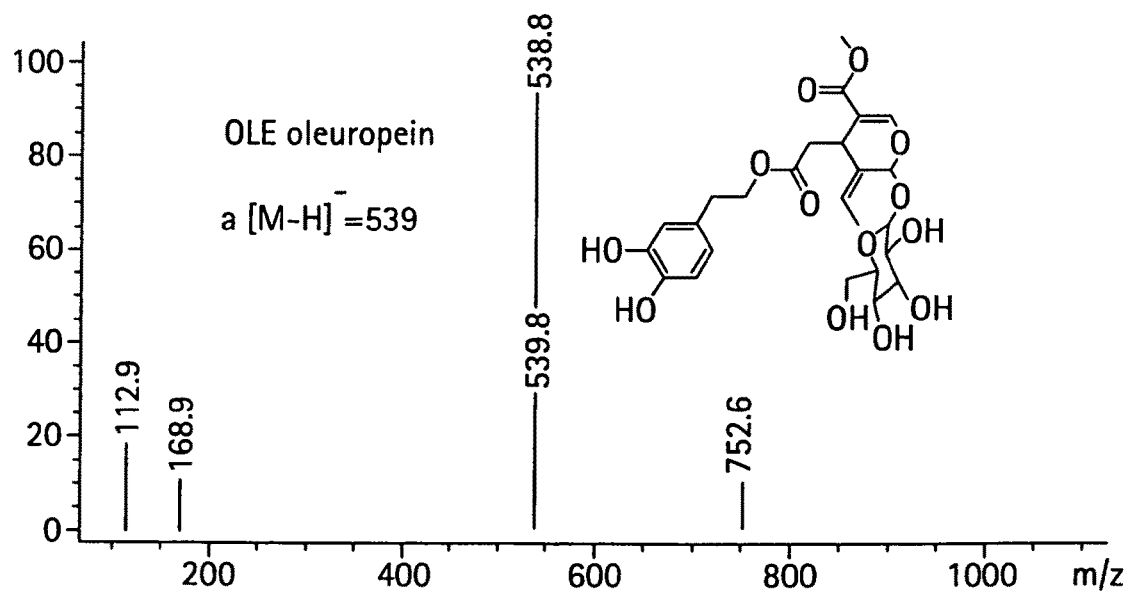
Figure 11G:
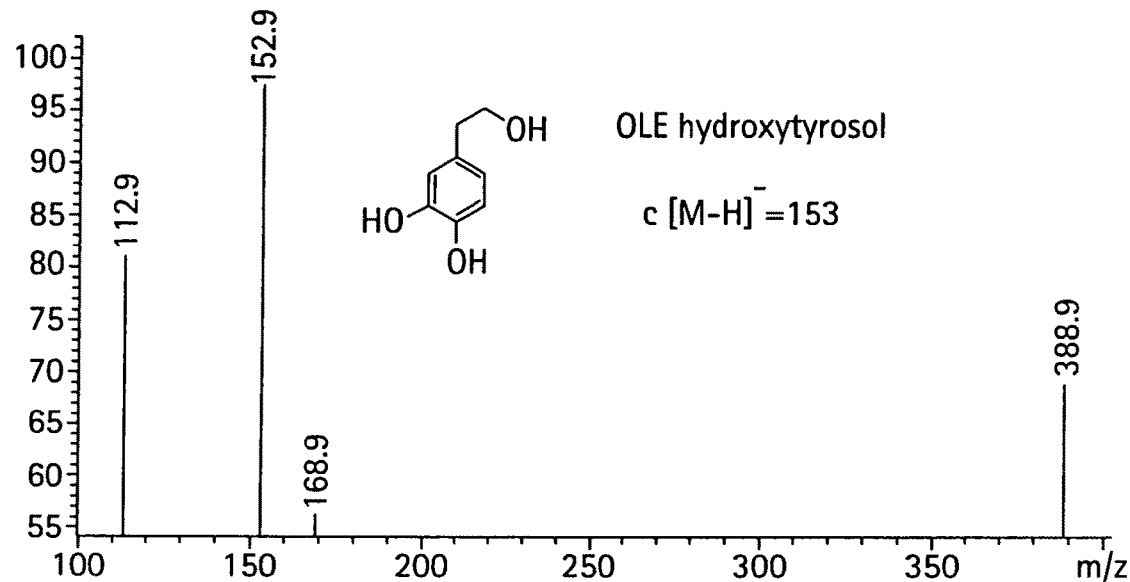
Figure 11H:
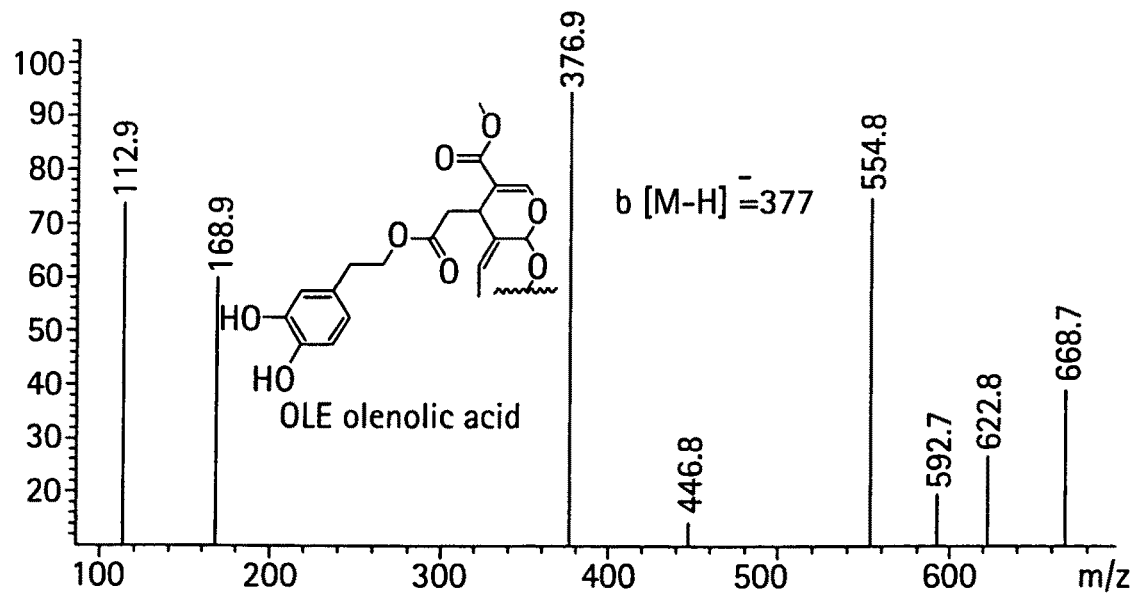
Figure 12A:
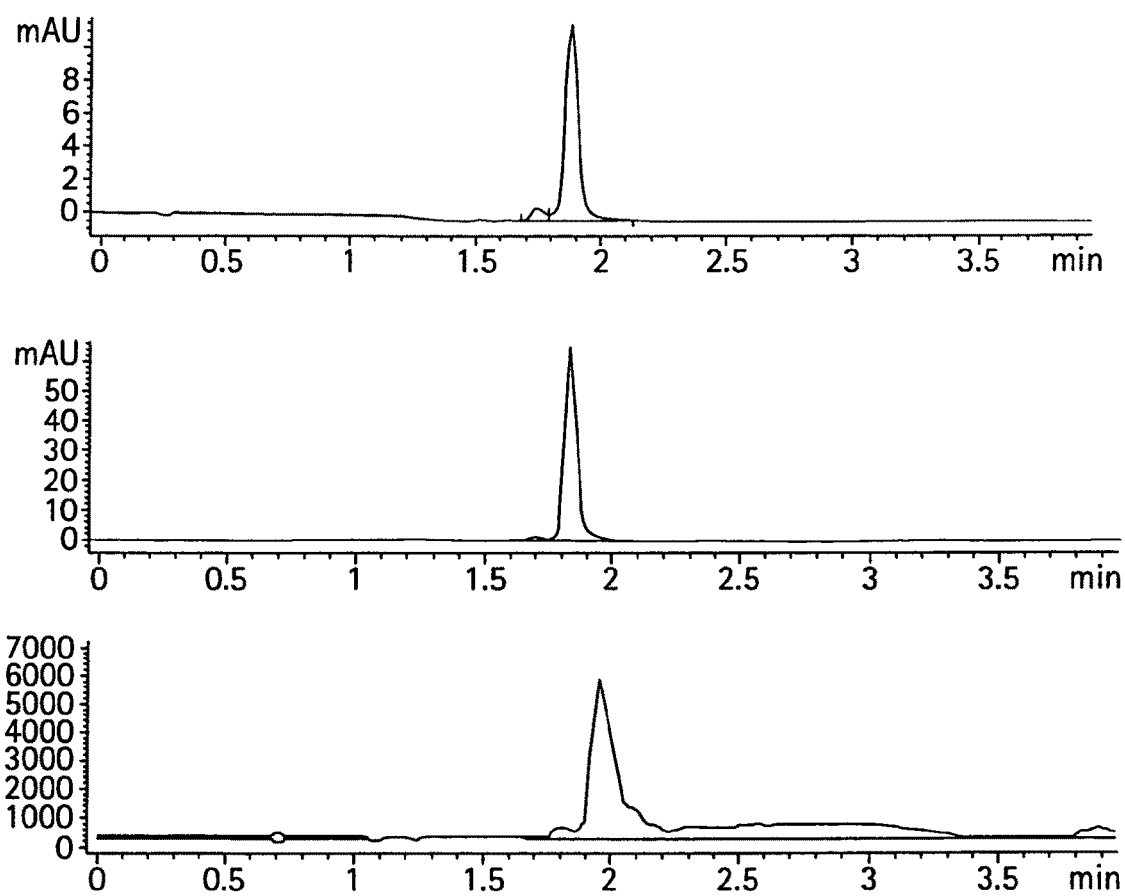
FIG. 12 Shows the results of the quantitation of oleuropein and metabolites in serum and urine of mice fed oleuropein.
Figure 12B:
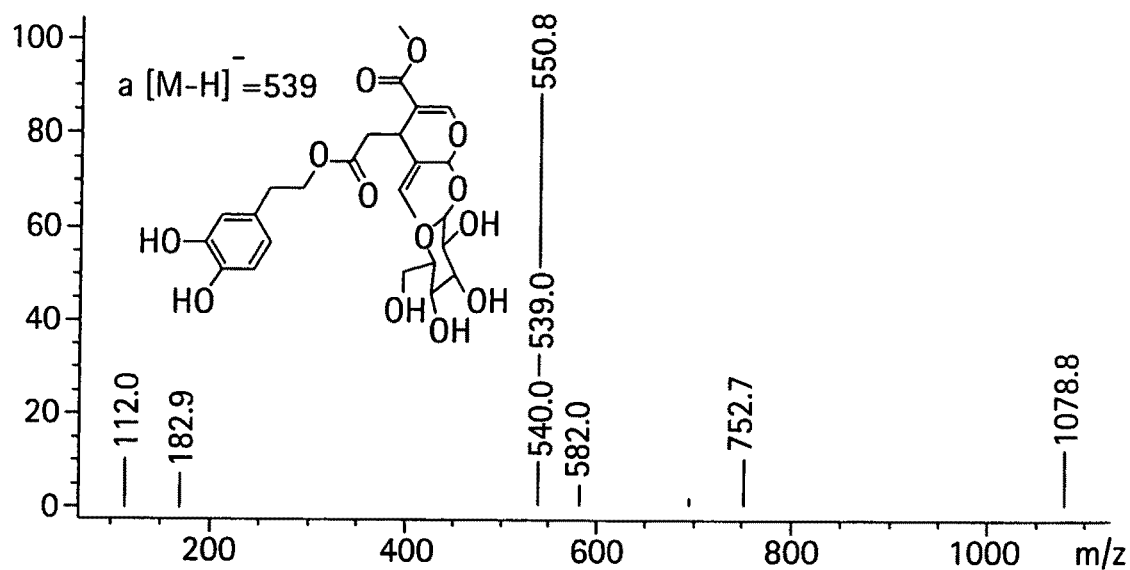
Figure 12C:
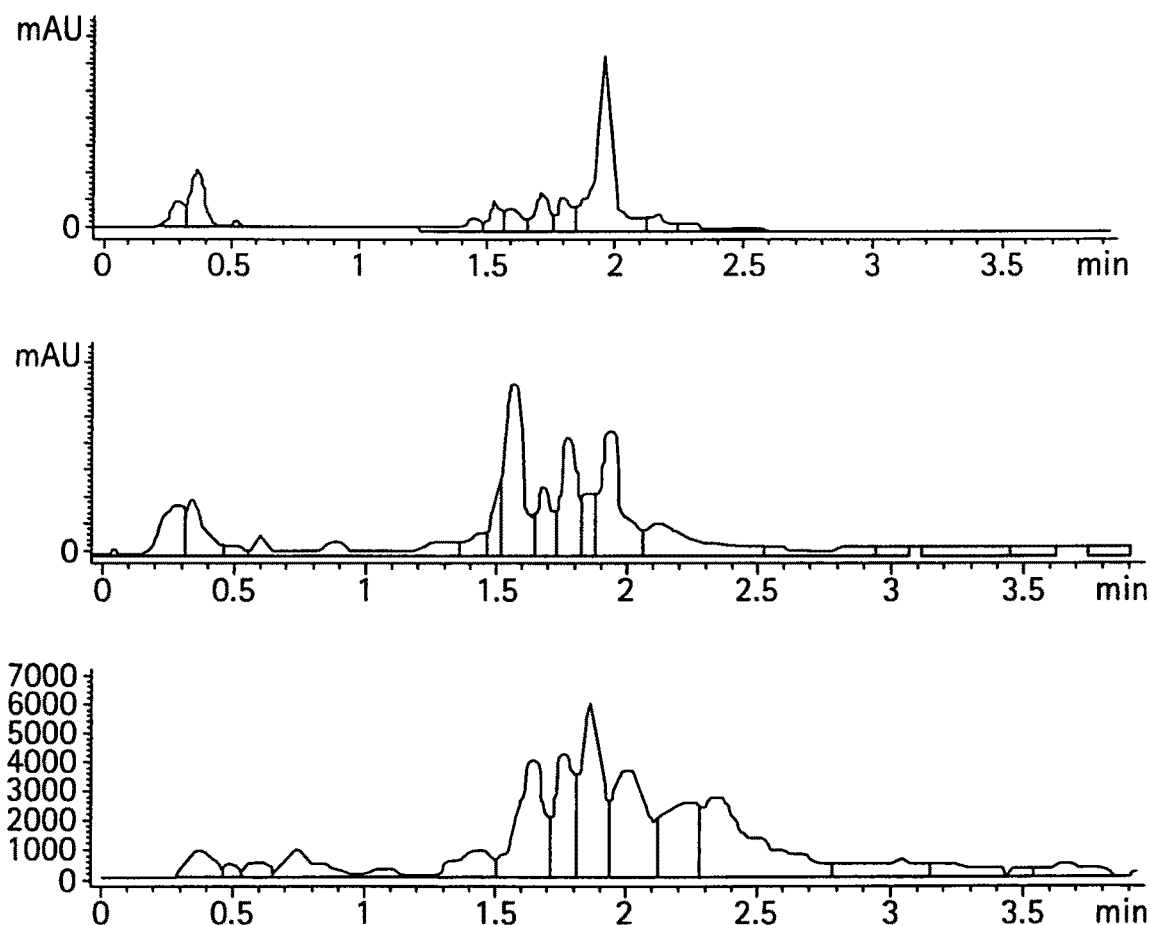
Figure 12D:
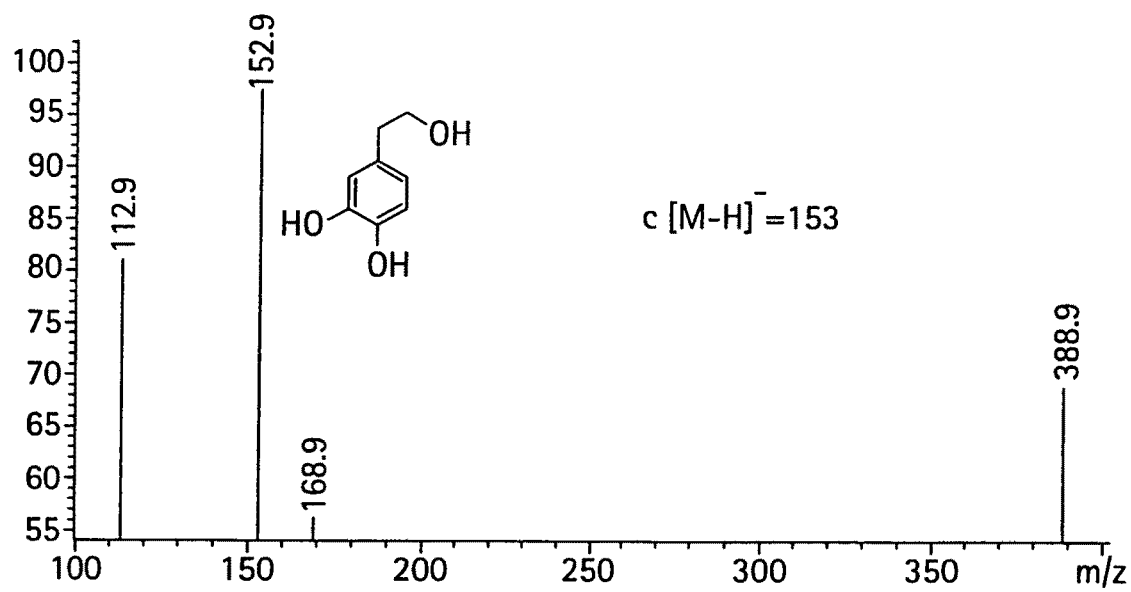
Figure 12F:
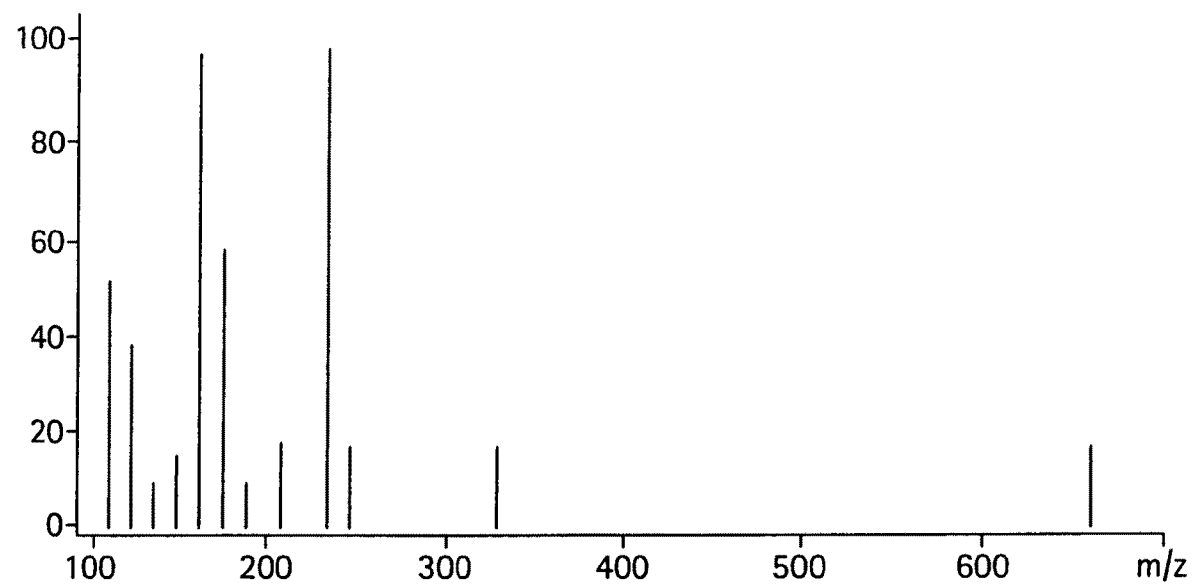

FIG. 11C-LC represents the LC profile of OLE. Several peaks were detected. Peaks A at 1.82 min is the major peak, peaks B, and C are moderate and minor respectively.

MS of OLE Identified Oleuropein, Oleuropein Aglycone and Hydroxytyrosol.

FIGS. 11C-MS of OLE A, OLE B, and OLE C represent MS of LC peaks A, B, C respectively. MS of peaks A, B, and C identified mass peaks at $[M-H]^-=539$, 377 and 153 correspond to oleuropein, oleuropein aglycone and hydroxytyrosol respectively.

Heavy metals, pesticides, fungicides & herbicides were analyzed and not detected in the samples.

Summary and Discussion of Results:

LC-MS results show that peak 6 oleuropein consists of a single major peak at $[M-H]^-=539$ corresponds to oleuropein. The purity of this sample is equal to or even better than the standard. The relative size of the peak $[M-H]^-=1079$ is less in peak 6 oleuropein than in the standard.

Figure 10:
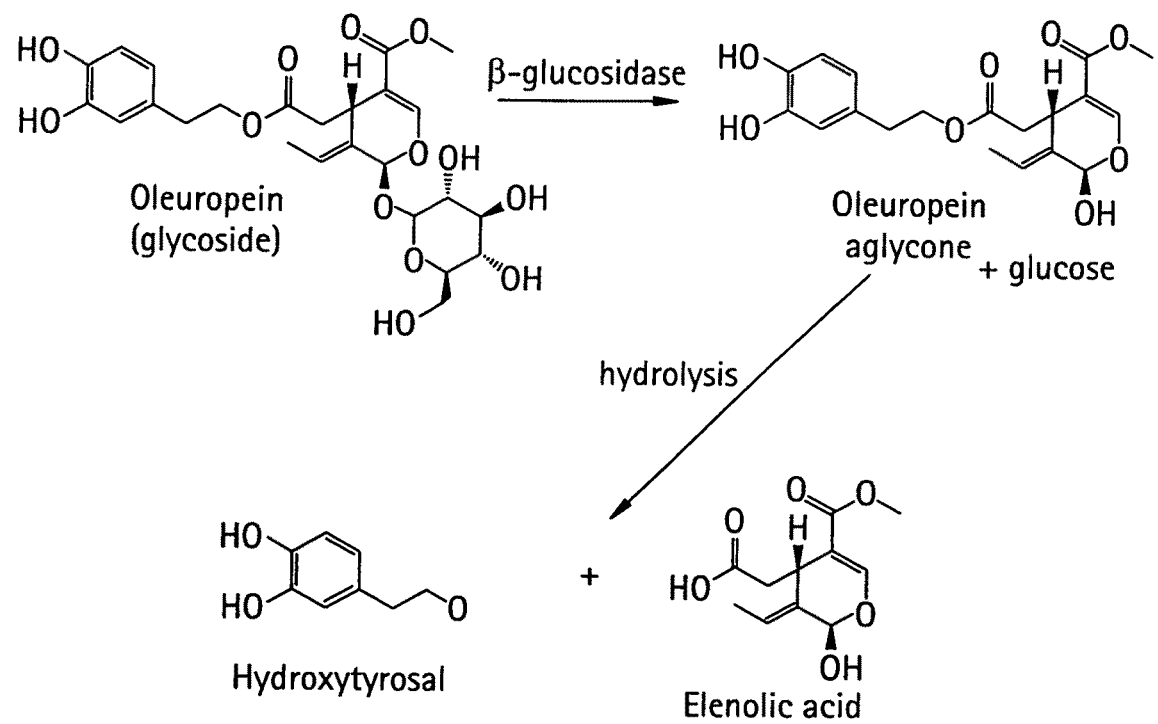
FIG. 10 Shows the chemical structure of oleuropein and its major metabolites.

LC-MS of OLE indicates that in addition to oleuropein, oleuropein aglycone and hydroxytyrosol are also present. Oleuropein is a heterosidic ester of elenolic acid and hydroxytyrosol (3,4-dihydroxy-phenylethanol), containing a molecule of glucose, upon β-glycosidase action it yields oleuropein agylcone. Hydrolysis of oleuropein aglycon yields hydroxytyrosol and elenolic acid. The structural relationships among these compounds are shown in FIG. 10. These molecules are major metabolites of oleuropein thus their presence in the OLE is expected. Elenolic acid has no UV absorbance thus it cannot be detected in LC-MS analysis.

Oleuropein can also be prepared from olive leaves by extracting with 50% aqueous methanol. After evaporation of methanol, the aqueous phase can be extracted with chloroform and then saturated with NaCl and filtered. Oleuropein and other phenolic compounds can be extracted with ethyl acetate. The ethyl acetate phase was totally evaporated to dryness. Oleuropein can be further purified and characterized by LC-MS as described above.

Example 5

Oleuropein is Bioavailable: it is Absorbed and Well Tolerated in Animals

A. Bioavailability Studies

It is important to establish that chronic administration of oleuropein results in the absorption of the biologically active material in vivo. In addition, it is necessary to determine the physiologically achievable and relevant concentrations in tissue, blood, and urine, and to compare these with concentrations that show activity in vitro or in cell culture.

To verify that we can administer oleuropein chronically to mice, we added purified oleuropein to drinking water at concentrations of 5 µg/ml, 50 µg/ml, 500 µg/ml, and 5 mg/ml. The water intake of mice averages 5 ml per mouse per day, these dosages of oleuropein result in daily doses of 0.025 mg, 0.25 mg, 2.5 mg, and 25 mg per mouse per day (equivalent to 1, 10, 100, and 1000 mg/kg body weight). 5 male and 5 female C57BL/6 wild-type mice were used for each dose of oleuropein, and housed them in metabolic cages that allow precise determination of water intake and quantitative urine collection.

B. LC-MS Quantitation

After seven days to 4 months of chronic steady-state administration, mice blood and urine were collected. 100 µl of serum or urine were extracted with 1 ml ethyl acetate, evaporated to dryness, and reconstituted with 25 µl water and 5 µl was injected for LC-MS analysis.

LC-MS quantitation was performed using an HP1100 equipped with diode array detector and ESI-mass spectrometer. LC was done using a C18 column (4×20 mm), with a 4 minute elution using a gradient of 5-95% $CH_3CN$—$H_2O$ containing 1% acetic acid. The diode array recordings were made at 280 nm and 230 nm, and the ESI mass spectrum was made in negative detection mode. Purified oleuropein, and hydroxytyrosol (synthesized by us) were used as standards. The injection volumes were 5 µl. Experiments were optimized by infusion of the standards in negative scan mode to investigate the [M-H] ion of oleuropein glycoside (m/z 539), oleuropein aglycone (m/z 377), and hydroxytyrosol (m/z 153).

C. Summary of Results

FIG. 12 shows results from LC-MS analysis of mice blood and urine after 4 months of chronic steady-state administration. Oleuropein standard shows a single peak by LC (12A) with mass of 539 (m/z 539) (12B). In comparison, the LC profile of serum (12C-D) and urine (12E-F) contain mainly hydroxytyrosol (m/z 153) as well as other derivatives and metabolites. Our results show that 1) we can administer oleuropein in a dose-dependent manner chronically to mice, 2) oleuropein is absorbed by the mice and metabolized to hydroxytyrosol, and 3) we can quantitate the amount of oleuropein and hydroxytyrosol in the serum and urine of mice by LC-MS.

In summary, our results show that oleuropein is bioavailable. It is absorbed and well tolerated in animals. It is metabolized to hydroxytyrosol, which is secreted in urine.

Example 6

Inhibition of HIV-1 Fusion by Oleuropein and Hydroxytyrosol

Materials and Methods
Oleuropein (Ole) and Hydroxytyrosol (HT)

Oleuropein (Ole) was purified from olive leaf extract, characterized, and standardized by liquid chromatography-coupled mass spectrometry (LC-MS) [3]. Hydroxytyrosol (HT) was prepared by stepwise hydrolysis of Ole with (β-glucosidase (Sigma G4511) in 80 mM sodium acetate, pH 5.0 using 1 Unit/mole substrate at 37° C. for 1 hr. This treatment removes the glucose moiety from Ole and yields oleuropein aglycone (Ole-AG). Ole-AG was subsequently hydrolyzed with esterase (Sigma E0887) in 50 mM sodium phosphate buffer at pH 7.5 at 1 Unit/mole substrate at 25° C. for 1 hr to yield hydroxytyrosol and elenolic acid. The mixture was separated by HPLC and standardized by LC-MS. HT was also prepared by chemical synthesis from 3,4-dihydroxylphenylacetic ester (DHPA).

Cell Lines and HIV-1

Uninfected MT2 and H9 cell lines, and HIV-1$_{IIIB}$ chronically infected H9 (H9/HIV-1$_{IIIB}$) and HIV-1/IIIB virus, were obtained through the AIDS Research and Reference Reagent Program, NIAID, NIH. MT-2 cells [4, 5] were obtained from D. Richman, and H9 and HIV-1IIIB virus stocks [6, 7] from R. Gallo. The cell lines were cultured in RPMI medium 1640 containing 100 U/ml penicillin, 100 µg/ml streptomycin, 2 mM L-glutamine, and 10% heat-inactivated fetal calf serum. Viral stocks were prepared and standardized as described [8].

Anti-HIV and Cytotoxicity Assays

The effects of Ole and HT on acute HIV infection and viral replication were measured by assays on syncytial formation in cell-cell HIV-1 transmission and on HIV-1 core protein p24 expression as described [8]. Cytotoxicity was evaluated by the MTT assay [8].

Molecular Modeling

Molecular modeling was performed by molecular docking, molecular dynamics (MD) simulation and free energy calculations [9, 10]. Docking was performed with Autodock version 3.0.5 [11]. The relaxation of docking structure obtained was then implemented under Discovery from Insight II (Accelrys Inc., San Diego, Calif., U.S.A.) using 500 steps of Steepest Descent followed by Conjugate Gradient until the root mean square of the energy gradient reaches a value of 0.01 kcal/molÅ.

HIV-1 gp41 Fusion Peptides C34 and N36

HIV-1 gp41 fusion peptides, N36 and C34 were synthesized by solid phase FMOC method (GeneMed, CA) and purified by HPLC. The sequences of these peptides are (Ac-SGIVQQQNNLLRAIEAQQHLLQLTVWGIKQLQARIL-NH$_2$) and (Ac-WMEWDREINNYTSLIHSLIEESQN-QQEKNEQELL-NH$_2$) respectively. Corresponding viral peptides N36 and C34 prepared from HIV-1 were obtained through the NIH AIDS Research and Reference Reagent Program, NIAID, NIH [12] and used as standards for purification and bioassays.

Fusion Complex Formation

Fusion complex formation was carried out by incubating equimolar amounts of HIV-1 gp41 fusion peptides N36 and C34 in PBS (Phosphate Buffer Saline, containing 50 mM sodium phosphate, pH 7.2 and 150 mM NaCl) at 10 or 20 µM each at 37° C. Peptide N36 was first incubated either alone or with various concentrations of Ole or HT for 30 min. Next, an equimolar amount of C34 was added and the samples incubated for 30 min.

Native Polyacrylamide Gel Electrophoresis (N-PAGE)

N-PAGE was carried out as previously reported [13] with modifications that involve fusion peptide concentration, order of reactions, and time of incubation in fusion complex formation. Tris-glycine gels (18%, Invitrogen, Carlsbad, Calif.) were electrophoresed at 120 V for 2 h, stained with Coomassie Blue and analyzed by densitometry.

Circular Dichroism (CD) Spectroscopy

CD spectra were recorded on an AVIV 62-DS CD spectrometer, using 1 mm sample cells and a fixed temperature of 4° C. [8]. Each spectrum is a smoothed average of 10 scans. The bandwidth for each measurement was 1 nm. CD intensities are expressed as mean residue ellipticities [θ] (degrees cm$^2$/dmol). Prior to calculation of the final ellipticity, all spectra were corrected by subtracting the reference spectra of PBS without peptides.

Results
Preparation and LC-MS Analysis of Oleuropein (Ole) and Hydroxytyrosol (HT)

Figure 13A:
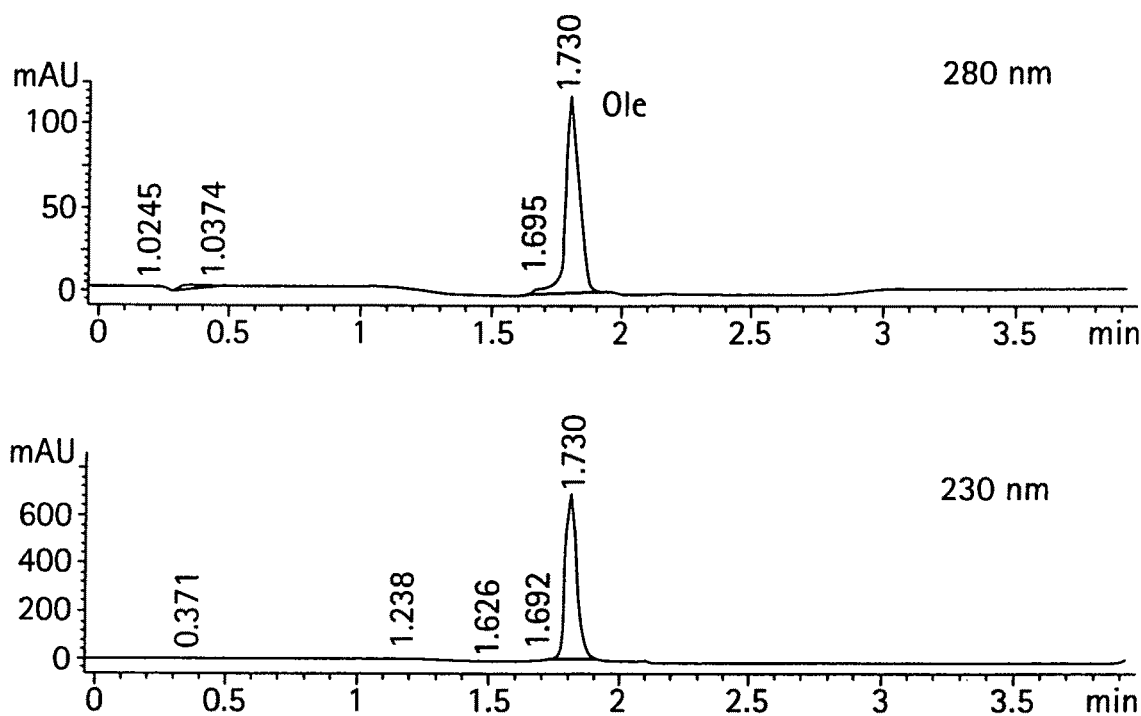
FIG. 13. LC-MS analysis of Ole and HT, metabolism of Ole and chemical synthesis of HT
A. LC elution profile of Ole. B. MS analysis of Ole, showing one major component with a molecular mass of 539. C. LC elution profile of HT. D. MS analysis of HT, showing one major component with a molecular mass of 153. E. Metabolism of Ole, showing major reactions in the production of HT from Ole. F. Chemical synthesis of HT.
Figure 13B:
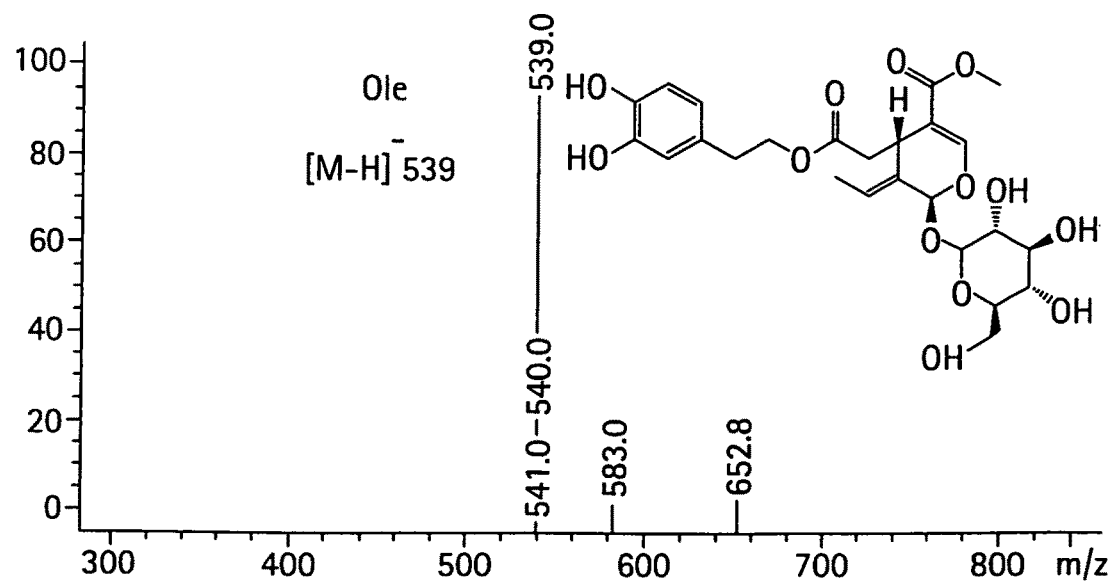
Figure 13C:
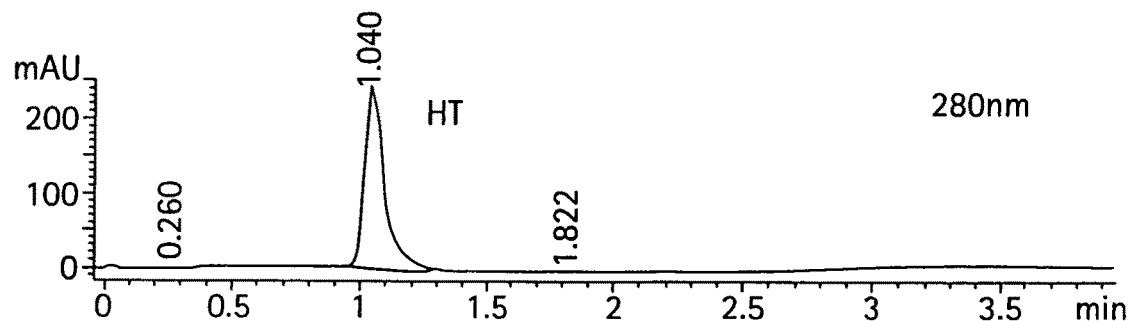
Figure 13D:
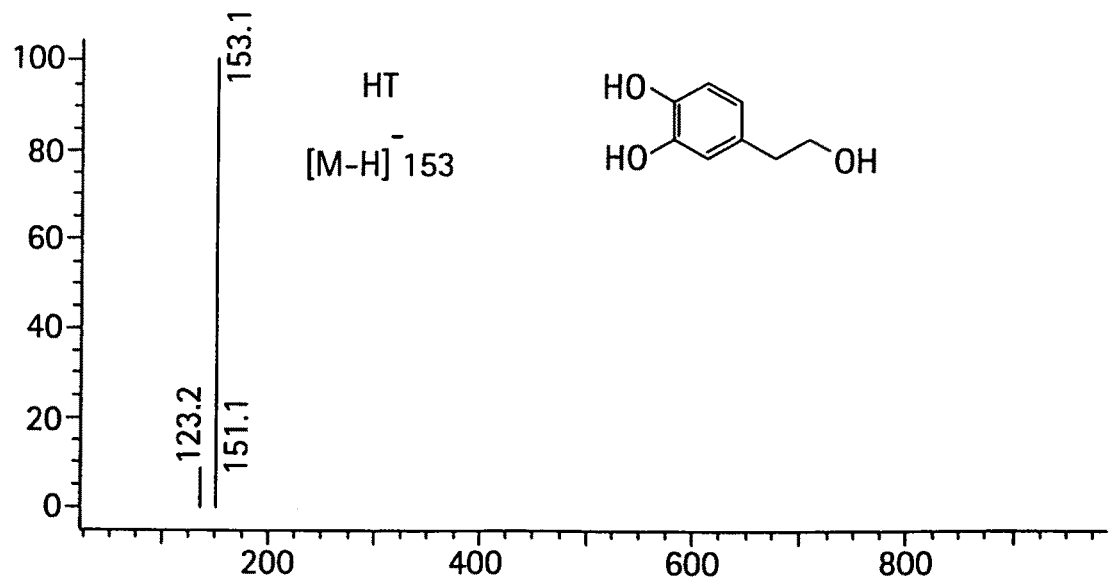
Figure 13E:
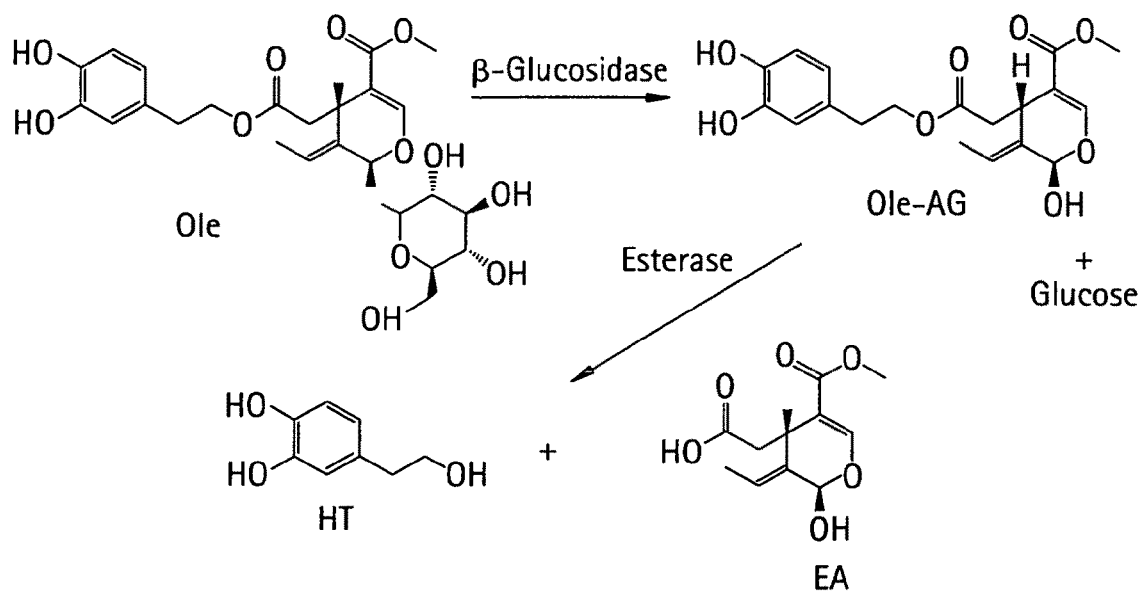
Figure 13F:
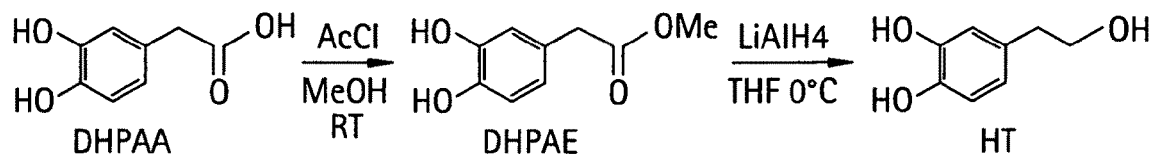

FIGS. 13A-1B and 13C-1D represent LC-MS analysis of Ole and HT. Ole fractionates as a single peak by HPLC at 1.848 min with m/z of 539 and HT as a single peak by HPLC at 1.108 min with m/z of 153. FIG. 13E shows the major steps in Ole metabolism. These are also the basic reactions in HT preparation from Ole. First, the glucose moiety is removed by P-glycosidase to yield oleuropein aglycone (Ole-AG). Next, Ole-AG is hydrolyzed by esterase to yield HT and elenolic acid (EA). FIG. 13F shows chemical synthesis of HT using 3,4-dihydroxylphenylacetic acid (DHPAA) as the starting material. Two major steps are involved: 1) acetylation with acetyl chloride (AcCl), and 2) reduction by LiAlH$_4$ to yield HT. Chemically synthesized HT was purified and characterized by LC-MS, and demonstrates identical biological, chemical and physical properties as natural HT prepared from Ole from olive leaf extract.

Ole and HT Inhibit HIV-1 Infection and Replication, but are not Toxic to Target Cells Ole and HT exhibit dose dependent inhibition of HIV-1 infection and replication as measured by syncytial formation and p24 production (Table 6). The average $EC_{50}$ for Ole is 55 nM for syncytial formation and 73 nM for p24 production. The corresponding $EC_{50}$s are 61 nM and 68 nM for HT. No cytotoxicity was detected, either by MTT assay or trypan blue dye exclusion, over a 10,000-fold concentration range from 1 nM to 10 μM. The $EC_{50}$s for inhibition on fusion complex, 6HB formation are also presented in Table 6.

Ole and HT Bind to the Conserved Hydrophobic Pocket on the Surface of the Central Trimeric Coiled-Coil of HIV-1 gp41

Inhibition of syncytial formation by Ole and HT reflects effects on early events during viral infection/entry, including CD4 receptor and coreceptor binding as well as viral fusion. To probe anti-HIV mechanisms of Ole and HT, we carried out molecular docking and MD calculations of these small molecules with viral targets. We found that Ole and HT bind to the conserved hydrophobic pocket on the surface of the central trimeric coiled-coil of the HIV-1 gp41 fusion domain.

Figure 14A:
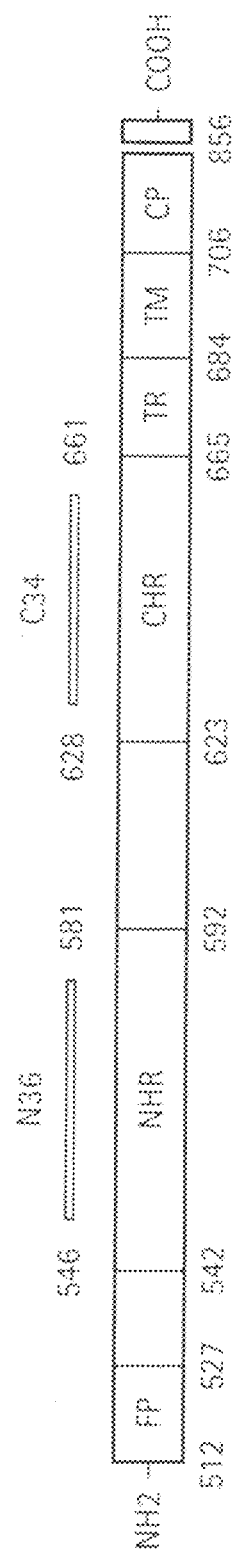
FIG. 14. HIV-1 gp41 and the formation of fusion core 6HB.
A. Structure map of 1-HIV-1 gp41, FP (fusion peptide), NHR (N-terminal heptad repeat), CHR (C-terminal heptad repeat), TR (tryptophan-rich), TM (transmembrane), and CP (cytoplasmic) domains. Residue numbers correspond to positions in gp160 of HIV-1HXB2. B. Formation of 6HB by N36 and C34 helices, showing the trimeric coiled-coil core of N36 and the surrounding three C34s. C. and D. Effect of Ole and HT on fusion core, 6HB formation, showing the binding of Ole or HT to the N36 trimeric coiled-coil core thus inhibiting 6HB formation.
Figure 14D:
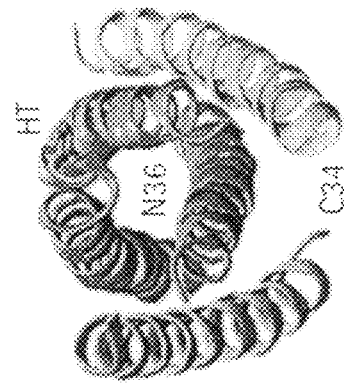
Figure 14C:
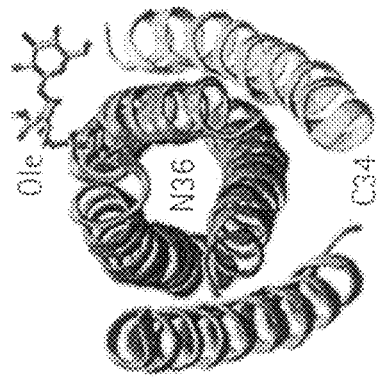
Figure 14B:
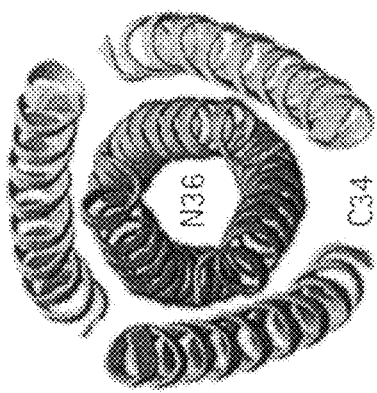

HIV-1 envelope glycoprotein (Env) mediates viral entry by fusing virus to target cells. Env is trimeric on the virion surface. Each monomer contains a surface subunit, gp120, for virus binding to CD4 receptor and coreceptors [14-17] and a noncovalently associated transmembrane subunit, gp41, that mediates fusion of the virus with the target cell [18, 19]. FIG. 14A shows the structure of HIV-1 gp41. Like other type I transmembrane proteins, HIV-1 gp41 consists of extracellular (ectodomain), transmembrane, and cytoplasmic domains. The ectodomain contains four functional regions: the fusion peptide, N-terminal heptad repeat (NHR), C-terminal heptad repeat (CHR), and a tryptophan-rich region. Binding of gp120 to the cellular receptor CD4 and co-receptor triggers conformational changes in gp41 that induce fusion [20-23]. This increases exposure of two heptad repeat motifs, NHR and CHR, and insertion of the fusion peptide into the target membrane [20-23]. Subsequently NHR and CHR fold in an antiparallel manner to create the six-helix bundle 6HB composed of a trimeric NHR coiled-coil core surrounded by three CHR helices that pack in the grooves of the coiled-coil as seen in FIG. 14B [24-26]. Formation of the 6HB promotes fusion between viral and cellular membranes and is essential for viral entry and infection [25, 26]. Ole and HT interact with the NHR coiled-coil trimer N36 helices and interfere with the formation of 6HB with the CHR, C34, as shown in FIGS. 14C and 14D.

Figure 15E:
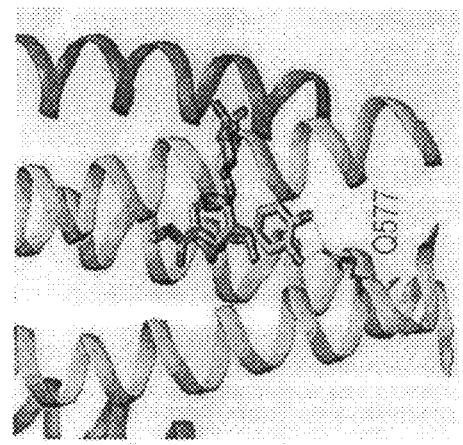
FIG. 15. Molecular docking of Ole and HT with HIV-1 gp41
A. Structures of the 5-helical gp41 bundle. B. Structure of Ole. The 9 freely rotating bonds are shown. C. and D. The predicted binding structures of Ole (C) and HT (D) inside the HIV-1 gp41 hydrophobic site. gp41 is shown as a surface model and Ole and HT are shown as stick models. Both molecules form stable hydrogen bonds with Q577 (green) on N36 peptide. E. and F. Ribbon representation showing hydrogen binding of gp41 5HB with Ole (E) and HT (F). The trimeric coiled-coil core of N36 peptides are pink and C34 peptides green. The Ole and HT molecules are shown as stick formation and hydrogen bonds with Q577 are in green dashed lines.
Figure 15F:
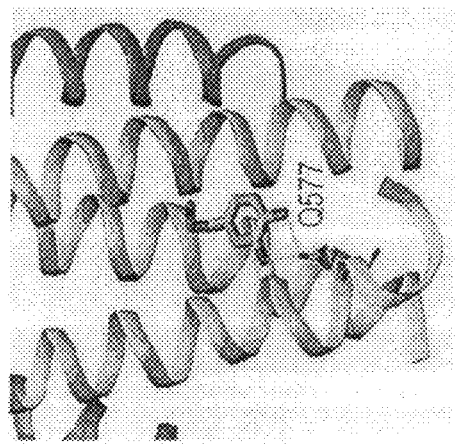
Figure 15C:
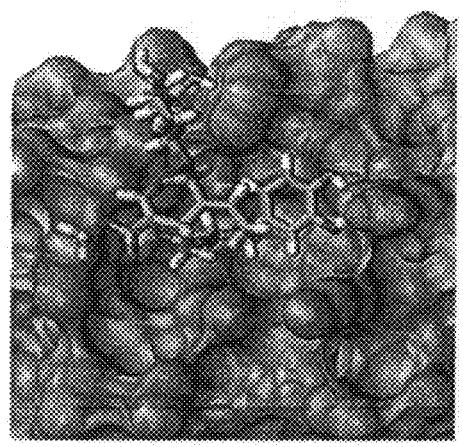
Figure 15D:
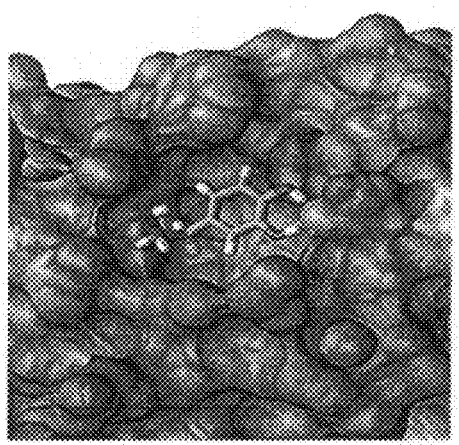
Figure 15A:
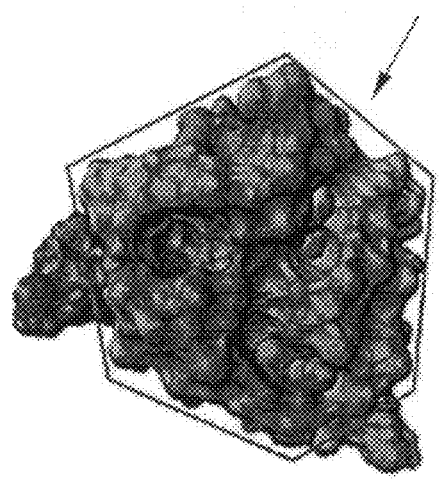
Figure 15B:
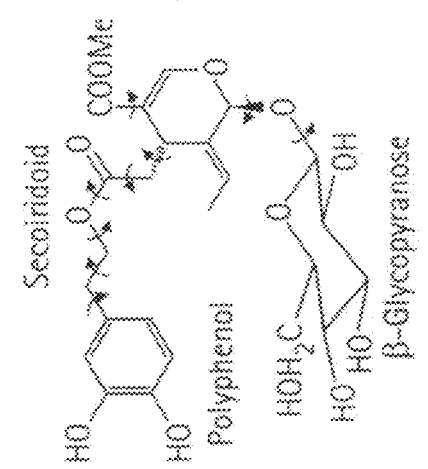

We used the crystal structure of the HIV-1 gp41 fusion complex, PDB code 1AIK [20] as a reference for our modeling work. To provide a ligand binding site, one of the C34 helices was removed from the 6HB (FIG. 15A). FIG. 15B shows the chemical structure of Ole with the 9 free rotatable bonds selected in our modeling interaction.

Molecular simulations suggest that the conserved hydrophobic cavity of the gp41 N36 trimer coiled-coil is the most likely binding site for Ole and HT. This cavity is mainly occupied by W628, W631 and neighboring I635 and D632. The predicted binding structures of Ole and HT are shown in FIGS. 15C and 15D respectively. Ole and HT form stable hydrogen bonds with Q577 on the N36 peptide. FIGS. 15E and 15F are ribbon representations of the predicted binding site of Ole and HT. 5HB, consisting of three N36-peptides (pink, residues 546-581) and two C34 peptides (green, residues 628-661), is used for docking calculations. Only one groove is exposed for the binding of small molecules. Both Ole and HT occupy the binding site similarly, with the diphenol ring forming stable hydrogen bonds with Q577. This blocks the close contacts between the hydrophobic groove in the gp41 NHR and the indole rings of W631 and W628, thus interfering with the formation of 6HB. In addition to hydrogen binding, hydrophobic interactions with I573, G 572, and L 568 also play important roles in the interaction.

Native PAGE Shows that Ole and HT Inhibit HIV-1 Fusion Core 6HB Formation

To test the predictions from molecular modeling, we examined the effect of Ole and HT on the formation of fusion complex 6HB by electrophoretic mobility shift using native-PAGE (FIG. 16A). The electrodes were connected from cathode (negative terminal on top) to anode (positive terminal on bottom) and the peptides move in the electric field according to their charge and size. Peptides carrying net negative charges, such as C34, moves toward the positive terminal (bottom) whereas peptides carrying net positive charges, such as N36, moves toward the negative terminal or remain at the top of the well. Incubation of N36 and C34 resulted in the formation of the 6HB fusion complex which is larger than C34, moves slower than free C34, and thus migrates to the middle of the gel. Pre-incubation of N36 with Ole or HT results in inhibition of 6HB formation. A dose-dependent disappearance of 6HB band was detected with concomitant appearance of the free C34 band. Total inhibition is achieved at 100 nM Ole or HT with $EC_{50}$s around 66 and 58 nM. These results confirm the predictions from molecular modeling.

CD Analysis Indicates that Ole and HT Inhibit HIV-1 Fusion Core 6HB Formation

We also used CD analysis to confirm molecular modeling predictions (FIG. 16B). Because N36 and C34 are single stranded random coils, they do not assume ordered structure in solution, so they display characteristic random coil CD spectra. However, formation of fusion complex 6HB results in a distinctive CD spectrum, including a saddle-shaped negative peak between 210-220 nm in the far UV region and a significant increase in molar ellipticity (θ) at 222 nm. Preincubation of N36 with Ole or HT interrupts 6HB formation and results in a dose dependent shift of the CD spectra from helical to random coil with $EC_{50}$s of 62 nM for Ole and 60 nM for HT.

TABLE 6

Anti-HIV Activity and Inhibition on HIV-1 Fusion Core Formation

| | Anti-HIV Activity[a] | | Inhibitory Activity[b] $EC_{50}$ (nM) Fusion Core Formation | |
|---|---|---|---|---|
| | $EC_{50}$ (nM) | | $IC_{50}$ (nM) | 6HB (N36 + C34) |
| Compound | Syncytium | P24 | Cytotoxicity | N-PAGE | CDSA |
| Ole | 55 ± 5 | 73 ± 8 | >10,000 | 66 ± 5 | 62 ± 6 |
| HT | 61 ± 6 | 68 ± 8 | >10,000 | 58 ± 8 | 60 ± 4 |

[a]$EC_{50}$, effective concentration at 50% inhibition; $IC_{50}$, cytotoxicity concentration at 50% inhibition.
[b]N-PAGE, native polyacrylamide gel electrophoresis; CDSA, circular dichroism spectroscopy analysis.
Values are means ± SD of triplicates in three independent determinations.

Discussion

Ole and HT are small molecules with molecular weights of 539 and 153 respectively. Their inhibition of the fusion-promoting refolding of gp41 is an excellent example of how small molecules can block formation of protein-protein complexes. We narrowed down the target of binding to a hydrophobic pocket on the gp41 inner core. This pocket is highly conserved among the different HIV clades. Consistent with this, we found that Ole and HT are active against a panel of HIV-1 primary isolates that includes both M and T tropic strains from different clades. Our results suggest that Ole and HT may be useful against other viruses with type I transmembrane envelope glycoprotein, including severe acute respiratory syndrome associated coronavirus [23, 27], respiratory syncytial virus, Ebola virus [28], measles virus [29], and avian flu [30, 31].

Fuzeon (T-20 or Enfuvirtide) is the only FDA approved HIV fusion inhibitor [32, 33]. It is a peptide derived from the CHR region of gp41 that partially overlaps with the C34 sequence. Fuzeon is commercially produced by chemical synthesis. Because of its large size—it consists of 36 amino acids with a molecular weight of 4492—its manufacturing process is very complex, involving 106 chemical steps [34, 35]. In contrast, our typical process for chemical synthesis of HT involves only two steps: acetylation and reduction (FIG. 13F). In addition, Ole and HT can also be easily prepared from natural olive leaf extract in only two steps: deglycosylation and oxidation (FIG. 13E). The fact that Ole and HT act both outside and inside of the cellular environments in viral entry and integration offers unique benefits to these small molecules against viral resistance.

REFERENCES

[1] S. M. Hammer, Clinical practice. Management of newly diagnosed HIV infection, N Engl J Med 353 (2005) 1702-1710.
[2] J. Cohen, Therapies. Confronting the limits of success, Science 296 (2002) 2320-2324.
[3] S. Lee-Huang, L. Zhang, P. L. Huang, and Y. T. Chang, Anti-HIV activity of olive leaf extract (OLE) and modulation of host cell gene expression by HIV-1 infection and OLE treatment, Biochem Biophys Res Commun 307 (2003) 1029-1037.
[4] T. Haertle, C. J. Carrera, D. B. Wasson, L. C. Sowers, D. D. Richman, and D. A. Carson, Metabolism and anti-human immunodeficiency virus-1 activity of 2-halo-2',3'-dideoxyadenosine derivatives, J Biol Chem 263 (1988) 5870-5875.
[5] S. Harada, Y. Koyanagi, and N. Yamamoto, Infection of HTLV-III/LAV in HTLV-I-carrying cells MT-2 and MT-4 and application in a plaque assay, Science 229 (1985) 563-566.
[6] D. L. Mann, S. J. O'Brien, D. A. Gilbert, Y. Reid, M. Popovic, E. Read-Connole, R. C. Gallo, and A. F. Gazdar, Origin of the HIV-susceptible human CD4+ cell line H9, AIDS Res Hum Retroviruses 5 (1989) 253-255.
[7] M. Popovic, M. G. Sarngadharan, E. Read, and R. C. Gallo, Detection, isolation, and continuous production of cytopathic retroviruses (HTLV-III) from patients with AIDS and pre-AIDS, Science 224 (1984) 497-500.
[8] S. Lee-Huang, V. Maiorov, P. L. Huang, A. Ng, H. C. Lee, Y. T. Chang, N. Kallenbach, P. L. Huang, and H. C. Chen, Structural and functional modeling of human lysozyme reveals a unique nonapeptide, HL9, with anti-HIV activity, Biochemistry 44 (2005) 4648-4655.
[9] D. A. Case, T. E. Cheatham, 3rd, T. Darden, H. Gohlke, R. Luo, K. M. Merz, Jr., A. Onufriev, C. Simmerling, B. Wang, and R. J. Woods, The Amber biomolecular simulation programs, J Comput Chem 26 (2005) 1668-1688.
[10] Y. Duan, C. Wu, S. Chowdhury, M. C. Lee, G. Xiong, W. Zhang, R. Yang, P. Cieplak, R. Luo, T. Lee, J. Caldwell, J. Wang, and P. Kollman, A point-charge force field for molecular mechanics simulations of proteins based on condensed-phase quantum mechanical calculations, J Comput Chem 24 (2003) 1999-2012.
[11] D. S. Goodsell, G. M. Morris, and A. J. Olson, Automated docking of flexible ligands: applications of AutoDock, J Mol Recognit 9 (1996) 1-5.
[12] S. A. Gallo, K. Sackett, S. S. Rawat, Y. Shai, and R. Blumenthal, The stability of the intact envelope glycoproteins is a major determinant of sensitivity of HIV/SIV to peptidic fusion inhibitors, J Mol Biol 340 (2004) 9-14.
[13] S. Liu, Q. Zhao, and S. Jiang, Determination of the HIV-1 gp41 fusogenic core conformation modeled by synthetic peptides: applicable for identification of HIV-1 fusion inhibitors, Peptides 24 (2003) 1303-1313.
[14] Y. Feng, C. C. Broder, P. E. Kennedy, and E. A. Berger, HIV-1 entry cofactor: functional cDNA cloning of a seven-transmembrane, G protein-coupled receptor, Science 272 (1996) 872-877.
[15] P. D. Kwong, R. Wyatt, J. Robinson, R. W. Sweet, J. Sodroski, and W. A. Hendrickson, Structure of an HIV gp120 envelope glycoprotein in complex with the CD4 receptor and a neutralizing human antibody, Nature 393 (1998) 648-659.
[16] C. D. Rizzuto, R. Wyatt, N. Hernandez-Ramos, Y. Sun, P. D. Kwong, W. A. Hendrickson, and J. Sodroski, A conserved HIV gp120 glycoprotein structure involved in chemokine receptor binding, Science 280 (1998) 1949-1953.
[17] Q. J. Sattentau, A. G. Dalgleish, R. A. Weiss, and P. C. Beverley, Epitopes of the CD4 antigen and HIV infection, Science 234 (1986) 1120-1123.
[18] D. C. Chan, and P. S. Kim, HIV entry and its inhibition, Cell 93 (1998) 681-684.
[19] J. Moore, B. Jameson, R. Weiss, and Q., in Viral Fusion Mechanisms, in Benz, J., (Ed.), CRC Press, Boca Raton, Fla., 1993, pp. 233-289.
[20] D. C. Chan, D. Fass, J. M. Berger, and P. S. Kim, Core structure of gp41 from the HIV envelope glycoprotein, Cell 89 (1997) 263-273.
[21] D. M. Eckert, and P. S. Kim, Mechanisms of viral membrane fusion and its inhibition, Annu Rev Biochem 70 (2001) 777-810.
[22] M. Lu, S. C. Blacklow, and P. S. Kim, A trimeric structural domain of the HIV-1 transmembrane glycoprotein, Nat Struct Biol 2 (1995) 1075-1082.
[23] Y. Xu, Z. Lou, Y. Liu, H. Pang, P. Tien, G. F. Gao, and Z. Rao, Crystal structure of severe acute respiratory syndrome coronavirus spike protein fusion core, J Biol Chem 279 (2004) 49414-49419.
[24] S. Jiang, K. Lin, N. Strick, and A. R. Neurath, HIV-1 inhibition by a peptide, Nature 365 (1993) 113.
[25] K. Tan, J. Liu, J. Wang, S. Shen, and M. Lu, Atomic structure of a thermostable subdomain of HIV-1 gp41, Proc Natl Acad Sci USA 94 (1997) 12303-12308.
[26] W. Weissenhorn, A. Dessen, S. C. Harrison, J. J. Skehel, and D. C. Wiley, Atomic structure of the ectodomain from HIV-1 gp41, Nature 387 (1997) 426-430.
[27] B. Tripet, M. W. Howard, M. Jobling, R. K. Holmes, K. V. Holmes, and R. S. Hodges, Structural characterization of the SARS-coronavirus spike S fusion protein core, J Biol Chem 279 (2004) 20836-20849.
[28] W. Weissenhorn, A. Carfi, K. H. Lee, J. J. Skehel, and D. C. Wiley, Crystal structure of the Ebola virus membrane fusion subunit, GP2, from the envelope glycoprotein ectodomain, Mol Cell 2 (1998) 605-616.
[29] D. M. Lambert, S. Barney, A. L. Lambert, K. Guthrie, R. Medinas, D. E. Davis, T. Bucy, J. Erickson, G. Merutka, and S. R. Petteway, Jr., Peptides from conserved regions of paramyxovirus fusion (F) proteins are potent inhibitors of viral fusion, Proc Natl Acad Sci USA 93 (1996) 2186-2191.

[30] D. Normile, Avian influenza. New H5N1 strain emerges in southern China, Science 314 (2006) 742.

[31] D. Q. Wei, Q. S. Du, H. Sun, and K. C. Chou, Insights from modeling the 3D structure of H5N1 influenza virus neuraminidase and its binding interactions with ligands, Biochem Biophys Res Commun 344 (2006) 1048-1055.

[32] V. Oldfield, G. M. Keating, and G. Plosker, Enfuvirtide: a review of its use in the management of HIV infection, Drugs 65 (2005) 1139-1160.

[33] D. Robertson, US FDA approves new class of HIV therapeutics, Nat Biotechnol 21 (2003) 470-471.

[34] B. L. Bray, Large-scale manufacture of peptide therapeutics by chemical synthesis, Nat Rev Drug Discov 2 (2003) 587-593.

[35] A. Castagna, P. Biswas, A. Beretta, and A. Lazzarin, The appealing story of HIV entry inhibitors: from discovery of biological mechanisms to drug development, Drugs 65 (2005) 879-904.

Example 7

Effect of Oleuropein and Hydroxytyrosol on HIV-1 Integrase

Material and Methods
Oleuropein (Ole) and Hydroxytyrosol (HT)

Ole and HT used in this study were prepared and purified from olive leaf extract as described in the preceding article.

Target Cells, HIV-1, Anti-HIV and Cytotoxicity Assays

Target cells MT2, H9, HIV-1$_{IIIB}$ chronically infected H9 (H9/HIV-1$_{IIIB}$) and HIV-1/IIIB virus, were obtained through the AIDS Research and Reference Reagent Program, NIAID, NIH. MT-2 cells were from D. Richman [7, 8]. H9 cells and HIV-1IIIB virus stocks were from R. Gallo [9, 10]. The cell lines were cultured in RPMI medium 1640 containing 100 U/ml penicillin, 100 µg/ml streptomycin, 2 mM L-glutamine, and 10% heat-inactivated fetal calf serum. Viral stocks were prepared and standardized as described previously [11]. Anti-HIV activity was measured by the microliter syncytial formation and HIV-1 p24 production assays [11]. Cytotoxicity was determined by the MTT assay [11].

Molecular Modeling

A combination of molecular docking, molecular dynamics (MD) simulation and free energy calculations [12, 13] were performed to probe the interactions of Ole or HT with viral targets. Docking was performed with AutoDock version 3.0.5 [14]. Relaxation of docking structure obtained was carried out by the program Discovery from Insight II (Accelrys Inc., San Diego, Calif., U.S.A.), using 500 steps of Steepest Descent followed by Conjugate Gradient until the root mean square (RMS) of the energy gradient reaches 0.01 kcal/molÅ.

HIV-1 Integrase

HIV-1 integrase was expressed in *E. coli* from pIN (F185H/C280S) and purified according to previously reported method [15]. This recombinant clone makes the integrase protein more soluble and stable without affecting in vitro activity. HIV-1 integrase protein (F185H/C280S) was used as a standard for purification and assay. The integrase clone pIN (F185H/C280S) and the standard integrase protein were obtained through the NIH AIDS Research and Reference Reagent Program, NIAID, NIH from Dr. Robert Craigie [16].

Integrase Substrates

Oligonucleotide substrates were synthesized and purified as described previously [17]. Three types of substrates were synthesized with sequences that correspond to the U3 and U5 ends of HIV-LTR: (i) the 21-nucleotide minus strand of U3 end HIV-LTR 5'-GAGTGAATTAGCCCTTCCAGT-3' (SEQ ID NO: 41), and the U5 HIV-LTR, 5'-GTGTG-GAAAATCTCTAGCAGT-3' (SEQ ID NO: 42), as well as their complementary strands, for assaying the 3'-processing reaction; (ii) the 19-mer U3-GT, and U5-GT (i.e., U3 and U5 minus the 3'-end dinucleotide GT) for assaying heterologous integration (strand transfer); and (iii) a 38-mer dumbbell substrate with the sequence 5'-TGCTAGTTCTAGCAGGCCCT-TGGGCCGGCGCTTGCGCC-3' (SEQ ID NO: 43), for assaying the dis-integration.

Radiolabeling and Preparation of the Substrates

The integrase substrates were 5'-end radiolabeled as reported previously [17]. Briefly, 1 µg of the oligonucleotide was 5'-end labeled with 100 µCi of [α-$^{32}$P] ATP (3000 Ci/mmol; 1 Ci=37 GBq; A-mersham) by 20 units of polynucleotide T4 kinase in a final volume of 40 µl of kinase buffer (Boehringer Mannheim) at 37° C. for 60 min. The reaction was stopped by EDTA (25 mM) and heat inactivation. Unincorporated label was removed by two passages through a Sephadex G-25 spin column (Boehringer Mannheim). The purified labeled oligonucleotide was then annealed with an equimolar amount of unlabeled complementary strand in 10 mM Tris HCl, pH 7.5/1 mM EDTA/100 mM NaCl at 95° C. for 5 min followed by slow cooling. The dumbbell substrate was self-annealed under the same conditions.

Integrase Assays

Integrase assays were carried out in 20 mM Hepes, pH 7.5/10 mM MgCl$_2$ or MnCl$_2$/10 mM dithiothreitol/0.05% Nonidet P-40 (integrase buffer) with 40 pmol of HIV-1 integrase and 20 ng of 5'-end radiolabeled substrates specific for 3'-processing (21-mer U3), strand-transfer (19-mer U3-GT)) or disintegration (38-mer dumbbell) in the presence or absence of Ole or HT in a final volume of 10 µl at 37° C. for 60 min. For 3'-processing and disintegration, the reactions were stopped by the addition of 10 µl of 90% formamide/0.025% bromophenol blue/0.025% xylene cyanol/89 mM Tris/89 mM boric acid/2 mM EDTA, pH 8.0. Samples were heated at 75° C. for 3 mM, load at 10 µl/well onto 18% polyacrylamide denaturing (7.5 M urea) gels in TBE buffer and electrophoresed at 200 V constant voltage at room temperature for 2 h. The results were visualized by autoradiography of wet gels. For strand-transfer (integration), pUC18 plasmid DNA (50 ng) was used as the target for the integration of viral DNA into heterologous plasmid DNA. The reaction was stopped by 0.1% SDS and integration products monitored on 1% agarose gels at 10 µl/well in TBE buffer at 100 V constant voltage at room temperature for 45 min. The results were visualized by autoradiography of dried gels.

Results

Ole and HT Bind to the Catalytic Site of HIV-1 Integrase

To examine the molecular interactions of Ole and HT with HIV integrase, we performed a series of docking simulations. In these studies, we focused on the catalytic core domain (CCD) of the viral enzyme, because the linkages between the CCD and both the N- and C-terminal domains (NTD and CTD) are flexible and have been not precisely determined. We used the crystal structure 1QS4 (pdb ID) as the starting structure [18], because it is the only structure has an inhibitor (5CITEP) bound in the active site. To keep the binding pocket available, we removed the ligand (5CITEP) from the CCD. Before docking, the missing residues in the loop region and the point mutation at position 185 were restored with AMBER software. The K185 mutation was converted to the native F185.

Figure 17A:
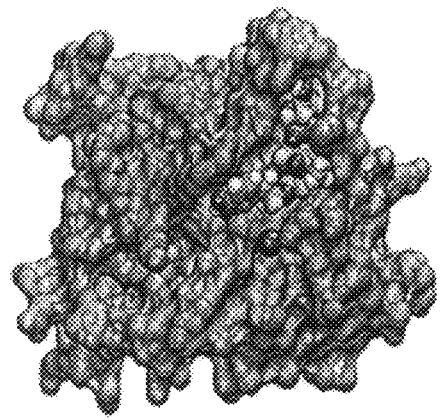
FIG. 17. Molecular docking of Ole and HT with HIV-1 integrase
The predicted binding structures of Ole (A) and HT (B) inside the HIV-1 integrase catalytic site. Integrase is shown as a surface model, while Ole and HT are shown as van der Waals models and the purple sphere represents $Mg^{2+}$. Hydrogen bonds formed by Ole (C) and HT (D) with integrase are indicated as green dotted lines, and the integrase backbone is represented by the cyan ribbon.
Figure 17B:
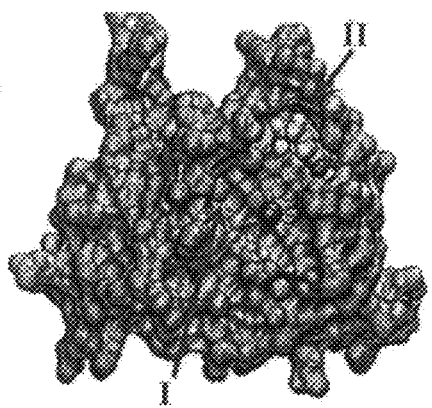

FIGS. 17A and 17B represent the predicted bound conformations of Ole and HT within the active site of HIV-1 integrase. Two unique binding regions have been identified within the integrase active site [2, 4], referred to as regions I and II (FIG. 17B). Region I, near the active site center, encompasses the conserved DDE motif, D64-D116-E152 in HIV-1 integrase. These residues are highly conserved in all integrases, retrotransposases and other DNA-processing enzymes (polynucleotide transferases). Mutation of any of these acidic amino acids abolishes integrase activities and viral replication. D64 and D116 are involved in the formation of coordination complex with divalent metal (Mg2+ or Mn2+). A second metal (Mg2+ or Mn2+) can be coordinated between D116 and E152 once HIV-1 integrase binds its DNA substrates (20, 21). Metal ion coordination with viral integrase and the phosphodiester backbone of the DNA substrates are likely to occur during 3'-processing and strand-transfer reactions. Region II is close to the active catalytic loop (amino acid residues 139-147), and involves the flexible loop formed by amino acid residues 140-149. This loop region has been identified as the DNA binding site which is important for integrase action [19].

Figure 17C:
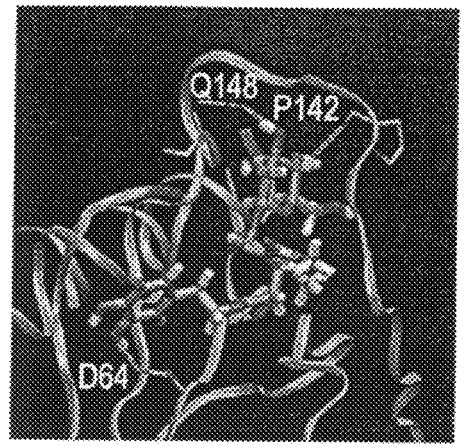
Figure 17D:
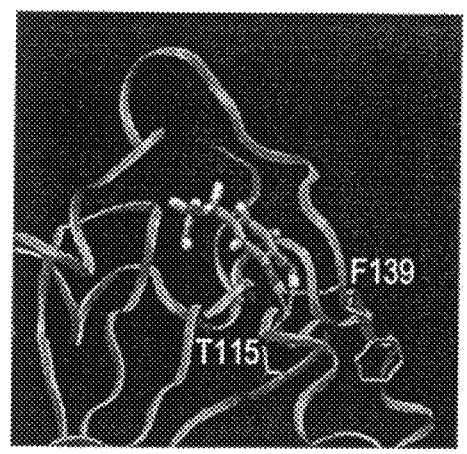

As seen in FIG. 17A, Ole binds to both regions I and II. The β-glycopyranose moiety of Ole interacts with residues in region II whereas the dihydroxyphenol ring occupies region I. FIGS. 17C and 17D are ribbon representation of the HIV-integrase CCD showing major strong H-bonding sites with Ole and HT. The flexible loop widens the active site region and allows the sugar ring of Ole to dock with strong H-bond with P142 and Q148 as well as form weak interactions with S147. The dihydroxyphenol moiety of Ole binds to region I with a strong H-bond interaction with D64 and a weak H bond-network interactions with K156 and K159. This suggests that Ole would be a strong integrase binding inhibitor because it interacts with residues in both regions I and II. On the other hand, the dihydroxyphenol ring of HT binds to region II with strong H bond interaction with F139 and nearby T115, and weak interactions with E138 and Q 148. Since the dihydroxyphenol ring is capable of binding both regions I and II, HT maintains the ability to bind the integrase active site even if mutations occur. Thus the likelihood of resistance development should be less than inhibitors that bind to a single site. Thus, interaction modeling suggests that Ole and HT bind to both regions I and II, so they would be expected to be effective against metal coordination as well as substrate binding. Modeling results therefore predict that Ole and HT would inhibit all of the three HIV-1 integrase activities.

Ole and HT Inhibit 3'-Processing Activity of HIV-1 Integrase

Modeling predictions that Ole and HT may affect HIV-integrase activity were tested in all of the three activities, namely 3'-processing, strand transfer (integration) and disintegration. Results of HIV-1 integrase inhibitory activities of Ole and HT are summarized in Table 7 with their anti-HIV activities.

Figure 18A:
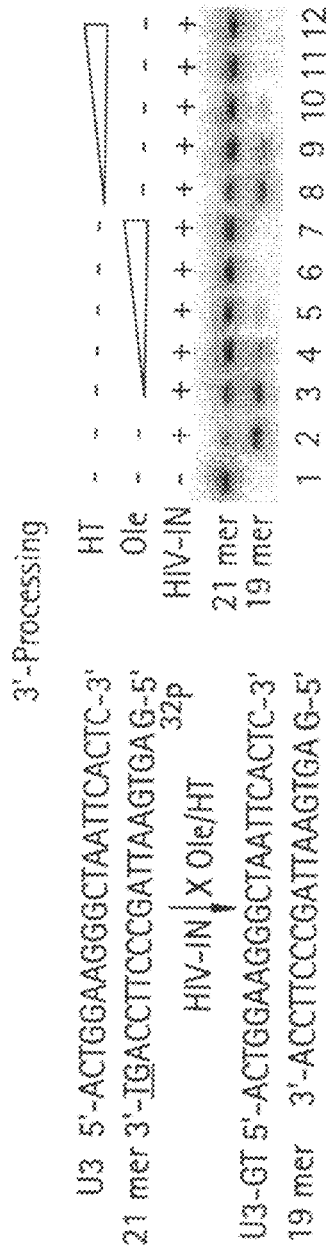
FIG. 18. The effect of Ole and HT on HIV-1 integrase 3'-processing, strand transfer and disintegration activities
A. The effect of Ole and HT on HIV-1 integrase 3'-processing activity
Left: Schematic representation of the 3'-processing activity of HIV-1 integrase. A 5'-$^{32}$P-labeled 21-mer of HIV-1 LTR U3 double-stranded (ds) DNA was used as the substrate. Specific cleavage of the dinucleotide GT from the 3' end of the substrate results in the formation of 19-mer 3'-recessed U3-GT.
Right: Inhibition of HIV-1 integrase 3'-processing activity by Ole and HT. Inhibition was monitored by the formation of labeled 19-mer product. Lane 1, the 21-mer substrate, 5'-$^{32}$P-labeled U3. Lane 2, cleavage of the 3' GT of the 21-mer substrate by HIV-1 integrase results in the formation of the 19-mer 3'-recessed U3-GT. Lanes 3-7 or 8-12, in the presence of 25, 50, 75, 100, and 200 nM Ole or HT.
B. The effect of Ole and HT on HIV-1 integrase strand transfer activity
Left: Schematic representation of strand transfer (integration). Pre-cleaved 5'-$^{32}$P-labeled U3-GT 19-mer was used as the viral substrate and, unlabeled pUC18 DNA (2.69 kb) was used as the heterologous target substrate.
Right: Inhibition of strand-transfer activity of HIV-1 integrase by Ole and HT. Integration was monitored by the conversion of the unlabeled plasmid into labeled DNA. Lanes 1,5'-$^{32}$P-labeled size marker, HindIII fragments of λ phage DNA. Lanes 2, target substrate, pUC18; because it is unlabeled, it is not seen in the autoradiogram. Lanes 3, the product of integration (ST) by HIV-1 integrase. The integration of the 5'$^{32}$P-labeled U3-GT into pUC18 results in the appearance of labeled band at 2.69 kb, corresponding to the size of pUC18. Lanes 4-8, in the presence of 25, 50, 75, 100 and 200 nM Ole or HT.
C. The effect of Ole and HT on HIV-1 integrase disintegration activity
Left: Schematic representation of the disintegration activity of HIV-1 integrase. The 5' $^{32}$P-labeled 38-mer dumbbell was used as the substrate and shown with the predicted secondary structure. Disintegration yields a $^{32}$P-labeled 14-mer consisting of the viral sequences in the hairpin stem and a 24-mer unlabeled target sequence that has been repaired.
Right: Inhibition of disintegration activity of HIV-1 integrase by Ole and HT. Lane 1, the 5' $^{32}$P-labeled 38-mer dumbbell substrate. Lane 2, treatment with HIV-1 integrase results in the formation of the 5' $^{32}$P-labeled 14-mer disintegration product. Lanes 3, 4, 5, 6, 7 disintegration assays in the presence of 25, 50, 75, 100, and 200 nM Ole. Lanes 8, 9, 10, 11, 12, in the presence of 25, 50, 75, 100 and 200 nM HT.

FIG. 18A shows the 3'-processing reaction and results. 5' [$^{32}$P] labeled 21-mer double-stranded oligonucleotide that mimics the U3 HIV-1 LTR was used as a substrate. 3'-processing by HIV-1 integrase, removes the dinucleotide GT from the 3' end of the labeled minus strand of the 21-mer substrate and yields a 3' recessed product (U3-GT) with 19 nucleotides in length. Ole or HT inhibits the 3'-processing activity of HIV-1 integrase. FIG. 18A demonstrates dose-dependent inhibition of 3'-processing by Ole and HT as detected by 7.5 M urea denaturating polyacrylamide gel electrophoresis. Inhibition of the formation of the 19-mer product from the 21-mer substrate increases with the increase of Ole or HT concentration from 25 to 100 nM. The degree of inhibition depends on the concentrations of the HIV-1 integrase, the substrate and the inhibitor. Under our assay conditions, $EC_{50}$s of 46 and 54 nM were obtained for Ole and HT respectively, and total inhibition was observed at 100 nM. Substrate U5 HIV-LTR showed similar results.

Ole and HT Inhibit Strand-Transfer Activity of HIV-1 Integrase

Figure 18B:
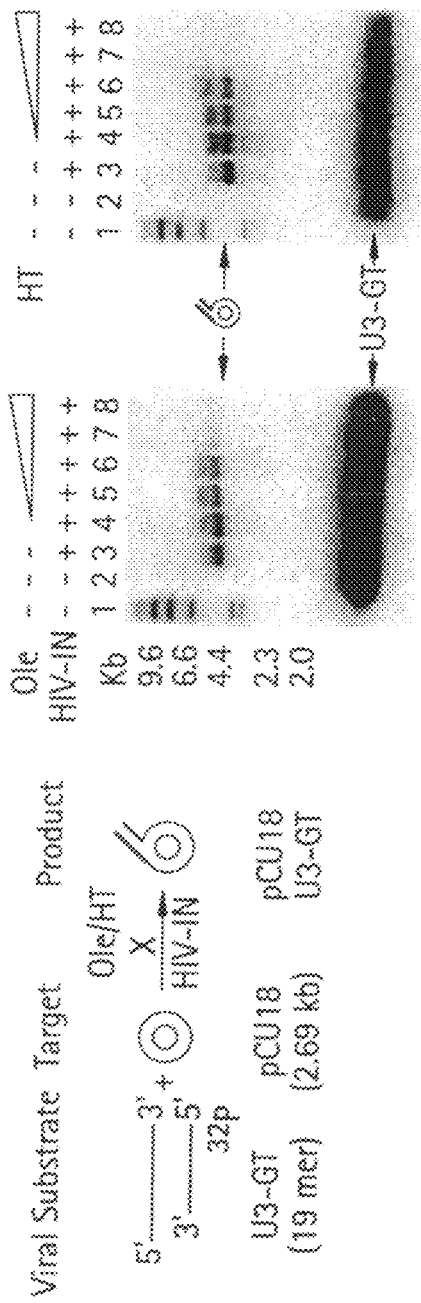

The effect of Ole and HT on the strand-transfer activity of HIV-1 integrase was tested by a quantitative heterologous integration assay. FIG. 18B shows the design and results of this assay: U3-GT, a 5' [$^{32}$P] labeled and 3'-recessed 19-mer was used as the viral substrate. To focus on strand transfer, a supercoiled pUC18 plasmid DNA of 2.69 kb was used as the heterologous target. Incubation of the 5' [$^{32}$P] labeled viral substrate with unlabeled target in the presence of HIV-1 integrase results in the integration of the labeled 19-mer viral substrate into the 2.69 kb target plasmid. Integration was monitored by the conversion of unlabeled plasmid to labeled DNA in agarose gel electrophoresis as seen in the figure. Under these conditions, any inhibition detected must be specific for strand transfer and not for 3' processing. Ole and HT demonstrated dose-dependent inhibition of the strand-transfer activity of HIV-1 integrase with $EC_{50}$s of 56 and 43 nM respectively.

Ole and HT are Effective Against Disintegration Activity of HIV-1 Integrase

Figure 18C:
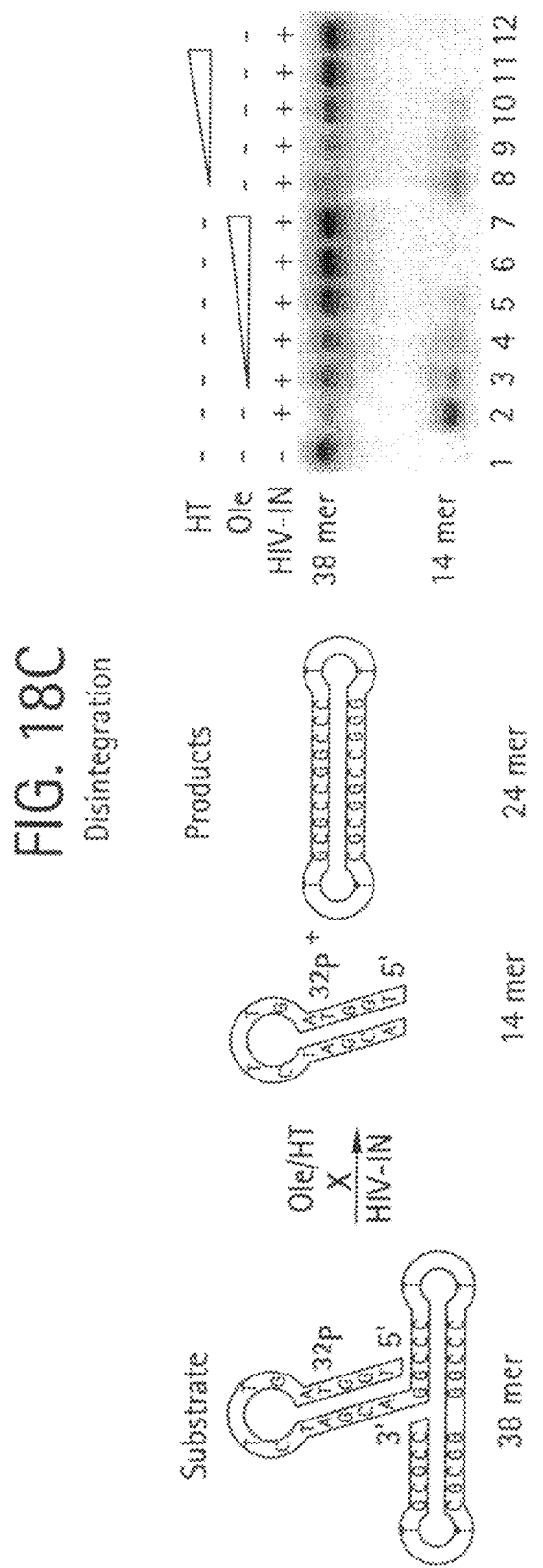

FIG. 18C shows a schematic representation of disintegration reaction and assay results. Disintegration is the reverse of integration and involves concerted strand-cleavage and ligation reactions [20]. Strand cleavage takes place precisely at the junction between the viral and the target sequences and is coupled with the rejoining of the cleaved target sequences. The disintegration substrate is a dumbbell shaped 38-mer oligonucleotide that mimics the recombination intermediate of HIV-1 integration. It contains 5' [$^{32}$P] labeled virus-specific U5-LTR sequence of 14-mer in the stem of the hairpin loop and arbitrary target DNA sequences of 24-mer in the base of the dumbbell [21, 22]. The folded structure of the annealed substrate shown is based on reports obtained from hairpin formation by similar sequences [23, 24]. Dis-integration of the 5' [$^{32}$P] labeled dumbbell by HIV-1 integrase is expected to give two products, a 5' [$^{32}$P] labeled 14-mer hairpin loop viral sequence and an unlabeled 24-mer closed circular target DNA. In the presence of HIV-integrase, the production of labeled 14-mer hairpin loop was detected by 7.5 M urea denaturating polyacrylamide gel electrophoresis and autoradiography of the gel, whereas the 24-mer product, the target DNA, was not seen in the autoradiography because it is unlabeled. This product can be detected by UV shadowing of the gel or by the use of 3'-labeled substrate. In the presence of Ole or HT, dose-dependent inhibition on the formation of the labeled 14-mer disintegration product was observed with $EC_{50}$s of 28 or 18 nM respectively.

TABLE 7

Anti-HIV Activity and Inhibition on HIV-1 Integrase Activity

| | Anti-HIV Activity[a] | | | Inhibitory Activity[b] EC$_{50}$ (nM) | | |
|---|---|---|---|---|---|---|
| | EC$_{50}$ (nM) | | IC$_{50}$ (nM) | HIV-1 Integrase Activities | | |
| Compound | Syncytium | P24 | Cytotoxicity | 3'-Proc | ST | Dis-In |
| Ole | 55 ± 5 | 73 ± 8 | >10,000 | 46 ± 6 | 56 ± 5 | 28 ± 3 |
| HT | 61 ± 6 | 68 ± 8 | >10,000 | 54 ± 5 | 43 ± 5 | 18 ± 2 |

[a]EC$_{50}$, effective concentration at 50% inhibition; IC$_{50}$, cytotoxicity concentration at 50% inhibition.
[b]3'-Proc, 3'-processing; ST, strand transfer; Dis-In, disintegration.
Values are means ± SD of triplicates in three independent determinations Discussion Several classes of HIV integrase inhibitors have been reported [4, 23], but none is clinically available yet. Lack of structural information for the intact protein, issues regarding different active site conformations dependent on crystal structure, and uncertain oligo-meric character of the enzyme protein have impeded the discovery of a clinically useful HIV-integrase inhibitor [4, 23]. Thus, molecular modeling becomes a key component in both the design of new integrase inhibitors and the identification of important protein-ligand interactions. There are 14 crystal structures of HIV-integrase available from the Protein Data Bank (PDB); however, only one has an inhibitor bound in the active site: 1QS4 [18]. We believe that this crystal structure contains the inhibitor would be the most relevant active site conformation on which to conduct the docking simulations with our anti-HIV small molecules, Ole and HT, despite previously reported crystal-packing effects associated with this structure [24].

The docking results reported here show good correlation with experimental data and provide a valuable tool for both evaluating compounds and designing more potent inhibitors. Ole and HT exhibit dose dependent inhibition in all of the three activities of HIV-1 integrase: 3'-processing, strand transfer and disintegration with EC$_{50}$s all in the nM range. These compounds also showed good antiviral efficacy both in cell-to-cell transmission of HIV-1 as assayed by syncytial formation and in HIV-1 replication as assayed by p24 production. However, they are not toxic in the effective dose ranges and even at the concentration of 1,000 times EC$_{50}$ (Table 7).

To our knowledge, Ole and HT are the first group of small molecules capable of multiple actions against the AIDS virus, inhibiting both viral entry and integration. To act both outside and inside of the cellular environments represents a great advantage of this novel class of drugs. The structure-function information described here should facilitate the design of innovative multi-functional HIV-1 inhibitors.

REFERENCES

[1] P. O. Brown, Retroviruses, in Coffin, J., Hughes, S., and Varmus, H., (Eds.) Cold Spring Harbor Press, Cold Spring Harbor, 1998, 161-203.

[2] T. K. Chiu, and D. R. Davies, Structure and function of HIV-1 integrase, Curr Top Med Chem 4 (2004) 965-977.

[3] K. Zhu, C. Dobard, and S. A. Chow, Requirement for integrase during reverse transcription of human immunodeficiency virus type 1 and the effect of cysteine mutations of integrase on its interactions with reverse transcriptase, J Virol 78 (2004) 5045-5055.

[4] Y. Pommier, A. A. Johnson, and C. Marchand, Integrase inhibitors to treat HIV/AIDS, Nat Rev Drug Discov 4 (2005) 236-248.

[5] P. A. Sherman, and J. A. Fyfe, Human immunodeficiency virus integration protein expressed in Escherichia coli possesses selective DNA cleaving activity, Proc Natl Acad Sci USA 87 (1990) 5119-5123.

[6] S. A. Chow, K. A. Vincent, V. Ellison, and P. O. Brown, Reversal of integration and DNA splicing mediated by integrase of human immunodeficiency virus, Science 255 (1992) 723-726.

[7] T. Haertle, C. J. Carrera, D. B. Wasson, L. C. Sowers, D. D. Richman, and D. A. Carson, Metabolism and anti-human immunodeficiency virus-1 activity of 2-halo-2',3'-dideoxyadenosine derivatives, J Biol Chem 263 (1988) 5870-5875.

[8] S. Harada, Y. Koyanagi, and N. Yamamoto, Infection of HTLV-III/LAV in HTLV-1-carrying cells MT-2 and MT-4 and application in a plaque assay, Science 229 (1985) 563-566.

[9] D. L. Maim, S. J. O'Brien, D. A. Gilbert, Y. Reid, M. Popovic, E. Read-Connole, R. C. Gallo, and A. F. Gazdar, Origin of the HIV-susceptible human CD4+ cell line H9, AIDS Res Hum Retroviruses 5 (1989) 253-255.

[10] M. Popovic, M. G. Sarngadharan, E. Read, and R. C. Gallo, Detection, isolation, and continuous production of cytopathic retroviruses (HTLV-III) from patients with AIDS and pre-AIDS, Science 224 (1984) 497-500.

[11] S. Lee-Huang, V. Maiorov, P. L. Huang, A. Ng, H. C. Lee, Y. T. Chang, N. Kallenbach, P. L. Huang, and H. C. Chen, Structural and functional modeling of human lysozyme reveals a unique nonapeptide, HL9, with anti-HIV activity, Biochemistry 44 (2005) 4648-4655.

[12] D. A. Case, T. E. Cheatham, 3rd, T. Darden, H. Gohlke, R. Luo, K. M.-merz, Jr., A. Onufriev, C. Simmerling, B. Wang, and R. J. Woods, The Amber biomolecular simulation programs, J Comput Chem 26 (2005) 1668-1688.

[13] Y. Duan, C. Wu, S. Chowdhury, M. C. Lee, G. Xiong, W. Zhang, R. Yang, P. Cieplak, R. Luo, T. Lee, J. Caldwell, J. Wang, and P. Kollman, A point-charge force field for molecular mechanics simulations of proteins based on condensed-phase quantum mechanical calculations, J Comput Chem 24 (2003) 1999-2012.

[14] D. S. Goodsell, G. M. Morris, and A. J. Olson, Automated docking of flexible ligands: applications of AutoDock, J Mol Recognit 9 (1996) 1-5.

[15] T. M. Jenkins, A. Engelman, R. Ghirlando, and R. Craigie, A soluble active mutant of HIV-1 integrase: involvement of both the core and carboxyl-terminal domains in multi-merization, J Biol Chem 271 (1996) 7712-7718.

[16] M. Li, and R. Craigie, Processing of viral DNA ends channels the HIV-1 integration reaction to concerted integration, J Biol Chem 280 (2005) 29334-29339.

[17] S. Lee-Huang, P. L. Huang, A. S. Bourinbaiar, H. C. Chen, and H. F. Kung, Inhibition of the integrase of human immunodeficiency virus (HIV) type 1 by anti-HIV plant proteins MAP30 and GAP31, Proc Natl Acad Sci USA 92 (1995) 8818-8822.

[18] Y. Goldgur, R. Craigie, G. H. Cohen, T. Fujiwara, T. Yoshinaga, T. Fujishita, H. Sugimoto, T. Endo, H. Murai, and D. R. Davies, Structure of the HIV-1 integrase catalytic domain complexed with an inhibitor: a platform for antiviral drug design, Proc Natl Acad Sci USA 96 (1999) 13040-13043.

[19] C. Marchand, A. A. Johnson, R. G. Karki, G. C. Pais, X. Zhang, K. Cowansage, T. A. Patel, M. C. Nicklaus, T. R. Burke, Jr., and Y. Pommier, Metal-dependent inhibition of HIV-1 integrase by beta-diketo acids and resistance of the soluble double-mutant (F185K/C280S), Mol Pharmacol 64 (2003) 600-609.

[20] K. A. Vincent, V. Ellison, S. A. Chow, and P. O. Brown, Characterization of human immunodeficiency virus type 1 integrase expressed in *Escherichia coli* and analysis of variants with amino-terminal mutations, J Virol 67 (1993) 425-437.

[21] M. J. Blom-mers, J. A. Walters, C. A. Haasnoot, J. M. Aelen, G. A. van der Marel, J. H. van Boom, and C. W. Hilbers, Effects of base sequence on the loop folding in DNA hairpins, Biochemistry 28 (1989) 7491-7498.

[22] S. A. Chow, and P. O. Brown, Substrate features important for recognition and catalysis by human immunodeficiency virus type 1 integrase identified by using novel DNA substrates, J Virol 68 (1994) 3896-3907.

[23] L. Q. Al-Mawsawi, V. Fikkert, R. Dayam, M. Witvrouw, T. R. Burke, Jr., C. H. Borchers, and N. Neamati, Discovery of a small-molecule HIV-1 integrase inhibitor-binding site, Proc Natl Acad Sci USA 103 (2006) 10080-10085.

[24] C. A. Sotriffer, H. Ni, and J. A. McCammon, Active site binding modes of HIV-1 integrase inhibitors, J Med Chem 43 (2000) 4109-4117.

---

What is claimed is:

1. A method for treating a human suffering from obesity consisting essentially of administering to said human a therapeutically effective amount of an olive leaf extract to treat said obesity in the human.

2. The method according to claim 1 wherein the olive leaf extract contains oleuropein.

3. The method according to claim 1 wherein the olive leaf extract is therapeutically effective to modulate adipocyte differentiation in the human.

4. The method according to claim 1 wherein the olive leaf extract is therapeutically effective to modulate adipocyte dedifferentiation and transdifferentiation in the human.

5. The method according to claim 1 wherein the olive leaf extract is therapeutically effective to modulate adipocyte transdifferentiation in the human.

6. The method according to claim 1 wherein the olive leaf extract is therapeutically effective to reduce the number of adipocytes in the human.

7. The method according to claim 1 wherein the human suffering from obesity also suffers from an obesity-related disease selected from the group consisting of diabetes, dyslipidemia, hypertension, cardiovascular disease, and asthma.

8. The method according to claim 1 wherein the olive leaf extract is administered for at least one month.

9. The method according to claim 1 wherein the human suffering from obesity also suffers from one or more diseases selected from the group consisting of metabolic syndrome, type 2 diabetes and human immunodeficiency virus infection.

* * * * *

SEQUENCE LISTING

```
<160> NUMBER OF SEQ ID NOS: 43

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggatgtcgtg tctgtggaga                                                    20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
tgaggagagt tacttggtcg                                                    20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
gagatttctc tgtatggcac c                                                  21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ctgcaaatga gacactttct c                                                  21

<210> SEQ ID NO 5
<211> LENGTH: 20
<212> TYPE: DNA
```

```
<213> ORGANISM: Artificial Sequence
<220> FEATURE:
<223> OTHER INFORMATION: primer

<400> SEQUENCE: 5
gtacctggaa acttgtctcc                                              20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gttcaatgcg aacttcagtc                                              20

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
ggtgaatggc ctgcctccct acaa                                         24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
cacagaatga tggccgcaat gaat                                         24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
tggagcttca gaagctcaac acca                                         24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
atctcgttgt ctgagtacca gtcc                                         24

<210> SEQ ID NO 11
<211> LENGTH: 16
<212> TYPE: DNA
<213> ORGANISM: Artificial Sequence
<220> FEATURE:
<223> OTHER INFORMATION: primer

<400> SEQUENCE: 11
catgagagcc ctcaca                                                  16
```

<210> SEQ ID NO 12
<211> LENGTH: 16
<212> TYPE: DNA
<213> ORGANISM: Artificial Sequence
<220> FEATURE:
<223> OTHER INFORMATION: primer

<400> SEQUENCE: 12
agagcgacac ctagac                                                    16

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
gtgcagatct tggtggtagt agc                                            23

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
agagccaatc cttatcccga agtt                                           24

<210> SEQ ID NO 15
<211> LENGTH: 505
<212> TYPE: PRT
<213> ORGANISM: Homo sapiens

<400> SEQUENCE: 15

Met Gly Glu Thr Leu Gly Asp Ser Pro Ile Asp Pro Glu Ser Asp Ser
 1               5                  10                  15

Phe Thr Asp Thr Leu Ser Ala Asn Ile Ser Gln Glu Met Thr Met Val
                20                  25                  30

Asp Thr Glu Met Pro Phe Trp Pro Thr Asn Phe Gly Ile Ser Ser Val
            35                  40                  45

Asp Leu Ser Val Met Glu Asp His Ser His Ser Phe Asp Ile Lys Pro
        50                  55                  60

Phe Thr Thr Val Asp Phe Ser Ser Ile Ser Thr Pro His Tyr Glu Asp
65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Lys Pro His Glu
        115                 120                 125

Glu Pro Ser Asn Ser Leu Met Ala Ile Glu Cys Arg Val Cys Gly Asp
    130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

```
Cys Arg Phe Gln Lys Cys Leu Ala Val Gly Met Ser His Asn Ala Ile
            195                 200                 205
Arg Phe Gly Arg Met Pro Gln Ala Glu Lys Glu Lys Leu Leu Ala Glu
        210                 215                 220
Ile Ser Ser Asp Ile Asp Gln Leu Asn Pro Glu Ser Ala Asp Leu Arg
225                 230                 235                 240
Ala Leu Ala Lys His Leu Tyr Asp Ser Tyr Ile Lys Ser Phe Pro Leu
                245                 250                 255
Thr Lys Ala Lys Ala Arg Ala Ile Leu Thr Gly Lys Thr Thr Asp Lys
            260                 265                 270
Ser Pro Phe Val Ile Tyr Asp Met Asn Ser Leu Met Met Gly Glu Asp
        275                 280                 285
Lys Ile Lys Phe Lys His Ile Thr Pro Leu Gln Glu Gln Ser Lys Glu
290                 295                 300
Val Ala Ile Arg Ile Phe Gln Gly Cys Gln Phe Arg Ser Val Glu Ala
                305                 310                 315                 320
Val Gln Glu Ile Thr Glu Tyr Ala Lys Ser Ile Pro Gly Phe Val Asn
            325                 330                 335
Leu Asp Leu Asn Asp Gln Val Thr Leu Leu Lys Tyr Gly Val His Glu
        340                 345                 350
Ile Ile Tyr Thr Met Leu Ala Ser Leu Met Asn Lys Asp Gly Val Leu
355                 360                 365
Ile Ser Glu Gly Gln Gly Phe Met Thr Arg Glu Phe Leu Lys Ser Leu
        370                 375                 380
Arg Lys Pro Phe Gly Asp Phe Met Glu Pro Lys Phe Glu Phe Ala Val
385                 390                 395                 400
Lys Phe Asn Ala Leu Glu Leu Asp Asp Ser Asp Leu Ala Ile Phe Ile
                405                 410                 415
Ala Val Ile Ile Leu Ser Gly Asp Arg Pro Gly Leu Leu Asn Val Lys
            420                 425                 430
Pro Ile Glu Asp Ile Gln Asp Asn Leu Leu Gln Ala Leu Glu Leu Gln
        435                 440                 445
Leu Lys Leu Asn His Pro Glu Ser Ser Gln Leu Phe Ala Lys Leu Leu
450                 455                 460
Gln Lys Met Thr Asp Leu Arg Gln Ile Val Thr Glu His Val Gln Leu
465                 470                 475                 480
Leu Gln Val Ile Lys Lys Thr Glu Thr Asp Met Ser Leu His Pro Leu
                485                 490                 495
Leu Gln Glu Ile Tyr Lys Asp Leu Tyr
            500                 505

<210> SEQ ID NO 16
<211> LENGTH: 225
<212> TYPE: DNA
<213> ORGANISM: Homo sapiens

<400> SEQUENCE: 16
atgcaggcgc aggacaggca gctggcaggg cagctgctgc ggctgcgggc ccagctgcac      60
cgactgaaga tggaccaagc ctgtcacctg caccaggagc tgctggatga ggccgagctg     120
gagctggagc tggagcccgg ggccggccta gccctggccc cgctgctgcg gcacctgggc     180
ctcacgcgca tgaacatcag cgcccggcgc ttcaccctct gctga                     225

<210> SEQ ID NO 17
<211> LENGTH: 303
<212> TYPE: DNA
```

<213> ORGANISM: Homo sapiens

<400> SEQUENCE: 17

| | | | | | |
|---|---|---|---|---|---|
| atggttgagc | ccttcttggg | aacctggaag | ctggtctcca | gtgaaaactt | tgaggattac | 60 |
| atgaaagaac | tgggagtgaa | tttcgcagcc | cggaacatgg | cagggttagt | gaaaccgaca | 120 |
| gtaactatta | gtgttgatgg | gaaaatgatg | accataagaa | cagaaagttc | tttccaggac | 180 |
| actaagatct | ccttcaagct | ggggaagaa | tttgatgaaa | ctacagcaga | caaccggaaa | 240 |
| gtaaaggtca | gaactaattc | ttcctggtgt | tcaacaatca | ggaaaaagtt | agaaggtggt | 300 |
| tag | | | | | | 303 |

<210> SEQ ID NO 18
<211> LENGTH: 1071
<212> TYPE: DNA
<213> ORGANISM: Homo sapiens

<400> SEQUENCE: 18

| | | | | | |
|---|---|---|---|---|---|
| gcagttctgg | tcctcctagg | agcggccgcc | tgcgcggcgc | ggccccgtgg | tcggatgctg | 60 |
| ggcggcagag | aggccgaggc | gcacgcgcgg | ccctacatgg | cgtcggtgca | gctgaacggc | 120 |
| gcgcacctgt | gcgcaggcgt | cctggtggcg | gagcggtggg | tgctgagcgc | ggcgcactgc | 180 |
| ctggaggacg | cggccgacgg | gaaggtgcag | gttctcctgg | gcgcgcactc | cctgtcgcag | 240 |
| ccggagccct | ccaagcgcct | gtacgacgtg | ctccgcgcag | tgccccaccc | ggacagccag | 300 |
| cccgacacca | tcgaccacga | cctcctgctg | ctacagctgt | cggagaaggc | cacactgggc | 360 |
| cctgctgtgc | gcccctgcc | ctggcagcgc | gtggaccgcg | acgtggcacc | gggaactctc | 420 |
| tgcgacgtgg | ccggctgggg | catagtcaac | cacgcgggcc | gccgcccgga | cagcctgcag | 480 |
| cacgtgctct | tgccagtgct | ggaccgcgcc | acctgcaacc | ggcgcacgca | ccacgacggc | 540 |
| gccatcaccg | agcgcttgat | gtgcgcggag | agcaatcgcc | gggacagctg | caagggtgac | 600 |
| tccgggggcc | cgctggtgtg | cggggcgtg | ctcgagggc | tggtcacctc | gggctcgcgc | 660 |
| gtttgcggca | accgcaagaa | gcccgggatc | tacacccgcg | tggcgagcta | tgcggcctgg | 720 |
| atcgacagcg | tcctggccta | gggtgccggg | gcctgaaggt | cagggtcacc | caagcaacaa | 780 |
| agtcccgagc | aatgaagtca | tccactcctg | catctggttg | gtctttattg | agcacctact | 840 |
| atatgcagaa | ggggaggccg | aggtgggagg | atcattggat | ctcaggagtt | ggagatcagc | 900 |
| atgggccacg | tagcgcgact | ccatctctac | aaataaataa | aaattagctg | ggcaattggc | 960 |
| gggcatggag | gtgggtgctt | gtagttccag | ctactcagga | ggctgaggtg | ggaggatgac | 1020 |
| ttgaacgcag | gaggctgagg | ctgcagtgag | ttgtgattgc | accactgccc | t | 1071 |

<210> SEQ ID NO 19
<211> LENGTH: 118
<212> TYPE: PRT
<213> ORGANISM: Homo sapiens

<400> SEQUENCE: 19

Asp Ala His Lys Val Leu Ser Ala Leu Gln Ala Val Gln Gly Leu Leu
  1               5                  10                  15

Val Ala Gln Gly Arg Ala Asp Ser Gln Ala Gln Leu Leu Leu Ser Thr
             20                  25                  30

Val Val Gly Val Phe Thr Ala Pro Gly Leu His Leu Lys Gln Pro Phe
         35                  40                  45

Val Gln Gly Leu Ala Leu Tyr Thr Pro Val Val Leu Pro Arg Ser Leu
     50                  55                  60

```
Asp Phe Thr Glu Arg Asp Val Ala Ala Glu Lys Ile Asp Arg Phe Met
 65                  70                  75                  80

Gln Ala Val Thr Gly Trp Lys Thr Gly Cys Ser Leu Met Gly Ala Ser
                 85                  90                  95

Val Asp Ser Thr Leu Ala Phe Asn Thr Tyr Val His Phe Gln Gly Lys
            100                 105                 110

Ala Asn Leu Ser Ala Gly
            115

<210> SEQ ID NO 20
<211> LENGTH: 1926
<212> TYPE: DNA
<213> ORGANISM: Homo sapiens

<400> SEQUENCE: 20
```

| | | | | | |
|---|---|---|---|---|---|
| gttgttctgg | gtactacagc | agaagggtat | gcggaagcga | gcaccccagt | ctgagatggc | 60 |
| tcctgccggt | gtgagcctga | gggccaccat | cctctgcctc | ctggcctggg | ctggcctggc | 120 |
| tgcaggtgac | cgggtgtaca | tacacccctt | ccacctcgtc | atccacaatg | agagtacctg | 180 |
| tgagcagctg | gcaaaggcca | atgccggaa | gcccaaagac | cccaccttca | tacctgctcc | 240 |
| aattcaggcc | aagacatccc | ctgtggatga | aaaggcccta | caggaccagc | tggtgctagt | 300 |
| cgctgcaaaa | cttgacaccg | aagacaagtt | gagggccgca | atggtcggga | tgctggccaa | 360 |
| cttcttgggc | ttccgtatat | atggcatgca | cagtgagcta | tggggcgtgg | tccatggggc | 420 |
| caccgtcctc | tccccaacgg | ctgtctttgg | caccctggcc | tctctctatc | tgggagcctt | 480 |
| ggaccacaca | gctgacaggc | tacaggcaat | cctgggtgtt | ccttggaagg | acaagaactg | 540 |
| cacctcccgg | ctggatgcgc | acaaggtcct | gtctgccctg | caggctgtac | agggcctgct | 600 |
| agtgcccag | gcagggctg | atagccaggc | ccagctgctg | ctgtccacgg | tggtgggcgt | 660 |
| gttcacagcc | ccaggcctgc | acctgaagca | gccgtttgtg | cagggcctgg | ctctctatac | 720 |
| ccctgtggtc | ctcccacgct | ctctggactt | cacagaactg | gatgttgctg | ctgagaagat | 780 |
| tgacaggttc | atgcaggctg | tgacaggatg | gaagactggc | tgctccctga | cgggagccag | 840 |
| tgtggacagc | accctggctt | tcaacaccta | cgtccacttc | caaggaaga | tgaagggctt | 900 |
| ctccctgctg | gccgagcccc | aggagttctg | ggtggacaac | agcacctcag | tgtctgttcc | 960 |
| catgctctct | ggcatgggca | ccttccagca | ctggagtgac | atccaggaca | acttctcggt | 1020 |
| gactcaagtg | tccttcactg | agagcgcctg | cctgctgctg | atccagcctc | actatgcctc | 1080 |
| tgacctggac | aagtggagg | gtctcacttt | ccagcaaaac | tccctcaact | ggatgaagaa | 1140 |
| actgtctccc | cggaccatcc | acctgaccat | gccccaactg | gtgctgcaag | atcttatga | 1200 |
| cctgcaggac | ctgctcgccc | aggctgagct | gccccgccatt | ctgcacaccg | agctgaacct | 1260 |
| gcaaaaattg | agcaatgacc | gcatcagggt | gggggaggtg | ctgaacagca | ttttttttga | 1320 |
| gcttgaagcg | gatgagagag | agcccacaga | gtctacccaa | cagcttaaca | agcctgaggt | 1380 |
| cttggaggtg | accctgaacc | gcccattcct | gtttgctgtg | tatgatcaaa | gcgccactgc | 1440 |
| cctgcacttc | ctgggccgcg | tggccaaccc | gctgagcaca | gcatgaggcc | agggccccag | 1500 |
| aacacagtgc | ctggcaaggc | ctctgcccct | ggcctttgag | gcaaaggcca | gcagcagata | 1560 |
| acaaccccgg | acaaatcagc | gatgtgtcac | ccccagtctc | cccacctttc | ttctaatgag | 1620 |
| tcgactttga | gctggaaagc | agccgtttct | ccttggtcta | agtgtgctgc | atggagtgag | 1680 |
| cagtagaagc | ctgcagcggc | acaaatgcac | ctcccagttt | gctgggttta | ttttagaaa | 1740 |
| tgggggtggg | gaggcaagaa | ccagtgttta | gcgcgggact | actgttccaa | aaagaattcc | 1800 |

```
aaccgaccag cttgtttgtg aaacaaaaaa gtgttcccct ttcaagttga gaacaaaaat    1860
tgggttttaa aattaaagta tacatttttg cattgcaaaa aaaaaaaaaa aaaaaaaaaa    1920
aaaaaa                                                               1926

<210> SEQ ID NO 21
<211> LENGTH: 330
<212> TYPE: PRT
<213> ORGANISM: Homo sapiens

<400> SEQUENCE: 21

Met Leu Leu Leu Ile Asn Val Ile Leu Thr Leu Trp Val Ser Cys Ala
 1               5                  10                  15

Asn Gly Gln Val Lys Pro Cys Asp Phe Pro Asp Ile Lys His Gly Gly
            20                  25                  30

Leu Phe His Glu Asn Met Arg Arg Pro Tyr Phe Pro Val Ala Val Gly
        35                  40                  45

Lys Tyr Tyr Ser Tyr Tyr Cys Asp Glu His Phe Glu Thr Pro Ser Gly
    50                  55                  60

Ser Tyr Trp Asp Tyr Ile His Cys Thr Gln Asn Gly Trp Ser Pro Ala
65                  70                  75                  80

Val Pro Cys Leu Arg Lys Cys Tyr Phe Pro Tyr Leu Glu Asn Gly Tyr
                85                  90                  95

Asn Gln Asn Tyr Gly Arg Lys Phe Val Gln Gly Asn Ser Thr Glu Val
           100                 105                 110

Ala Cys His Pro Gly Tyr Gly Leu Pro Lys Ala Gln Thr Thr Val Thr
       115                 120                 125

Cys Thr Glu Lys Gly Trp Ser Pro Thr Pro Arg Cys Ile Arg Val Arg
   130                 135                 140

Thr Cys Ser Lys Ser Asp Ile Glu Ile Glu Asn Gly Phe Ile Ser Glu
145                 150                 155                 160

Ser Ser Ser Ile Tyr Ile Leu Asn Lys Glu Ile Gln Tyr Lys Cys Lys
                165                 170                 175

Pro Gly Tyr Ala Thr Ala Asp Gly Asn Ser Ser Gly Ser Ile Thr Cys
           180                 185                 190

Leu Gln Asn Gly Trp Ser Ala Gln Pro Ile Cys Ile Asn Ser Ser Glu
       195                 200                 205

Lys Cys Gly Pro Pro Pro Ile Ser Asn Gly Asp Thr Thr Ser Phe
   210                 215                 220

Leu Leu Lys Val Tyr Val Pro Gln Ser Arg Val Glu Tyr Gln Cys Gln
225                 230                 235                 240

Pro Tyr Tyr Glu Leu Gln Gly Ser Asn Tyr Val Thr Cys Ser Asn Gly
                245                 250                 255

Glu Trp Ser Glu Pro Pro Arg Cys Ile His Pro Cys Ile Ile Thr Glu
           260                 265                 270

Glu Asn Met Asn Lys Asn Asn Ile Lys Leu Lys Gly Arg Ser Asp Arg
       275                 280                 285

Lys Tyr Tyr Ala Lys Thr Gly Asp Thr Ile Glu Phe Met Cys Lys Leu
   290                 295                 300

Gly Tyr Asn Ala Asn Thr Ser Ile Leu Ser Phe Gln Ala Val Cys Arg
305                 310                 315                 320

Glu Gly Ile Val Glu Tyr Pro Arg Cys Glu
                325                 330

<210> SEQ ID NO 22
<211> LENGTH: 878
```

```
<212> TYPE: DNA
<213> ORGANISM: Homo sapiens

<400> SEQUENCE: 22
agtcggtgtc tcagccacag cggcttcacc atgcacagct gggagcgcct ggcagttctg      60
gtcctcctag gagcggccgc ctgcgcggcg ccgccccgtg gtcggatcct gggcggcaga     120
gaggccgagg cgcacgcgcg gccctacatg cgtcggtgc agctgaacgg cgcgcacctg     180
tgcggcggcg tcctggtggc ggagcagtgg gtgctgagcg cggcgcactg cctggaggac     240
gcggccgacg ggaaggtgca ggttctcctg ggcgcgcact ccctgtcgca gccggagccc     300
tccaagcgcc tgtacgacgt gctccgcgca gtgcccacc cggacagcca gcccgacacc     360
atcgaccacg acctcctgct gctacagctg tcggagaagg ccacactggg ccctgctgtg     420
cgcccctgc cctggcagcg cgtggaccgc gacgtggcac cgggaactct ctgcgacgtg     480
gccggctggg gcatagtcaa ccacgcgggc cgccgcccgg acagcctgca gcacgtgctc     540
ttgccagtgc tggaccgcgc cacctgcaac cggcgcacgc accacgacgg cgccatcacc     600
gagcgcttga tgtgcgcgga gagcaatcgc cgggacagct gcaagggtga ctccgggggc     660
ccgctggtgt gcgggggcgt gctcgagggc gtggtcacct cgggctcgcg cgtttgcggc     720
aaccgcaaga agcccgggat ctacacccgc gtggcgagct atgcggcctg gatcgacagc     780
gtcctggcct agggtgccgg ggctgaagg tcagggtcac ccaagcaaca aagtcccgag     840
cattgaagtc atccactcct gcaaaaaaaa aaaaaaaa                             878

<210> SEQ ID NO 23
<211> LENGTH: 3549
<212> TYPE: DNA
<213> ORGANISM: Homo sapiens

<400> SEQUENCE: 23
cccctcttcc tcctcctcaa gggaaagctg cccacttcta gctgccctgc catcccctt      60
aaagggcgac ttgctcagcg ccaaaccgcg gctccagccc tctccagcct ccggctcagc     120
cggctcatca gtcggtccgc gccttgcagc tcctccagag ggacgcgccc cgagatggag     180
agcaaagccc tgctcgtgct gactctggcc gtgtggctcc agagtctgac cgcctcccgc     240
ggaggggtgg ccgccgccga ccaaagaaga gattttatcg acatcgaaag taaatttgcc     300
ctaaggaccc ctgaagacac agctgaggac acttgccacc tcattcccgg agtagcagag     360
tccgtggcta cctgtcattt caatcacagc agcaaaacct tcatggtgat ccatggctgg     420
acggtaacag gaatgtatga gagttgggtg ccaaaacttg tggccgccct gtacaagaga     480
gaaccagact ccaatgtcat tgtggtggac tggctgtcac gggctcagga gcattaccca     540
gtgtccgcgg gctacaccaa actggtggga caggatgtgg cccggtttat caactggatg     600
gaggaggagt ttaactaccc tctggacaat gtccatctct tgggatacag ccttggagcc     660
catgctgctg gcattgcagg aagtctgacc aataagaaag tcaacagaat tactggcctc     720
gatccagctg gacctaactt tgagtatgca gaagccccga tcgtctttc tcctgatgat     780
gcagattttg tagacgtctt acacacattc accagagggt cccctggtcg aagcattgga     840
atccagaaac cagttgggca tgttgacatt tacccgaatg gaggtacttt tcagccagga     900
tgtaacattg gagaagctat ccgcgtgatt gcagagagag acttggaga tgtggaccag     960
ctagtgaagt gctcccacga cgcgctccat catctcttca tcgactctct gttgaatgaa    1020
gaaaatccaa gtaaggccta caggtgcagt tccaaggaag cctttgagaa agggctctgc    1080
ttgagttgta gaaagaaccg ctgcaacaat ctgggctatg agatcaataa agtcagagcc    1140
```

```
aaaagaagca gcaaaatgta cctgaagact cgttctcaga tgccctacaa agtcttccat    1200
taccaagtaa agattcattt ttctgggact gagagtgaaa cccataccaa tcaggccttt    1260
gagatttctc tgtatggcac cgtggccgag agtgagaaca tcccattcac tctgcctgaa    1320
gtttccacaa ataagaccta ctccttccta atttacacag aggtagatat tggagaacta    1380
ctcatgttga agctcaaatg gaagagtgat tcatacttta gctggtcaga ctggtggagc    1440
agtcccggct tcgccattca gaagatcaga gtaaaagcag gagagactca gaaaaaggtg    1500
atcttctgtt ctagggagaa agtgtctcat ttgcagaaag gaaaggcacc tgcggtattt    1560
gtgaaatgcc atgacaagtc tctgaataag aagtcaggct gaaactgggc gaatctacag    1620
aacaaagaac ggcatgtgaa ttctgtgaag aatgaagtgg aggaagtaac ttttacaaaa    1680
catacccagt gtttggggtg tttcaaaagt ggattttcct gaatattaat cccagcccta    1740
cccttgttag ttattttagg agacagtctc aagcactaaa aagtggctaa ttcaatttat    1800
ggggtatagt ggccaaatag cacatcctcc aacgttaaaa gacagtggat catgaaaagt    1860
gctgttttgt cctttgagaa agaaataatt gtttgagcgc agagtaaaat aaggctcctt    1920
catgtggcgt attgggccat agcctataat tggttagaac ctcctatttt aattggaatt    1980
ctggatcttt cggactgagg ccttctcaaa ctttactcta agtctccaag aatacagaaa    2040
atgcttttcc gcggcacgaa tcagactcat ctacacagca gtatgaatga tgttttagaa    2100
tgattccctc ttgctattgg aatgtggtcc agacgtcaac caggaacatg taacttggag    2160
agggacgaag aaagggtctg ataaacacag aggttttaaa cagtccctac cattggcctg    2220
catcatgaca aagttacaaa ttcaaggaga tataaaatct agatcaatta attcttaata    2280
ggctttatcg tttattgctt aatccctctc tcccccttct tttttgtctc aagattatat    2340
tataataatg ttctctgggt aggtgttgaa aatgagcctg taatcctcag ctgacacata    2400
atttgaatgg tgcagaaaaa aaaaagatac cgtaatttta ttattagatt ctccaaatga    2460
ttttcatcaa tttaaaatca ttcaatatct gacagttact cttcagtttt aggcttacct    2520
tggtcatgct tcagttgtac ttccagtgcg tctcttttgt tcctggcttt gacatgaaaa    2580
gataggtttg agttcaaatt ttgcattgtg tgagcttcta cagattttag acaaggaccg    2640
tttttactaa gtaaaagggt ggagaggttc ctggggtgga ttcctaagca gtgcttgtaa    2700
accatcgcgt gcaatgagcc agatggagta ccatgagggt tgttatttgt tgtttttaac    2760
aactaatcaa gagtgagtga acaactattt ataaactaga tctcctatttt ttcagaatgc    2820 tcttctacgt ataaatatga aatgataaag atgtcaaata tctcagaggc tatagctggg    2880
aacccgactg tgaaagtatg tgatatctga acacatacta gaaagctctg catgtgtgtt    2940
gtccttcagc ataattcgga agggaaaaca gtcgatcaag ggatgtattg gaacatgtcg    3000
gagtagaaat tgttcctgat gtgccagaac ttcgaccctt tctctgagag atgatcgt      3060 gcctataaat agtaggacca atgttgtgat taacatcatc aggcttggaa tgaattctct    3120
ctaaaaataa aatgatgtat gatttgttgt tggcatcccc tttattaatt cattaaattt    3180
ctggatttgg gttgtgaccc agggtgcatt aacttaaaag attcactaaa gcagcacata    3240
gcactgggaa ctctggctcc gaaaaacttt gttatatata tcaaggatgt tctggcttta    3300
cattttattt attagctgta aatacatgtg tggatgtgta aatggagctt gtacatattg    3360
gaaaggtcat tgtggctatc tgcatttata aatgtgtggt gctaactgta tgtgtcttta    3420
tcagtgatgg tctcacagag ccaactcact cttatgaaat gggctttaac aaaacaagaa    3480
agaaacgtac ttaactgtgt gaagaaatgg aatcagcttt taataaaatt gacaacattt    3540
``` tattaccac                                                             3549

<210> SEQ ID NO 24
<211> LENGTH: 2315
<212> TYPE: DNA
<213> ORGANISM: Homo sapiens

<400> SEQUENCE: 24
gctcagccgg ctcatcagtc ggtccgcgcc ttgcagctcc tccagaggga cgcgccccga      60
gatggagagc aaagccctgc tcgtgctgac tctggccgtg tggctccaga gtctgaccgc     120
ctcccgcgga ggggtggccg ccgccgacca agaagagat tttatcgaca tcgaaagtaa     180
atttgcccta aggaccctg aagacacagc tgaggacact tgccacctca ttcccggagt     240
agcagagtcc gtggctacct gtcatttcaa tcacagcagc aaaaccttca tggtgatcca     300
tggctggacg gtaacaggaa tgtatgagag ttgggtgcca aaacttgtgg ccgccctgta     360
caagagagaa ccagactcca atgtcattgt ggtggactgg ctgtcacggg ctcaggagca     420
ttacccagtg tccgcgggct acaccaaact ggtgggacag gatgtggccc ggtttatcaa     480
ctggatggag gaggagttta actaccctct ggacaatgtc catctcttgg gatacagcct     540
tggagcccat gctgctggca ttgcaggaag tctgaccaat aagaaagtca acagaattac     600
tggcctcgat ccagctggac ctaactttga gtatgcagaa gccccgagtc gtctttctcc     660
tgatgatgca gattttgtag acgtcttaca cacattcacc agagggtccc ctggtcgaag     720
cattggaatc cagaaaccag ttgggcatgt tgacatttac ccgaatggag gtacttttca     780
gccaggatgt aacattggag aagctatccg cgtgattgca gagagaggac ttggagatgt     840
ggaccagcta gtgaagtgct cccacgagcg ctccattcat ctcttcatcg actctctgtt     900
gaatgaagaa atccaagta aggcctacag gtgcagttcc aaggaagcct tgagaaagg     960 gctctgcttg agttgtagaa agaaccgctg caacaatctg ggctatgaga tcagtaaagt    1020
cagagccaaa agaagcagca aaatgtacct gaagactcgt tctcagatgc cctacaaagt    1080
cttccattac caagtaaaga ttcatttttc tgggactgag agtgaaaccc ataccaatca    1140
ggcctttgag atttctctgt atggcaccgt ggccgagagt gagaacatcc cattcactct    1200
gcctgaagtt tccacaaata agacctactc cttcctaatt tacacagagg tagatattgg    1260
agaactactc atgttgaagc tcaaatggaa gagtgattca tactttagct ggtcagactg    1320
gtggagcagt cccggcttcg ccattcagaa gatcagagta aaagcaggag agactcagaa    1380
aaaggtgatc ttctgttcta gggagaaagt gtctcatttg cagaaaggaa aggcacctgc    1440
ggtatttgtg aaatgccatg acaagtctct gaataagaag tcaggctgaa actgggcgaa    1500
tctacagaac aaagaacggc atgtgaattc tgtgaagaat gaagtggagg aagtaacttt    1560
tacaaaacat acccagtgtt tggggtgttt caaaagtgga ttttcctgaa tattaatccc    1620
agccctaccc ttgttagtta ttttaggaga cagtctcaag cactaaaaag tggctaattc    1680
aatttatggg gtatagtggc caaatagcac atcctccaac gttaaagac agtggatcat    1740 gaaaagtgct gttttgtcct ttgagaaaga ataattgtt tgagcgcaga gtaaaataag    1800
gctccttcat gtggcgtatt gggccatagc ctataattgg ttagaacctc ctattttaat    1860
tggaattctg atctttcgg actgaggcct tctcaaactt tactctaagt ctccaagaat    1920
acagaaaatg cttttccgcg gcacgaatca gactcatcta cacagcagta tgaatgatgt    1980
tttagaatga ttccctcttg ctattggaat gtggtccaga cgtcaaccag gaacatgtaa    2040
cttggagagg gacgaagaaa gggtctgata aacacagagg ttttaaacag tccctaccat    2100

```
tggcctgcat catgacaaag ttacaaattc aaggagatat aaaatctaga tcaattaatt      2160
cttaataggc tttatcgttt attgcttaat ccctctctcc cccttctttt ttgtctcaag      2220
attatattat aataatgttc tctgggtagg tgttgaaaat gagcctgtaa tcctcagctg      2280
acacataatt tgaatggtgc aaaaaaaaaa aaaaa                                 2315

<210> SEQ ID NO 25
<211> LENGTH: 2922
<212> TYPE: DNA
<213> ORGANISM: Homo sapiens

<400> SEQUENCE: 25
agcctgggct ctgtgagact gaggtggcgg tcagccggag tgagtgttgg ggtcctgggg        60
cacctgcctt acatggcttg tttatgaaca ttaaagggaa gaagttgaag cttgaggagc       120
gaggatggca gtcaacaaag gcctcacctt gctggatgga gacctccctg agcaggagaa       180
tgtgctgcag cgggtcctgc agctgccggt ggtgagtggc acctgcgaat gcttccagaa       240
gacctacacc agcactaagg aagcccaccc cctggtggcc tctgtgtgca atgcctatga       300
gaagggcgtg cagagcgcca gtagcttggc tgcctggagc atggagccgg tggtccgcag       360
gctgtccacc cagttcacag ctgccaatga gctggcctgc cgaggcttgg accacctgga       420
ggaaaagatc cccgccctcc agtacccccc tgaaaagatt gcttctgagc tgaaggacac       480
catctccacc cgcctccgca gtgccagaaa cagcatcagc gttcccatcg cgagcacttc       540
agacaaggtc ctgggggccg ctttggccgg gtgcgagctt gctgggggg tggccagaga       600 cactgcggaa tttgctgcca acactcgagc tggccgactg gcttctggag gggccgactt       660
ggccttgggc agcattgaga aggtggtgga gtacctcctc cctgcagaca aggaagagtc       720
agcccctgct cctggacacc agcaagccca gaagtctccc aaggccaagc caagcctctt       780
gagcagggtt ggggctctga ccaacaccct ctctcgatac accgtgcaga ccatggcccg       840
ggccctggag cagggccaca ccgtggccat gtggatccca ggcgtggtgc ccctgagcag       900
cctggcccag tggggtgcct cagtggccat gcaggcggtg tcccggcgga ggagcgaagt       960
gcgggtaccc tggctgcaca gcctcgcagc cgcccaggag gaggatcatg aggaccagac      1020
agacacggag ggagaggaca cggaggagga ggaagaattg gagactgagg agaacaagtt      1080
cagtgaggta gcagccctgc caggccctcg aggcctcctg ggtggtgtgg cacatacccct     1140 gcagaagacc ctccagacca ccatctcggc tgtgacatgg gcacctgcag ctgtgctggg      1200
catggcaggg agggtgctgc acctcacacc agccctgct gtctcctcaa ccaaggggag      1260
ggccatgtcc ctatcagatg ccctgaaggg cgttactgac aacgtggtgg acacagtggt      1320
gcattacgtg ccgctcccca ggctgtcgct gatggagccc gagagcgaat tcgggacat      1380 cgacaaccca ccagccgagg tcgagcgccg ggaggcggag cgcagagcgt ctggggcgcc      1440
gtccgccggc ccggagcccg ccccgcgtct cgcacagccc cgccgcagcc tgcgcagcgc      1500
gcagagcccc ggcgcgcccc ccggccccggg cctggaggac gaagtcgcca cgcccgcagc      1560
gccgcgcccg ggcttcccgg ccgtgccccg cgagaagcca agcgcaggg tcagcgacag      1620 cttcttccgg cccagcgtca tggagcccat cctgggccgc acgcattaca gccagctgcg      1680
caagaagagc tgagtcgccg caccagccgc gcgcccggg gccggcgggt ttctctaaca      1740
aataaacaga acccgcactg cccaggcgag cgttgccact ttcaaagtgg tccctgggg      1800 agctcagcct catcctgatg atgctgccaa ggcgcacttt ttattttat tttattttta      1860 tttttttttt agcatccttt tggggcttca ctctcagagc cagttttaa gggacaccag      1920
```

-continued

```
agccgcagcc tgctctgatt ctatggcttg gttgttacta taagagtaat tgcctaactt      1980 gattttcat ctctttaacc aaacttgtgg ccaaaagata tttgaccgtt tccaaaattc       2040
agattctgcc tctgcggata aatatttgcc acgaatgagt aactcctgtc accactctga      2100
aggtccagac agaaggtttt gacacattct tagcactgaa ctcctctgtg atctaggatg      2160
atctgttccc cctctgatga acatcctctg atgatctagg ctcccagcag gctactttga      2220
agggaacaat cagatgcaaa agctcttggg tgtttattta aaatactagt gtcactttct      2280
gagtacccgc cgcttcacag gctgagtcca ggcctgtgtg cttgtagag ccagctgctt       2340 gctcacagcc acatttccat ttgcatcatt actgccttca cctgcatagt cactcttttg      2400
atgctgggga accaaaatgg tgatgatata tagactttat gtatagccac agttcatccc      2460
caaccctagt cttcgaaatg ttaatatttg ataaatctag aaaatgcatt catacaatta      2520
cagaattcaa atattgcaaa aggatgtgtg tctttctccc cgagctcccc tgttcccctt      2580
cattgaaaac caccacggtg ccatctcttg tgtatgcagg gctatgcacc tgcaggcacg      2640
tgtgtatgca ctccccgctt gtgtttacac aagctgtggg gtgttacgca tgcctgcttt      2700
tttcacttaa taatacagct tggagagatt tttgtatcac attataaatc ccactcgctc      2760
tttttgatgg ccacataata actactgcat aatatggata cgccttattt gatttaacta      2820
gttccctaat gatggacttt taagttgttt cctttttttt tctttttttgc tactgcaaac      2880 gatgctataa taaatgtcct tatcaaaaaa aaaaaaaaaa aa                          2922
```

<210> SEQ ID NO 26
<211> LENGTH: 509
<212> TYPE: PRT
<213> ORGANISM: Homo sapiens

<400> SEQUENCE: 26

```
Met Pro Ser Gly Phe Gln Gln Ile Gly Ser Glu Asp Gly Glu Pro Pro
  1               5                  10                  15

Gln Gln Arg Val Thr Gly Thr Leu Val Leu Ala Val Phe Ser Ala Val
             20                  25                  30

Leu Gly Ser Leu Gln Phe Gly Tyr Asn Ile Gly Val Ile Asn Ala Pro
         35                  40                  45

Gln Lys Val Ile Glu Gln Ser Tyr Asn Glu Thr Trp Leu Gly Arg Gln
     50                  55                  60

Gly Pro Glu Gly Pro Ser Ser Ile Pro Pro Gly Thr Leu Thr Thr Leu
 65                  70                  75                  80

Trp Ala Leu Ser Val Ala Ile Phe Ser Val Gly Gly Met Ile Ser Ser
                 85                  90                  95

Phe Leu Ile Gly Ile Ile Ser Gln Trp Leu Gly Arg Lys Arg Ala Met
            100                 105                 110

Leu Val Asn Asn Val Leu Ala Val Leu Gly Gly Ser Leu Met Gly Leu
        115                 120                 125

Ala Asn Ala Ala Ala Ser Tyr Glu Met Leu Ile Leu Gly Arg Phe Leu
    130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Ile Ala Gln Val Leu Gly Leu
            180                 185                 190

Glu Ser Leu Leu Gly Thr Ala Ser Leu Trp Pro Leu Leu Leu Gly Leu
```

```
                195                 200                 205
Thr Val Leu Pro Ala Leu Leu Gln Leu Val Leu Leu Pro Phe Cys Pro
210                 215                 220

Glu Ser Pro Arg Tyr Leu Tyr Ile Ile Gln Asn Leu Glu Gly Pro Ala
225                 230                 235                 240

Arg Lys Ser Leu Lys Arg Leu Thr Gly Trp Ala Asp Val Ser Gly Val
                245                 250                 255

Leu Ala Glu Leu Lys Asp Glu Lys Arg Lys Leu Glu Arg Glu Arg Pro
                260                 265                 270

Leu Ser Leu Leu Gln Leu Leu Gly Ser Arg Thr His Arg Gln Pro Leu
                275                 280                 285

Ile Ile Ala Val Val Leu Gln Leu Ser Gln Gln Leu Ser Gly Ile Asn
            290                 295                 300

Ala Val Phe Tyr Tyr Ser Thr Ser Ile Phe Glu Thr Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Leu Val Glu Arg Ala Gly Arg Arg Thr Leu
                340                 345                 350

His Leu Leu Gly Leu Ala Gly Met Cys Gly Cys Ala Ile Leu Met Thr
            355                 360                 365

Val Ala Leu Leu Leu Leu Glu Arg Val Pro Ala Met Ser Tyr Val Ser
370                 375                 380

Ile Val Ala Ile Phe Gly Phe Val Ala Phe Phe Glu Ile Gly Pro Gly
385                 390                 395                 400

Pro Ile Pro Trp Phe Ile Val Ala Glu Leu Phe Ser Gln Gly Pro Arg
                405                 410                 415

Pro Ala Ala Met Ala Val Ala Gly Phe Ser Asn Trp Thr Ser Asn Phe
                420                 425                 430

Ile Ile Gly Met Gly Phe Gln Tyr Val Ala Glu Ala Met Gly Pro Tyr
            435                 440                 445

Val Phe Leu Leu Phe Ala Val Leu Leu Leu Gly Phe Phe Ile Phe Thr
450                 455                 460

Phe Leu Arg Val Pro Glu Thr Arg Gly Arg Thr Phe Asp Gln Ile Ser
465                 470                 475                 480

Ala Ala Phe His Arg Thr Pro Ser Leu Leu Glu Gln Glu Val Lys Pro
                485                 490                 495

Ser Thr Glu Leu Glu Tyr Leu Gly Pro Asp Glu Asn Asp
                500                 505

<210> SEQ ID NO 27
<211> LENGTH: 4194
<212> TYPE: DNA
<213> ORGANISM: Homo sapiens

<400> SEQUENCE: 27
agcagagctg cggccggggg aacccagttt ccgaggaact tttcgccggc gccgggccgc      60
ctctgaggcc agggcaggac acgaacgcgc ggagcggcgg cggcgactga gagccggggc     120
cgcggcggcg ctccctagga agggccgtac gaggcggcgg gcccggcggg cctcccggag     180
gaggcggctc cgccatggac gagccaccct tcagcgaggc ggctttggag caggcgctgg     240
gcgagccgtg cgatctggac gcggcgctgc tgaccgacat cgaagacatg cttcagctta     300
tcaacaacca agacagtgac ttccctggcc tatttgaccc accctatgct gggagtgggg     360 caggggggcac agaccctgcc agccccgata ccagctcccc aggcagcttg tctccacctc     420
```

```
ctgccacatt gagctcctct cttgaagcct tcctgagcgg gccgcaggca gcgccctcac    480
ccctgtcccc tccccagcct gcacccactc cattgaagat gtacccgtcc atgcccgctt    540
tctcccctgg gcctggtatc aaggaagagt cagtgccact gagcatcctg cagaccccca    600
ccccacagcc cctgccaggg gccctcctgc cacagagctt cccagcccca gccccaccgc    660
agttcagctc caccctgtg ttaggctacc ccagccctcc gggaggcttc tctacaggaa    720
gccctcccgg gaacacccag cagccgctgc ctggcctgcc actggcttcc ccgccagggg    780
tcccgcccgt ctccttgcac acccaggtcc agagtgtggt cccccagcag ctactgacag    840
tcacagctgc ccccacggca gccctgtaa cgaccactgt gacctcgcag atccagcagg    900
tcccggtcct gctgcagccc cacttcatca aggcagactc gctgcttctg acagccatga    960
agacagacgg agccactgtg aaggcggcag gtctcagtcc cctggtctct ggcaccactg   1020
tgcagacagg gcctttgccg accctggtga gtggcggaac catcttggca acagtcccac   1080
tggtcgtaga tgcggagaag ctgcctatca accggctcgc agctggcagc aaggcccggg   1140
cctctgccca gagccgtgga gagaagcgca cagcccacaa cgccattgag aagcgctacc   1200
gctcctccat caatgacaaa atcattgagc tcaaggatct ggtggtgggc actgaggcaa   1260
agctgaataa atctgctgtc ttgcgcaagg ccatcgacta cattcgcttt ctgcaacaca   1320
gcaaccagaa actcaagcag gagaacctaa gtctgcgcac tgctgtccac aaaagcaaat   1380
ctctgaagga tctggtgtcg gcctgtggca gtggagggaa cacagacgtg ctcatggagg   1440
gcgtgaagac tgaggtggag gacacactga ccccacccc ctcggatgct ggctcacctt   1500
tccagagcag ccccttgtcc cttggcagca ggggcagtgg cagcggtggc agtggcagtg   1560
actcggagct gacagcccca gtctttgagg acagcaaggc aaagccagag cagcggccgt   1620
ctctgcacag ccggggcatg ctggaccgct cccgcctggc cctgtgcacg ctcgtcttcc   1680
tctgcctgtc ctgcaacccc ttggcctcct gctgggggc ccggggcttc cccagccct   1740
cagataccac cagcgtctac catagccctg gccgcaacgt gctgggcacc gagagcagag   1800
atggccctgg ctgggcccag tggctgctgc ccccagtggt ctggctgctc aatgggctgt   1860
tggtgctcgt ctccttggtg cttctctttg tctacggtga gccagtcaca cggccccact   1920
caggccccgc cgtgtacttc tggaggcatc gcaagcaggc tgacctggac ctggcccggg   1980
gagactttgc ccaggctgcc cagcagctgt ggctggccct gcgggcactg gccggcccc   2040
tgcccacctc ccacctggac ctggcttgta gcctcctctg gaacctcatc cgtcacctgc   2100
tgcagcgtct ctgggtgggc cgctggctgg caggccggg aggggcctg cagcaggact   2160
gtgctctgcg agtggatgct agcgccagcc cccgagacgc agccctggtc taccataagc   2220
tgcaccagct gcacaccatg gggaagcaca caggcgggca cctcactgcc accaacctgg   2280
cgctgagtgc cctgaacctg gcagagtgtg caggggatgc cgtgtctgtg gcgacgctgg   2340
ccgagatcta tgtggcggct gcattgagag tgaagaccag tctcccacgg gccttgcatt   2400
ttctgacacg cttcttcctg agcagtgccc gccaggcctg cctggcacag agtggctcag   2460
tgcctcctgc catgcagtgg ctctgccacc ccgtgggcca ccgtttcttc gtggatgggg   2520
actggtccgt gctcagtacc ccatgggaga gcctgtacag cttggccggg aacccagtgg   2580
accccctggc ccaggtgact cagctattcc gggaacatct cttagagcga gcactgaact   2640
gtgtgaccca gccaacccc agccctgggt cagctgatgg ggacaaggaa ttctcggatg   2700
ccctcgggta cctgcagctg ctgaacagct gttctgatgc tgcgggggct cctgcctaca   2760
gcttctccat cagttccagc atggccacca ccaccggcgt agacccggtg ccaagtggt   2820
```

| | |
|---|---|
| gggcctctct gacagctgtg gtgatccact ggctgcggcg ggatgaggag gcggctgagc | 2880 |
| ggctgtgccc gctggtggag cacctgcccc gggtgctgca ggagtctgag agacccctgc | 2940 |
| ccagggcagc tctgcactcc ttcaaggctg cccgggccct gctgggctgt gccaaggcag | 3000 |
| agtctggtcc agccagcctg accatctgtg agaaggccag tgggtacctg caggacagcc | 3060 |
| tggctaccac accagccagc agctccattg acaaggccgt gcagctgttc ctgtgtgacc | 3120 |
| tgcttcttgt ggtgcgcacc agcctgtggc ggcagcagca gccccggcc ccggcccag | 3180 |
| cagcccaggg caccagcagc aggcccagg cttccgccct tgagctgcgt ggcttccaac | 3240 |
| gggacctgag cagcctgagg cggctggcac agagcttccg gcccgccatg cggagggtgt | 3300 |
| tcctacatga ggccacggcc cggctgatgg cgggggccag ccccacacgg acacaccagc | 3360 |
| tcctcgaccg cagtctgagg cggcgggcag gccccggtgg caaaggaggc gcggtggcgg | 3420 |
| agctggagcc gcggcccacg cggcgggagc acgcggaggc cttgctgctg gcctcctgct | 3480 |
| acctgccccc cggcttcctg tcggcgcccg ggcagcgcgt gggcatgctg gctgaggcgg | 3540 |
| cgcgcacact cgagaagctt ggcgatcgcc ggctgctgca cgactgtcag cagatgctca | 3600 |
| tgcgcctggg cggtgggacc actgtcactt ccagctagac cccgtgtccc cggcctcagc | 3660 |
| acccctgtct ctagccactt tggtcccgtg cagcttctgt cctgcgtcga agctttgaag | 3720 |
| gccgaaggca gtgcaagaga ctctggcctc cacagttcga cctgcggctg ctgtgtgcct | 3780 |
| tcgcggtgga aggcccgagg ggcgcgatct tgaccctaag accggcggcc atgatggtgc | 3840 |
| tgacctctgg tggccgatcg gggcactgca ggggccgagc catttgggg ggccccctc | 3900 |
| cttgctctgc aggcacctta gtggctttt tcctcctgtg tacaggaag agaggggtac | 3960 |
| atttccctgt gctgacggaa gccaacttgg ctttcccgga ctgcaagcag ggctctgccc | 4020 |
| cagaggcctc tctctccgtc gtgggagaga gacgtgtaca tagtgtaggt cagcgtgctt | 4080 |
| agcctcctga cctgaggctc ctgtgctact ttgccttttg caaactttat tttcatagat | 4140 |
| tgagaagttt tgtacagaga attaaaaatg aaattattta taatctggaa aaaa | 4194 |

<210> SEQ ID NO 28
<211> LENGTH: 1837
<212> TYPE: DNA
<213> ORGANISM: Homo sapiens

<400> SEQUENCE: 28

| | |
|---|---|
| gagccgcgca cgggactggg aaggggaccc acccgagggt ccagccacca gccccctcac | 60 |
| taatagcggc caccccggca gcggcggcag cagcagcagc gacgcagcgg cgacagctca | 120 |
| gagcagggag gccgcgccac ctgcgggccg gccggagcgg gcagcccag gccccctccc | 180 |
| cgggcacccg cgttcatgca acgcctggtg gcctgggacc cagcatgtct ccccctgccg | 240 |
| ccgccgccgc ctgcctttaa atccatggaa gtggccaact tctactacga ggcggactgc | 300 |
| ttggctgctg cgtacggcgg caaggcggcc cccgcgcgcg ccccgcggc cagacccggg | 360 |
| ccgcgcccc ccgccggcga gctgggcagc atcggcgacc acgagcgcgc catcgacttc | 420 |
| agcccgtacc tggagccgct gggcgcgccg caggccccgg cgcccgccac ggccacggac | 480 |
| accttcgagg cggctccgcc cgcgcccgcc ccgcgcccg cctcctcgg gcagcaccac | 540 |
| gacttcctct ccgacctctt ctccgacgac tacgggggca agaactgcaa gaagccggcc | 600 |
| gagtacggct acgtgagcct ggggcgcctg ggggccgcca agggcgcgct gcaccccggc | 660 |
| tgcttcgcgc ccctgcaccc accgcccccg ccgccgccgc cgcccgccga gctcaaggcg | 720 |
| gagccgggct tcgagcccgc ggactgcaag cggaaggagg aggccggggc gccgggcggc | 780 |

-continued

```
ggcgcaggca tggcggcggg cttcccgtac gcgctgcgcg cttacctcgg ctaccaggcg      840
gtgccgagcg gcagcagcgg gagcctctcc acgtcctcct cgtccagccc gcccggcacg      900
ccgagccccg ctgacgccaa ggcgcccccg accgcctgct acgcggggc  cgcgccggcg      960 ccctcgcagg tcaagagcaa ggccaagaag accgtggaca agcacagcga cgagtacaag     1020
atccggcgcg agcgcaacaa catcgccgtg cgcaagagcc gcgacaaggc caagatgcgc     1080
aacctggaga cgcagcacaa ggtcctggag ctcacggccg agaacgagcg gctgcagaag     1140
aaggtggagc agctgtcgcg cgagctcagc accctgcgga acttgttcaa gcagctgccc     1200
gagcccctgc tcgcctcctc cggccactgc tagcgcggcc cccgcgcgcg tcccctgcc      1260 ggccggggct gagactccgg ggagcgcccc gcccgcgcc  ctcgcccccg ccccggcgg      1320 cgccggcaaa actttggcac tggggcactt ggcagcgcgg ggagcccgtc ggtaatttta     1380 atatttatt  atatatatat atctatattt ttgtccaaac caaccgcaca tgcagatggg     1440
gctcccgccc gtggtgttat ttaaagaaga aacgtctatg tgtacagatg aatgataaac     1500
tctctgcttc tccctctgcc cctctccagg cgccggcggg cgggccggtt cgaagttga      1560 tgcaatcggt ttaaacatgg ctgaacgcgt gtgtacacgg gactgacgca acccacgtgt     1620
aactgtcagc cgggccctga gtaatcgctt aaagatgttc ctacgggctt gttgctgttg     1680
atgttttgtt ttgttttgtt ttttggtctt tttttgtatt ataaaaaata atctatttct     1740
atgagaaaag aggcgtctgt atattttggg aatcttttcc gtttcaagca ttaagaacac     1800
ttttaataaa ctttttttg  agaatggtta caaagcc                              1837
```

<210> SEQ ID NO 29
<211> LENGTH: 3549
<212> TYPE: DNA
<213> ORGANISM: Homo sapiens

<400> SEQUENCE: 29

```
cccctcttcc tcctcctcaa gggaaagctg cccacttcta gctgccctgc catccccttt       60
aaagggcgac ttgctcagcg ccaaaccgcg gctccagccc tctccagcct ccggctcagc      120
cggctcatca gtcggtccgc gccttgcagc tcctccagag ggacgcgccc cgagatggag      180
agcaaagccc tgctcgtgct gactctggcc gtgtggctcc agagtctgac cgcctcccgc      240
ggaggggtgg ccgccgccga ccaaagaaga gattttatcg acatcgaaag taaatttgcc      300
ctaaggaccc ctgaagacac agctgaggac acttgccacc tcattcccgg agtagcagag      360
tccgtggcta cctgtcattt caatcacagc agcaaaacct tcatggtgat ccatggctgg      420
acggtaacag gaatgtatga gagttgggtg ccaaaacttg tggccgccct gtacaagaga      480
gaaccagact ccaatgtcat tgtggtggac tggctgtcac gggctcagga gcattaccca      540
gtgtccgcgg gctacaccaa actggtggga caggatgtgg cccggtttat caactggatg      600
gaggaggagt ttaactaccc tctggacaat gtccatctct gggatacag  ccttggagcc      660 catgctgctg gcattgcagg aagtctgacc aataagaaag tcaacagaat tactggcctc      720
gatccagctg gacctaactt tgagtatgca gaagccccga gtcgtctttc tcctgatgat      780
gcagattttg tagacgtctt acacacattc accagagggt cccctggtcg aagcattgga      840
atccagaaac cagttgggca tgttgacatt tacccgaatg gaggtacttt tcagccagga      900
tgtaacattg gagaagctat ccgcgtgatt gcagagagag acttggaga tgtggaccag      960 ctagtgaagt gctcccacga gcgctccatt catctcttca tcgactctct gttgaatgaa     1020
gaaaatccaa gtaaggccta caggtgcagt tccaaggaag cctttgagaa agggctctgc     1080
```

```
ttgagttgta gaaagaaccg ctgcaacaat ctgggctatg agatcaataa agtcagagcc    1140
aaaagaagca gcaaaatgta cctgaagact cgttctcaga tgccctacaa agtcttccat    1200
taccaagtaa agattcattt ttctgggact gagagtgaaa cccataccaa tcaggccttt    1260
gagatttctc tgtatggcac cgtggccgag agtgagaaca tcccattcac tctgcctgaa    1320
gtttccacaa ataagaccta ctccttccta atttacacag aggtagatat tggagaacta    1380
ctcatgttga agctcaaatg aagagtgat tcatacttta gctggtcaga ctggtggagc    1440
agtcccggct tcgccattca gaagatcaga gtaaaagcag gagagactca gaaaaggtg    1500 atcttctgtt ctagggagaa agtgtctcat ttgcagaaag gaaaggcacc tgcggtattt    1560
gtgaaatgcc atgacaagtc tctgaataag aagtcaggct gaaactgggc gaatctacag    1620
aacaaagaac ggcatgtgaa ttctgtgaag aatgaagtgg aggaagtaac ttttacaaaa    1680
catacccagt gtttggggtg tttcaaaagt ggattttcct gaatattaat cccagcccta    1740
cccttgttag ttattttagg agacagtctc aagcactaaa aagtggctaa ttcaatttat    1800
ggggtatagt ggccaaatag cacatcctcc aacgttaaaa gacagtggat catgaaaagt    1860
gctgttttgt cctttgagaa agaaataatt gtttgagcgc agagtaaaat aaggctcctt    1920
catgtggcgt attgggccat agcctataat tggttagaac ctcctatttt aattggaatt    1980
ctggatcttt cggactgagg ccttctcaaa ctttactcta agtctccaag aatacagaaa    2040 atgctttttcc gcggcacgaa tcagactcat ctacacagca gtatgaatga tgttttagaa    2100
tgattccctc ttgctattgg aatgtggtcc agacgtcaac caggaacatg taacttggag    2160
agggacgaag aaagggtctg ataaacacag aggttttaaa cagtccctac cattggcctg    2220
catcatgaca aagttacaaa ttcaaggaga tataaaatct agatcaatta attcttaata    2280
ggctttatcg tttattgctt aatccctctc tcccccttct tttttgtctc aagattatat    2340
tataataatg ttctctgggt aggtgttgaa aatgagcctg taatcctcag ctgacacata    2400
atttgaatgg tgcagaaaaa aaaaagatac cgtaattta ttattagatt ctccaaatga    2460
ttttcatcaa tttaaaatca ttcaatatct gacagttact cttcagtttt aggcttacct    2520
tggtcatgct tcagttgtac ttccagtgcg tctcttttgt tcctggcttt gacatgaaaa    2580
gataggtttg agttcaaatt ttgcattgtg tgagcttcta cagattttag acaaggaccg    2640
tttttactaa gtaaaagggt ggagaggttc ctggggtgga ttcctaagca gtgcttgtaa    2700
accatcgcgt gcaatgagcc agatggagta ccatgagggt tgttatttgt tgttttaac     2760 aactaatcaa gagtgagtga acaactattt ataaactaga tctcctattt ttcagaatgc    2820
tcttctacgt ataaatatga atgataaag atgtcaaata tctcagaggc tatagctggg    2880
aacccgactg tgaaagtatg tgatatctga acacatacta gaaagctctg catgtgtgtt    2940
gtccttcagc ataattcgga agggaaaaca gtcgatcaag ggatgtattg gaacatgtcg    3000
gagtagaaat tgttcctgat gtgccagaac ttcgacccct tctctgagag agatgatcgt    3060
gcctataaat agtaggacca atgttgtgat taacatcatc aggcttggaa tgaattctct    3120
ctaaaaataa aatgatgtat gatttgttgt tggcatcccc tttattaatt cattaaattt    3180
ctggatttgg gttgtgaccc agggtgcatt aacttaaaag attcactaaa gcagcacata    3240
gcactgggaa ctctggctcc gaaaaacttt gttatatata tcaaggatgt tctggctta    3300 cattttattt attagctgta aatacatgtg tggatgtgta aatggagctt gtacatattg    3360
gaaaggtcat tgtggctatc tgcatttata aatgtgtggt gctaactgta tgtgtcttta    3420
tcagtgatgg tctcacagag ccaactcact cttatgaaat gggctttaac aaaacaagaa    3480
```
agaaacgtac ttaactgtgt gaagaaatgg aatcagcttt taataaaatt gacaacattt    3540
tattaccac                                                             3549

<210> SEQ ID NO 30
<211> LENGTH: 402
<212> TYPE: PRT
<213> ORGANISM: Homo sapiens

<400> SEQUENCE: 30

Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
            20                  25                  30

His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
    210                 215                 220

Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
                245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
                325                 330                 335

Pro Leu His Val Ala Gln Ala Leu Gln Lys Val Lys Ile Glu Val Asn
            340                 345                 350

Glu Ser Gly Thr Val Ala Ser Ser Ser Thr Ala Val Ile Val Ser Ala

```
              355                 360                 365
Arg Met Ala Pro Glu Glu Ile Ile Met Asp Arg Pro Phe Leu Phe Val
        370                 375                 380

Val Arg His Asn Pro Thr Gly Thr Val Leu Phe Met Gly Gln Val Met
385                 390                 395                 400

Glu Pro

<210> SEQ ID NO 31
<211> LENGTH: 4592
<212> TYPE: DNA
<213> ORGANISM: Homo sapiens

<400> SEQUENCE: 31
aggctgttga ggctgggcca tctcctcctc acttccattc tgactgcagt ctgtggttct   60
gattccatac cagaggggct caggatgctg ttgctgggag ctgttctact gctattagct  120
ctgcccggtc atgaccagga aaccacgact caagggcccg agtcctgct  tcccctgccc   180 aagggggcct gcacaggttg gatggcgggc atcccagggc atccgggcca taatggggcc  240
ccaggccgtg atggcagaga tggcacccct ggtgagaagg gtgagaaagg agatccaggt  300
cttattggtc ctaagggaga catcggtgaa accggagtac ccggggctga aggtccccga  360
ggctttccgg gaatccaagg caggaaagga gaacctggag aaggtgccta tgtataccgc  420
tcagcattca gtgtgggatt ggagacttac gttactatcc ccaacatgcc cattcgcttt  480
accaagatct tctacaatca gcaaaaccac tatgatggct ccactggtaa attccactgc  540
aacattcctg gctgtacta  ctttgcctac cacatcacag tctatatgaa ggatgtgaag  600
gtcagcctct tcaagaagga caaggctatg ctcttcacct atgatcagta ccaggaaaat  660
aatgtggacc aggcctccgg ctctgtgctc ctgcatctgg aggtgggcga ccaagtctgg  720
ctccaggtgt atggggaagg agagcgtaat ggactctatg ctgataatga caatgactcc  780
accttcacag gctttcttct ctaccatgac accaactgat caccactaac tcagagcctc  840
ctccaggcca acagccccca agtcaattaa aggctttca gtacggttag aagttgatt   900 attatttagt tggaggcctt tagatattat tcattcattt actcattcat ttattcattc  960
attcatcaag taactttaaa aaatcatat gctatgttcc cagtcctggg gagcttcaca  1020
aacatgacca gataactgac tagaaagaag tagttgacag tgctattttg tgcccactgt  1080
ctctcctgat gctcatatca atcctataag gcacagggaa caagcattct cctgttttta  1140
cagattgtat cctgaggctg agagagttaa gtgaatgtct aaggtcacac agtattaagt  1200
gacagtgcta gaaatcaaac ccagagctgt ggactttgtt cactagactg tgccctttta  1260
tagaggtaca tgttctcttt ggagtgttgg taggtgtctg tttcccacct cacctgagag  1320
ccattgaatt tgccttcctc atgaattaaa acctccccca agcagagctt cctcagagaa  1380
agtggttcta tgatgaagtc ctgtcttgga aggactacta ctcaatggcc cctgcactac  1440
tctacttcct cttacctatg tcccttctca tgcctttccc tccaacgggg aaagccaact  1500
ccatctctaa gtgctgaact catccctgtt cctcaaggcc acctggccag gagcttctct  1560
gatgtgatat ccacttttt  tttttttgag atggagtctc actctgtcac ccaggctgga  1620
gtacagtgac acgacctcgg ctcactgcag cctccttctc ctgggtccaa gcaattattg  1680
tgcctcagcc tcccgagtag ctgagacttc aggtgcattc accacacat  ggctaatttt  1740 tgtattttta gtagaaatgg gtttcgtca  tgttggccag gctggtctcg aactcctggc  1800
ctaggtgatc caccgcctc  gacctcccaa agtgctggga ttacaggcat gagccaccat  1860
```

```
gcccagtcga tatctcactt tttattttgc catggatgag agtcctgggt gtgaggaaca   1920
cctcccacca ggctagaggc aactgcccag gaaggactgt gcttccgtca cctctaaatc   1980
ccttgcagat ccttgataaa tgcctcatga agaccaatct cttgaatccc atatctaccc   2040
agaattaact ccattccagt ctctgcatgt aatcagtttt atccacagaa acattttcat   2100
tttaggaaat ccctggtttt aagtatcaat ccttgttcag ctggacaata tgaatctttt   2160
ccactgaagt tagggatgac tgtgattttc agaacacgtc cagaattttt catcaagaag   2220
gtagcttgag cctgaaatgc aaaacccatg gaggaattct gaagccattg tctccttgag   2280
taccaacagg gtcagggaag actgggcctc ctgaatttat tattgttctt taagaattac   2340
aggttgaggt agttgatggt ggtaaacatt ctctcaggag acaataactc cagtgatgtt   2400
cttcaaagat tttagcaaaa acagagtaaa tagcattctc tatcaatata taaatttaaa   2460
aaactatctt tttgcttaca gttttaaatt ctgaacaatt ctctcttata tgtgtattgc   2520
taatcattaa ggtattattt tttccacata taaagctttg tcttttttgtt gttgttgttg   2580
tttttaagat ggagtttccc tctgttgcca ggctagagtg cagtggcatg atctcggctt   2640
actgcaacct ttgcctccca ggttcaagcg attcttctgc ctcagcctcc cgagtagctg   2700
ggaccacagg tgcctaccac catgccaggc taattttttgt attttttagta aagacagggt   2760
ttcaccatat tggccaggct ggtctcgaac tcctgacctt gtgatctgcc cgcctccatt   2820
tttgttgtta ttttttgaga agatagata tgaggtttag agaggatga agaggtgaga   2880
gtaagccttg tgttagtcag aactctgtgt tgtgaatgtc attcacaaca gaaaacccaa   2940
aatattatgc aaactactgt aagcaagaaa aataaaggaa aaatggaaac atttattcct   3000
ttgcataata gaaattacca gagttgttct gtctttagat aaggtttgaa ccaaagctca   3060
aaacaatcaa gacccttttc tgtatgtcct tctgttctgc cttccgcagt gtaggcttta   3120
ccctcaggtg ctacacagta tagttctagg gtttccctcc cgatatcaaa aagactgtgg   3180
cctgcccagc tctcgtatcc ccaagccaca ccatctggct aaatggacat catgttttct   3240
ggtgatgccc aaagaggaga gaggaagctc tctttcccag atgccccagc aagtgtaacc   3300
ttgcatctca ttgctctggc tgagttgtgt gcctgtttct gaccaatcac tgagtcagga   3360
ggatgaaata ttcatattga cttaattgca gcttaagtta ggggtatgta gaggtatttt   3420
ccctaaagca aaattgggac actgttatca gaaataggag agtggatgat agatgcaaaa   3480
taatacctgt ccacaacaaa ctcttaatgc tgtgtttgag ctttcatgag tttcccagag   3540
agacatagct ggaaaattcc tattgatttt ctctaaaatt tcaacaagta gctaaagtct   3600
ggctatgctc acagtctcac atctggttgg ggtgggctcc ttacagaaca cgctttcaca   3660
gttaccctaa actctctggg gcagggttat tcctttgtgg aaccagaggc acagagagag   3720
tcaactgagg ccaaaagagg cctgagagaa actgaggtca agatttcagg attaatggtc   3780
ctgtgatgct ttgaagtaca attgtggatt tgtccaattc tctttagttc tgtcagcttt   3840
tgcttcatat atttttagcgc tctattatta gatatataca tgtttagtat tatgtcttat   3900
tggtgcattt actctcttat cattatgtaa tgtccttctt tatctgtgat aattttctgt   3960
gttctgaagt ctactttgtc taaaaataac atacgcactc aacttccttt tctttcttcc   4020
ttcctttctt tcttccttcc tttctttctc tctctctctc tttccttcct tccttcctcc   4080
ttttctttct ctctctctct ctctctcttt ttttgacaga ctctcgttct gtggccctgg   4140
ctggagttca gtggtgtgat cttggctcac tgctacctct accatgagca attctcctgc   4200
ctcagcctcc caagtagctg gaactacagg ctcatgccac tgcgcccagc taattttttgt   4260
```

```
atttttcgta gagacggggt ttcaccacat tcgtcaggtt ggtttcaaac tcctgacttt    4320
gtgatccacc cgcctcggcc tcccaaagtg ctgggattac aggcatgagc catcacacct    4380
ggtcaacttt cttttgatta gtgttttttgt ggtatatctt tttccatcat gttactttaa    4440
atatatctat attattgtat ttaaaatgtg tttcttacag actgcatgta gttgggtata    4500 attttatcc agtctaaaaa tatctgtctt ttaattggtg tttagacaat ttatatttaa    4560
taaaattgtt gaatttaaaa aaaaaaaaaa aa                                  4592

<210> SEQ ID NO 32
<211> LENGTH: 1125
<212> TYPE: DNA
<213> ORGANISM: Homo sapiens

<400> SEQUENCE: 32
ttctgccctc gagcccaccg ggaacgaaag agaagctcta tctcgcctcc aggagcccag     60
ctatgaactc cttctccaca agcgccttcg gtccagttgc cttctccctg ggctgctcc    120 tggtgttgcc tgctgccttc cctgccccag tacccccagg agaagattcc aaagatgtag    180
ccgccccaca cagacagcca ctcacctctt cagaacgaat tgacaaacaa attcggtaca    240
tcctcgacgg catctcagcc ctgagaaagg agacatgtaa caagagtaac atgtgtgaaa    300
gcagcaaaga ggcactggca gaaaacaacc tgaaccttcc aaagatggct gaaaaagatg    360
gatgcttcca atctggattc aatgaggaga cttgcctggt gaaaatcatc actggtcttt    420
tggagtttga ggtataccta gagtacctcc agaacagatt tgagagtagt gaggaacaag    480
ccagagctgt gcagatgagt acaaaagtcc tgatccagtt cctgcagaaa aaggcaaaga    540
atctagatgc aataaccacc cctgacccaa ccacaaatgc cagcctgctg acgaagctgc    600
aggcacagaa ccagtggctg caggacatga caactcatct cattctgcgc agctttaagg    660
agttcctgca gtccagcctg agggctcttc ggcaaatgta gcatgggcac ctcagattgt    720
tgttgttaat gggcattcct tcttctggtc agaaacctgt ccactgggca cagaacttat    780
gttgttctct atggagaact aaaagtatga gcgttaggac actattttaa ttatttttaa    840
tttattaata tttaaatatg tgaagctgag ttaatttatg taagtcatat ttatattttt    900
aagaagtacc acttgaaaca ttttatgtat tagttttgaa ataataatgg aaagtggcta    960
tgcagtttga atatcctttg tttcagagcc agatcatttc ttggaaagtg taggcttacc   1020
tcaaataaat ggctaactta tacatatttt taagaaata tttatattgt atttatataa   1080
tgtataaatg gttttatac caataaatgg catttttaaaa aattc                   1125

<210> SEQ ID NO 33
<211> LENGTH: 212
<212> TYPE: PRT
<213> ORGANISM: Homo sapiens

<400> SEQUENCE: 33

Met Asn Ser Phe Ser Thr Ser Ala Phe Gly Pro Val Ala Phe Ser Leu
  1               5                  10                  15

Gly Leu Leu Leu Val Leu Pro Ala Ala Phe Pro Ala Pro Val Pro Pro
                 20                  25                  30

Gly Glu Asp Ser Lys Asp Val Ala Ala Pro His Arg Gln Pro Leu Thr
             35                  40                  45

Ser Ser Glu Arg Ile Asp Lys Gln Ile Arg Tyr Ile Leu Asp Gly Ile
         50                  55                  60

Ser Ala Leu Arg Lys Glu Thr Cys Asn Lys Ser Asn Met Cys Glu Ser
 65                  70                  75                  80
```

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 34
<211> LENGTH: 233
<212> TYPE: PRT
<213> ORGANISM: Homo sapiens

<400> SEQUENCE: 34

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 35
<211> LENGTH: 10049
<212> TYPE: DNA
<213> ORGANISM: Homo sapiens

<400> SEQUENCE: 35

| | | | | | |
|---|---|---|---|---|---|
| gcgccgcctc | cttcggcgtt | cgccccacgg | accggcaggc | ggcggaccgc | ggcccaggct | 60 |
| gaagctcagg | gccctgtctg | ctctgtggac | tcaacagttt | gtggcaagac | aagctcagaa | 120 |
| ctgagaagct | gtcaccacag | ttctggaggc | tgggaagttc | aagatcaaag | tgccagcaga | 180 |
| ttcagtgtca | tgtgaggacg | tgcttcctgc | ttcatagata | agagtagctt | ggagctcggc | 240 |
| ggcacaacca | gcaccatctg | gtcgcgatgg | tggacacgga | aagcccactc | tgcccccctct | 300 |
| ccccactcga | ggccggcgat | ctagagagcc | cgttatctga | agagttcctg | caagaaatgg | 360 |
| gaaacatcca | agagatttcg | caatccatcg | gcgaggatag | ttctggaagc | tttggctttta | 420 |
| cggaatacca | gtatttagga | agctgtcctg | gctcagatgc | tcggtcatc | acggacacgc | 480 |
| tttcaccagc | ttcgagcccc | tcctcggtga | cttatcctgt | ggtccccggc | agcgtggacg | 540 |
| agtctcccag | tggagcattg | aacatcgaat | gtagaatctg | cggggacaag | gcctcaggct | 600 |
| atcattacgg | agtccacgcg | tgtgaaggct | gcaagggctt | ctttcggcga | acgattcgac | 660 |
| tcaagctggt | gtatgacaag | tgcgaccgca | gctgcaagat | ccagaaaaag | aacagaaaca | 720 |
| aatgccagta | ttgtcgattt | cacaagtgcc | tttctgtcgg | gatgtcacac | aacgcgattc | 780 |
| gttttggacg | aatgccaaga | tctgagaaag | caaaactgaa | agcagaaatt | cttacctgtg | 840 |
| aacatgacat | agaagattct | gaaactgcag | atctcaaatc | tctggccaag | agaatctacg | 900 |
| aggcctactt | gaagaacttc | aacatgaaca | aggtcaaagc | ccgggtcatc | ctctcaggaa | 960 |
| aggccagtaa | caatccacct | tttgtcatac | atgatatgga | gacactgtgt | atggctgaga | 1020 |
| agacgctggt | ggccaagctg | gtggccaatg | gcatccagaa | caaggaggcg | gaggtccgca | 1080 |
| tctttcactg | ctgccagtgc | acgtcagtgg | agaccgtcac | ggagctcacg | gaattcgcca | 1140 |
| aggccatccc | aggcttcgca | aacttggacc | tgaacgatca | agtgacattg | ctaaaatacg | 1200 |
| gagtttatga | ggccatattc | gccatgctgt | cttctgtgat | gaacaaagac | gggatgctgg | 1260 |
| tagcgtatgg | aaatgggttt | ataactcgtg | aattcctaaa | aagcctaagg | aaaccgttct | 1320 |
| gtgatatcat | ggaacccaag | tttgattttg | ccatgaagtt | caatgcactg | gaactggatg | 1380 |
| acagtgatat | ctcccttttt | gtggctgcta | tcatttgctg | tggagatcgt | cctggccttc | 1440 |
| taaacgtagg | acacattgaa | aaaatgcagg | agggtattgt | acatgtgctc | agactccacc | 1500 |
| tgcagagcaa | ccacccggac | gatatctttc | tcttcccaaa | acttcttcaa | aaaatgcag | 1560 |
| acctccggca | gctggtgacg | gagcatgcgc | agctggtgca | gatcatcaag | aagacggagt | 1620 |
| cggatgctgc | gctgcacccg | ctactgcagg | agatctacag | ggacatgtac | tgagttcctt | 1680 |
| cagatcagcc | acaccttttc | caggagttct | gaagctgaca | gcactacaaa | ggagacgggg | 1740 |
| gagcagcacg | attttgcaca | aatatccacc | actttaacct | tagagcttgg | acagtctgag | 1800 |
| ctgtaggtaa | ccggcatatt | attccatatc | tttgttttaa | ccagtacttc | taagagcata | 1860 |
| gaactcaaat | gctggggggta | ggtggctaat | ctcaggactg | ggaagattac | ggcgaattat | 1920 |
| gctcaatggt | ctgattttaa | ctcacccgat | gttaatcaat | gcacattgct | ttagatcaca | 1980 |
| ttcgtgattt | accatttaat | taactggtaa | cctcaaaatt | cgtggcctgt | cttcccattc | 2040 |
| accccgcttt | tgactattgt | gctcctttat | aattctgaaa | actaatcagc | acttttaac | 2100 |
| aatgtttata | atcctataag | tctagatgta | tccaaaggtg | aagtatgtaa | aaagcagcaa | 2160 |

```
aatatttatt tcaaagactt cacttctgtt tcctgaatct aaagaaagac aacatgctgc    2220
tttttaatca taggatggag aattttaaag aactgtttgg gccaggcaca gtcgctcata    2280
cttgtaatcc cagcactttg ggaggccgag gcgggtggat cacaaggtca gcagatcgag    2340
accatcctgg ccaacatggt gaaaccctgt ctctactaaa aatacaaaaa ttagccgggt    2400
gtggtggcac atgcctgtaa tcccagctac tcgggaagct gaggcaggag aattgcttga    2460
accagggagt tggaggttgc agtgagctaa gactgcacca ctgcactcca gcctggtgac    2520
agaacgagac tctgtcttaa aaacaaacaa acaaaaaaaa aatctgttag ataagctatc    2580
aaaatgcagc tgttgttttg tttttggctc actgttttcg tggttgtaac taatatgtgg    2640
aaaggcccat ttccaggttt gcgtagaaga gcccagaaaa cagagtctca agaccccgc     2700 tctggactgt cataagctag cacccgtggt aagcgggacg agacaagctc ccgaagcccg    2760
ccagcttcct gctccactca gctccgtcca gtcaacctga acccacccag tccagctgtc    2820
tgtgggaatg gtggtgttct tagggacaga ctgacacctt acttgtcagt gttcctccgg    2880
gccccatttg gcagctcccg tatcttttgt tatgttgctt ttaaagatat gatgttttat    2940
tgttttaact cttggtgaca gtagatgctc tctggagcgc agacgaggca catgtgtctt    3000
catagcctgg gctgggtggg agccagtcac cctgcggatc gagagagggg gtagagtctt    3060
cttcaaatgg cagttttact tcaaatggca gatttcacaa gagttggtta ttttttacaa    3120
tggtttaggt tgttaagtct cctttgtatg taaggtagtt ttttcaacat ctaaaatttt    3180
tgttttagcc ttcaaaacca acttaccaac ctcagtccag ctgggaaggc agcgttgatt    3240
atggtagttt gtcaagaata tatggacctg gaaacacttt ctctctctgt ccacctggta    3300
gataaattgt cctgttgaga attttttagat ctggactgga actgccagga ccaccgcctc    3360
cagggagtcg ctgggcacct ggaggtatcg tcgatgcctc tccccatct ttagaaaatt      3420 tggctcttct gaggtcatta ttattttaag aatgattagg attgataagg gtcccatgac    3480
cagcattatg aaaatgcgag agtgggaagg acacagtgtg agacttccac tagaaaaaag    3540
tgaaagttag ggttaggaca tccttttta aaaattacaa atttagtccg ttttggtttt     3600
tgtaatcagg ctaggcacag tggctcacac atggaatccc agcactttgg gaggccgagg    3660
tgggaggatc acttgagccc aggagttcga gaccagccta ggcaacatag caagaccctg    3720
tctgtacaca aaatttaaaa attagttcat cggggtggca cacatcagta gtcccagcta    3780
ctctgcaggc tgaggtggga ggattgcttg aacccaggag gtcgaggctg cagtgagctg    3840
tgatctcacc actgcattcc agcctgggtg acagagttag attccaccct ctcccacccc    3900
ggcaaaaaaa aaaaaaaaag atgcaatcaa aggggctgtt ggccagcaat ggcagcagca    3960
gcggcgggca gtctgcccaa gtgtcttagg aaccaaaagc aaataaaagt gtttccatat    4020
atgccaccag ccaagtggcc atcctaattc agaaagaagc tagcctttga gtgtctgtca    4080
tggtgcatcc gtttcagtat tatttcctaa aatgagaagc ccctgtgtca acaagatcca    4140
ggggctggag cccaatgcca agcctgtgtt gtccccagcg accctgcagc tgctcgctct    4200
gatgtaccct gtgccattca aggagatgtg gtccaggaaa gtgagcctca tggttttcag    4260
agaagtcatt gttctgttta cattttcata aaacctgttt aaaatagctc cccgtctcag    4320
gctttcagca gtaacagtga gctgactggc aagttcgatg ttagctcccg ggacactcag    4380
cagcgatggt gagcatttg gtttccttaa ggcccagcaa gacttccagg gacatctctg     4440
gtgaagccag aatggagaca cccgtgacct caggctgaaa gtcactcgac attggtctct    4500
tgtgttgata gggaaggaaa tcaggcattc ctatttcttt aaataacaaa accactaatt    4560
```

```
gccactcaat gctggaatat tttgggtcac ctaatcatag atttctcagg gcatcaatac    4620
tcaaatatag gctgattatg ccccagttca aatgggaact attaacagag tgcatttctt    4680
gcttgctggg tttcaacaga catcagccaa agaacaaaa gagatgtcag acagattcc     4740 aggagtgtcg gagcacatgt gtggcacccg ctccctctgg cagcgaatgt aggaagtcgc    4800
caaatttacc cactcttcaa caagtcattg tttaaacacg ttttttcatt ttctcaactt    4860
ttaatagcaa aaagtgccaa agtcctcaga gacctaacag ccttggtcta ccgtgctgac    4920
cagggtgaag gcacggcgag ggactcctcc cagacgtgcc tcttgtgtgc cagctggctg    4980
tggctcggga gcagacgcag gcctctccat tgtccagggg agcctggcgg cgcatccctc    5040
ctctcccacc tcctggcact tccagctggg tgtcccacat gttggattcc gtccccacca    5100
cacttccaga gaccggagaa ctgtgcaggg cctaaggccg tttggatgaa ttgtcaaaac    5160
aagatgcttc cagttacagc ggcaggagcg ggactgggag cacgggctga cggctgctgg    5220
tgcctttctt cccacctcgc ttgcctgttt ccgcttgacc cttcctccag ctccgatgag    5280
aagagtataa agcatcttcc taacggggtgt gtttgctata cgaacataat ggacgtgaag    5340
tggggcagaa acccagaact cagcattcaa ggatgcccag gagagctgtc cctgttttaa    5400
agagctgtgt tttgttttgt ttcgcattta gagagcagac aaggcaccct tctgctgcgc    5460
tgatacgttt cttacactgg gccattttag acccccaggg aaacagcctt cctggagcgt    5520
tgtctggagg ttccagggac agggcagcct cccagagccg agcaagagct caaggtacaa    5580
atgagagatt tgctataccg tgagaagtca acaacttagc caccacttcc ccgcaatgga    5640
ccatgtaaca aatacctcag caggccctgc aaaaggccat gctagagctg aggcgcacag    5700
cctgtggcct ctgtagttag ggcaggtggg atggagactc cttgagtgca cacacctgag    5760
cctgcccaca cacaggggag cagcatctcg tatgacgtct ggaaggaact tcggttgtgt    5820
aaagggagcc ttgaagatac gtgcaaaagg tgctacccca atttggtgaa actgacattg    5880
ggcacgtctt gggcttagga gaagcggccg atggtcccgg cctgcagtga caaaccccccc   5940 tccccgcacc gccccccagca cccccctctcc tcttcacctc ttcctgctgg ccacgaggaa    6000
gccacttcct cagagagacc ctaccagatg cggatggaaa cagatgcacc aaagcaagcc    6060
ctgatgaaac cgcgacttcc taaggtctgt ctcctctgaa cttgcacctg ggcctctctg    6120
tgtttggttc caagcacttc ccacctcaaa ctcccatttt caaaccactg tatctctgcg    6180
cacatctgct acttaccagc cgcatacatg atggagggtt ttttggtcct gatccagtgg    6240
ccacacctgt ctttgaaatg tctcactgaa ctccagtttt aaaatagatt cattgcttca    6300
acacagcaag cccaatgcac ccagctaaga ctggcttgac cgacagcctg cctttggtg     6360 ggggcttcc tggggcctgg ggaaagctgg ccaccttcaa cagctggtac ctcttcaaca     6420
gtgtggcctt tcaaaatgca gatgccacca ggagaacatg cccacagctc accacctatg    6480
gatgccatgg ctctgggcag ctttcaaagc aggttcctgt ggtctcctca gctgtttgag    6540
ggggtaacag caaatcagcc tccatttaa aatgaaaaca ccagcctcca gatgtagggc      6600
ctgctgggtg ttgctagccg ctggtcccca ggcacggtgc actttctcca cctcctgcag    6660 cctcccctgtt gtttctagac tcttgcacct ggtgagtgca aggataggtg acccagggggc   6720 ctgcagcctt gtcctcagct cccatctcct ggactgccag cctcaccctc tgcagttagc    6780
atggttggcc tgatgcaggg atcccgaggg attacttttt agaccttctt tcacattcag    6840
aaaagtagta tagattcagg agaggcaaga aaattatgct gtccatagaa gtcacccatg    6900
aagactgatg ccaccacctg aaggctcatg attgttaaaa atgtccacgg gaacctctcg    6960
```

```
tccacaggag gtttgtctca acacttccca tttttacggc attggcattg ccaagcatgg    7020
ggaagtatct gctcttctca tgttaaaagt ggcccagctt ttcttaactc agtccaagct    7080
gacttgttta gctgcactgg aatttcttac caaccaaata tttgcatcga gcaaggggg    7140 ctgtgtgcac ctccctaatg gcagcgatga tggctgctgt cattcaagcc catcttcaga    7200
cgtcacagtc tggaagtgaa atgtccacaa acatctgtgg cagaaaaggc tatacggacc    7260
acccagttgt gctgcagctt tacagagcaa ggaagggttg tggcaaataa atgattaacc    7320
tgcctcgact gtgctgaggg caacaaaggc catctcacca aaggattatt cgatgccatt    7380
aaatcatccc gtgaccttcc tgcttccgag tccatggcct tgcccaggg catgtactcc    7440 cctgagaggc cttctgccta gaaagatcta tgactgggtt ccaaagttga ggcctaggtt    7500
tttgctggga tttagatatt ttcaggcacc attttgacag cattcaggaa aacgttatt    7560 gaccccatag actagggtaa gaataaaggc aataaatttg gtctgactca gaatatagga    7620
gatccatata tttctctgga aaccacagtg tacactaaaa tgtgaaattg aaggttttgt    7680 taaaagaaa aagataatga gcttcatgct ttgtttaatt acataatgat ttccattacg    7740
ctatttctgt gaaatgcagc aggttcttaa acgttatttc agtggcatgg gctggaagct    7800
tatcacaaaa agccatgtgt gtggccttat cagaacagaa agagacaggc tggtgcccaa    7860
ggctgctgcc tgctccacct tttgccagct ctggacatct gaggacgtcc cggcagatct    7920
ggaatggggc cctcaactga ccatttgctt ctcagaattt cagtttgaga catgagaggt    7980
ataatcagtt acttttctcc ccccagagaa accctttgt gaggggagag gagctatggt    8040
atgtggttca gctgaaacac atacaactgc atcctttgg agtcctttgc caacaaaaac    8100
agaccaacag accagatggt gtccatgttc aatatcatgt cttgatggac gcagctgatg    8160
acctcaaata cttgagtggt ctcatggctg ttagatggat tatttgaaaa aaaaaaaaa    8220 aaaagagaga aaaataatt gattttaca tcagagatag caaactaaga cctggggagg    8280
ggggtcagct tttattttat tttatttttt ttaagtttgc tagttgggtc aaatgtgagg    8340
aggagggagt ctacctgcca cctcttctct tgcccctctt ctgccacac atccagcatc    8400 caaaatccat tcatttaatg aattgataaa gtgccgtgca aactggtgca caaacaggcc    8460
cccagtccac gcagcctggc tcctaggaaa agtggtgacc gggcgtgggg gggcatgccg    8520
cagccctggg acacagtcgg gcaccttccc cggaccccca ggccttggct gtgcctcaag    8580
tcagagaggg tcagccttca ggccccggag acgagtgact ggccgatcat ttcacaataa    8640
aatcactcac ttttggcaac ttcactttt taaggcaca gtcagttcct tttctcatgt    8700
acctcacaaa agatgaagac catgtagtac tcttttggt aaagttacag tgttcatgtt    8760
aaatatcact ttttctaca ttgtgtggta aaaagaacta cgttaatagc tatatcttaa    8820
atactgtgat ttgactttt gaaaaatatc ctaatacaaa tattttacta acttacaatc    8880
actcatttaa taagaaacat ttggattctt ttgaaatcag tgttaattga ctcatattct    8940
taaaagcctg gctcttgacc ctattggaaa cacaaggaa gctgaaatca acatctaaa    9000 atacactgcg tacacgtgtg cgtgcacaca cacacacaca cacacacaca cacagctctt    9060
catttctcct gagccatgca gaatttactt tcaatgtgga aatctgttcc ctttaccaca    9120
ctgtatatgc acagagcaca agagaggcta tctctagtca cttccaccag cgaggcctta    9180
gactccgtat tagaggccac cgatttcata caacagtgtt tcgctaaaga ccccttcacta    9240 ttcttgttta gtaaatagct gtctgctctt cagggaactg ttacctatgg gttattacca    9300
aagaacgctg gcaattggaa atgtcctgat ggaaattctt tgcacgtgcc ggttctctgg    9360
```

```
catcctccag gtggcccaac ccaaagcaga aagcagaaac cacagacccc gtgagtctcc    9420
ccataccttg tttccaataa cttggcaaaa cttcttggtg catattggtt acaccctctg    9480
ggattcataa tgccattagg ctaaaaccct aagagagagg gttgacagaa acacacgcga    9540
gaatgaggca gatcccagag caaggactgg gcccagactc tccacatgtg ctctactagt    9600
gagtgcctta tactctcagt attttggggc ttacagcttc ttatttgtgc taaaaaggtg    9660
cagttccaaa gtaggaactg ccacacaggc cccagcatcc tctctccaac ttcataccct    9720
tctcctggtg gggggagcgg gcatccagga cctccggaat caaggatgtg cagagaagag    9780
cgaaagtaat ttttctagtc acatgaactg attggttcca ggcaattaga aaatggctat    9840 aaaataaccct taattttaaa aaaaatctt gggtcttcgt tttcctatta ggagactgaa    9900
ctgaccacat gtattgattt atatcctgaa tatatgggaa cttctgtgtt tgggatgtcc    9960
tactgtaaga ctgatgaatg tacagagtta atttcagggt acagttttgc cttaatggtt    10020
ttaaaaaata aactattttt taaaatttt                                     10049
```

<210> SEQ ID NO 36
<211> LENGTH: 468
<212> TYPE: PRT
<213> ORGANISM: Homo sapiens

<400> SEQUENCE: 36

```
Met Val Asp Thr Glu Ser Pro Leu Cys Pro Leu Ser Pro Leu Glu Ala
 1               5                  10                  15

Gly Asp Leu Glu Ser Pro Leu Ser Glu Glu Phe Leu Gln Glu Met Gly
            20                  25                  30

Asn Ile Gln Glu Ile Ser Gln Ser Ile Gly Glu Asp Ser Ser Gly Ser
        35                  40                  45

Phe Gly Phe Thr Glu Tyr Gln Tyr Leu Gly Ser Cys Pro Gly Ser Asp
    50                  55                  60

Gly Ser Val Ile Thr Asp Thr Leu Ser Pro Ala Ser Ser Pro Ser Ser
65                  70                  75                  80

Val Thr Tyr Pro Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
            100                 105                 110

His Tyr Gly Val His Ala Cys Glu Gly Cys Lys Gly Phe Phe Arg Arg
        115                 120                 125

Thr Ile Arg Leu Lys Leu Val Tyr Asp Lys Cys Asp Arg Ser Cys Lys
    130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Ile Glu Asp Ser Glu Thr Ala Asp Leu Lys Ser Leu Ala Lys
        195                 200                 205

Arg Ile Tyr Glu Ala Tyr Leu Lys Asn Phe Asn Met Asn Lys Val Lys
    210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255
```

```
Lys Leu Val Ala Asn Gly Ile Gln Asn Lys Glu Ala Glu Val Arg Ile
            260                 265                 270
Phe His Cys Cys Gln Cys Thr Ser Val Glu Thr Val Thr Glu Leu Thr
        275                 280                 285
Glu Phe Ala Lys Ala Ile Pro Gly Phe Ala Asn Leu Asp Leu Asn Asp
    290                 295                 300
Gln Val Thr Leu Leu Lys Tyr Gly Val Tyr Glu Ala Ile Phe Ala Met
305                 310                 315                 320
Leu Ser Ser Val Met Asn Lys Asp Gly Met Leu Val Ala Tyr Gly Asn
                325                 330                 335
Gly Phe Ile Thr Arg Glu Phe Leu Lys Ser Leu Arg Lys Pro Phe Cys
            340                 345                 350
Asp Ile Met Glu Pro Lys Phe Asp Phe Ala Met Lys Phe Asn Ala Leu
        355                 360                 365
Glu Leu Asp Asp Ser Asp Ile Ser Leu Phe Val Ala Ala Ile Ile Cys
    370                 375                 380
Cys Gly Asp Arg Pro Gly Leu Leu Asn Val Gly His Ile Glu Lys Met
385                 390                 395                 400
Gln Glu Gly Ile Val His Val Leu Arg Leu His Leu Gln Ser Asn His
                405                 410                 415
Pro Asp Asp Ile Phe Leu Phe Pro Lys Leu Leu Gln Lys Met Ala Asp
            420                 425                 430
Leu Arg Gln Leu Val Thr Glu His Ala Gln Leu Val Gln Ile Ile Lys
        435                 440                 445
Lys Thr Glu Ser Asp Ala Ala Leu His Pro Leu Leu Gln Glu Ile Tyr
    450                 455                 460
Arg Asp Met Tyr
465

<210> SEQ ID NO 37
<211> LENGTH: 1863
<212> TYPE: DNA
<213> ORGANISM: Homo sapiens

<400> SEQUENCE: 37
actgatgtct tgactcatgg gtgtattcac aaattctgtt acttcaagtc ttttctttt       60 aacggattga tcttttgcta gatagagaca aaatatcagt gtgaattaca gcaaaccct      120 attccatgct gttatgggtg aaactctggg agattctcct attgacccag aaagcgattc     180
cttcactgat acactgtctg caaacatatc acaagaaatg accatggttg acacagagat     240
gccattctgg cccaccaact tgggatcag ctccgtggat ctctccgtaa tggaagacca      300
ctcccactcc tttgatatca gcccttcac tactgttgac ttctccagca tttctactcc      360
acattacgaa gacattccat tcacaagaac agatccagtg gttgcagatt acaagtatga     420
cctgaaactt caagagtacc aaagtgcaat caaagtggga cctgcatctc caccttatta     480
ttctgagaag actcagctct acaataagcc tcatgaagag ccttccaact ccctcatggc     540
aattgaatgt cgtgtctgtg gagataaagc ttctggattt cactatggag ttcatgcttg     600
tgaaggatgc aagggtttct tccggagaac aatcagattg aagcttatct atgacagatg     660
tgatcttaac tgtcggatcc acaaaaaaag tagaaataaa tgtcagtact gtcggtttca     720
gaaatgcctt gcagtgggga tgtctcataa tgccatcagg tttgggcgga tgccacaggc     780
cgagaaggag aagctgttgg cggagatctc cagtgatatc gaccagctga atccagagtc     840
cgctgaccct cggggccctg caaaacattt gtatgactca tacataaagt ccttcccgct     900
```

```
gaccaaagca aaggcgaggg cgatcttgac aggaaagaca acagacaaat caccattcgt    960
tatctatgac atgaattcct taatgatggg agaagataaa atcaagttca aacacatcac   1020
ccccctgcag gagcagagca aagaggtggc catccgcatc tttcagggct gccagtttcg   1080
ctccgtggag gctgtgcagg agatcacaga gtatgccaaa agcattcctg gttttgtaaa   1140
tcttgacttg aacgaccaag taactctcct caaatatgga gtccacgaga tcatttacac   1200
aatgctggcc tccttgatga ataaagatgg ggttctcata tccgagggcc aaggcttcat   1260
gacaagggag tttctaaaga gcctgcgaaa gccttttggt gactttatgg agcccaagtt   1320
tgagtttgct gtgaagttca atgcactgga attagatgac agcgacttgg caatatttat   1380
tgctgtcatt attctcagtg gagaccgccc aggtttgctg aatgtgaagc ccattgaaga   1440
cattcaagac aacctgctac aagccctgga gctccagctg aagctgaacc accctgagtc   1500
ctcacagctg tttgccaagc tgctccagaa aatgacagac ctcagacaga ttgtcacgga   1560
acacgtgcag ctactgcagg tgatcaagaa gacggagaca gacatgagtc ttcacccgct   1620
cctgcaggag atctacaagg acttgtacta gcagagagtc ctgagccact gccaacattt   1680
cccttcttcc agttgcacta ttctgaggga aaatctgaca cctaagaaat ttactgtgaa   1740
aaagcatttt aaaaagaaaa ggttttagaa tatgatctat tttatgcata ttgtttataa   1800
agacacattt acaatttact tttaatatta aaaattacca tattatgaaa aaaaaaaaa   1860
aaa                                                                  1863

<210> SEQ ID NO 38
<211> LENGTH: 505
<212> TYPE: PRT
<213> ORGANISM: Homo sapiens

<400> SEQUENCE: 38

Met Gly Glu Thr Leu Gly Asp Ser Pro Ile Asp Pro Glu Ser Asp Ser
 1               5                  10                  15

Phe Thr Asp Thr Leu Ser Ala Asn Ile Ser Gln Glu Met Thr Met Val
                20                  25                  30

Asp Thr Glu Met Pro Phe Trp Pro Thr Asn Phe Gly Ile Ser Ser Val
            35                  40                  45

Asp Leu Ser Val Met Glu Asp His Ser His Ser Phe Asp Ile Lys Pro
        50                  55                  60

Phe Thr Thr Val Asp Phe Ser Ser Ile Ser Thr Pro His Tyr Glu Asp
 65                  70                  75                  80

Ile Pro Phe Thr Arg Thr Asp Pro Val Val Ala Asp Tyr Lys Tyr Asp
                85                  90                  95

Leu Lys Leu Gln Glu Tyr Gln Ser Ala Ile Lys Val Glu Pro Ala Ser
            100                 105                 110

Pro Pro Tyr Tyr Ser Glu Lys Thr Gln Leu Tyr Asn Lys Pro His Glu
        115                 120                 125

Glu Pro Ser Asn Ser Leu Met Ala Ile Glu Cys Arg Val Cys Gly Asp
    130                 135                 140

Lys Ala Ser Gly Phe His Tyr Gly Val His Ala Cys Glu Gly Cys Lys
145                 150                 155                 160

Gly Phe Phe Arg Arg Thr Ile Arg Leu Lys Leu Ile Tyr Asp Arg Cys
                165                 170                 175

Asp Leu Asn Cys Arg Ile His Lys Lys Ser Arg Asn Lys Cys Gln Tyr
            180                 185                 190

Cys Arg Phe Gln Lys Cys Leu Ala Val Gly Met Ser His Asn Ala Ile
```

```
                195                 200                 205
Arg Phe Gly Arg Met Pro Gln Ala Glu Lys Glu Lys Leu Leu Ala Glu
210                 215                 220

Ile Ser Ser Asp Ile Asp Gln Leu Asn Pro Glu Ser Ala Asp Leu Arg
225                 230                 235                 240

Ala Leu Ala Lys His Leu Tyr Asp Ser Tyr Ile Lys Ser Phe Pro Leu
                245                 250                 255

Thr Lys Ala Lys Ala Arg Ala Ile Leu Thr Gly Lys Thr Thr Asp Lys
            260                 265                 270

Ser Pro Phe Val Ile Tyr Asp Met Asn Ser Leu Met Met Gly Glu Asp
        275                 280                 285

Lys Ile Lys Phe Lys His Ile Thr Pro Leu Gln Glu Gln Ser Lys Glu
    290                 295                 300

Val Ala Ile Arg Ile Phe Gln Gly Cys Gln Phe Arg Ser Val Glu Ala
305                 310                 315                 320

Val Gln Glu Ile Thr Glu Tyr Ala Lys Ser Ile Pro Gly Phe Val Asn
                325                 330                 335

Leu Asp Leu Asn Asp Gln Val Thr Leu Leu Lys Tyr Gly Val His Glu
            340                 345                 350

Ile Ile Tyr Thr Met Leu Ala Ser Leu Met Asn Lys Asp Gly Val Leu
        355                 360                 365

Ile Ser Glu Gly Gln Gly Phe Met Thr Arg Glu Phe Leu Lys Ser Leu
    370                 375                 380

Arg Lys Pro Phe Gly Asp Phe Met Glu Pro Lys Phe Glu Phe Ala Val
385                 390                 395                 400

Lys Phe Asn Ala Leu Glu Leu Asp Asp Ser Asp Leu Ala Ile Phe Ile
                405                 410                 415

Ala Val Ile Ile Leu Ser Gly Asp Arg Pro Gly Leu Leu Asn Val Lys
            420                 425                 430

Pro Ile Glu Asp Ile Gln Asp Asn Leu Leu Gln Ala Leu Glu Leu Gln
        435                 440                 445

Leu Lys Leu Asn His Pro Glu Ser Ser Gln Leu Phe Ala Lys Leu Leu
    450                 455                 460

Gln Lys Met Thr Asp Leu Arg Gln Ile Val Thr Glu His Val Gln Leu
465                 470                 475                 480

Leu Gln Val Ile Lys Lys Thr Glu Thr Asp Met Ser Leu His Pro Leu
                485                 490                 495

Leu Gln Glu Ile Tyr Lys Asp Leu Tyr
            500                 505

<210> SEQ ID NO 39
<211> LENGTH: 3734
<212> TYPE: DNA
<213> ORGANISM: Homo sapiens

<400> SEQUENCE: 39
gcggagcgtg tgacgctgcg gccgccgcgg acctggggat taatgggaaa agttttggca      60
ggagcgggag aattctgcgg agcctgcggg acggcggcgg tggcgccgta ggcagccggg     120
acagtgttgt acagtgtttt gggcatgcac gtgatactca cacagtggct tctgctcacc     180
aacagatgaa gacagatgca ccaacgaggc tgatgggaac caccctgtag aggtccatct     240
gcgttcagac ccagacgatg ccagagctat gactgggcct gcaggtgtgg cgccgagggg     300
agatcagcca tggagcagcc acaggaggaa gcccctgagg tccgggaaga ggaggagaaa     360
gaggaagtgg cagaggcaga aggagcccca gagctcaatg ggggaccaca gcatgcactt     420
```

```
ccttccagca gctacacaga cctctcccgg agctcctcgc caccctcact gctggaccaa      480
ctgcagatgg gctgtgacgg ggcctcatgc ggcagcctca acatggagtg ccgggtgtgc      540
ggggacaagg catcgggctt ccactacggt gttcatgcat gtgaggggtg caagggcttc      600
ttccgtcgta cgatccgcat gaagctggag tacgagaagt gtgagcgcag ctgcaagatt      660
cagaagaaga accgcaacaa gtgccagtac tgccgcttcc agaagtgcct ggcactgggc      720
atgtcacaca acgctatccg ttttggtcgg atgccggagg ctgagaagag gaagctggtg      780
gcagggctga ctgcaaacga ggggagccag tacaacccac aggtggccga cctgaaggcc      840
ttctccaagc acatctacaa tgcctacctg aaaaacttca acatgaccaa aaagaaggcc      900
cgcagcatcc tcaccggcaa agccagccac acggcgccct tgtgatccca cgacatcgag      960
acattgtggc aggcagagaa ggggctggtg tggaagcagt tggtgaatgg cctgcctccc     1020
tacaaggaga tcagcgtgca cgtcttctac cgctgccagt gcaccacagt ggagaccgtg     1080
cgggagctca ctgagttcgc caagagcatc cccagcttca gcagcctctt cctcaacgac     1140
caggttaccc ttctcaagta tggcgtgcac gaggccatct tcgccatgct ggcctctatc     1200
gtcaacaagg acgggctgct ggtagccaac ggcagtggct tgtcacccg tgagttcctg     1260 cgcagcctcc gcaaacccctt cagtgatatc attgagccta agtttgaatt tgctgtcaag     1320
ttcaacgccc tggaacttga tgacagtgac ctggccctat tcattgcggc catcattctg     1380
tgtggagacc ggccaggcct catgaacgtt ccacgggtgg aggctatcca ggacaccatc     1440
ctgcgtgccc tcgaattcca cctgcaggcc aaccaccctg atgcccagta cctcttcccc     1500
aagctgctgc agaagatggc tgacctgcgg caactggtca ccgagcacgc ccagatgatg     1560
cagcggatca agaagaccga aaccgagacc tcgctgcacc ctctgctcca ggagatctac     1620
aaggacatgt actaacggcg gcacccaggc ctccctgcag actccaatgg ggccagcact     1680 ggagggggccc acccacatga cttttccatt gaccagccct tgagcacccg gcctggagca     1740
gcagagtccc acgatcgccc tcagacacat gacacccacg gcctctggct ccctgtgccc     1800
tctctcccgc ttcctccagc cagctctctt cctgtctttg ttgtctccct ctttctcagt     1860
tcctctttct tttctaattc ctgttgctct gtttcttcct ttctgtaggt ttctctcttc     1920
ccttctccct tgccctccct ttctctctcc accccccacg tctgtcctcc tttcttattc     1980
tgtgagatgt tttgtattat ttcaccagca gcatagaaca ggacctctgc ttttgcacac     2040
cttttcccca ggagcagaag agagtgggc ctgccctctg ccccatcatt gcacctgcag     2100
gcttaggtcc tcacttctgt ctcctgtctt cagagcaaaa gacttgagcc atccaaagaa     2160
acactaagct ctctgggcct gggttccagg gaaggctaag catggcctgg actgactgca     2220
gccccctata gtcatggggt ccctgctgca aaggacagtg ggcaggaggc cccaggctga     2280
gagccagatg cctccccaag actgtcattg cccctccgat gctgaggcca cccactgacc     2340
caactgatcc tgctccagca gcacacctca gccccactga cacccagtgt ccttccatct     2400
tcacactggt ttgccaggcc aatgttgctg atggccccct gcactggccg ctggacggca     2460
ctctcccagc ttggaagtag gcagggttcc ctccaggtgg gccccacct cactgaagag      2520 gagcaagtct caagagaagg aggggggatt ggtggttgga ggaagcagca cacccaattc     2580 tgccccctagg actcggggtc tgagtcctgg ggtcaggcca gggagagctc ggggcaggcc     2640
ttccgccagc actcccactg ccccctgcc cagtagcagc cgcccacatt gtgtcagcat      2700
ccagggccag ggcctggcct cacatccccc tgctcctttc tctagctggc tccacggag      2760 ttcaggcccc actcccctg aagctgcccc tccagcacac acacataagc actgaaatca     2820
```

```
ctttacctgc aggctccatg cacctccctt ccctccctga ggcaggtgag aacccagaga    2880
gaggggcctg caggtgagca gcagggctg ggccaggtct ccggggaggc aggggtcctg     2940
caggtcctgg tgggtcagcc cagcacctgc tcccagtggg agcttcccgg gataaactga   3000
gcctgttcat tctgatgtcc atttgtccca atagctctac tgccctcccc ttccccttta   3060
ctcagcccag ctggccacct agaagtctcc ctgcacagcc tctagtgtcc ggggaccttg   3120
tgggaccagt cccacaccgc tggtccctgc cctcccctgc tcccaggttg aggtgcgctc   3180
acctcagagc agggccaaag cacagctggg catgccatgt ctgagcggcg cagagccctc   3240
caggcctgca ggggcaaggg gctggctgga gtctcagagc acagaggtag gagaactggg   3300
gttcaagccc aggcttcctg ggtcctgcct ggtcctccct cccaaggagc cattctgtgt   3360
gtgactctgg gtggaagtgc ccagcccctg cccctacggg cgctgcagcc tcccttccat   3420
gccccaggat cactctctgc tggcaggatt cttcccgctc cccacctacc cagctgatgg   3480
gggttggggt gcttcctttc aggccaaggc tatgaaggga cagctgctgg gacccacctc   3540
cccctccccg gccacatgcc gcgtccctgc cccgacccgg gtctggtgct gaggatacag   3600
ctcttctcag tgtctgaaca atctccaaaa ttgaaatgta tattttgct aggagcccca    3660 gcttcctgtg ttttaatat aaatagtgta cacagactga cgaaacttta aataaatggg    3720
aattaaatat ttaa                                                      3734
```

<210> SEQ ID NO 40
<211> LENGTH: 441
<212> TYPE: PRT
<213> ORGANISM: Homo sapiens

<400> SEQUENCE: 40

```
Met Glu Gln Pro Gln Glu Ala Pro Glu Val Arg Glu Glu Glu
 1               5                  10                  15

Lys Glu Val Ala Glu Ala Glu Gly Ala Pro Glu Leu Asn Gly Gly
                20                  25                  30

Pro Gln His Ala Leu Pro Ser Ser Ser Tyr Thr Asp Leu Ser Arg Ser
            35                  40                  45

Ser Ser Pro Pro Ser Leu Leu Asp Gln Leu Gln Met Gly Cys Asp Gly
        50                  55                  60

Ala Ser Cys Gly Ser Leu Asn Met Glu Cys Arg Val Cys Gly Asp Lys
    65                  70                  75                  80

Ala Ser Gly Phe His Tyr Gly Val His Ala Cys Glu Gly Cys Lys Gly
                    85                  90                  95

Phe Phe Arg Arg Thr Ile Arg Met Lys Leu Glu Tyr Glu Lys Cys Glu
                100                 105                 110

Arg Ser Cys Lys Ile Gln Lys Lys Asn Arg Asn Lys Cys Gln Tyr Cys
            115                 120                 125

Arg Phe Gln Lys Cys Leu Ala Leu Gly Met Ser His Asn Ala Ile Arg
        130                 135                 140

Phe Gly Arg Met Pro Glu Ala Glu Lys Arg Lys Leu Val Ala Gly Leu
    145                 150                 155                 160
```

-continued

```
Thr Ala Asn Glu Gly Ser Gln Tyr Asn Pro Gln Val Ala Asp Leu Lys
            165                 170                 175

Ala Phe Ser Lys His Ile Tyr Asn Ala Tyr Leu Lys Asn Phe Asn Met
        180                 185                 190

Thr Lys Lys Lys Ala Arg Ser Ile Leu Thr Gly Lys Ala Ser His Thr
    195                 200                 205

Ala Pro Phe Val Ile His Asp Ile Glu Thr Leu Trp Gln Ala Glu Lys
210                 215                 220

Gly Leu Val Trp Lys Gln Leu Val Asn Gly Leu Pro Pro Tyr Lys Glu
225                 230                 235                 240

Ile Ser Val His Val Phe Tyr Arg Cys Gln Cys Thr Thr Val Glu Thr
                245                 250                 255

Val Arg Glu Leu Thr Glu Phe Ala Lys Ser Ile Pro Ser Phe Ser Ser
            260                 265                 270

Leu Phe Leu Asn Asp Gln Val Thr Leu Leu Lys Tyr Gly Val His Glu
        275                 280                 285

Ala Ile Phe Ala Met Leu Ala Ser Ile Val Asn Lys Asp Gly Leu Leu
    290                 295                 300

Val Ala Asn Gly Ser Gly Phe Val Thr Arg Glu Phe Leu Arg Ser Leu
305                 310                 315                 320

Arg Lys Pro Phe Ser Asp Ile Ile Glu Pro Lys Phe Glu Phe Ala Val
                325                 330                 335

Lys Phe Asn Ala Leu Glu Leu Asp Asp Ser Asp Leu Ala Leu Phe Ile
            340                 345                 350

Ala Ala Ile Ile Leu Cys Gly Asp Arg Pro Gly Leu Met Asn Val Pro
        355                 360                 365

Arg Val Glu Ala Ile Gln Asp Thr Ile Leu Arg Ala Leu Glu Phe His
    370                 375                 380

Leu Gln Ala Asn His Pro Asp Ala Gln Tyr Leu Phe Pro Lys Leu Leu
385                 390                 395                 400

Gln Lys Met Ala Asp Leu Arg Gln Leu Val Thr Glu His Ala Gln Met
                405                 410                 415

Met Gln Arg Ile Lys Lys Thr Glu Thr Glu Thr Ser Leu His Pro Leu
            420                 425                 430

Leu Gln Glu Ile Tyr Lys Asp Met Tyr
        435                 440

<210> SEQ ID NO 41
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 41
gagtgaatta gcccttccag t                                           21

<210> SEQ ID NO 42
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 42
gtgtggaaaa tctctagcag t                                           21

<210> SEQ ID NO 43
```

```
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 43
tgctagttct agcaggccct tgggccggcg cttgcgcc                    38
```